(12) United States Patent
Kawashima et al.

(10) Patent No.: US 7,977,371 B2
(45) Date of Patent: Jul. 12, 2011

(54) PYRROLE DERIVATIVE HAVING UREIDO GROUP AND AMINOCARBONYL GROUP AS SUBSTITUENTS

(75) Inventors: Kenji Kawashima, Ikoma (JP); Hiroshi Enomoto, Ikoma (JP); Noriko Ishizaka, Ikoma (JP); Minoru Yamamoto, Ikoma (JP); Kazuhiro Kudou, Ikoma (JP); Masaaki Murai, Ikoma (JP); Takaaki Inaba, Ikoma (JP); Kazuyoshi Okamoto, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 150 days.

(21) Appl. No.: 12/449,794

(22) PCT Filed: Feb. 26, 2008

(86) PCT No.: PCT/JP2008/053297
§ 371 (c)(1),
(2), (4) Date: Aug. 25, 2009

(87) PCT Pub. No.: WO2008/105408
PCT Pub. Date: Sep. 4, 2008

(65) Prior Publication Data
US 2010/0099675 A1 Apr. 22, 2010

(30) Foreign Application Priority Data
Feb. 26, 2007 (JP) ................... 2007-045582

(51) Int. Cl.
A61K 31/5377 (2006.01)
A61K 31/497 (2006.01)
A61K 31/496 (2006.01)
A61K 31/454 (2006.01)
A61K 31/4439 (2006.01)
A61K 31/427 (2006.01)
A61K 31/422 (2006.01)
A61K 31/403 (2006.01)
A61K 31/4025 (2006.01)
A61K 31/40 (2006.01)
C07D 417/12 (2006.01)
C07D 413/12 (2006.01)
C07D 409/04 (2006.01)
C07D 405/12 (2006.01)
C07D 407/10 (2006.01)
C07D 401/12 (2006.01)
C07D 401/04 (2006.01)
C07D 403/12 (2006.01)
C07D 403/10 (2006.01)

(52) U.S. Cl. ................... 514/423; 514/326; 514/254.01; 514/414; 514/378; 514/365; 514/255.05; 514/343; 514/235.5; 546/279.1; 546/208; 548/537; 548/465; 548/247; 548/204; 544/372; 544/141; 544/405

(58) Field of Classification Search .................. 514/423; 548/537
See application file for complete search history.

(56) References Cited

U.S. PATENT DOCUMENTS
7,015,218 B1 3/2006 Ushio et al.
2001/0020034 A1 9/2001 Larson et al.

FOREIGN PATENT DOCUMENTS
WO WO 98/52558 A1 11/1998
WO WO 00/71532 A1 11/2000
WO WO 03/086371 A2 10/2003
(Continued)

OTHER PUBLICATIONS

Bessatsu Igaku no Agumi (Journal of Clinical and Experimental Medicine, Supplement) Cytokines, Iso kara Risho Oyo made (from Basic to Clinical Research) pp. 28-35 (1992) (with translation of relevant portion, p. 31, Table 1).
(Continued)

Primary Examiner — Joseph Kosack
Assistant Examiner — Matthew Coughlin
(74) Attorney, Agent, or Firm — Holtz, Holtz, Goodman & Chick, PC

(57) ABSTRACT

Objects of the present invention are to study on the synthesis of a novel pyrrole derivative having a ureido group and an aminocarbonyl group as substituents or a salt thereof, to find a pharmacological effect of the derivative or a salt thereof, and to find a medicinal agent which has a prophylactic and/or therapeutic effect on a retinal disease or the like through oral administration. A compound represented by the general formula (1) or a salt thereof has an inhibitory activity against the production of interleukin-6 and/or an inhibitory effect on choroidal neovascularization, and is therefore useful as a prophylactic and/or therapeutic agent for a disease associated with interleukin-6, an ocular inflammatory disease and/or a retinal disease. In the formula, the ring A represents a benzene ring or the like; $R^1$ represents a halogen atom, a hydrogen atom, a lower alkyl group or the like; $R^2$ represents a halogen atom, a lower alkyl group which may have a substituent, a lower alkenyl group, a lower alkynyl group which may have a substituent, a lower cycloalkyl group, an aryl group, a hydroxy group, a lower alkoxy group which may have a substituent or the like; and n represents 0, 1, 2, 3 or the like.

(1)

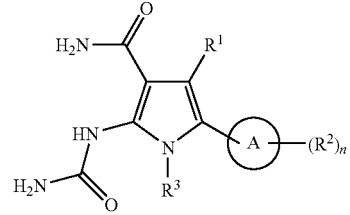

23 Claims, No Drawings

FOREIGN PATENT DOCUMENTS

WO   WO 2005/113534 A2   12/2005
WO   WO 2005/123671 A1   12/2005

OTHER PUBLICATIONS

K. Izumi et al, "Suppression of Choroidal Neovascularization by Blocking Interleukin-6 Receptor Signaling" *Invest. Ophthalmol. Vis. Sci.*, 47, E-Abstract 905 (2006).

N. Namura et al, "Increased concentration of pentosidine, an advanced glycation end product, and interleukin-6 in the vitreous of patients . . .", *Diabetes Res. Clin. Pract.*, 61, pp. 93-101 (2003).

H. Funatsu et al, "Vitreous Levels of Interleukin-6 and Vascular Endothelial Growth Factor Are Related to Diabetic Macular Edema", *Ophthamology*, 110, pp. 1690-1696 (2003).

STN Registry files CAS No. 375823-41-9, 2001.

M.T. Garcia-Lopez et al, "New Routes for the Sunthesis of Pyrrolo-[3,2-d]-pyrimidine Systems Starting from a Common Pyrrole Derivative", *J. Chem. Soc. Perkin Transactions 1*, 5, pp. 483-487 (1978).

Communication dated Jul. 14, 2010 (7 pages) in EP 08 72 0883 including the International Search Report and European Search Opinion.

PYRROLE DERIVATIVE HAVING UREIDO GROUP AND AMINOCARBONYL GROUP AS SUBSTITUENTS

This application is the United States national phase application of International Application PCT/JP2008/053297 filed Feb. 26, 2008.

TECHNICAL FIELD

The present invention relates to a novel pyrrole derivative having a ureido group and an aminocarbonyl group as substituents or a salt thereof which is useful as a pharmaceutical. The derivative has an inhibitory activity against the production of interleukin-6 (hereinafter referred to as "IL-6") and/or an inhibitory effect on choroidal neovascularization, and is therefore useful as a prophylactic and/or therapeutic agent for a disease considered to be associated with IL-6, an ocular inflammatory disease and/or a retinal disease.

BACKGROUND ART

IL-6 is a cytokine that was discovered as a B-cell differentiation inducing factor and has a variety of bioactivities such as antibody production system, induction of biosynthesis of acute phase protein in the liver, and acceleration of proliferation of hematopoietic stem cells based on its synergistic effect with interleukin-3.

Accordingly, if the production of IL-6 can be regulated, prevention and/or treatment of a disease considered to be associated with IL-6 can be realized.

As the disease considered to be associated with IL-6, for example, polyclonal B cell disorders (such as intra-atrial myxoma, Castleman syndrome, rheumatoid arthritis, cervical cancer, acquired immunodeficiency syndrome and alcoholic liver cirrhosis), lymphoid tumors (such as multiple myeloma and Lennert T lymphoma), mesangioproliferative nephritis, renal cell carcinoma, psoriasis and the like have been known (Bessatsu Igaku no Ayumi (Journal of Clinical and Experimental Medicine, Supplement) Cytokines, Kiso kara'Rinsho Oyo made (from Basic to Clinical Research), 28-35 (1992)).

Further, recently, correlation between IL-6 and ocular inflammatory diseases such as age-related macular degeneration, diabetic retinopathy and diabetic macular edema has also become known (Invest. Ophthalmol. Vis. Sci. 47, E-Abstract 905 (2006), Diabetes. Res. Clin. Pract. 61, 93-101 (2003), and Ophthalmology, 110, 1690-1696 (2003)).

Further, a lot of medicinal agents for regulating IL-6 have been known, and for example, WO 2003/086371 describes that a benzimidazole derivative having an EP4 agonistic effect inhibits IL-6 production, and STN Registry files CAS No. 375823-41-9 describes MRA which is an anti-IL-6 receptor antibody.

On the other hand, J. Chem. Soc. Perkin Transactions 1, 5, 483-487 (1978) describes a pyrrole derivative having a ureido group as a substituent. Further, WO 2005/123671 describes, as a therapeutic agent for an immune or allergic disease, a pyrrole derivative having an aminocarbonyl group as a substituent. However, a pyrrole derivative having both ureido group and aminocarbonyl group as substituents is an entirely unknown compound, and as a matter of course, the use thereof is also not known.

DISCLOSURE OF THE INVENTION

Problems that the Invention is to Solve

It is a very interesting subject to study the synthesis of a novel pyrrole derivative having a ureido group and an aminocarbonyl group as substituents or a salt thereof, and to find a pharmacological effect of the derivative or a salt thereof, and particularly, it is a very interesting subject to find a medicinal agent, which has a prophylactic and/or therapeutic effect on a retinal disease or the like through oral administration of the medicinal agent.

Means for Solving the Problems

The present inventors conducted studies of the synthesis of a novel pyrrole derivative having a ureido group and an aminocarbonyl group as substituents or a salt thereof, and succeeded in creating a large number of novel compounds.

Further, as a result of various studies of a pharmacological effect of the derivative or a salt thereof, the present inventors found that the derivative or a salt thereof has an inhibitory activity against IL-6 production and/or an inhibitory effect on choroidal neovascularization through oral administration, and thus, the present invention has been completed.

That is, the present invention relates to a compound represented by the following general formula (1) or a salt thereof (hereinafter referred to as "the present compound") and a pharmaceutical composition containing the same. Further, a preferred invention of the medical use thereof relates to an inhibitor of IL-6 production, a prophylactic and/or therapeutic agent for a disease considered to be associated with IL-6, a prophylactic and/or therapeutic agent for an ocular inflammatory disease and a prophylactic and/or therapeutic agent for a retinal disease. Examples of the diseases to be targeted by the pharmaceutical composition include diseases considered to be associated with IL-6, ocular inflammatory diseases and/or retinal diseases, and specific examples thereof include age-related macular degeneration, retinopathy of prematurity, polypoidal choroidal vasculopathy, retinal vein occlusion, diabetic retinopathy, diabetic macular edema, keratitis, conjunctivitis and uveitis, and particularly preferred examples thereof include age-related macular degeneration, diabetic retinopathy and diabetic macular edema.

A particularly preferred medical use invention is an invention relating to a prophylactic or therapeutic agent for these diseases containing the present compound as an active ingredient.

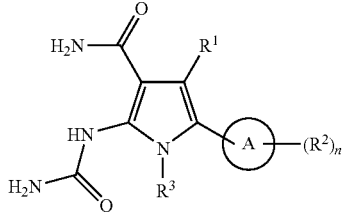

(1)

[The ring A represents a benzene ring or a monocyclic aromatic heterocyclic ring;

$R^1$ represents a halogen atom, a hydrogen atom, a lower alkyl group which may have a substituent, a formyl group or a lower alkylcarbonyl group which may have a substituent;

$R^2$ represents a halogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a hydroxy group, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent, a heterocyclic oxy group which may have a substituent, a formyl group, a lower alkylcarbonyl group which may have a substituent, an arylcarbonyl group which may have a substituent, a carboxy group, a lower alkoxycarbonyl group which may have a substituent, an aryloxycarbonyl group which may have a substituent, a lower alkylcarbonyloxy group which may have a substituent, an arylcarbonyloxy group which may have a substituent, a mercapto group, a lower alkylthio group which may have a substituent, a lower cycloalkylthio group which may have a substituent, an arylthio group which may have a substituent, a lower alkylsulfinyl group which may have a substituent, an arylsulfinyl group which may have a substituent, a lower alkylsulfonyl group which may have a substituent, an arylsulfonyl group which may have a substituent, a cyano group, a nitro group, $-NR^{a1}R^{a2}$, $-CONR^{b1}R^{b2}$, $-SONR^{c1}R^{c2}$, $-SO_2NR^{d1}R^{d2}$ or $-OCONR^{e1}R^{e2}$;

$R^3$ represents a hydrogen atom, a lower alkyl group which may have a substituent, an aryl group which may have a substituent or an acyl group which may have a substituent;

$R^{a1}$, $R^{a2}$, $R^{b1}$, $R^{b2}$, $R^{c1}$, $R^{c2}$, $R^{d1}$, $R^{d2}$, $R^{e1}$, and $R^{e2}$ are the same or different and represent a hydrogen atom, a lower alkyl group which may have a substituent or an aryl group which may have a substituent, and further, $R^{a1}$ and $R^{a2}$, $R^{b1}$ and $R^{b2}$, $R^{c1}$ and $R^{c2}$, $R^{d1}$ and $R^{d2}$ or $R^{e1}$ and $R^{e2}$ may be joined to each other to form a nitrogen-containing heterocyclic ring which may have a substituent;

n represents 0, 1, 2, 3, 4 or 5; and provided that when n is 2, 3, 4 or 5, $R^2$ may be the same or different. The same shall apply hereinafter.]

Advantage of the Invention

The present invention provides a novel pyrrole derivative having a ureido group and an aminocarbonyl group as substituents or a salt thereof. The present compound has an excellent inhibitory activity against IL-6 production and/or inhibitory effect on choroidal neovascularization, and is therefore useful as an inhibitor of IL-6 production, a prophylactic and/or therapeutic agent for a disease considered to be associated with IL-6, a prophylactic and/or therapeutic agent for an ocular inflammatory disease and a prophylactic and/or therapeutic agent for a retinal disease.

More specifically, the present compound is useful as a prophylactic or therapeutic agent for age-related macular degeneration, retinopathy of prematurity, polypoidal choroidal vasculopathy, retinal vein occlusion, diabetic retinopathy, diabetic macular edema, keratitis, conjunctivitis, uveitis or the like.

BEST MODE FOR CARRYING OUT THE INVENTION

Hereinafter, definitions of terms and phrases (atoms, groups, rings and the like) to be used in this specification will be described in detail. Further, when the other definitions of terms and phrases are applied to the definitions of terms and phrases mentioned below, preferred ranges of the respective definitions and the like can also be applied.

The "halogen atom" refers to a fluorine, chlorine, bromine, or iodine atom.

The "lower alkyl group" refers to a straight-chain or branched alkyl group having 1 to 6 carbon atoms. Specific examples thereof include methyl, ethyl, n-propyl, n-butyl, n-pentyl, n-hexyl, isopropyl, isobutyl, sec-butyl, tert-butyl and isopentyl groups.

The "lower alkenyl group" refers to a straight-chain or branched alkenyl group having 2 to 6 carbon atoms. Specific examples thereof include vinyl, propenyl, butenyl, pentenyl, hexenyl, ethylpropenyl and methylbutenyl groups.

The "lower alkynyl group" refers to a straight-chain or branched alkynyl group having 2 to 6 carbon atoms. Specific examples thereof include ethynyl, propynyl, butynyl, pentynyl and hexynyl groups.

The "lower cycloalkyl group" refers to a cycloalkyl group having 3 to 8 carbon atoms. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon group, or a bicyclic or tricyclic condensed polycyclic aromatic hydrocarbon having 6 to 14 carbon atoms. Specific examples thereof include phenyl, naphthyl, anthryl and phenanthryl groups.

The "lower alkoxy group" refers to a group formed by substituting the hydrogen atom of a hydroxy group with a lower alkyl group. Specific examples thereof include methoxy, ethoxy, n-propoxy, n-butoxy, n-pentyloxy, n-hexyloxy, isopropoxy, isobutoxy, sec-butoxy, tert-butoxy and isopentyloxy groups.

The "lower alkenyloxy group" refers to a group formed by substituting the hydrogen atom of a hydroxy group with a lower alkenyl group. Specific examples thereof include vinyloxy, propenyloxy, butenyloxy, pentenyloxy, hexenyloxy, ethylpropenyloxy and methylbutenyloxy groups.

The "lower alkynyloxy group" refers to a group formed by substituting the hydrogen atom of a hydroxy group with a lower alkynyl group. Specific examples thereof include ethynyloxy, propynyloxy, butynyloxy, pentynyloxy and hexynyloxy groups.

The "lower cycloalkyloxy group" refers to a group formed by substituting the hydrogen atom of a hydroxy group with a lower cycloalkyl group. Specific examples thereof include cyclopropyloxy, cyclobutyloxy, cyclopentyloxy, cyclohexyloxy, cycloheptyloxy and cyclooctyloxy groups.

The "aryloxy group" refers to a group formed by substituting the hydrogen atom of a hydroxy group with an aryl group. Specific examples thereof include phenoxy, naphthoxy, anthryloxy and phenanthryloxy groups.

The "lower alkylcarbonyl group" refers to a group formed by substituting the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl and isopentylcarbonyl groups.

The "arylcarbonyl group" refers to a group formed by substituting the hydrogen atom of a formyl group with an aryl group. Specific examples thereof include phenylcarbonyl, naphthylcarbonyl, anthrylcarbonyl and phenanthrylcarbonyl groups.

The "lower alkoxycarbonyl group" refers to a group formed by substituting the hydrogen atom of a formyl group with a lower alkoxy group. Specific examples thereof include methoxycarbonyl, ethoxycarbonyl, n-propoxycarbonyl, n-butoxycarbonyl, n-pentyloycarbonyl, n-hexyloxycarbonyl, isopropoxycarbonyl, isobutoxycarbonyl, sec-butoxycarbonyl, tert-butoxycarbonyl and isopentyloxycarbonyl groups.

The "aryloxycarbonyl group" refers to a group formed by substituting the hydrogen atom of a formyl group with an aryloxy group. Specific examples thereof include phenoxycarbonyl, naphthoxycarbonyl, anthryloxycarbonyl and phenanthryloxycarbonyl groups.

The "lower alkylcarbonyloxy group" refers to a group formed by substituting the hydrogen atom of a hydroxy group with a lower alkylcarbonyl group. Specific examples thereof include methylcarbonyloxy, ethylcarbonyloxy, n-propylcarbonyloxy, n-butylcarbonyloxy, n-pentylcarbonyloxy, n-hexylcarbonyloxy, isopropylcarbonyloxy, isobutylcarbonyloxy, sec-butylcarbonyloxy, tert-butylcarbonyloxy and isopentylcarbonyloxy groups.

The "arylcarbonyloxy group" refers to a group formed by substituting the hydrogen atom of a hydroxy group with an arylcarbonyl group. Specific examples thereof include phenylcarbonyloxy, naphthylcarbonyloxy, anthrylcarbonyloxy and phenanthrylcarbonyloxy groups.

The "lower alkylthio group" refers to a group formed by substituting the hydrogen atom of a mercapto group with a lower alkyl group. Specific examples thereof include methylthio, ethylthio, n-propylthio, n-butylthio, n-pentylthio, n-hexylthio, isopropylthio, isobutylthio, sec-butylthio, tert-butylthio and isopentylthio groups.

The "lower cycloalkylthio group" refers to a group formed by substituting the hydrogen atom of a mercapto group with a lower cycloalkyl group. Specific examples thereof include cyclopropylthio, cyclobutylthio, cyclopentylthio, cyclohexylthio, cycloheptylthio and cyclooctylthio groups.

The "arylthio group" refers to a group formed by substituting the hydrogen atom of a mercapto group with an aryl group. Specific examples thereof include phenylthio, naphthylthio, anthrylthio and phenanthrylthio groups.

The "lower alkylsulfinyl group" refers to a group formed by substituting the hydroxy group of a sulfinate group with a lower alkyl group. Specific examples thereof include methylsulfinyl, ethylsulfinyl, n-propylsulfinyl, n-butylsulfinyl, n-pentylsulfinyl, n-hexylsulfinyl, isopropylsulfinyl, isobutylsulfinyl, sec-butylsulfinyl, tert-butylsulfinyl and isopentylsulfinyl groups.

The "arylsulfinyl group" refers to a group formed by substituting the hydroxy group of a sulfinate group with an aryl group. Specific examples thereof include phenylsulfinyl, naphthylsulfinyl, anthrylsulfinyl and phenanthrylsulfinyl groups.

The "lower alkylsulfonyl group" refers to a group formed by substituting the hydroxy group of a sulfonate group with a lower alkyl group. Specific examples thereof include methylsulfonyl, ethylsulfonyl, n-propyl sulfonyl, n-butylsulfonyl, n-pentyl sulfonyl, n-hexylsulfonyl, isopropylsulfonyl, isobutylsulfonyl, sec-butylsulfonyl, tert-butylsulfonyl and isopentylsulfonyl groups.

The "arylsulfonyl group" refers to a group formed by substituting the hydroxy group of a sulfonate group with an aryl group. Specific examples thereof include phenylsulfonyl, naphthylsulfonyl, anthrylsulfonyl and phenanthrylsulfonyl groups.

The "acyl group" refers to a group formed by removing the hydroxy group from the carboxy group of a saturated aliphatic monocarboxylic acid, an unsaturated aliphatic monocarboxylic acid, a carbocyclic monocarboxylic acid or a heterocyclic monocarboxylic acid.

Specific examples of the saturated aliphatic monocarboxylic acid include straight-chain or branched groups having 1 to 7 carbon atoms such as formic acid, acetic acid, propionic acid, butyric acid, isobutyric acid, valeric acid, isovaleric acid and pivalic acid.

Specific examples of the unsaturated aliphatic monocarboxylic acid include straight-chain or branched groups having 3 to 7 carbon atoms such as acrylic acid, propiolic acid, methacrylic acid, crotonic acid and isocrotonic acid.

Specific examples of the carbocyclic monocarboxylic acid include groups having 7 to 12 carbon atoms such as benzoic acid, naphthoic acid and toluic acid.

Specific examples of the heterocyclic monocarboxylic acid include groups having 5 or 6 carbon atoms such as furancarboxylic acid, thiophenecarboxylic acid, nicotinic acid and isonicotinic acid.

The "heterocyclic ring" refers to a saturated or unsaturated monocyclic heterocyclic ring, or a bicyclic or tricyclic condensed polycyclic heterocyclic ring having one or plural heteroatoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings, each of which has a nitrogen atom in the ring; tetrahydrofuran and tetrahydropyran rings, each of which has an oxygen atom in the ring; tetrahydrothiophene and tetrahydrothiopyran rings, each of which has a sulfur atom in the ring; oxazolidine, isoxazolidine and morpholine rings, each of which has a nitrogen atom and an oxygen atom in the ring; and thiazolidine, isothiazolidine and thiomorpholine rings, each of which has a nitrogen atom and a sulfur atom in the ring.

Further, such a saturated monocyclic heterocyclic ring may be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chroman, isochroman, dihydrobenzothiophene, dihydroisobenzothiophene, thiochroman, isothiochroman, dihydrobenzoxazole, dihydrobenzisoxazole, dihydrobenzoxazine, dihydrobenzothiazole, dihydrobenzoisothiazole, dihydrobenzothiazine, xanthene, 4a-carbazole or perimidine ring.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, pyrazine and triazine rings, each of which has a nitrogen atom in the ring; dihydrofuran, furan, dihydropyran and pyran rings, each of which has an oxygen atom in the ring; dihydrothiophene, thiophene, dihydrothiopyran and thiopyran rings, each of which has a sulfur atom in the ring; dihydrooxazole, oxazole, dihydroisoxazole, isoxazole, dihydrooxazine and oxazine rings, each of which has a nitrogen atom and an oxygen atom in the ring; and dihydrothiazole, thiazole, dihydroisothiazole, isothiazole, dihydrothiazine and thiazine rings, each of which has a nitrogen atom and a sulfur atom in the ring.

Further, such an unsaturated monocyclic heterocyclic ring may be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromen, isochromen, benzothiophene, isobenzothiophene, thiochromen, isothiochromen, benzoxazole, benzisoxazole, benzoxazine, benzothiazole, benzoisothiazole, benzothiazine, phenoxanthine, carbazole, β-carboline, phenanthridine, acridine, phenanthroline, phenazine, phenothiazine or phenoxazine ring.

Among the above-mentioned heterocyclic rings, preferred is a pyrrolidine, piperidine, piperazine, morpholine, dihydroindole, pyrrole, pyridine, pyrazine, furan, thiophene, pyran, isoxazole or thiazole ring, and particularly preferred is a pyrrolidine; piperidine, piperazine, morpholine, pyridine, pyrazine or thiophene ring.

The "monocyclic aromatic heterocyclic ring" refers to a ring that exhibits aromaticity among the unsaturated monocyclic heterocyclic rings. Specific examples thereof include pyrrole, pyrazole, imidazole, triazole, pyridine, pyridazine, pyrimidine, pyrazine, triazine, furan, thiophene, oxazole, isoxazole, thiazole and isothiazole rings.

The "heterocyclic group" refers to a residue formed by removing one hydrogen atom from a heterocyclic ring.

The "heterocyclic oxy group" refers to a group formed by substituting the hydrogen atom of a hydroxy group with a heterocyclic group.

The "heterocyclic carbonyl group" refers to a group formed by substituting the hydrogen atom of a formyl group with a heterocyclic group.

The "heterocyclic oxy carbonyl group" refers to a group formed by substituting the hydrogen atom of a formyl group with a heterocyclic oxy group.

The "nitrogen-containing heterocyclic ring" refers to a ring containing one or plural nitrogen atoms in the ring among the heterocyclic rings. Specific examples thereof include pyrrolidine, piperidine, piperazine, homopiperazine, morpholine, pyrrole and pyridine rings.

The "lower alkyl group which may have a substituent", "lower alkenyl group which may have a substituent", "lower alkynyl group which may have a substituent", "lower alkoxy group which may have a substituent", "lower alkenyloxy group which may have a substituent", "lower alkynyloxy group which may have a substituent", "lower alkylcarbonyl group which may have a substituent", "lower alkoxycarbonyl group which may have a substituent", "lower alkylcarbonyloxy group which may have a substituent", "lower alkylthio group which may have a substituent", "lower alkylsulfinyl group which may have a substituent" and/or "lower alkylsulfonyl group which may have a substituent" refers to a "lower alkyl group", a "lower alkenyl group", a "lower alkynyl group", a "lower alkoxy group", a "lower alkenyloxy group", a "lower alkynyloxy group", a "lower alkylcarbonyl group", a "lower alkoxycarbonyl group", a "lower alkylcarbonyloxy group", a "lower alkylthio group", a "lower alkylsulfinyl group" and/or a "lower alkylsulfonyl group" which may have one or plural substituents selected from the group consisting of a halogen atom, a lower cycloalkyl group, an aryl group which may have a substituent, a heterocyclic group which may have a substituent, a hydroxy group, a lower alkoxy group which may have a substituent, a lower cycloalkyloxy group, an aryloxy group, a heterocyclic oxy group, a formyl group, a lower alkylcarbonyl group, an arylcarbonyl group which may have a substituent, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group which may have a substituent, an arylthio group, a nitro group, a cyano group, —CONR$^s$R$^t$ and —NR$^u$R$^v$.

The "lower cycloalkyl group which may have a substituent", "aryl group which may have a substituent", "heterocyclic ring which may have a substituent", "lower cycloalkyloxy group which may have a substituent", "aryloxy group which may have a substituent", "heterocyclic oxy group which may have a substituent", "arylcarbonyl group which may have a substituent", "aryloxycarbonyl group which may have a substituent", "arylcarbonyloxy group which may have a substituent", "lower cycloalkylthio group which may have a substituent", "arylthio group which may have a substituent", "arylsulfinyl group which may have a substituent", "arylsulfonyl group which may have a substituent", "acyl group which may have a substituent" and/or "nitrogen-containing heterocyclic ring which may have a substituent" refers to a "lower cycloalkyl group", an "aryl group", a "heterocyclic ring", a "lower cycloalkyloxy group", an "aryloxy group", a "heterocyclic oxy group", an "arylcarbonyl group", an "aryloxycarbonyl group", an "arylcarbonyloxy group", a "lower cycloalkylthio group", an "arylthio group", an "arylsulfinyl group", an "arylsulfonyl group", an "acyl group" and/or a "nitrogen-containing heterocyclic ring" which may have one or plural substituents selected from the group consisting of a halogen atom, a lower alkyl group which may have a substituent, a lower alkenyl group, a lower alkynyl group, a lower cycloalkyl group, an aryl group, a heterocyclic group, a hydroxy group, a lower alkoxy group, a lower cycloalkyloxy group, an aryloxy group, a heterocyclic oxy group, a carbonyl group (an oxo group), a formyl group, a lower alkylcarbonyl group, an arylcarbonyl group, a heterocyclic carbonyl group, a carboxy group, a lower alkoxycarbonyl group, an aryloxycarbonyl group, a heterocyclic oxy carbonyl group, a mercapto group, a lower alkylthio group, an arylthio group, a nitro group, a cyano group, —CONR$^s$R$^t$ and —NR$^u$R$^v$.

Here, R$^s$, R$^t$, R$^u$ and R$^v$ are the same or different and represent a hydrogen atom, a lower alkyl group, a lower alkyl group which may have a substituent, a lower alkenyl group, a lower alkynyl group, a lower cycloalkyl group, an aryl group or a heterocyclic group, and further, R$^s$ and R$^t$ or R$^u$ and R$^v$ may be joined to each other to form a nitrogen-containing heterocyclic ring which may have a substituent.

Here, the substituent of the "group which may have a substituent" may be a "group which may have a substituent", and the same shall in turn apply up to three times.

Further, the "group substituted with a group" refers to a group substituted with one or plural groups.

The term "plural groups" as used herein refers to a maximum number of substitutable groups which may be the same or different, and the number of the groups is preferably 2 and/or 3, particularly preferably 2.

Further, the concept of the "group" also includes the "atom", "group" and "ring" defined above and the like.

In the present invention, when "n" represents 2, 3, 4 or 5, the plural R$^2$ may be the same or different.

Further, when "n" represents 0, R$^2$ does not exist. That is, it shows that the ring A does not have the substituent R$^2$.

The "inhibitor of IL-6 production" as used herein refers to a compound which inhibits the production of IL-6 thereby to exhibit a pharmaceutical effect.

The "ocular inflammatory disease" and/or "retinal disease" as used herein includes age-related macular degeneration, retinopathy of prematurity, polypoidal choroidal vasculopathy, retinal vein occlusion, diabetic retinopathy, diabetic macular edema, keratitis, conjunctivitis, uveitis and the like, and preferably include age-related macular degeneration, diabetic retinopathy and diabetic macular edema.

Incidentally, the above-mentioned specific diseases are described for the purpose of understanding the invention better and are not meant to limit the scope of the invention.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalene sulfonate or sulfosalicylic acid; quaternary ammonium salts with methyl bromide, methyl iodide or the like salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; and salts with an organic amine such as triethylenediamine, 2-aminoethanol, 2,2-iminobis(ethanol), 1-deoxy-1-methylamino-2-D-sorbitol, 2-amino-2-hydroxymethyl-1,3-propanediol, procaine or N,N-bis(phenylmethyl)-1,2-ethanediamine.

In the case where there are geometric isomers or optical isomers in the present compound, these isomers are also included in the scope of the present invention.

Further, the present compound may be in the form of a hydrate or a solvate.

Further, in the case where there is proton tautomerism in the present compound, the tautomeric isomers thereof are also included in the present invention.

In the case where there are crystalline polymorphisms and/or crystalline polymorphism groups (crystalline polymorphism systems) in the present compound, these crystalline polymorphisms and/or crystalline polymorphism groups (crystalline polymorphism systems) are also included in the present invention. Here, the crystalline polymorphism groups (crystalline polymorphism systems) mean individual crystal forms in respective stages when the crystal forms are changed by conditions for the production, crystallization, storage or the like of these crystals and/or states thereof (the states also include a formulated state) and/or all the processes thereof.

(a) Preferred examples of the present compound include compounds in which the respective groups are as defined below and salts thereof in the compounds represented by the general formula (1) and salts thereof:

(a1) the ring A represents a benzene ring or a monocyclic aromatic heterocyclic ring; and/or (a2) $R^1$ represents a halogen atom, a hydrogen atom, a lower alkyl group which may have a substituent, a formyl group or a lower alkylcarbonyl group; and/or (a3) $R^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group which may have a substituent, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group which may have a substituent, a lower cycloalkylthio group, an arylthio group which may have a substituent, a lower alkylsulfinyl group, an arylsulfinyl group, a lower alkylsulfonyl group, an arylsulfonyl group, a cyano group, a nitro group, $-NR^{a1}R^{a2}$, $-CONR^{b1}R^{b2}$, $-SONR^{c1}R^{c2}$, $-SO_2NR^{d1}R^{d2}$ or $-OCONR^{e1}R^{e2}$; and/or (a4) $R^3$ represents a hydrogen atom, a lower alkyl group, an aryl group or an acyl group; and/or (a5) $R^{a1}$, $R^{a2}$, $R^{b1}$, $R^{b2}$, $R^{c1}$, $R^{c2}$, $R^{d1}$, $R^{d2}$, $R^{e1}$ and $R^{e2}$ are the same or different and represent a hydrogen atom, a lower alkyl group or an aryl group, and further, $R_{a1}$ and $R^{a2}$, $R^{b1}$ and $R^{b2}$, $R^{c1}$ and $R^{c2}$, $R^{d1}$ and $R^{d2}$ or $R^{e1}$ and $R^{e2}$ may be joined to each other to form a nitrogen-containing heterocyclic ring; and/or (a6) n represents 0, 1, 2, 3, 4 or 5; and/or (a7) provided that when n is 2, 3, 4 or 5, $R^2$ may be the same or different.

That is, preferred examples of the present compound include, in the compounds represented by the general formula (1), compounds which comprise one or a combination of two or more selected from the above (a1), (a2), (a3), (a4), (a5), (a6) and/or (a7) and salts thereof.

(b) More preferred examples of the present compound include compounds in which the respective groups are as defined below and salts thereof in the compounds represented by the general formula (1) and salts thereof:

(b1) the ring A represents a benzene ring or a monocyclic aromatic heterocyclic ring; and/or (b2) $R^1$ represents a halogen atom, a hydrogen atom, a lower alkyl group which may have a substituent, a formyl group or a lower alkylcarbonyl group; and/or (b3) $R^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group which may have a substituent, a lower cycloalkylthio group, an arylthio group, an arylthio group substituted with a nitro group, a lower alkylsulfinyl group, an arylsulfinyl group, a lower alkylsulfonyl group, an arylsulfonyl group, a cyano group, a nitro group, $-NR^{a1}R^{b1}$, $-CONR^{b1}R^{b2}$, $-SONR^{c1}R^{c2}$, $-SO_2NR^{d1}R^{d2}$ or $-OCONR^{e1}R^{e2}$; and/or (b4) provided that when $R^1$ and/or $R^2$ represents a lower alkyl group which may have a substituent, a lower alkynyl group which may have a substituent, a lower alkoxy group which may have a substituent or a lower alkylthio group which may have a substituent, the lower alkyl group, the lower alkynyl group, the lower alkoxy group or the lower alkylthio group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a heterocyclic group substituted with a carbonyl group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, an arylthio group, a lower alkylthio group substituted with a lower alkoxycarbonyl group, a cyano group and —NR$^{f1}$R$^{f2}$; and/or (b5) R$^3$ represents a hydrogen atom, a lower alkyl group, an aryl group or an acyl group; and/or (b6) R$^{a1}$, R$^{a2}$, R$^{b1}$, R$^{b2}$, R$^{c1}$, R$^{c2}$, R$^{d1}$, R$^{d2}$, R$^{e1}$ and R$^{e2}$ are the same or different and represent a hydrogen atom, a lower alkyl group or an aryl group, and further, R$^{a1}$ and R$^{a2}$, R$^{b1}$ and R$^{b2}$, R$^{c1}$ and R$^{c2}$, R$^{d1}$ and R$^{d2}$ or R$^{e1}$ and R$^{e2}$ may be joined to each other to form a nitrogen-containing heterocyclic ring; and/or (b7) R$^{f1}$ and R$^{f2}$ are the same or different and represent a hydrogen atom, a lower alkyl group which may have a substituent, a lower cycloalkyl group or an aryl group, and further, R$^{f1}$ and R$^{f2}$ may be joined to each other to form a nitrogen-containing heterocyclic ring which may have a lower alkyl group substituted with a hydroxy group or a carbonyl group as a substituent; and/or (b8) provided that when R$^{f1}$ and/or R$^{f2}$ represents a lower alkyl group which may have a substituent, the lower alkyl group represents a group which may be substituted with one or plural groups selected from the group consisting of a lower cycloalkyl group, an aryl group, a heterocyclic group, a hydroxy group, a lower alkoxy group, a lower cycloalkyloxy group, an aryloxy group, a heterocyclic oxy group and —NR$^{g1}$R$^{g2}$; and/or (b9) R$^{g1}$ and R$^{g2}$ are the same or different and represent a hydrogen atom or a lower alkyl group, and further, R$^{g1}$ and R$^{g2}$ may be joined to each other to form a nitrogen-containing heterocyclic ring; and/or (b10) n represents 0, 1, 2, 3, 4 or 5; and/or (b11) provided that when n is 2, 3, 4 or 5, R$^2$ may be the same or different.

That is, more preferred examples of the present compound include, in the compounds represented by the general formula (1), compounds which comprise one or a combination of two or more selected from the above (b1), (b2), (b3), (b4), (b5), (b6), (b7), (b8), (b9), (b10) and/or (b11) and salts thereof.

(c) Further more preferred examples of the present compound include compounds in which the respective groups are as defined below and salts thereof in the compounds represented by the general formula (1) and salts thereof:

(c1) the ring A represents a benzene ring or a monocyclic aromatic heterocyclic ring; and/or (c2) R$^1$ represents a halogen atom, a hydrogen atom, a lower alkyl group, a lower alkyl group substituted with a hydroxy group, a lower alkyl group substituted with a lower alkoxy group, a lower alkyl group substituted with —NR$^{h1}$R$^{h2}$, a formyl group or a lower alkylcarbonyl group; and/or (c3) R$^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group, a lower alkylthio group substituted with a cyano group, a lower cycloalkylthio group, an arylthio group, an arylthio group substituted with a nitro group, a lower alkylsulfinyl group, an arylsulfinyl group, a lower alkylsulfonyl group, an arylsulfonyl group, a cyano group, a nitro group, —CONR$^{b1}$R$^{b2}$, —SONR$^{c1}$R$^{c2}$, —SO$_2$NR$^{d1}$R$^{d2}$ or —OCONR$^{e1}$R$^{e2}$; and/or (c4) provided that when R$^2$ represents a lower alkyl group which may have a substituent, the lower alkyl group represents a group which may be substituted with one or plural groups selected from the group consisting of a halogen atom, a hydroxy group, a lower alkoxy group, a mercapto group, a lower alkylthio group and —NR$^{11}$R$^{12}$; and/or (c5) provided that when R$^2$ represents a lower alkynyl group which may have a substituent, the lower alkynyl group represents a group which may be substituted with one or plural groups selected from the group consisting of a lower cycloalkyl group, an aryl group, a hydroxy group, a lower alkoxy group, a lower cycloalkyloxy group, an aryloxy group and —NR$^{j1}$R$^{j2}$; and/or (c6) provided that when R$^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a heterocyclic group substituted with a carbonyl group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, a lower alkylthio group substituted with a lower alkoxycarbonyl group, an arylthio group, a cyano group and —NR$^{f1}$R$^{f2}$; and/or (c7) provided that when R$^2$ represents a lower alkylthio group which may have a substituent, the lower alkylthio group represents a group which may be substituted with one or plural groups selected from the group consisting of a hydroxy group, a lower alkoxy group, a mercapto group, a lower alkylthio group and a cyano group; and/or (c8) R$^3$ represents a hydrogen atom, a lower alkyl group, an aryl group or an acyl group; and/or (c9) R$^{a1}$, R$^{a2}$, R$^{b1}$, R$^{b2}$, R$^{c1}$, R$^{c2}$, R$^{d1}$, R$^{d2}$, R$^{e1}$ and R$^{e2}$ are the same or different and represent a hydrogen atom, a lower alkyl group or an aryl group, and further, R$^{a1}$ and R$^{a2}$, R$^{b1}$ and R$^{b2}$, R$^{c1}$ and R$^{c2}$, R$^{d1}$ and R$^{d2}$ or R$^{e1}$ and R$^{e2}$ may be joined to each other to form a nitrogen-containing heterocyclic ring; and/or (c10) R$^{f1}$ and R$^{f2}$ are the same or different and represent a hydrogen atom, a lower alkyl group, a lower alkyl group substituted with a lower cycloalkyl group, a lower alkyl group substituted with an aryl group, a lower alkyl group substituted with a heterocyclic group, a lower alkyl group substituted with a hydroxy group, a lower alkyl group substituted with a lower alkoxy group, a lower alkyl group substituted with a lower cycloalkyloxy group, a lower alkyl group substituted with an aryloxy group, a lower alkyl group substituted with a heterocyclic oxy group, a lower alkyl group substituted with —NR$^{g1}$R$^{g2}$, lower cycloalkyl group or an aryl group, and further, R$^{f1}$ and R$^{f2}$ may be joined to each other to form a nitrogen-containing heterocyclic ring which may have a lower alkyl group substituted with a hydroxy group or a carbonyl group as a substituent; and/or (c11) R$^{g1}$ and R$^{g2}$ are the same or different and represent a hydrogen atom or a lower alkyl group, and further, R$^{g1}$ and R$^{g2}$ may be joined to each other to form a nitrogen-containing heterocyclic ring; and/or (c12) R$^{h1}$ and R$^{h2}$ are the same or different and represent a hydrogen atom or a lower alkyl group, and further, R$^{h1}$ and R$^{h2}$ may be joined to each other to form a nitrogen-containing heterocyclic ring; and/or (c13) R$^{i1}$ and R$^{i2}$ are the same or different and represent a hydrogen atom, a lower alkyl group, a lower alkyl group substituted with a lower cycloalkyl group, a lower alkyl group substituted with an aryl group, a lower alkyl group substituted with a hydroxy group, a lower alkyl group substituted with a lower alkoxy group, a lower alkyl group substituted with a lower cycloalkyloxy group or a lower alkyl group substituted with an aryloxy group, and further, R$^{i1}$ and R$^{i2}$ may be joined to each other to form a nitrogen-containing heterocyclic ring; and/or (c14) R$^{j1}$ and R$^{j2}$ are the same or different and represent a hydrogen atom or a lower alkyl group, and further, R$^{j1}$ and R$^{j2}$ may be joined to each other to form a nitrogen-containing heterocyclic ring; and/or (c15) n represents 0, 1, 2 or 3; and/or (c16) provided that when n is 2 or 3, R$^2$ may be the same or different.

That is, further more preferred examples of the present compound include, in the compounds represented by the general formula (1), compounds which comprise one or a combination of two or more selected from the above (c1), (c2), (c3), (c4), (c5), (c6), (c7), (c8), (c9), (c10), (c11), (c12), (c13), (c14), (c15), and/or (b16) and salts thereof.

(d) Still further more preferred examples of the present compound include compounds in which the respective groups are as defined below and salts thereof in the compounds represented by the general formula (1) and salts thereof:

(d1) the ring A represents a benzene ring or a monocyclic aromatic heterocyclic ring; and/or (d2) R$^1$ represents a halogen atom, a hydrogen atom, a lower alkyl group, a lower alkyl group substituted with a hydroxy group, a lower alkyl group substituted with a lower alkoxy group, a lower alkyl group substituted with —NR$^{h1}$R$^{h2}$, a formyl group or a lower alkylcarbonyl group; and/or (d3) R$^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group, a lower alkylthio group substituted with a cyano group, an arylthio group, an arylthio group substituted with a nitro group, a cyano group, a nitro group, —NR$^{a1}$R$^{a2}$ or OCONR$^{e1}$R$^{e2}$; and/or (d4) provided that when R$^2$ represents a lower alkyl group which may have a substituent, the lower alkyl group represents a group which may be substituted with one or plural groups selected from the group consisting of a halogen atom, a hydroxy group, a lower alkoxy group, a mercapto group, a lower alkylthio group and —NR$^{i1}$R$^{i2}$; and/or (d5) provided that when R$^2$ represents a lower alkynyl group which may have a substituent, the lower alkynyl group represents a group which may be substituted with one or plural groups selected from the group consisting of a lower cycloalkyl group, an aryl group, a hydroxy group, a lower alkoxy group, a lower cycloalkyloxy group, an aryloxy group and —NR$^{j1}$R$^{j2}$; and/or (d6) provided that when R$^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, an arylthio group, a cyano group and —NR$^{f1}$R$^{f2}$; and/or (d7) R$^3$ represents a hydrogen atom or a lower alkyl group; and/or (d8) R$^{a1}$, R$^{a2}$, R$^{e1}$ and R$^{e2}$ are the same or different and represent a hydrogen atom or a lower alkyl group; and/or (d9) R$^{f1}$ and R$^{f2}$ are the same or different and represent a hydrogen atom, a lower alkyl group, a lower alkyl group substituted with a lower cycloalkyl group, a lower alkyl group substituted with an aryl group, a lower alkyl group substituted with a heterocyclic group, a lower alkyl group substituted with a hydroxy group, a lower alkyl group substituted with a lower alkoxy group, a lower alkyl group substituted with a lower cycloalkyloxy group, a lower alkyl group substituted with an aryloxy group, a lower alkyl group substituted with a heterocyclic oxy group, a lower alkyl group substituted with —NR$^{g1}$R$^{g2}$ or a lower cycloalkyl group, and further, R$^{f1}$ and R$^{f2}$ may be joined to each other to form a nitrogen-containing heterocyclic ring; and/or (d10) R$^{g1}$ and R$^{g2}$ are the same or different and represent a hydrogen atom or a lower alkyl group; and/or (d11) R$^{h1}$ and R$^{h2}$ are the same or different and represent a hydrogen atom or a lower alkyl group; and/or (d12) R$^{i1}$ and R$^{i2}$ are the same or different and represent a hydrogen atom, a lower alkyl group, a lower alkyl group substituted with a lower cycloalkyl group, a lower alkyl group substituted with an aryl group, a lower alkyl group substituted with a hydroxy group, a lower alkyl group substituted with a lower alkoxy group, a lower alkyl group substituted with a lower cycloalkyloxy group or a lower alkyl group substituted with an aryloxy group; and/or (d13) R$^{j1}$ and R$^{j2}$ are the same or different and represent a hydrogen atom or a lower alkyl group; and/or (d14) n represents 0, 1, 2 or 3; and/or (d15) provided that when n is 2 or 3, R$^2$ may be the same or different.

That is, still further more preferred examples of the present compound include, in the compounds represented by the general formula (1), compounds which comprise one or a combination of two or more selected from the above (d1), (d2), (d3), (d4), (d5), (d6), (d7), (d8), (d9), (d10), (d11), (d12), (d13), (d14) and/or (d15) and salts thereof.

(e) Particularly preferred examples of the present compound include compounds in which the respective groups are as defined below and salts thereof in the compounds represented by the general formula (1) and salts thereof:

(e1) the ring A represents a benzene ring or a monocyclic aromatic heterocyclic ring; and/or (e2) $R^1$ represents a halogen atom, a hydrogen atom, a lower alkyl group, a lower alkyl group substituted with a hydroxy group, a lower alkyl group substituted with $-NR^{h1}R^{h2}$ or a formyl group; and/or (e3) $R^2$ represents a halogen atom, a lower alkyl group which may have a substituent, a lower alkenyl group, a lower alkynyl group which may have a substituent, an aryl group, a heterocyclic group, a hydroxy group, a lower alkoxy group which may have a substituent, a lower alkenyloxy group, a lower alkynyloxy group, an aryloxy group substituted with a nitro group, a formyl group, a lower alkoxycarbonyl group, a lower alkylcarbonyloxy group, a lower alkylthio group, a lower alkylthio group substituted with a cyano group, an arylthio group substituted with a nitro group, a cyano group, a nitro group, $-NR^{a1}R^{a2}$ or $-OCONR^{e1}R^{e2}$; and/or (e4) provided that when $R^2$ represents a lower alkyl group which may have a substituent, the lower alkyl group represents a group which may be substituted with one or plural groups selected from the group consisting of a halogen atom, a hydroxy group, a lower alkylthio group and $-NR^{i1}R^{i2}$; and/or (e5) provided that when $R^2$ represents a lower alkynyl group which may have a substituent, the lower alkynyl group represents a group which may be substituted with one or plural groups selected from the group consisting of an aryl group, a hydroxy group and $-NR^{j1}R^{j2}$; and/or (e6) provided that when $R^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a hydroxy group, a lower alkoxy group, a lower alkoxy group substituted with an aryl group, a lower alkoxy group substituted with a lower alkoxy group, an aryloxy group, a heterocyclic oxy group, an arylcarbonyl group substituted with a halogen atom, a heterocyclic carbonyl group, a lower alkoxycarbonyl group, a lower alkylthio group, a cyano group and $-NR^{f1}R^{f2}$; and/or (e7) $R^3$ represents a hydrogen atom; and/or (e8) $R^{a1}$ and $R^{a2}$ represent a hydrogen atom; and/or (e9) $R^{e1}$ and $R^{e2}$ are the same or different and represent a hydrogen atom or a lower alkyl group; and/or (e10) $R^{f1}$ and $R^{f2}$ are the same or different and represent a hydrogen atom, a lower alkyl group, a lower alkyl group substituted with an aryl group, a lower alkyl group substituted with a heterocyclic group, a lower alkyl group substituted with a hydroxy group, a lower alkyl group substituted with $-NR^{g1}R^{g2}$ or a lower cycloalkyl group, and further, $R^{f1}$ and $R^{f2}$ may be joined to each other to form a nitrogen-containing heterocyclic ring; and/or (e11) $R^{g1}$ and $R^{g2}$ represent a lower alkyl group; and/or (e12) $R^{h1}$ and $R^{h2}$ are the same or different and represent a hydrogen atom or a lower alkyl group; and/or (e13) $R^{i1}$ and $R^{i2}$ are the same or different and represent a hydrogen atom, a lower alkyl group, a lower alkyl group substituted with an aryl group or a lower alkyl group substituted with a hydroxy group; and/or (e14) $R^{j1}$ and $R^{j2}$ represent a lower alkyl group; and/or (e15) n represents 0, 1, 2 or 3; and/or (e16) provided that when n is 2 or 3, $R^2$ may be the same or different.

That is, particularly preferred examples of the present compound include, in the compounds represented by the general formula (1), compounds which comprise one or a combination of two or more selected from the above (e1), (e2), (e3), (e4), (e5), (e6), (e7), (e8), (e9), (e10), (e11), (e12), (e13), (e14), (e15) and/or (e16) and salts thereof.

(f) Particularly preferred examples of the present compound in terms of inhibitory activity against IL-6 include compounds in which the respective groups are as defined below and salts thereof in the compounds represented by the general formula (1) and salts thereof:

(f1) the ring A represents a benzene ring or a monocyclic aromatic heterocyclic ring; and/or (f2) $R^1$ represents a halogen atom, a hydrogen atom, a lower alkyl group, a lower alkyl group substituted with a hydroxy group, a lower alkyl group substituted with $-NR^{h1}R^{h2}$ or a formyl group; and/or (f3) $R^2$ represents a halogen atom, a lower alkyl group which may have a substituent, a lower alkenyl group, a lower alkynyl group, a lower alkynyl group substituted with a hydroxy group, an aryl group, a heterocyclic group, a hydroxy group, a lower alkoxy group which may have a substituent, a lower alkenyloxy group, a lower alkynyloxy group, a lower alkoxycarbonyl group, a lower alkylcarbonyloxy group, a lower alkylthio group, a cyano group, a nitro group, $-NR^{a1}R^{a2}$ or $-OCONR^{e1}R^{e2}$; and/or (f4) provided that when $R^2$ represents a lower alkyl group which may have a substituent, the lower alkyl group represents a group which may be substituted with one or plural groups selected from the group consisting of a halogen atom, a hydroxy group and a lower alkylthio group; and/or (f5) provided that when $R^2$ represents a lower alkoxy group which may have a substituent, the lower alkoxy group represents a group which may be substituted with one or plural groups selected from the group consisting of a halogen atom, a lower cycloalkyl group, a heterocyclic group, a heterocyclic group substituted with a lower alkyl group, a hydroxy group, a lower alkylthio group, a cyano group and $-NR^{f1}R^{f2}$; and/or (f6) $R^3$ represents a hydrogen atom; and/or (f7) $R^{a1}$ and $R^{a2}$ represent a hydrogen atom; and/or (f8) $R^{e1}$ and $R^{e2}$ are the same or different and represent a hydrogen atom or a lower alkyl group; and/or (f9) $R^{f1}$ and $R^{f2}$ are the same or different and represent a hydrogen atom, a lower alkyl group, a lower alkyl group substituted with a hydroxy group or a lower cycloalkyl group, and further, $R^{f1}$ and $R^{f2}$ may be joined to each other to form a nitrogen-containing heterocyclic ring; and/or (f10) $R^{h1}$ and $R^{h2}$ are the same or different and represent a hydrogen atom or a lower alkyl group; and/or (F11) n represents 0, 1, 2 or 3; and/or (f12) provided that when n is 2 or 3, $R^2$ may be the same or different.

That is, particularly preferred examples of the present compound in terms of inhibitory activity against IL-6 include, in the compounds represented by the general formula (1), compounds which comprise one or a combination of two or more selected from the above (f1), (f2), (f3), (f4), (f5), (f6), (f7), (f8), (f9), (f10), (f11) and/or (f12) and salts thereof.

(g) Preferred examples of the ring A in the present compound include the case where, in the general formula (1), the ring A represents benzene, pyridine, pyrazine or thiophene; more preferred examples thereof include the case where, in the general formula (1), the ring A represents benzene, pyridine or thiophene; and particularly preferred examples thereof include the case where, in the general formula (1), the ring A represents benzene.

In this connection, compounds which satisfy these requirements and the requirements of the above (a), (b), (c), (d), (e) and/or (f) and salts thereof are more preferred.

(h) Preferred examples of $R^1$ and $R^3$ in the present compound include the case where, in the general formula (1), $R^1$ represents a hydrogen atom and $R^3$ represents a hydrogen atom.

In this connection, compounds which satisfy this requirement and the requirements of the above (a), (b), (c), (d), (e) and/or (f) and salts thereof are more preferred.

(i) Preferred examples of n in the present compound include the case where, in the general formula (1), n represents 0, 1 or 2; and more preferred examples thereof include the case where, in the general formula (1), n represents 1 or 2.

In this connection, compounds which satisfy these requirements and the requirements of the above (a), (b), (c), (d), (e) and/or (f) and salts thereof are more preferred.

(j) Preferred examples of the present compound in terms of inhibitory effect on choroidal neovascularization include compounds in which the respective groups are as defined below and salts thereof in the compounds represented by the general formula (1) and salts thereof:

(j1) the ring A represents a benzene ring; and/or
(j2) $R^1$ represents a hydrogen atom; and/or
(j3) $R^2$ represents a halogen atom, a lower alkynyl group, a hydroxy group, a lower alkoxy group which may have a substituent, a lower alkylthio group which may have a substituent or a cyano group; and/or
(j4) provided that when $R^2$ represents a lower alkoxy group which may have a substituent or a lower alkylthio group which may have a substituent, the lower alkoxy group or the lower alkylthio group represents a group which may be substituted with one or plural groups selected from the group consisting of a hydroxy group, a lower alkoxy group, a mercapto group, a lower alkylthio group and a cyano group; and/or
(j5) $R^3$ represents a hydrogen atom; and/or
(j6) n represents 0, 1 or 2; and/or
(j7) provided that when n is 2, $R^2$ may be the same or different.

That is, preferred examples of the present compound in terms of inhibitory effect on choroidal neovascularization include, in the compounds represented by the general formula (1), compounds which comprise one or a combination of two or more selected from the above (j1), (j2), (j3), (j4), (j5), (j6) and/or (j7) and salts thereof.

(k) More preferred examples of the present compound in terms of inhibitory effect on choroidal neovascularization include compounds in which the respective groups are as defined below and salts thereof in the compounds represented by the general formula (1) and salts thereof:

(k1) the ring A represents a benzene ring; and/or
(k2) $R^1$ represents a hydrogen atom; and/or
(k3) $R^2$ represents a halogen atom, a lower alkynyl group, a hydroxy group, a lower alkoxy group, a lower alkoxy group substituted with hydroxy group, a lower alkoxy group substituted with a cyano group, a lower alkylthio group or a cyano group; and/or
(k4) $R^3$ represents a hydrogen atom; and/or
(k5) n represents 0, 1 or 2; and/or
(k6) provided that when n is 2, $R^2$ may be the same or different.

That is, more preferred examples of the present compound in terms of inhibitory effect on choroidal neovascularization include, in the compounds represented by the general formula (1), compounds which comprise one or a combination of two or more selected from the above (k1), (k2), (k3), (k4), (k5) and/or (k6) and salts thereof.

(l) Particularly preferred examples of the present compound in terms of inhibitory effect on choroidal neovascularization include compounds in which the respective groups are as defined below and salts thereof in the compounds represented by the general formula (1) and salts thereof:

(11) the ring A represents a benzene ring;
(12) $R^1$ represents a hydrogen atom;
(13) $R^2$ represents a fluorine atom, a chlorine atom, a bromine atom, an ethynyl group, a hydroxy group, a methoxy group, an ethoxy group, a propoxy group, a hydroxyethyloxy group, a cyanomethyloxy group or a cyano group;
(14) $R^3$ represents a hydrogen atom;
(15) n represents 1 or 2; and/or
(16) provided that when n is 2, $R^2$ may be the same or different.

That is, particularly preferred examples of the present compound in terms of inhibitory effect on choroidal neovascularization include, in the compounds represented by the general formula (1), compounds which comprise one or a combination of two or more selected from the above (11), (12), (13), (14), (15) and/or (16) and salts thereof.

(m) The following compounds and salts thereof are shown as particularly preferred specific examples in the present compound.

2-Aminocarbonylamino-5-(4-bromophenyl)pyrrole-3-carboxamide.
2-Aminocarbonylamino-5-(pyridin-2-yl)pyrrole-3-carboxamide.
2-Aminocarbonylamino-5-phenylpyrrole-3-carboxamide.
2-Aminocarbonylamino-5-(4-biphenyl)pyrrole-3-carboxamide.
2-Aminocarbonylamino-5-(3-nitrophenyl)pyrrole-3-carboxamide.
2-Aminocarbonylamino-5-(4-fluorophenyl)pyrrole-3-carboxamide.
2-Aminocarbonylamino-5-(2-methoxyphenyl)pyrrole-3-carboxamide.
2-Aminocarbonylamino-5-(4-methylphenyl)pyrrole-3-carboxamide.
2-Aminocarbonylamino-5-(2-trifluoromethylphenyl)pyrrole-3-carboxamide.
2-Aminocarbonylamino-5-(4-cyanophenyl)pyrrole-3-carboxamide.
2-Aminocarbonylamino-5-(thiophen-2-yl)pyrrole-3-carboxamide.
2-Aminocarbonylamino-5-(2,5-dimethoxyphenyl)pyrrole-3-carboxamide.
2-Aminocarbonylamino-5-(5-fluoro-2-methoxyphenyl)pyrrole-3-carboxamide.
2-Aminocarbonylamino-5-(4-bromophenyl)-4-methylpyrrole-3-carboxamide.
2-Aminocarbonylamino-5-(5-chloro-2-methoxyphenyl)pyrrole-3-carboxamide.
2-Aminocarbonylamino-5-(5-chloro-2-methoxy-4-methylphenyl)pyrrole-3-carboxamide.
2-Aminocarbonylamino-5-(3-chlorophenyl)pyrrole-3-carboxamide.

2-Aminocarbonylamino-5-(2,5-dichlorophenyl)pyrrole-3-carboxamide.
2-Aminocarbonylamino-5-(3-fluorophenyl)pyrrole-3-carboxamide.
2-Aminocarbonylamino-5-(5-chloro-2-methoxyphenyl)-1-methylpyrrole-3-carboxamide.
2-Aminocarbonylamino-5-(4-ethoxycarbonylphenyl)pyrrole-3-carboxamide.
2-Aminocarbonylamino-5-(3-chloro-4-fluorophenyl)pyrrole-3-carboxamide.
2-Aminocarbonylamino-5-(3-chloro-4-methoxyphenyl)pyrrole-3-carboxamide.
2-Aminocarbonylamino-5-(3-cyanophenyl)pyrrole-3-carboxamide.
2-Aminocarbonylamino-5-(2-chlorophenyl)pyrrole-3-carboxamide.
2-Aminocarbonylamino-5-(5-methylthiophen-2-yl)pyrrole-3-carboxamide.
2-Aminocarbonylamino-5-(2-methylphenyl)pyrrole-3-carboxamide.
2-Aminocarbonylamino-5-(3-methylthiophenyl)pyrrole-3-carboxamide.
2-Aminocarbonylamino-5-(3-ethylthiophenyl)pyrrole-3-carboxamide
2-Aminocarbonylamino-5-(2-fluorophenyl)pyrrole-3-carboxamide.
2-Aminocarbonylamino-5-(5-chlorothiophen-2-yl)pyrrole-3-carboxamide.
2-Aminocarbonylamino-5-(2,5-dimethylthiophen-3-yl)pyrrole-3-carboxamide.
2-Aminocarbonylamino-5-(2,4,5-trifluorophenyl)pyrrole-3-carboxamide.
2-Aminocarbonylamino-5-(2,5-difluorophenyl)pyrrole-3-carboxamide.
2-Aminocarbonylamino-5-(4-aminophenyl)pyrrole-3-carboxamide.
2-Aminocarbonylamino-5-(2-hydroxyphenyl)pyrrole-3-carboxamide.
2-Aminocarbonylamino-5-(5-fluoro-2-hydroxyphenyl)pyrrole-3-carboxamide.
2-Aminocarbonylamino-5-(5-chloro-2-hydroxyphenyl)pyrrole-3-carboxamide.
2-Aminocarbonylamino-5-(2-cyanomethyloxyphenyl)pyrrole-3-carboxamide.
2-Aminocarbonylamino-5-(2-propyloxyphenyl)pyrrole-3-carboxamide
2-Aminocarbonylamino-5-(3-cyanomethyloxyphenyl)pyrrole-3-carboxamide.
2-Aminocarbonylamino-5-(2-ethoxyphenyl)pyrrole-3-carboxamide.
2-Aminocarbonylamino-5-[2-(pyridin-3-ylmethyloxy)phenyl]pyrrole-3-carboxamide.
2-Aminocarbonylamino-5-(2-cyclopropylmethyloxyphenyl)pyrrole-3-carboxamide.
2-Aminocarbonylamino-5-[2-(3-fluoropropyloxy)phenyl]pyrrole-3-carboxamide.
2-Aminocarbonylamino-5-[2-[2-(piperidin-1-yl)ethyloxy]phenyl]pyrrole-3-carboxamide.
2-Aminocarbonylamino-5-[2-(3-dimethylaminopropyloxy)phenyl]pyrrole-3-carboxamide.
2-Aminocarbonylamino-5-[2-(2-dimethylaminoethyloxy)phenyl]pyrrole-3-carboxamide.
2-Aminocarbonylamino-5-[2-[2-(1-methylpyrrolidin-2-yl)ethyloxy]phenyl]pyrrole-3-carboxamide.
2-Aminocarbonylamino-5-(5-fluoro-2-propyloxyphenyl)pyrrole-3-carboxamide.
2-Aminocarbonylamino-5-[5-fluoro-2-(3-hydroxypropyloxy)phenyl]pyrrole-3-carboxamide.
2-Aminocarbonylamino-5-(5-chloro-2-propyloxyphenyl)pyrrole-3-carboxamide.
2-Aminocarbonylamino-5-(5-chloro-2-cyanomethyloxyphenyl)pyrrole-3-carboxamide.
2-Aminocarbonylamino-5-(5-fluoro-2-ethoxyphenyl)pyrrole-3-carboxamide.
2-Aminocarbonylamino-5-(5-chloro-2-ethoxyphenyl)pyrrole-3-carboxamide.
5-(2-Allyloxy-5-chlorophenyl)-2-(aminocarbonylamino)pyrrole-3-carboxamide.
2-Aminocarbonylamino-5-[5-chloro-2-(2-propynyloxy)phenyl]pyrrole-3-carboxamide.
2-Aminocarbonylamino-5-[5-fluoro-2-(2-hydroxyethyloxy)phenyl]pyrrole-3-carboxamide.
2-Aminocarbonylamino-5-(2-acetoxyphenyl)pyrrole-3-carboxamide.
2-Aminocarbonylamino-5-(2-propylaminocarbonyloxyphenyl)pyrrole-3-carboxamide.
2-Aminocarbonylamino-4-chloro-5-(4-fluorophenyl)pyrrole-3-carboxamide.
2-Aminocarbonylamino-5-[2-[3-(pyrrolidin-1-yl)propyloxy]phenyl]pyrrole-3-carboxamide.
2-Aminocarbonylamino-5-[2-[2-(4-methylpiperazin-1-yl)ethyloxy]phenyl]pyrrole-3-carboxamide.
2-Aminocarbonylamino-5-[2-[2-(morpholin-4-yl)ethyloxy]phenyl]pyrrole-3-carboxamide.
2-Aminocarbonylamino-5-[2-[2-(pyrrolidin-1-yl)ethyloxy]phenyl]pyrrole-3-carboxamide.
2-Aminocarbonylamino-5-[2-[2-(4-methylpiperidin-1-yl)ethyloxy]phenyl]pyrrole-3-carboxamide.
2-Aminocarbonylamino-5-[2-[2-[N-(2-hydroxyethyl)-N-methylamino]ethyloxy]phenyl]pyrrole-3-carboxamide.
2-Aminocarbonylamino-5-[5-fluoro-2-[2-(pyrrolidin-1-yl)ethyloxy]phenyl]pyrrole-3-carboxamide.
2-Aminocarbonylamino-5-[5-fluoro-2-[2-(4-methylpiperidin-1-yl)ethyloxy]phenyl]pyrrole-3-carboxamide.
2-Aminocarbonylamino-5-[5-chloro-2-[2-(piperidin-1-yl)ethyloxy]phenyl]pyrrole-3-carboxamide.
2-Aminocarbonylamino-5-[5-chloro-2-[2-(4-methylpiperazin-1-yl)ethyloxy]phenyl]pyrrole-3-carboxamide.
2-Aminocarbonylamino-5-[5-chloro-2-[2-(4-hydroxyethylpiperidin-1-yl)ethyloxy]phenyl]pyrrole-3-carboxamide.
2-Aminocarbonylamino-5-[5-fluoro-2-[2-[N-(2-hydroxyethyl)-N-methylamino]ethyloxy]phenyl]pyrrole-3-carboxamide.
2-Aminocarbonylamino-5-[5-fluoro-2-(2-methylthioethyloxy)phenyl]pyrrole-3-carboxamide.
2-Aminocarbonylamino-5-[2-[2-(N-cyclohexyl-N-methylamino)ethyloxy]-5-fluorophenyl]pyrrole-3-carboxamide.
2-Aminocarbonylamino-5-(4-vinylphenyl)pyrrole-3-carboxamide.
2-Aminocarbonylamino-5-[4-(furan-3-yl)phenyl]pyrrole-3-carboxamide.
2-Aminocarbonylamino-5-[3-(3-hydroxypropynyl)phenyl]pyrrole-3-carboxamide.
2-Aminocarbonylamino-5-(3-ethynylphenyl)pyrrole-3-carboxamide.
2-Aminocarbonylamino-5-(3-hydroxymethylphenyl)pyrrole-3-carboxamide.
2-Aminocarbonylamino-5-(3-methylthiomethylphenyl)pyrrole-3-carboxamide.
2-Aminocarbonylamino-5-(3-chlorophenyl)-4-formylpyrrole-3-carboxamide.
2-Aminocarbonylamino-5-(3-chlorophenyl)-4-(hydroxymethyl)pyrrole-3-carboxamide.

2-Aminocarbonylamino-5-(3-chlorophenyl)-4-(methylaminomethyl)pyrrole-3-carboxamide.

2-Aminocarbonylamino-5-[2-(2-methylaminoethyloxy)phenyl]pyrrole-3-carboxamide.

The present compounds can be prepared according to the following methods. Each specific process for preparing the present compounds is described in detail in the following examples (section of Production Examples). The term "Hal" used in the following synthetic routes represents a halogen atom, $(R)_i$ means an arbitrary substituent represented as $R^2$, and the term "i" represents 0, 1, 2, 3 or 4.

The processes for preparing the present compounds are divided roughly into the methods described bellow, and the suitable method can be chosen according to the kind of substituent.

The present compound (I) can be synthesized according to synthetic route 1. Namely, the present compound (I) can be given by the reaction of compound (II) with trichloroacetyl isocyanate in an organic solvent such as tetrahydrofuran (as "THF" below) or N,N-dimethylformamide (as "DMF" below) at −80° C. to room temperature for 1 hour to 3 hours, and with ammonia in methanol solution at 0° C. to room temperature for 1 hour to 72 hours.

Synthetic Route 1

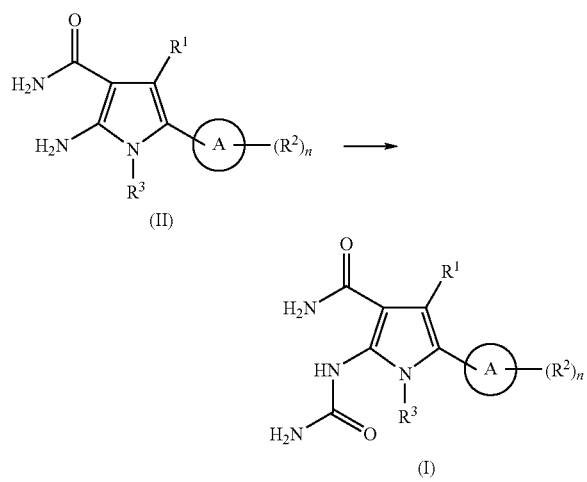

The compound (II)-(a) can be synthesized according to synthetic route 2-1. Namely, the compound (IV) can be given by the reaction of compound (III) in an organic solvent such as dichloromethane or THF in the presence of a halogenating reagent such as phenyltrimethylammonium tribromide or N-bromosuccinimide at 0° C. to 60° C. for 1 hour to 24 hours. The compound (II)-(a) can be given by the reaction of the obtainable compound (IV) with malonamamidine (V) in an organic solvent such as ethanol or DMF in the presence of a base such as sodium ethoxide or potassium carbonate at 0° C. to 60° C. for 1 hour to 48 hours.

Synthetic Route 2-1

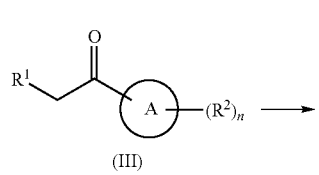

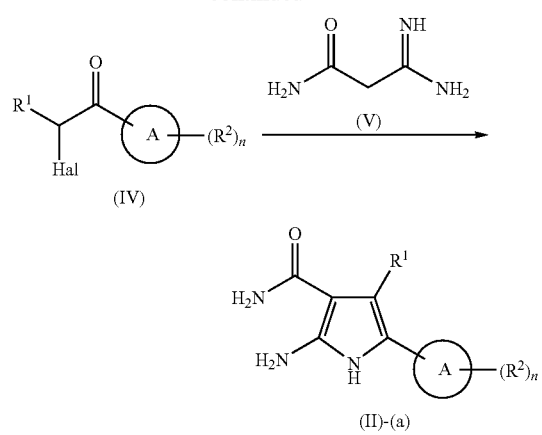

The compound (II)-(b) can be synthesized according to synthetic route 2-2. Namely, the compound (II)-(b) can be given by the reaction of compound (II)-(c) with an alkyl halide (VI) in an organic solvent such as THF or DMF in the presence of a base such as sodium hydroxide or sodium hydride at 0° C. to 100° C. for 1 hour to 24 hours.

Synthetic Route 2-2

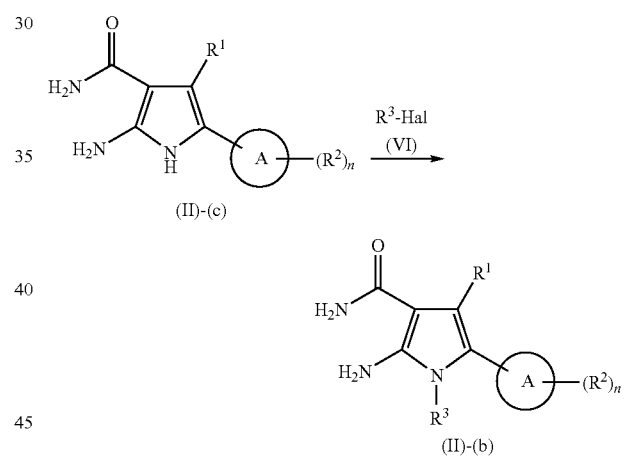

The compound (II)-(d) can be synthesized according to synthetic route 2-3. Namely, the compound (II)-(d) can be given by the reaction of compound (II)-(c) with tetrabutylammonium bromide and dimethyl sulfate in an organic solvent such as THF or DMF in the presence of a base such as sodium hydroxide or sodium hydride at 0° C. to 100° C. for 1 hour to 24 hours.

Synthetic Route 2-3

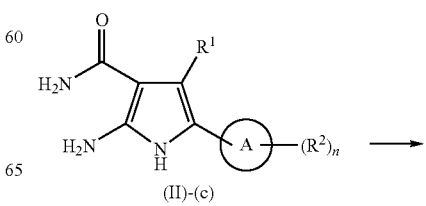

Synthetic Route 4

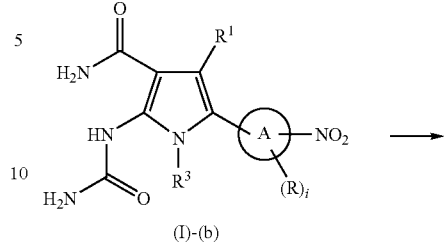

(I)-(b)

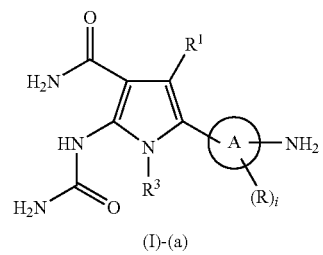

(I)-(a)

The present compounds (I)-(c) and (I)-(d) can be synthesized according to synthetic route 5. Namely, the present compound (I)-(c) can be given by the reaction of the present compound (I)-(e) in an organic solvent such as dichloromethane or chloroform in the presence of a Lewis acid such as boron tribromide at −80° C. to 0° C. for 1 hour to 6 hours. The present compound (I)-(d) can be given by the reaction of the obtainable present compound (I)-(c) with a halogenated compound (XI) in an organic solvent such as THF or DMF in the presence of a base such as potassium carbonate or sodium hydride at 0° C. to 100° C. for 1 hour to 24 hours.

Synthetic Route 5

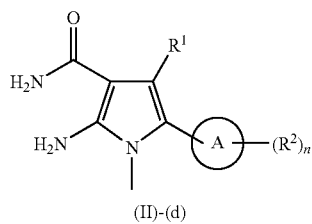

(II)-(d)

The compound (III)-(a) can be synthesized according to synthetic route 3. Namely, the compound (IX) can be given by the reaction of compound (VII) with mercaptopropionic acid ester (VIII) ($X^a$ represents a lower alkyl group) in an organic solvent such as 1,4-dioxane or DMF in the presence of a metal complex catalyst such as tetrakis(triphenylphosphine)palladium(0) or tris(dibenzylideneacetone)dipalladium(0) and in the presence of a base such as sodium hydrogencarbonate or N,N-diisopropylethylamine at room temperature to 150° C. for 1 hour to 48 hours. The compound (X) can be given by the reaction of the obtainable compound (IX) in an organic solvent such as THF or ethanol in the presence of a base such as sodium ethoxide at 0° C. to 80° C. for 1 hour to 24 hours. The compound (III)-(a) can be given by the reaction of the obtainable compound (X) with a halogenated compound (XI) in an organic solvent such as THF or DMF in the presence of a base such as potassium carbonate or sodium hydride at 0° C. to 80° C. for 1 hour to 24 hours. Further, $Y^a$ represents a lower alkyl group which may have substituents, an aryl group which may have substituents, or a heterocyclic group which may have substituents.

Synthetic Route 3

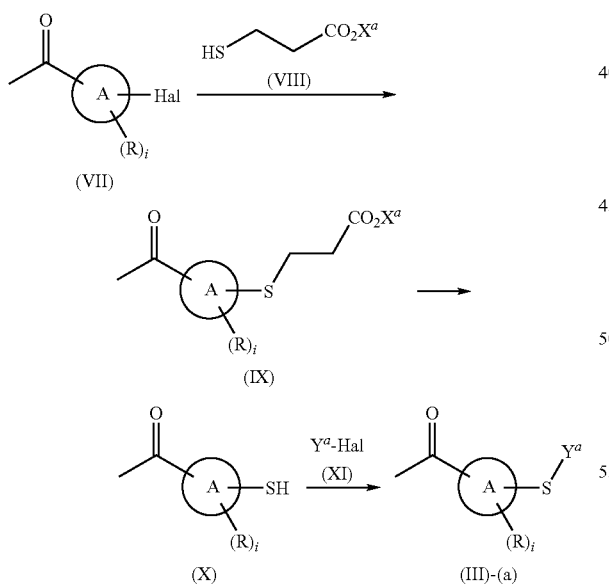

The present compound (I)-(a) can be synthesized according to synthetic route 4. Namely, the present compound (I)-(a) can be given by the reaction of the present compound (I)-(b) in an organic solvent such as methanol or DMF in the presence of palladium on carbon under hydrogen atmosphere at room temperature to 50° C. for 1 hour to 24 hours.

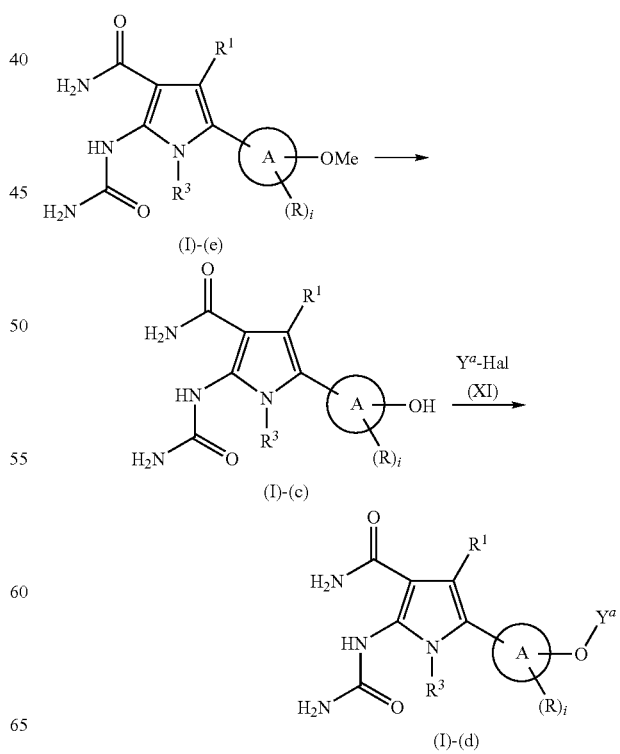

The present compounds (I)-(f), (I)-(g) and (I)-(h) can be synthesized according to synthetic route 6. Namely, the present compound (I)-(f) can be given by the reaction of the present compound (I)-(c) with an alkyl dihalide (XII) in an organic solvent such as THF or DMF in the presence of a base such as potassium carbonate or sodium hydride at 0° C. to 100° C. for 1 hour to 24 hours. The present compounds (I)-(g) and (I)-(h) can be given by the reaction of the obtainable present compound (I)-(f) with an amine (XIII) or a thiol (XIV) under no solvent or in an organic solvent such as DMF in the presence of a base such as potassium carbonate at room temperature to 150° C. for 1 hour to 24 hours. Further, $Y^b$ represents a lower alkyl group which may have substituents. And the term "j" used in this synthetic route represents 2, 3 or 4.

Synthetic Route 6

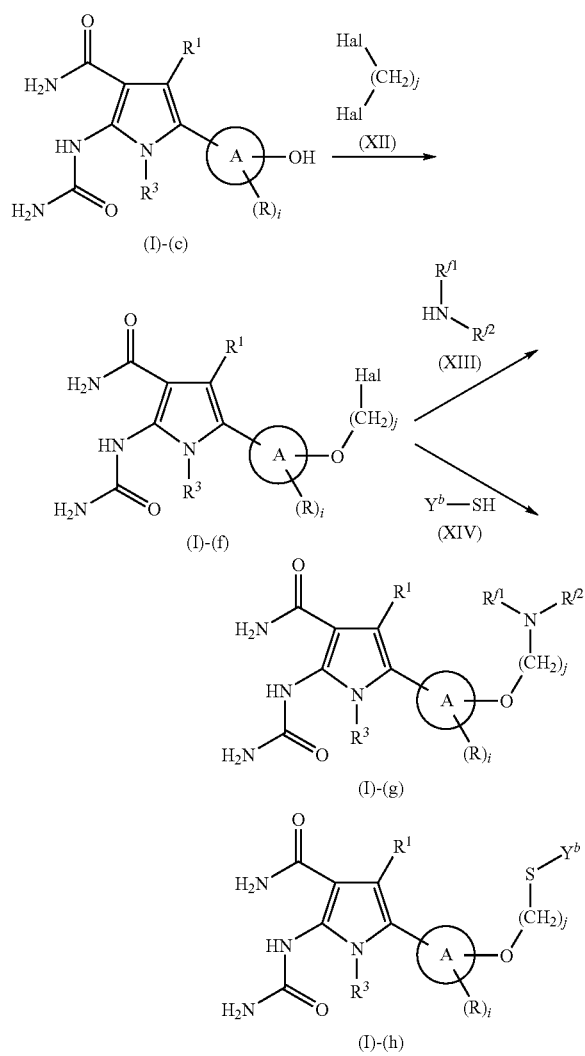

Synthetic Route 7

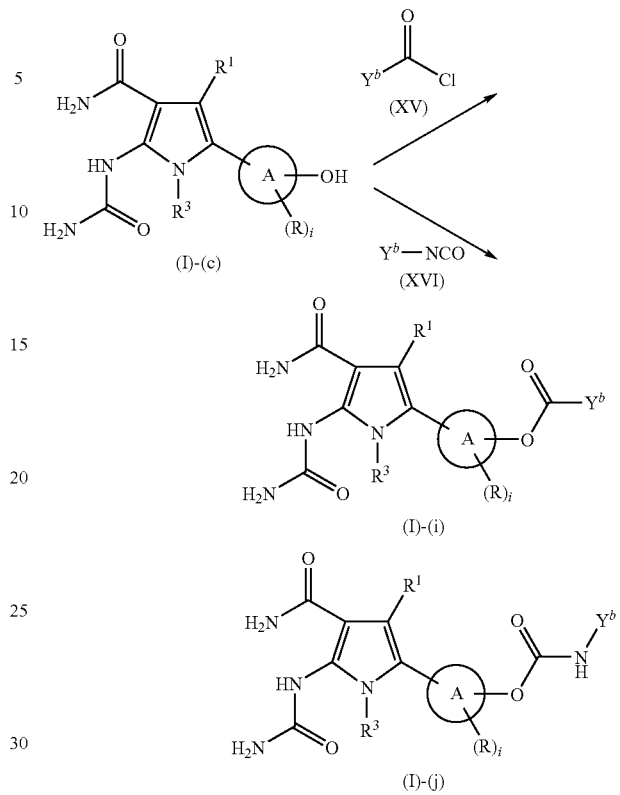

The present compounds (I)-(i) and (I)-(j) can be synthesized according to synthetic route 7. Namely, the present compounds (I)-(i) and (I)-(j) can be given by the reaction of the present compound (I)-(c) with a carbonyl chloride (XV) or an isocyanate (XVI) in an organic solvent such as THF or DMF in the presence of a base such as potassium carbonate or triethylamine at room temperature to 100° C. for 1 hour to 24 hours.

The present compound (I)-(k) can be synthesized according to synthetic route 8. Namely, the present compound (I)-(k) can be given by the reaction of the present compound (I)-(l) with a boronic acid (XVII) in a mixed solvent, which consists of an organic solvent such as 1,4-dioxane or DMF and water, in the presence of a metal complex catalyst such as tetrakis (triphenylphosphine)palladium(0) or tris(dibenzylideneacetone)dipalladium(0) and in the presence of a base such as sodium hydrogencarbonate or triethylamine at room temperature to 150° C. for 1 hour to 24 hours. Further, $Y^c$ represents an aryl group which may have substituents, or a heterocyclic group which may have substituents.

Synthetic Route 8

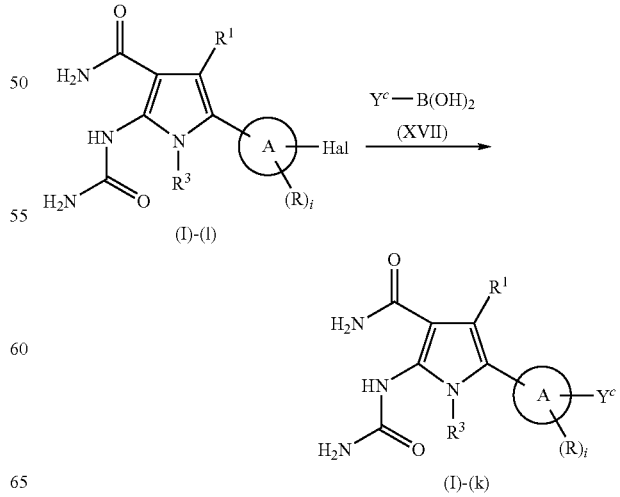

The present compounds (I)-(m), (I)-(n) and (I)-(o) can be synthesized according to synthetic route 9. Namely, the present compound (I)-(m) can be given by the reaction of the present compound (I)-(l) with an 1-alkyne (XVIII) in a mixed solvent, which consists of an organic solvent such as 1,4-dioxane or DMF and water, in the presence of a metal complex catalyst such as tetrakis(triphenylphosphine)palladium (0) or tris(dibenzylideneacetone)dipalladium(0), in the presence of a cuprate such as copper(I) iodide or copper(I) bromide and in the presence of a base such as sodium hydrogencarbonate or triethylamine at room temperature to 150° C. for 1 hour to 24 hours.

Further, the present compound (I)-(n) can be given by the reaction of the present compound (I)-(l) with a boronic acid ester (XIX) in a mixed solvent, which consists of an organic solvent such as 1,4-dioxane or DMF and water, in the presence of a metal complex catalyst such as tetrakis(triphenylphosphine)palladium(0) or tris(dibenzylideneacetone) dipalladium(0) and in the presence of a base such as sodium hydrogencarbonate or triethylamine at room temperature to 150° C. for 1 hour to 24 hours.

And the present compound (I)-(o) can be given by the reaction of the present compound (I)-(m) or (I)-(n) in an organic solvent such as methanol or DMF in the presence of palladium on carbon under hydrogen atmosphere at room temperature to 100° C. for 1 hour to 24 hours.

Synthetic Route 9

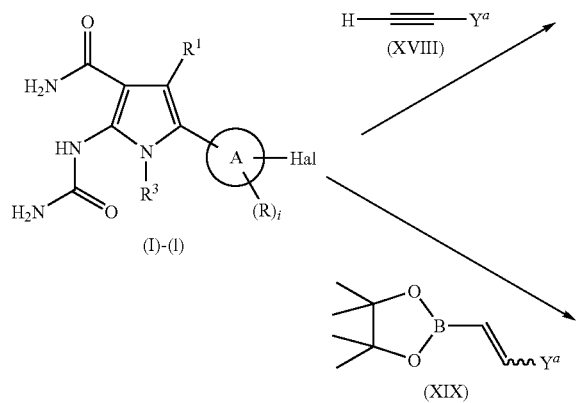

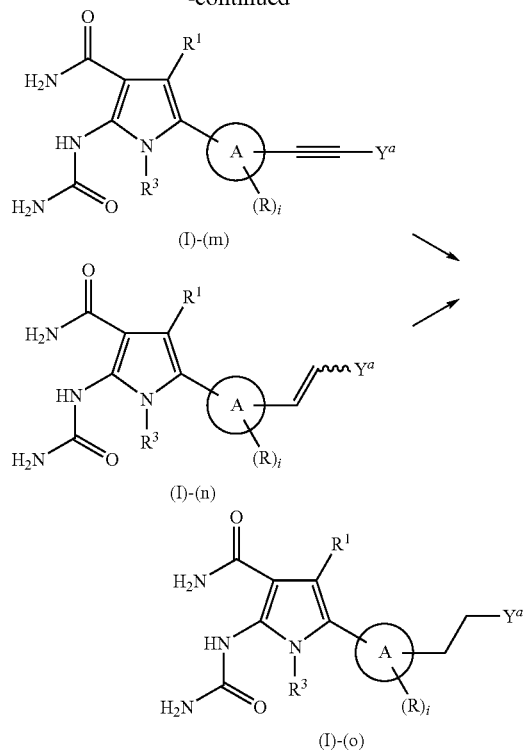

The present compounds (I)-(p), (I)-(q), (I)-(r) and (I)-(s) can be synthesized according to synthetic route 10. Namely, the present compound (I)-(p) can be given by the reaction of the present compound (I)-(t) in an organic solvent such as diethyl ether or THF in the presence of a reducing reagent such as diisobutylaluminum hydride at −80° C. to room temperature for 30 minutes to 6 hours. The present compound (I)-(q) can be given by the reaction of the obtainable present compound (I)-(p) in an organic solvent such as dichloromethane or dimethyl sulfoxide in the presence of a oxidizing reagent such as 2-iodoxybenzoic acid at −80° C. to room temperature for 30 minutes to 6 hours. The present compound (I)-(r) can be given by the reaction of the obtainable present compound (I)-(q) with an amine (XX) in an organic solvent such as methanol or THF at room temperature to 100° C. for 1 hour to 24 hours and moreover in the presence of a reducing reagent such as sodium borohydride or sodium cyanoborohydride at 0° C. to 100° C. for 1 hour to 24 hours.

Further, the present compound (I)-(s) can be given by the reaction of the present compound (I)-(q) with a thiol (XIV) in an organic solvent such as dichloromethane in the presence of trifluoroacetic acid at 0° C. to room temperature for 5 minutes to 1 hour and moreover in the presence of borane pyridine complex at 0° C. to room temperature for 5 minutes to 1 hour.

Synthetic Route 10

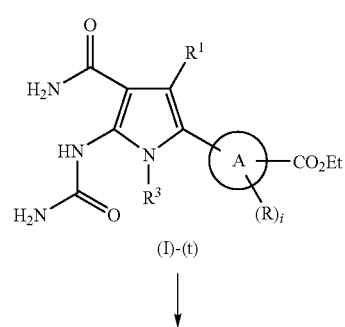

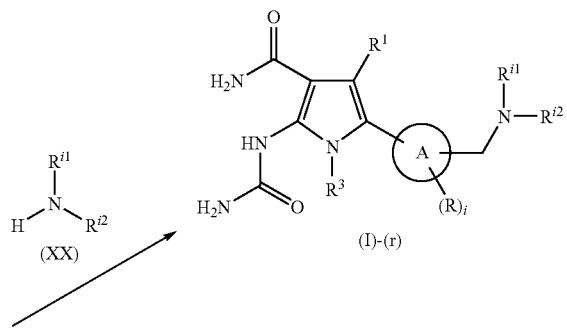

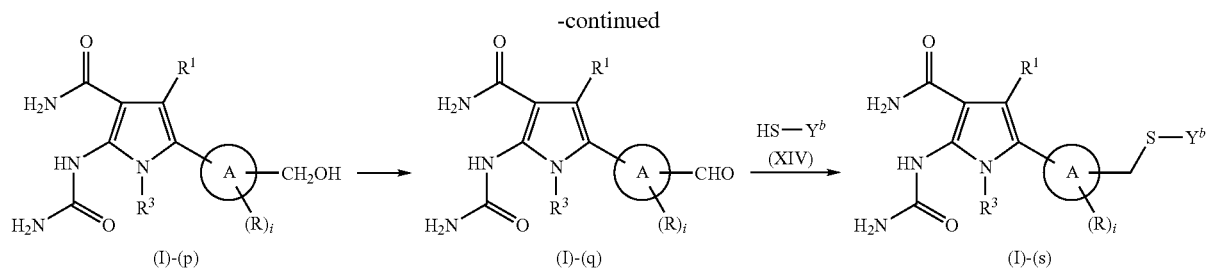

The present compounds (I)-(u), (I)-(v), (I)-(w) and (I)-(x) can be synthesized according to synthetic route 11. Namely, the present compound (I)-(u) can be given by the reaction of the present compound (I)-(y) with dichloromethyl methyl ether in an organic solvent such as dichloromethane in the presence of a Lewis acid such as titanium tetrachloride at −80° C. to room temperature for 1 hour to 24 hours. The present compound (I)-(v) can be given by the reaction of the obtainable present compound (I)-(u) in an organic solvent such as diethyl ether or THF in the presence of a reducing reagent such as sodium borohydride at −80° C. to room temperature for 30 minutes to 6 hours.

Further, the present compound (I)-(w) can be given by the reaction of the present compound (I)-(u) with an amine (XXI) in an organic solvent such as methanol or THF at room temperature to 100° C. for 1 hour to 24 hours and moreover in the presence of a reducing reagent such as sodium borohydride or sodium cyanoborohydride at 0° C. to 100° C. for 1 hour to 24 hours.

Further, the present compound (I)-(x) can be given by the reaction of the present compound (I)-(y) in an organic solvent such as dichloromethane or DMF in the presence of a halogenating reagent such as N-chlorosuccinimide or N-bromosuccinimide at room temperature to 80° C. for 1 hour to 24 hours.
Synthetic Route 11

The present compound prepared by the above synthetic routes can also be converted into the above-mentioned salt, hydrate or solvate using widely used techniques.

Further, as will be described in detail in the following Examples (under the item of Pharmacological Tests), firstly, when an inhibitory effect of the present compound on TNF-α-induced IL-6 production was studied using normal human skin fibroblast-derived CCD-1059Sk cells, the present compound exhibited an excellent inhibitory activity against IL-6 production.

As described above, IL-6 is associated with the incidence of various diseases, and the present compound having an excellent inhibitory activity against IL-6 is useful as a prophylactic and/or therapeutic agent for a disease considered to be associated with IL-6.

Further, when an inhibitory effect of the present compound through oral administration on choroidal neovascularization was studied using a rat model of choroidal neovascularization induced by krypton laser irradiation, the present compound exhibited an excellent inhibitory effect on choroidal neovascularization through oral administration.

Incidentally, this model is considered to be a model of an ocular inflammatory disease and/or a model of a retinal disease typified by age-related macular degeneration or the like, and therefore, the present compound is useful as a prophylactic and/or therapeutic agent for an ocular inflammatory

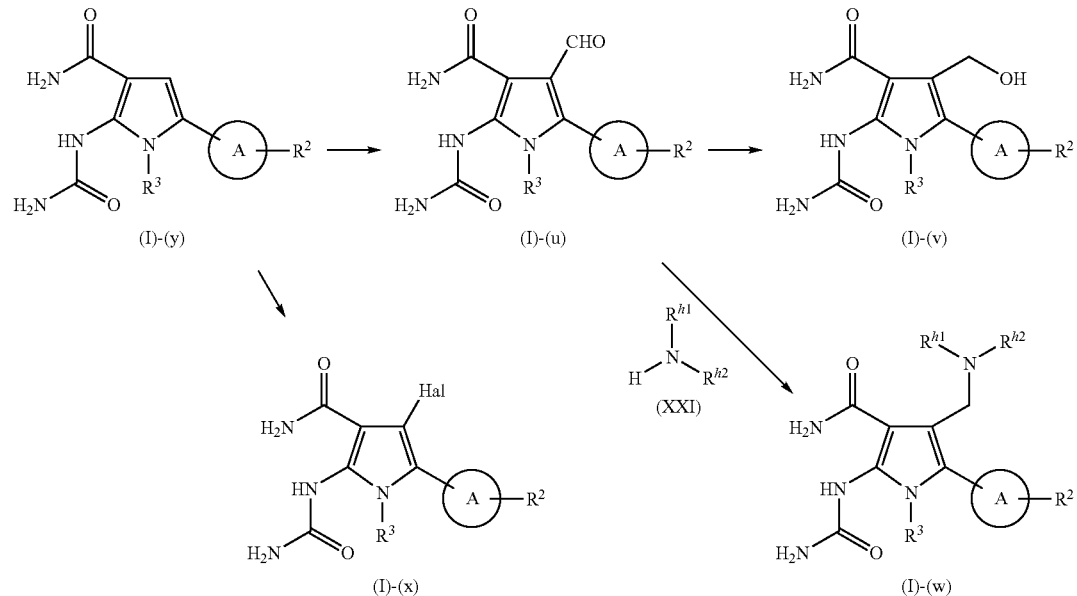

disease and/or a retinal disease, particularly for age-related macular degeneration, retinopathy of prematurity, polypoidal choroidal vasculopathy, retinal vein occlusion, diabetic retinopathy, diabetic macular edema, keratitis, conjunctivitis, uveitis or the like.

The present compound can be administered orally or parenterally. Examples of the mode of administration include oral administration, ophthalmic topical administration (such as eye drop administration, instillation in the conjunctival sac, intravitreal administration, subconjunctival administration and sub-Tenon's administration), intravenous administration and transdermal administration, and the present compound can be formulated into a preparation suitable for such an administration mode by properly selecting and using a pharmaceutically acceptable additive as needed.

Examples of the dosage form include, in the case of an oral preparation, a tablet, a capsule, a granule and a powder, and, in the case of a parenteral preparation, an injection, an eye drop, an eye ointment, an insert and an intraocular implant.

For example, in the case of a tablet, a capsule, a granule, a powder or the like, such a preparation can be prepared by properly selecting and using an excipient such as lactose, glucose, D-mannitol, anhydrous calcium hydrogen phosphate, starch or sucrose; a disintegrant such as carboxymethyl cellulose, calcium carboxymethyl cellulose, croscarmellose sodium, crosspovidone, starch, partially gelatinized starch or low-substituted hydroxypropyl cellulose; a binder such as hydroxypropyl cellulose, ethyl cellulose, gum arabic, starch, partially gelatinized starch, polyvinylpyrrolidone or polyvinyl alcohol; a lubricant such as magnesium stearate, calcium stearate, talc, hydrous silicon dioxide or a hydrogenated oil; a coating agent such as purified sucrose, hydroxypropylmethyl cellulose, hydroxypropyl cellulose, methyl cellulose, ethyl cellulose or polyvinylpyrrolidone; a corrigent such as citric acid, aspartame, ascorbic acid or menthol; or the like as needed.

An injection can be prepared by properly selecting and using a tonicity agent such as sodium chloride; a buffer such as sodium phosphate; a surfactant such as polyoxyethylene sorbitan monoolate; a viscosity-increasing agent such as methyl cellulose; or the like as needed.

An eye drop can be prepared by properly selecting and using a tonicity agent such as sodium chloride or concentrated glycerin; a buffer such as sodium phosphate or sodium acetate; a surfactant such as polyoxyethylene sorbitan monoolate, polyoxyl 40 stearate or polyoxyethylene hydrogenated castor oil; a stabilizer such as sodium citrate or sodium edetate; a preservative such as benzalkonium chloride or paraben; or the like as needed. The pH of the eye drop is permitted as long as it falls within the range that is acceptable as an ophthalmic preparation, but is preferably in the range of from 4 to 8.

An eye ointment can be prepared using a widely used base such as white petrolatum or liquid paraffin.

An insert can be prepared using a biodegradable polymer such as hydroxypropyl cellulose, hydroxypropylmethyl cellulose, a carboxy vinyl polymer or polyacrylic acid, and if necessary, an excipient, a binder, a stabilizer, a pH adjusting agent or the like can be properly selected and used as appropriate.

A preparation for intraocular implant can be prepared using a biodegradable polymer such as polylactic acid, polyglycolic acid, a lactic acid-glycolic acid copolymer or hydroxypropyl cellulose, and if necessary, an excipient, a binder, a stabilizer, a pH adjusting agent or the like can be properly selected and used as appropriate.

The dose of the present compound can be properly selected depending on the dosage form, symptoms, age, body weight of a patient or the like. For example, in the case of oral administration, it can be administered in an amount of from 0.01 to 5000 mg, preferably from 1 to 2500 mg, particularly preferably from 0.5 to 1000 mg per day in a single dose or several divided doses. In the case of an injection, it can be administered in an amount of from 0.00001 to 2000 mg, preferably from 0.0001 to 1500 mg, particularly preferably from 0.001 to 500 mg per day in a single dose or several divided doses. In the case of an eye drop, a preparation containing the present compound at a concentration of from 0.00001 to 10% (w/v), preferably from 0.0001 to 5% (w/v), particularly preferably from 0.001 to 1% (w/v) can be instilled into the eye once or several times a day. In the case of an eye ointment, a preparation containing the present compound in an amount of from 0.0001 to 2000 mg can be applied. In the case of an insert or a preparation for intraocular implant, a preparation containing the present compound in an amount of from 0.0001 to 2000 mg can be inserted or implanted.

Hereinafter, Production Examples of the present compound, Preparation Examples and results of Pharmacological Tests will be described. However, these examples are described for the purpose of understanding the invention better and are not meant to limit the scope of the invention.

Production Examples

Reference Example 1-1

2-Amino-5-(4-bromophenyl) pyrrole-3-carboxamide (Reference compound No. 1-1)

Under ice-cooling, sodium ethoxide (2.1 g, 30 mmol) was added to a suspension of malonamamidine hydrochloride (4.1 g, 30 mmol) in dehydrated ethanol (50 mL), and then the mixture was stirred for 20 minutes. Moreover, 2,4'-dibromoacetophenone (4.2 g, 15 mmol) was added thereto, and the whole was stirred at room temperature for 5 hours. After the insoluble solid was filtered out, the filtrate was concentrated in vacuo. The obtained residue was purified by silica gel column chromatography to give the title reference compound (0.37 g) as a black solid (Yield 9%).

| 2-Amino-5-(4-bromophenyl)pyrrole-3-carboxamide (Reference compound No. 1-1) | $^1$H-NMR (400 MHz, DMSO-$d_6$) δ 5.72 (s, 2H), 6.75 (d, J = 2.7 Hz, 1H), 7.34 (d, J = 8.7 Hz, 2H), 7.47 (d, J = 8.7 Hz, 2H), 10.66 (s, 1H) |
|---|---|
| 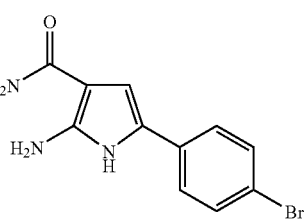 | |

Reference Example 1-2

2-Amino-5-(4-fluoro-2-methoxyphenyl)pyrrole-3-carboxamide (Reference compound No. 1-2)

Phenytrimethylammonium tribromide (5.8 g, 15 mmol) was added to a solution of 4'-fluoro-2'-methoxyacetophenone (2.5 g, 15 mmol) in anhydrous tetrahydrofuran (50 mL), and the mixture was stirred overnight at room temperature. After the insoluble solid was filtered out, the filtrate was concentrated in vacuo to give a mixture including 2-bromo-4'-fluoro-2'-methoxyacetophenone. A solution of this mixture in dehydrated ethanol (20 mL) was added to a suspension of malonamamidine hydrochloride (4.1 g, 30 mmol) and sodium ethoxide (2.1 g, 30 mmol) in dehydrated ethanol (80 mL) and the whole was stirred overnight at room temperature. The reaction mixture was concentrated in vacuo, the obtained residue was purified by silica gel column chromatography to give the title reference compound (0.84 g) as a black amorphous powder (Yield 22%).

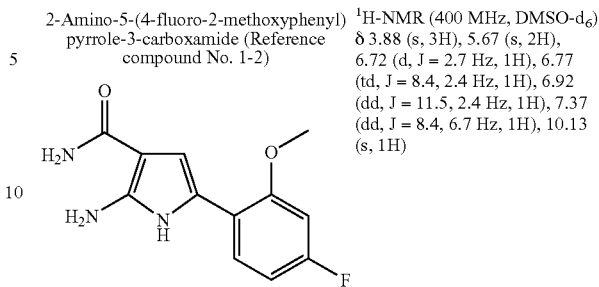

| | |
|---|---|
| 2-Amino-5-(4-fluoro-2-methoxyphenyl)pyrrole-3-carboxamide (Reference compound No. 1-2) | $^1$H-NMR (400 MHz, DMSO-$d_6$) δ 3.88 (s, 3H), 5.67 (s, 2H), 6.72 (d, J = 2.7 Hz, 1H), 6.77 (td, J = 8.4, 2.4 Hz, 1H), 6.92 (dd, J = 11.5, 2.4 Hz, 1H), 7.37 (dd, J = 8.4, 6.7 Hz, 1H), 10.13 (s, 1H) |

As described below, using commercially available compounds or reference compounds selected from No. 5-1 to 5-4, 6-1 or 7-1, reference compound No. 1-3 to 1-62 were obtained by a method similar to reference compound No. 1-1 or 1-2.

| | | |
|---|---|---|
| 2-Amino-5-(pyridin-2-yl)pyrrole-3-carboxamide (Reference compound No. 1-3) | 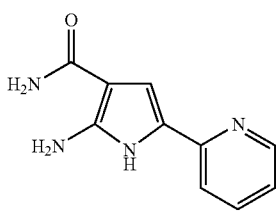 | $^1$H-NMR (500 MHz, DMSO-$d_6$) δ 5.76 (s, 2H), 6.96 (d, J = 2.7 Hz, 1H), 6.99 (ddd, J = 7.3, 4.9, 0.9 Hz, 1H), 7.37 (d, J = 8.2 Hz, 1H), 7.65 (ddd, J = 8.2, 7.3, 1.5 Hz, 1H), 8.37 (ddd, J = 8.2, 1.5, 0.9 Hz, 1H), 10.51 (s, 1H) |
| 2-Amino-5-(pyridin-3-yl)pyrrole-3-carboxamide (Reference compound No. 1-4) | 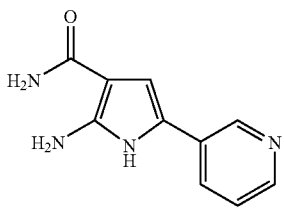 | $^1$H-NMR (500 MHz, DMSO-$d_6$) δ 5.79 (s, 2H), 6.69 (d, J = 2.4 Hz, 1H), 7.23 (m, 1H), 7.68 (m, 1H), 8.16 (dd, J = 4.6, 1.5 Hz, 1H), 8.62 (d, J = 2.4 Hz, 1H), 10.94 (s, 1H) |
| 2-Amino-5-phenylpyrrole-3-carboxamide (Reference compound No. 1-5) | 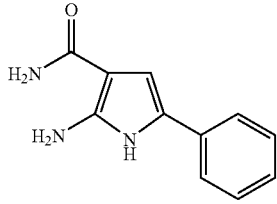 | $^1$H-NMR (400 MHz, DMSO-$d_6$) δ 5.65 (s, 2H), 6.69 (d, J = 2.7 Hz, 1H), 7.05 (t, J = 7.3 Hz, 1H), 7.29 (t, J = 7.3 Hz, 2H), 7.34 (d, J = 7.3 Hz, 2H), 10.59 (s, 1H) |
| 2-Amino-5-(4-biphenyl)pyrrole-3-carboxamide (Reference compound No. 1-6) | 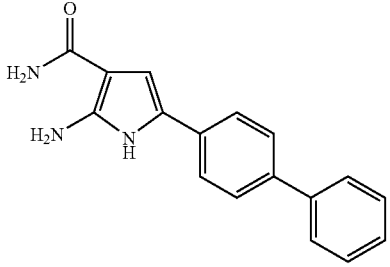 | $^1$H-NMR (500 MHz, DMSO-$d_6$) δ 5.72 (s, 2H), 6.77 (d, J = 2.7 Hz, 1H), 7.32 (m, 1H), 7.41-7.48 (m, 2H), 7.50 (d, J = 8.6 Hz, 2H), 7.63 (d, J = 8.6 Hz, 2H), 7.65-7.71 (m, 2H), 10.67 (s, 1H) |

| | -continued |
|---|---|
| 2-Amino-5-(3-nitrophenyl)pyrrole-3-carboxamide (Reference compound No. 1-7)<br>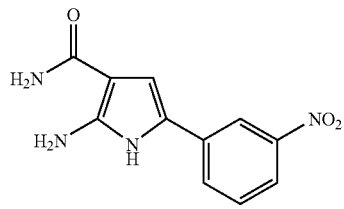 | $^1$H-NMR (400 MHz, DMSO-d$_6$)<br>δ 5.85 (s, 2H), 6.98 (d, J = 2.7 Hz, 1H), 7.57 (t, J = 8.1 Hz, 1H), 7.79 (ddd, J = 8.1, 1.8, 0.9 Hz, 1H), 7.84 (ddd, J = 8.1, 1.8, 0.9 Hz, 1H), 8.23 (t, J = 1.8 Hz, 1H), 10.96 (s, 1H) |
| 2-Amino-5-(4-nitrophenyl)pyrrole-3-carboxamide (Reference compound No. 1-8)<br>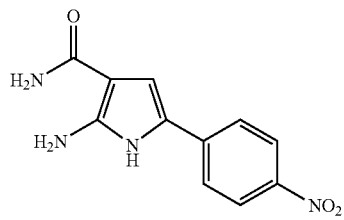 | $^1$H-NMR (400 MHz, DMSO-d$_6$)<br>δ 6.04 (s, 2H), 7.14 (d, J = 2.7 Hz, 1H), 7.53 (dd, J = 7.3, 2.0 Hz, 2H), 8.15 (dd, J = 7.3, 2.0 Hz, 2H), 10.99 (s, 1H) |
| 2-Amino-5-(4-fluorophenyl)pyrrole-3-carboxamide (Reference compound No. 1-9)<br>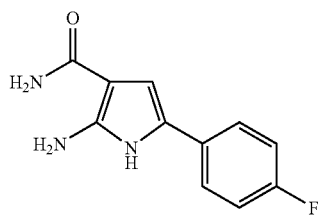 | $^1$H-NMR (400 MHz, DMSO-d$_6$)<br>δ 5.66 (s, 2H), 6.63 (d, J = 2.7 Hz, 1H), 7.12-7.17 (m, 2H), 7.38-7.44 (m, 2H), 10.59 (s, 1H) |
| 2-Amino-5-(2-methoxyphenyl)pyrrole-3-carboxamide (Reference compound No. 1-10)<br>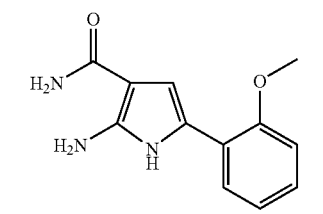 | $^1$H-NMR (400 MHz, DMSO-d$_6$)<br>δ 3.87 (s, 3H), 5.70 (s, 2H), 6.78 (d, J = 2.7 Hz, 1H), 6.91 (m, 1H), 7.00 (dd, J = 7.7, 1.6 Hz, 1H), 7.05 (m, 1H), 7.40 (dd, J = 7.7, 1.6 Hz, 1H), 10.11 (s, 1H) |
| 2-Amino-5-(4-methoxyphenyl)pyrrole-3-carboxamide (Reference compound No. 1-11)<br>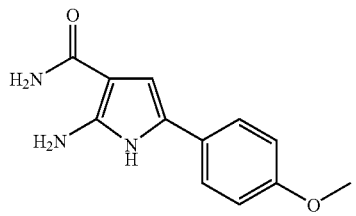 | $^1$H-NMR (400 MHz, DMSO-d$_6$)<br>δ 3.74 (s, 3H), 5.59 (s, 2H), 6.52 (d, J = 2.7 Hz, 1H), 6.89 (d, J = 8.8 Hz, 2H), 7.34 (d, J = 8.8 Hz, 2H), 10.47 (s, 1H) |

| | |
|---|---|
| 2-Amino-5-(2-trifluoromethylphenyl)pyrrole-3-carboxamide (Reference compound No. 1-12) 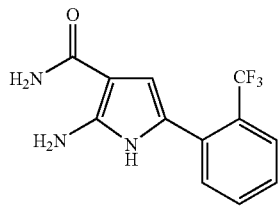 | ¹H-NMR (400 MHz, DMSO-d₆) δ 5.73 (s, 2H), 6.47 (s, 1H), 7.22-7.90 (m, 6H), 10.97 (s, 1H) |
| 2-Amino-5-(3-methoxyphenyl)pyrrole-3-carboxamide (Reference compound No. 1-13) 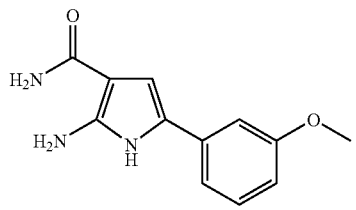 | ¹H-NMR (400 MHz, DMSO-d₆) δ 3.77 (s, 3H), 5.68 (s, 2H), 6.63 (m, 1H), 6.72 (d, J = 2.7 Hz, 1H), 6.97-7.04 (m, 2H), 7.20 (t, J = 8.1 Hz, 1H), 10.60 (s, 1H) |
| 2-Amino-5-(4-methylphenyl)pyrrole-3-carboxamide (Reference compound No. 1-14) 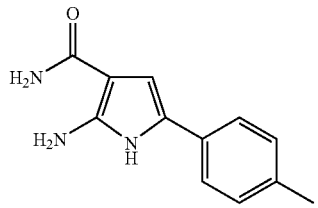 | ¹H-NMR (400 MHz, DMSO-d₆) δ 2.25 (s, 3H), 5.63 (s, 2H), 6.61 (d, J = 2.7 Hz, 1H), 7.11 (d, J = 7.9 Hz, 2H), 7.31 (d, J = 7.9 Hz, 2H), 10.52 (s, 1H) |
| 2-Amino-5-(4-chlorophenyl)pyrrole-3-carboxamide (Reference compound No. 1-15) 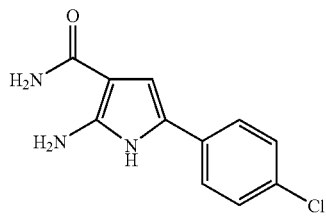 | ¹H-NMR (400 MHz, DMSO-d₆) δ 5.72 (s, 2H), 6.73 (d, J = 2.7 Hz, 1H), 7.34 (d, J = 8.8 Hz, 2H), 7.40 (d, J = 8.8 Hz, 2H), 10.66 (s, 1H) |
| 2-Amino-5-(4-cyanophenyl)pyrrole-3-carboxamide (Reference compound No. 1-16) 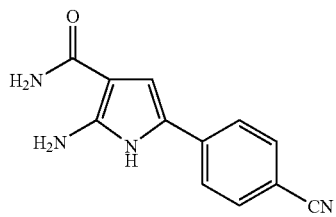 | ¹H-NMR (500 MHz, DMSO-d₆) δ 5.90 (s, 2H), 6.99 (d, J = 2.7 Hz, 1H), 7.50 (d, J = 8.6 Hz, 2H), 7.69 (d, J = 8.6 Hz, 2H), 10.85 (s, 1H) |

-continued

| | |
|---|---|
| 2-Amino-5-(thiophen-2-yl)pyrrole-3-carboxamide (Reference compound No. 1-17)<br>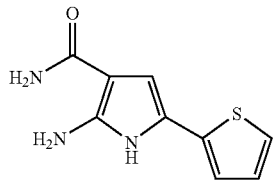 | $^1$H-NMR (500 MHz, DMSO-d$_6$) δ 5.72 (s, 2H), 6.49 (d, J = 2.7 Hz, 1H), 6.96 (dd, J = 4.9, 3.5 Hz, 1H), 7.00 (dd, J = 3.5, 0.9 Hz, 1H), 7.18 (dd, J = 4.9, 0.9 Hz, 1H), 10.62 (s, 1H) |
| 2-Amino-5-(2,5-dimethoxyphenyl)pyrrole-3-carboxamide (Reference compound No. 1-18)<br>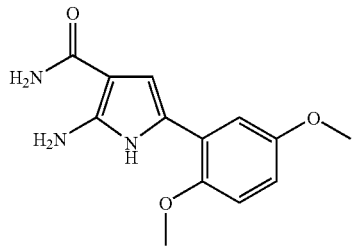 | $^1$H-NMR (400 MHz, DMSO-d$_6$) δ 3.72 (s, 3H), 3.81 (s, 3H), 5.72 (s, 2H), 6.62 (dd, J = 8.8, 2.9 Hz, 1H), 6.82 (d, J = 2.7 Hz, 1H), 6.92 (d, J = 8.8 Hz, 1H), 6.98 (d, J = 2.9 Hz, 1H), 10.15 (s, 1H) |
| 2-Amino-5-(5-fluoro-2-methoxyphenyl)pyrrole-3-carboxamide (Reference compound No. 1-19)<br>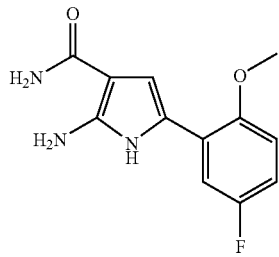 | $^1$H-NMR (400 MHz, DMSO-d$_6$) δ 3.86 (s, 3H), 5.76 (s, 2H), 6.83 (td, J = 8.8, 3.1 Hz, 1H), 6.91 (d, J = 2.7 Hz, 1H), 6.98 (dd, J = 8.8, 4.9 Hz, 1H), 7.19 (dd, J = 10.6, 3.1 Hz, 1H), 10.24 (s, 1H) |
| 2-Amino-5-(2-trifluoromethoxyphenyl)pyrrole-3-carboxamide (Reference compound No. 1-20)<br>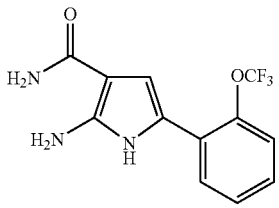 | $^1$H-NMR (400 MHz, DMSO-d$_6$) δ 5.78 (s, 2H), 6.74 (d, J = 2.7 Hz, 1H), 7.19 (m, 1H), 7.29-7.39 (m, 2H), 7.52 (dd, J = 7.9, 1.6 Hz, 1H), 10.42 (s, 1H) |
| 2-Amino-5-(5-chloro-2-methoxyphenyl)pyrrole-3-carboxamide (Reference compound No. 1-21)<br>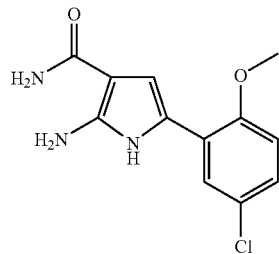 | $^1$H-NMR (400 MHz, DMSO-d$_6$) δ 3.87 (s, 3H), 5.75 (br s, 2H), 6.93 (d, J = 2.7 Hz, 1H), 7.00 (d, J = 8.8 Hz, 1H), 7.05 (dd, J = 8.8, 2.4 Hz, 1H), 7.42 (d, J = 2.4 Hz, 1H), 10.27 (s, 1H) |

| | |
|---|---|
| 2-Amino-5-(3-bromo-5-chloro-2-methoxy-phenyl)pyrrole-3-carboxamide (Reference compound No. 1-22) 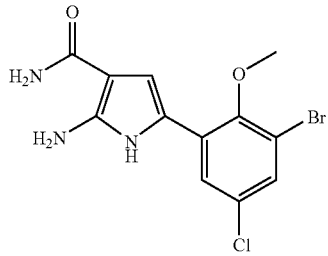 | $^1$H-NMR (500 MHz, DMSO-$d_6$) δ 3.69 (s, 3H), 5.85 (s, 2H), 7.02 (d, J = 2.7 Hz, 1H), 7.37 (d, J = 2.4 Hz, 1H), 7.47 (d, J = 2.4 Hz, 1H), 8.31 (s, 1H) |
| 2-Amino-5-(5-chloro-2-methoxy-4-methylphenyl)pyrrole-3-carboxamide (Reference compound No. 1-23) 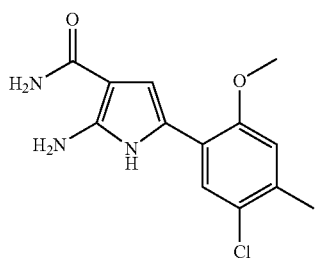 | $^1$H-NMR (500 MHz, DMSO-$d_6$) δ 2.29 (s, 3H), 3.87 (s, 3H), 5.70 (br s, 2H), 6.83 (d, J = 2.7 Hz, 1H), 6.99 (s, 1H), 7.40 (s, 1H), 10.20 (s, 1H) |
| 2-Amino-5-(3-chlorophenyl)pyrrole-3-carboxamide (Reference compound No. 1-24) 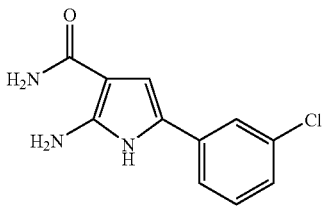 | $^1$H-NMR (400 MHz, DMSO-$d_6$) δ 5.75 (s, 2H), 6.81 (d, J = 2.7 Hz, 1H), 7.06 (dq, J = 7.6, 0.9 Hz, 1H), 7.24-7.39 (m, 2H), 7.45 (t, J = 1.7 Hz, 1H), 10.71 (s, 1H) |
| 2-Amino-5-(2-methoxy-5-nitrophenyl)pyrrole-3-carboxamide (Reference compound No. 1-25) 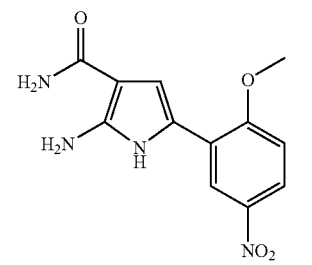 | $^1$H-NMR (500 MHz, DMSO-$d_6$) δ 4.02 (s, 3H), 5.80 (s, 2H), 7.08 (d, J = 3.1 Hz, 1H), 7.21 (d, J = 9.2 Hz, 1H), 7.94 (dd, J = 9.2, 2.7 Hz, 1H), 8.28 (d, J = 2.7 Hz, 1H), 10.51 (s, 1H) |
| 2-Amino-5-(2,5-dichlorophenyl)pyrrole-3-carboxamide (Reference compound No. 1-26) 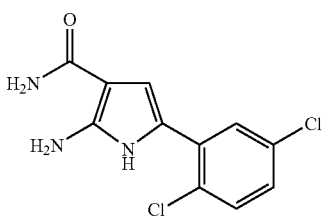 | $^1$H-NMR (400 MHz, DMSO-$d_6$) δ 5.83 (s, 2H), 7.06-7.18 (m, 2H), 7.43 (d, J = 8.5 Hz, 1H), 7.51 (d, J = 2.4 Hz, 1H), 10.60 (s, 1H) |

| | |
|---|---|
| 2-Amino-5-(3-fluorophenyl)pyrrole-3-carboxamide (Reference compound No. 1-27)<br />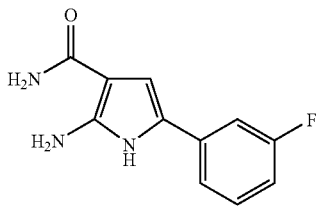 | $^1$H-NMR (400 MHz, DMSO-d$_6$) δ 5.74 (s, 2H), 6.79 (d, J = 2.7 Hz, 1H), 6.80-7.02 (m, 2H), 7.13-7.47 (m, 2H), 10.68 (s, 1H) |
| 2-Amino-5-(thiophen-3-yl)pyrrole-3-carboxamide (Reference compound No. 1-28)<br />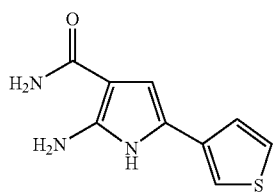 | $^1$H-NMR (400 MHz, DMSO-d$_6$) δ 5.68 (s, 2H), 6.49 (d, J = 2.7 Hz, 1H), 6.57 (br s, 2H), 7.17 (dd, J = 5.1, 1.2 Hz, 1H), 7.26 (dd, J = 2.9, 1.2 Hz, 1H), 7.50 (dd, J = 5.1, 2.9 Hz, 1H), 10.53 (s, 1H) |
| 2-Amino-5-(3-chloro-4-fluorophenyl)pyrrole-3-carboxamide (Reference compound No. 1-29)<br />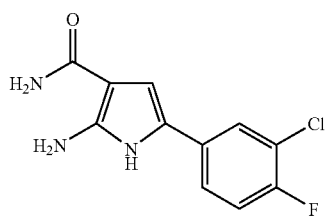 | $^1$H-NMR (400 MHz, DMSO-d$_6$) δ 5.75 (s, 2H), 6.63 (br s, 2H), 6.75 (d, J = 2.7 Hz, 1H), 7.30-7.40 (m, 2H), 7.57 (m, 1H), 10.71 (s, 1H) |
| 2-Amino-5-(3-chloro-4-methoxyphenyl)pyrrole-3-carboxamide (Reference compound No. 1-30)<br />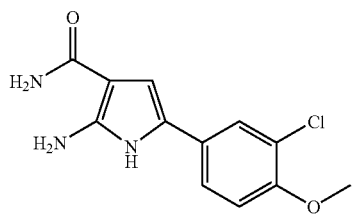 | $^1$H-NMR (400 MHz, DMSO-d$_6$) δ 3.84 (s, 3H), 4.75 (br s, 2H), 6.64 (s, 1H), 7.12 (m, 1H), 7.35 (m, 1H), 7.48 (m, 1H), 10.67 (s, 1H) |
| 2-Amino-5-(3-cyanophenyl)pyrrole-3-carboxamide (Reference compound No. 1-31)<br />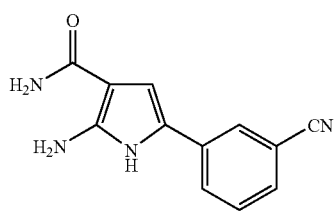 | $^1$H-NMR (400 MHz, DMSO-d$_6$) δ 5.83 (s, 2H), 6.89 (d, J = 2.7 Hz, 1H), 7.44 (dt, J = 7.6, 1.5 Hz, 1H), 7.48 (t, J = 7.6 Hz, 1H), 7.68 (dt, J = 7.6, 1.5 Hz, 1H), 7.78 (t, J = 1.5 Hz, 1H), 10.79 (s, 1H) |

-continued

| | |
|---|---|
| 2-Amino-5-(4-ethoxycarbonylphenyl)pyrrole-3-carboxamide (Reference compound No. 1-32)<br/>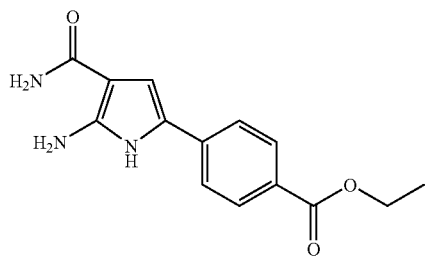 | $^1$H-NMR (400 MHz, DMSO-d$_6$) δ 1.31 (t, J = 7.2 Hz, 3H), 4.28 (q, J = 7.2 Hz, 2H), 5.83 (s, 2H), 6.94 (d, J = 2.7 Hz, 1H), 7.48 (d, J = 8.8 Hz, 2H), 7.86 (d, J = 8.8 Hz, 2H), 10.80 (s, 1H) |
| 2-Amino-5-(3-bromophenyl)pyrrole-3-carboxamide (Reference compound No. 1-33)<br/>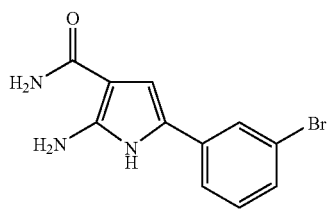 | $^1$H-NMR (500 MHz, DMSO-d$_6$) δ 5.74 (s, 2H), 6.80 (d, J = 2.7 Hz, 1H), 7.19 (dt, J = 7.8, 1.3 Hz, 1H), 7.24 (t, J = 7.8 Hz, 1H), 7.38 (dt, J = 7.8, 1.3 Hz, 1H), 7.59 (t, J = 1.8 Hz, 1H), 10.70 (s, 1H) |
| 2-Amino-5-(3-methylphenyl)pyrrole-3-carboxamide (Reference compound No. 1-34)<br/>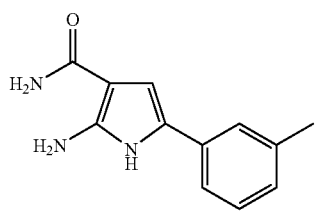 | $^1$H-NMR (400 MHz, DMSO-d$_6$) δ 2.29 (s, 3H), 5.64 (s, 2H), 6.68 (d, J = 2.7 Hz, 1H), 6.87 (d, J = 6.8 Hz, 1H), 7.15-7.22 (m, 2H), 7.24 (s, 1H), 10.55 (s, 1H) |
| 2-Amino-5-(3-trifluoromethylphenyl)pyrrole-3-carboxamide (Reference compound No. 1-35)<br/>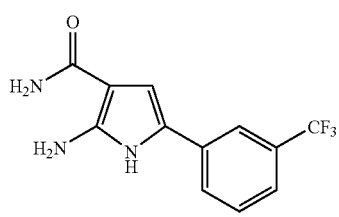 | $^1$H-NMR (400 MHz, DMSO-d$_6$) δ 5.79 (s, 2H), 6.90 (d, J = 2.9 Hz, 1H), 7.35 (d, J = 7.8 Hz, 1H), 7.51 (t, J = 7.8 Hz, 1H), 7.66 (d, J = 7.8 Hz, 1H), 7.72 (s, 1H), 10.84 (s, 1H) |
| 2-Amino-5-(3-ethoxycarbonylphenyl)pyrrole-3-carboxamide (Reference compound No. 1-36)<br/>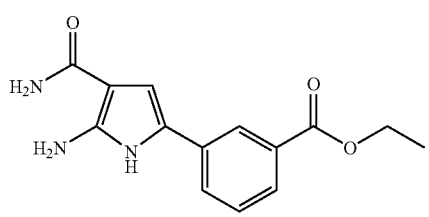 | $^1$H-NMR (400 MHz, DMSO-d$_6$) δ 1.34 (t, J = 7.1 Hz, 3H), 4.33 (q, J = 7.1 Hz, 2H), 5.73 (s, 2H), 6.83 (d, J = 2.4 Hz, 1H), 7.43 (t, J = 7.8 Hz, 1H), 7.60-7.66 (m, 2H), 8.01 (t, J = 1.7 Hz, 1H), 10.79 (s, 1H) |

| | |
|---|---|
| 2-Amino-5-(2-methylphenyl)pyrrole-3-carboxamide (Reference compound No. 1-37) 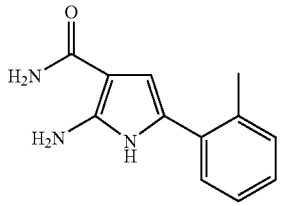 | $^1$H-NMR (400 MHz, DMSO-$d_6$) δ 2.40 (s, 3H), 5.62 (s, 2H), 6.49 (d, J = 2.7 Hz, 1H), 7.04 (td, J = 7.6, 1.1 Hz, 1H), 7.14-7.20 (m, 2H), 7.30 (d, J = 7.6 Hz, 1H), 10.32 (s, 1H) |
| 2-Amino-5-(3-methylthiophenyl)pyrrole-3-carboxamide (Reference compound No. 1-38) 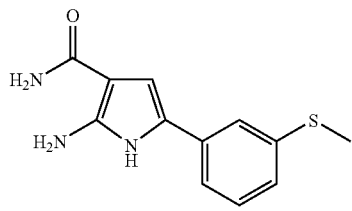 | $^1$H-NMR (400 MHz, DMSO-$d_6$) δ 2.49 (s, 3H), 5.69 (s, 2H), 6.75 (d, J = 2.7 Hz, 1H), 6.93 (dt, J = 7.7, 1.7 Hz, 1H), 7.17 (dt, J = 7.7, 1.7 Hz, 1H), 7.23 (t, J = 7.7 Hz, 1H), 7.29 (t, J = 1.7 Hz, 1H), 10.65 (s, 1H) |
| 2-Amino-5-(3-ethylthiophenyl)pyrrole-3-carboxamide (Reference compound No. 1-39) 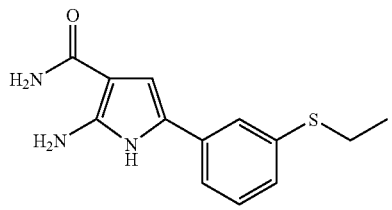 | $^1$H-NMR (400 MHz, DMSO-$d_6$) δ 1.25 (t, J = 7.3 Hz, 3H), 2.99 (q, J = 7.3 Hz, 2H), 5.69 (s, 2H), 6.75 (d, J = 2.7 Hz, 1H), 6.98 (dt, J = 6.8, 1.8 Hz, 1H), 7.20-7.26 (m, 2H), 7.35 (s, 1H), 10.65 (s, 1H) |
| 2-Amino-5-(5-methylthiophen-2-yl)pyrrole-3-carboxamide (Reference compound No. 1-40) 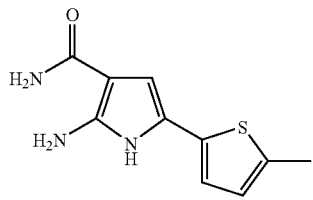 | $^1$H-NMR (500 MHz, DMSO-$d_6$) δ 2.38 (s, 3H), 5.68 (s, 2H), 6.36 (d, J = 2.7 Hz, 1H), 6.62 (m, 1H), 6.76 (d, J = 3.4 Hz, 1H), 10.52 (s, 1H) |
| 2-Amino-5-(2-fluorophenyl)pyrrole-3-carboxamide (Reference compound No. 1-41) 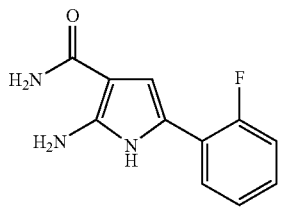 | $^1$H-NMR (500 MHz, DMSO-$d_6$) δ 5.75 (s, 2H), 6.80 (t, J = 2.6 Hz, 1H), 7.07 (m, 1H), 7.14-7.20 (m, 2H), 7.50 (td, J = 8.1, 1.5 Hz, 1H), 10.46 (s, 1H) |

| | |
|---|---|
| 2-Amino-5-(4-chloro-2-methoxyphenyl)pyrrole-3-carboxamide (Reference compound No. 1-42)<br>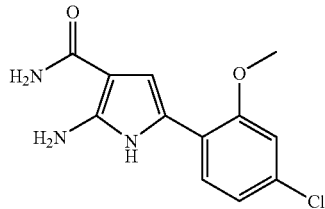 | $^1$H-NMR (400 MHz, DMSO-d$_6$) δ 3.90 (s, 3H), 5.72 (s, 2H), 6.82 (d, J = 2.7 Hz, 1H), 6.97 (dd, J = 8.5, 2.0 Hz, 1H), 7.05 (d, J = 2.0 Hz, 1H), 7.38 (d, J = 8.5 Hz, 1H), 10.18 (s, 1H) |
| 2-Amino-5-(pyrazin-2-yl)pyrrole-3-carboxamide (Reference compound No. 1-43)<br>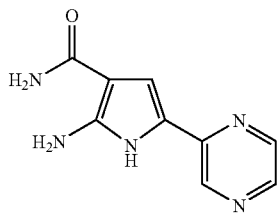 | $^1$H-NMR (400 MHz, DMSO-d$_6$) δ 5.90 (s, 2H), 7.16 (d, J = 2.7 Hz, 1H), 8.15 (d, J = 2.7 Hz, 1H), 8.36 (dd, J = 2.7, 1.7 Hz, 1H), 8.66 (d, J = 1.7 Hz, 1H), 10.70 (s, 1H) |
| 2-Amino-5-(5-chlorothiophen-2-yl)pyrrole-3-carboxamide (Reference compound No. 1-44)<br>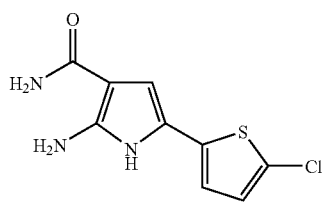 | $^1$H-NMR (500 MHz, DMSO-d$_6$) δ 5.78 (br s, 2H), 6.49 (d, J = 2.7 Hz, 1H), 6.82 (d, J = 3.7 Hz, 1H), 6.96 (d, J = 3.7 Hz, 1H), 10.69 (s, 1H) |
| 2-Amino-5-(2,3-dichlorophenyl)pyrrole-3-carboxamide (Reference compound No. 1-45)<br>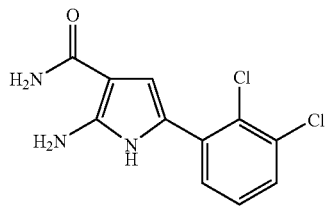 | $^1$H-NMR (500 MHz, DMSO-d$_6$) δ 5.80 (s, 2H), 7.00 (d, J = 2.4 Hz, 1H), 7.31 (t, J = 7.9 Hz, 1H), 7.36 (dd, J = 7.9, 1.6 Hz, 1H), 7.40 (dd, J = 7.9, 1.6 Hz, 1H), 10.53 (s, 1H) |
| 2-Amino-5-(2-chlorophenyl)pyrrole-3-carboxamide (Reference compound No. 1-46)<br>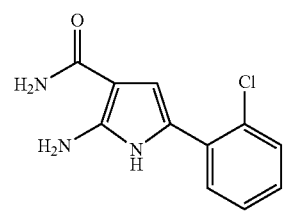 | $^1$H-NMR (500 MHz, DMSO-d$_6$) δ 5.75 (br s, 2H), 6.92 (d, J = 2.7 Hz, 1H), 7.11 (td, J = 7.9, 1.5 Hz, 1H), 7.30 (td, J = 7.9, 1.5 Hz, 1H), 7.42 (dd, J = 7.9, 1.5 Hz, 1H), 7.45 (dd, J = 7.9, 1.5 Hz, 1H), 10.43 (s, 1H) |

| | |
|---|---|
| 2-Amino-5-[4-(pyrrolidin-1-yl)phenyl]pyrrole-3-carboxamide (Reference compound No. 1-47)<br />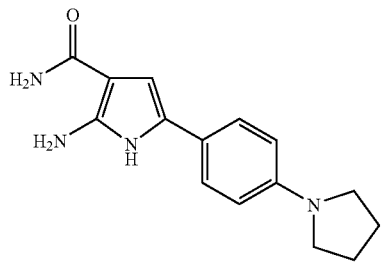 | ¹H-NMR (500 MHz, DMSO-d₆) δ 1.92-1.98 (m, 4H), 3.19-3.24 (m, 4H), 5.52 (s, 2H), 6.37 (d, J = 2.7 Hz, 1H), 6.50 (br s, 2H), 6.51 (d, J = 8.6 Hz, 2H), 7.25 (d, J = 8.6 Hz, 2H), 10.33 (s, 1H) |
| 2-Amino-5-[3-(4-nitrophenylthio)phenyl]pyrrole-3-carboxamide (Reference compound No. 1-48)<br />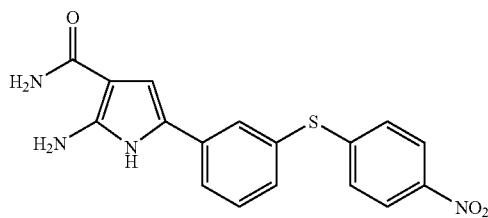 | ¹H-NMR (400 MHz, DMSO-d₆) δ 5.74 (s, 2H), 6.83 (d, J = 2.7 Hz, 1H), 7.24 (ddd, J = 7.8, 1.7, 1.2 Hz, 1H), 7.33 (dd, J = 7.0, 2.2 Hz, 2H), 7.45 (t, J = 7.8 Hz, 1H), 7.54 (ddd, J = 7.8, 1.7, 1.2 Hz, 1H), 7.64 (t, J = 1.7 Hz, 1H), 8.16 (dd, J = 7.0, 2.2 Hz, 2H), 10.74 (s, 1H) |
| 2-Amino-5-(2,5-dimethylthiophen-3-yl)pyrrole-3-carboxamide (Reference compound No. 1-49)<br />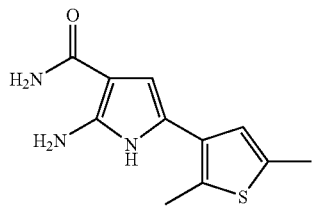 | ¹H-NMR (400 MHz, DMSO-d₆) δ 2.35 (s, 3H), 2.38 (s, 3H), 5.56 (s, 2H), 6.33 (d, J = 2.7 Hz, 1H), 6.80 (d, J = 1.2 Hz, 1H), 10.18 (s, 1H) |
| 2-Amino-5-(2,4,5-trifluorophenyl)pyrrole-3-carboxamide (Reference compound No. 1-50)<br />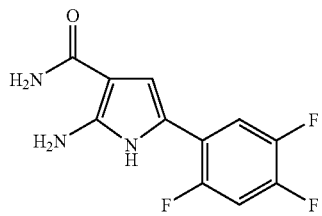 | ¹H-NMR (400 MHz, DMSO-d₆) δ 5.85 (s, 2H), 6.84 (t, J = 2.8 Hz, 1H), 7.46-7.62 (m, 2H), 10.59 (s, 1H) |
| 2-Amino-5-(2,5-difluorophenyl)pyrrole-3-carboxamide (Reference compound No. 1-51)<br />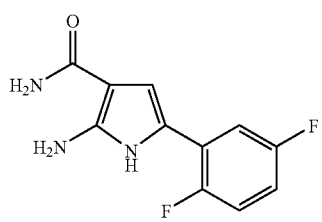 | ¹H-NMR (500 MHz, DMSO-d₆) δ 5.85 (s, 2H), 6.87 (m, 1H), 6.90 (t, J = 2.7 Hz, 1H), 7.20 (ddd, J = 11.3, 9.4, 4.6 Hz, 1H), 7.34 (ddd, J = 10.1, 6.4, 3.1 Hz, 1H), 10.59 (s, 1H) |

| | |
|---|---|
| 2-Amino-5-(3-methylthiophen-2-yl)pyrrole-3-carboxamide (Reference compound No. 1-52) 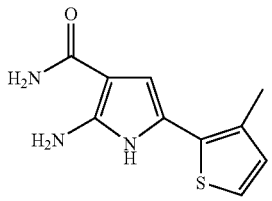 | $^1$H-NMR (400 MHz, DMSO-d$_6$) δ 2.25 (s, 3H), 3.95 (br s, 2H), 6.41 (d, J = 2.7 Hz, 1H), 6.86 (d, J = 4.9 Hz, 1H), 7.17 (d, J = 4.9 Hz, 1H), 10.21 (s, 1H) |
| 2-Amino-5-(2-fluoro-4-methoxyphenyl)pyrrole-3-carboxamide (Reference compound No. 1-53) 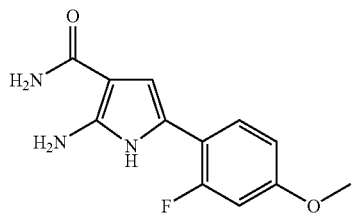 | $^1$H-NMR (400 MHz, DMSO-d$_6$) δ 3.76 (s, 3H), 5.67 (s, 2H), 6.62 (t, J = 2.6 Hz, 1H), 6.79 (dd, J = 8.8, 2.7 Hz, 1H), 6.84 (dd, J = 13.8, 2.7 Hz, 1H), 7.41 (t, J = 8.8 Hz, 1H), 10.36 (s, 1H) |
| 2-Amino-5-(3,4-difluorophenyl)pyrrole-3-carboxamide (Reference compound No. 1-54) 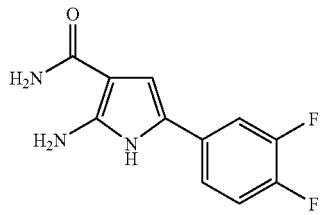 | $^1$H-NMR (500 MHz, DMSO-d$_6$) δ 5.75 (s, 2H), 6.73 (d, J = 2.7 Hz, 1H), 7.20 (m, 1H), 7.33-7.40 (m, 2H), 10.67 (s, 1H) |
| 2-Amino-5-(3-cyanomethylthiophenyl)pyrrole-3-carboxamide (Reference compound No. 1-55) 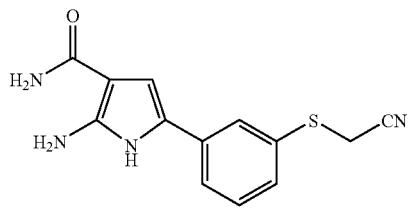 | $^1$H-NMR (500 MHz, DMSO-d$_6$) δ 4.22 (s, 2H), 5.74 (s, 2H), 6.79 (d, J = 2.7 Hz, 1H), 7.16 (m, 1H), 7.34-7.35 (m, 2H), 7.50 (m, 1H), 10.66 (s, 1H) |
| 2-Amino-5-(2-methylthiophenyl)pyrrole-3-carboxamide (Reference compound No. 1-56) 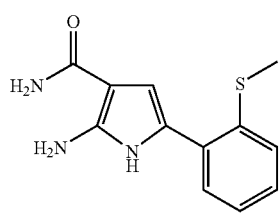 | $^1$H-NMR (400 MHz, DMSO-d$_6$) δ 2.42 (s, 3H), 5.67 (s, 2H), 6.63 (d, J = 2.7 Hz, 1H), 7.11-7.18 (m, 2H), 7.23-7.27 (m, 2H), 10.31 (s, 1H) |

| | |
|---|---|
| 2-Amino-5-(2-vinylphenyl)pyrrole-3-carboxamide (Reference compound No. 1-57) 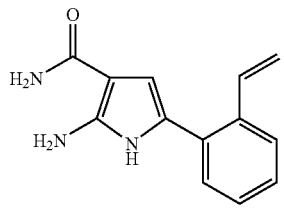 | $^1$H-NMR (400 MHz, DMSO-d$_6$) δ 5.27 (dd, J = 11.0, 1.6 Hz, 1H), 5.67 (s, 2H), 5.72 (dd, J = 17.6, 1.6 Hz, 1H), 6.33 (d, J = 2.7 Hz, 1H), 7.03 (dd, J = 17.6, 11.0 Hz, 1H), 7.17 (m, 1H), 7.25-7.31 (m, 2H), 7.54 (d, J = 7.3 Hz, 1H), 10.37 (s, 1H) |
| 2-Amino-5-(3,4-dichlorophenyl)pyrrole-3-carboxamide (Reference compound No. 1-58) 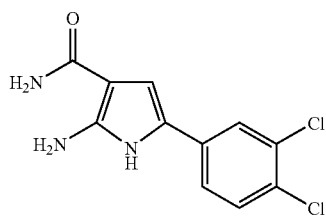 | $^1$H-NMR (400 MHz, DMSO-d$_6$) δ 5.81 (s, 2H), 6.85 (d, J = 2.4 Hz, 1H), 7.34 (dd, J = 8.5, 2.0 Hz, 1H), 7.52 (d, J = 8.5 Hz, 1H), 7.62 (d, J = 2.0 Hz, 1H), 10.77 (s, 1H) |
| 2-Amino-5-(2,4-difluorophenyl)pyrrole-3-carboxamide (Reference compound No. 1-59) 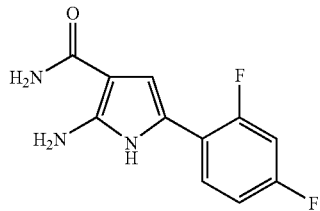 | $^1$H-NMR (400 MHz, DMSO-d$_6$) δ 5.76 (s, 2H), 6.75 (t, J = 2.7 Hz, 1H), 7.09 (td, J = 8.2, 2.7 Hz, 1H), 7.23 (ddd, J = 12.2, 9.3, 2.7 Hz, 1H), 7.52 (td, J = 9.3, 6.4 Hz, 1H), 10.50 (s, 1H) |
| 2-Amino-5-(4-methylthiophen-2-yl)pyrrole-3-carboxamide (Reference compound No. 1-60) 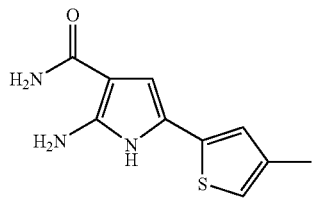 | $^1$H-NMR (400 MHz, DMSO-d$_6$) δ 2.16 (d, J = 1.2 Hz, 3H), 5.70 (s, 2H), 6.44 (d, J = 2.4 Hz, 1H), 6.75 (t, J = 1.2 Hz, 1H), 6.81 (d, J = 1.2 Hz, 1H), 10.57 (s, 1H) |
| 2-Amino-5-(3-fluoro-4-methoxyphenyl)pyrrole-3-carboxamide (Reference compound No. 1-61) 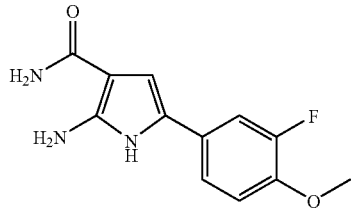 | $^1$H-NMR (400 MHz, DMSO-d$_6$) δ 3.82 (s, 3H), 5.66 (s, 2H), 6.60 (d, J = 2.7 Hz, 1H), 7.12 (t, J = 8.7 Hz, 1H), 7.17 (dd, J = 8.7, 2.1 Hz, 1H), 7.22 (dd, J = 13.3, 2.1 Hz, 1H), 10.56 (s, 1H) |

-continued

| | |
|---|---|
| 2-Amino-5-(3,5-difluorophenyl)pyrrole-3-carboxamide (Reference compound No. 1-62) 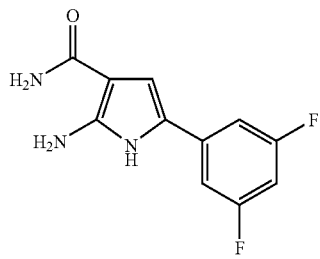 | $^1$H-NMR (500 MHz, DMSO-$d_6$) δ 5.84 (br s, 2H), 6.82 (tt, J = 9.3, 2.0 Hz, 1H), 6.88 (d, J = 2.4 Hz, 1H), 7.05 (dt, J = 7.9, 2.0 Hz, 2H), 10.80 (s, 1H) |

Reference Example 2

2-Amino-5-(4-bromophenyl)-4-methylpyrrole-3-carboxamide (Reference compound No. 2-1)

Under ice-cooling, sodium ethoxide (1.4 g, 20 mmol) was added to a suspension of malonamamidine hydrochloride (2.8 g, 20 mmol) in dehydrated ethanol (80 mL), and the mixture was stirred for 30 minutes. Moreover, 2,4'-dibromopropiophenone (2.9 g, 10 mmol) was added thereto, and the whole was stirred overnight at room temperature. After the reaction mixture was concentrated in vacuo, the residue was purified by silica gel column chromatography to give the title reference compound (0.12 g) as a white solid (Yield 4%).

| | |
|---|---|
| 2-Amino-5-(4-bromophenyl)-4-methyl-pyrrole-3-carboxamide (Reference compound No. 2-1) 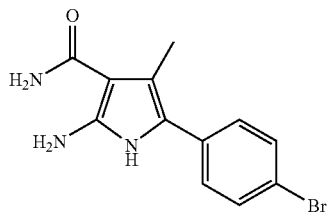 | $^1$H-NMR (400 MHz, DMSO-$d_6$) δ 2.24 (s, 3H), 5.67 (s, 2H), 6.29 (s, 2H), 7.24 (d, J = 8.6 Hz, 2H), 7.53 (d, J = 8.6 Hz, 2H), 10.29 (s, 1H) |

Reference Example 3

2-Amino-5-(5-chloro-2-methoxyphenyl)-1-methylpyrrole-3-carboxamide (Reference compound No. 3-1)

A suspension of 2-amino-5-(5-chloro-2-methoxyphenyl)pyrrole-3-carboxamide (Reference compound No. 1-21, 500 mg, 1.9 mmol), tetrabutylammonium bromide (61 mg, 0.19 mmol), dimethyl sulfate (210 μL, 2.2 mmol) and sodium hydroxide (90 mg, 2.3 mmol) in tetrahydrofuran (13 mL) was stirred at 60° C. for 3 hours. Tetrabutylammonium bromide (30 mg, 0.093 mmol), dimethyl sulfate (80 μL, 0.85 mmol) and sodium hydroxide (90 mg, 2.3 mmol) were added thereto, and moreover stirred at 60° C. for 4 hours. Water (30 mL) was added to the reaction solution, extracted with ethyl acetate (50 mL). The organic layer was washed with saturated aqueous ammonium chloride solution (50 mL) and brine (20 mL), dried over anhydrous magnesium sulfate. After the solvent was removed under reduced pressure, the residue was purified by silica gel column chromatography to give the title reference compound (28 mg) as a brown amorphous powder (Yield 5%).

| | |
|---|---|
| 2-Amino-5-(5-chloro-2-methoxyphenyl)-1-methylpyrrole-3-carboxamide (Reference compound No. 3-1) 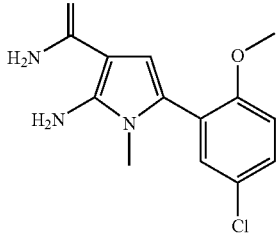 | $^1$H-NMR (400 MHz, DMSO-$d_6$) δ 3.09 (s, 3H), 3.77 (s, 3H), 5.96 (s, 2H), 6.28 (s, 1H), 7.08 (d, J = 8.8 Hz, 1H), 7.16 (d, J = 2.8 Hz, 1H), 7.36 (dd, J = 8.8, 2.8 Hz, 1H) |

Reference Example 4

3'-Mercaptoacetophenone (Reference compound No. 4-1)

A solution of 3'-bromoacetophenone (10 g, 50 mmol), N,N-diisopropylethylamine (18 mL, 0.10 mol), 3-mercaptopropionic acid 2-ethylhexyl ester (11 mL, 48 mmol), 4,5-bis(diphenylphosphino)-9,9-dimethylxanthene (0.29 g, 0.50 mmol) and tris(dibenzylideneacetone)palladium(0) (0.46 g, 0.50 mmol) in 1,4-dioxane (250 mL) was stirred at 100° C. for 2 days. After the reaction solution was filtered with celite, the filtrate was concentrated in vacuo until the volume became one third approximately. Water (200 mL) was added thereto, extracted with ethyl acetate (200 mL). The organic layer was washed with brine (200 mL) and dried over anhydrous magnesium sulfate. The solvent was removed under reduced pressure to give a mixture including 3-(3-acetylphenyl)thiopropionic acid 2-ethylhexyl ester (19 g). This mixture (17 g) was dissolved in tetrahydrofuran (200 mL), sodium ethoxide (7.0 g, 0.10 mol) in ethanol (40 mL) was added thereto, and then the whole was stirred at 50° C. for 2 hours. Water (200 mL) was added to the reaction solution and washed with ethyl acetate (200 mL). 1N Hydrochloric acid (100 mL) was added to the aqueous layer and extracted with ethyl acetate (300 mL), then the organic layer was washed with brine (100 mL) and dried over anhydrous magnesium sulfate. The solvent was removed under reduced pressure to give the title reference compound (6.2 g) as a brown oil (Yield 81%).

| | |
|---|---|
| 3'-Mercaptoacetophenone (Reference compound No. 4-1) 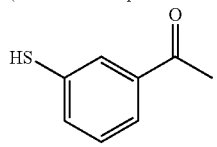 | ¹H-NMR (500 MHz, DMSO-d₆) δ 2.55 (s, 3H), 5.76 (s, 1H), 7.40 (t, J = 7.7 Hz, 1H), 7.54 (d, J = 7.7 Hz, 1H), 7.69 (d, J = 7.7 Hz, 1H), 7.87 (t, J = 1.7 Hz, 1H) |

As described below, using commercially available compounds, reference compound No. 4-2 was obtained by a method similar to reference compound No. 4-1.

| | |
|---|---|
| 2'-Mercaptoacetophenone (Reference compound No. 4-2) 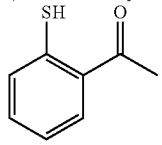 | ¹H-NMR (400 MHz, DMSO-d₆) δ 2.59 (s, 3H), 5.04 (s, 1H), 7.27 (td, J = 7.8, 1.5 Hz, 1H), 7.41 (td, J = 7.8, 1.5 Hz, 1H), 7.53 (dd, J = 7.8, 1.5 Hz, 1H), 8.02 (dd, J = 7.8, 1.5 Hz, 1H) |

Reference Example 5

3'-(Methylthio)acetophenone (Reference compound No. 5-1)

A suspension of 3'-mercaptoacetophenone (Reference compound No. 4-1, 1.5 g, 9.9 mmol), potassium carbonate (1.6 g, 12 mmol) and iodomethane (740 μL, 12 mmol) in N,N-dimethylformamide was stirred at 50° C. for 75 minutes. Water (50 mL) was added to the reaction mixture, extracted with a mixed solvent (50 mL) which consists of hexane and ethyl acetate (3:1). The organic layer was washed with brine (50 mL), dried over anhydrous magnesium sulfate. The solvent was removed under reduced pressure to give the title reference compound (1.3 g) as a brown oil (Yield 77%).

| | |
|---|---|
| 3'-(Methylthio)acetophenone (Reference compound No. 5-1) 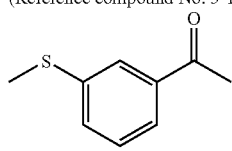 | ¹H-NMR (400 MHz, DMSO-d₆) δ 2.53 (s, 3H), 2.59 (s, 3H), 7.47 (t, J = 7.8 Hz, 1H), 7.53 (ddd, J = 7.8, 1.7, 1.2 Hz, 1H), 7.72 (dt, J = 7.8, 1.7 Hz, 1H), 7.76 (t, J = 1.7 Hz, 1H) |

As described below, using commercially available compounds or reference compound No. 4-1 or 4-2, reference compound No. 5-2 to 5-4 were obtained by a method similar to reference compound No. 5-1.

| | |
|---|---|
| 3'-(Ethylthio)acetophenone (Reference compound No. 5-2) 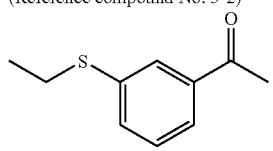 | ¹H-NMR (400 MHz, DMSO-d₆) δ 1.25 (t, J = 7.3 Hz, 3H), 2.58 (s, 3H), 3.05 (q, J = 7.3 Hz, 2H), 7.47 (t, J = 7.7 Hz, 1H), 7.57 (ddd, J = 7.7, 1.7, 1.2 Hz, 1H), 7.75 (ddd, J = 7.7, 1.7, 1.2 Hz, 1H), 7.81 (t, J = 1.7 Hz, 1H) |
| 2'-(Methylthio)acetophenone (Reference compound No. 5-3) 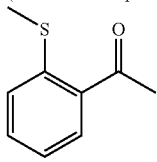 | ¹H-NMR (400 MHz, DMSO-d₆) δ 2.38 (s, 3H), 2.57 (s, 3H), 7.26 (td, J = 7.8, 1.5 Hz, 1H), 7.40 (d, J = 7.8 Hz, 1H), 7.56 (m, 1H), 7.99 (dd, J = 7.8, 1.5 Hz, 1H) |
| 3'-(Cyanomethylthio)acetophenone (Reference compound No. 5-4) 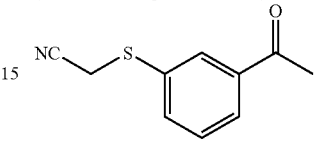 | ¹H-NMR (500 MHz, DMSO-d₆) δ 2.61 (s, 3H), 4.34 (s, 2H), 7.59 (t, J = 7.8 Hz, 1H), 7.76 (ddd, J = 7.8, 1.8, 1.2 Hz, 1H), 7.90 (dt, J = 7.8, 1.8 Hz, 1H), 8.01 (t, J = 1.8 Hz, 1H) |

Reference Example 6

3'-(4-Nitrophenylthio)acetophenone (Reference compound No. 6-1)

A suspension of 3'-mercaptoacetophenone (Reference compound No. 4-1, 0.50 g, 3.3 mmol), potassium carbonate (0.55 g, 4.0 mmol) and 4-fluoronitrobenzene (0.42 mL, 4.0 mmol) in N,N-dimethylformamide (20 mL) was stirred at room temperature for 8.5 hours. Water (30 mL) was added to the reaction mixture, extracted with mixed solvent (30 mL) which consists of hexane and ethyl acetate (3:1). The organic layer was washed with brine (30 mL), dried over anhydrous magnesium sulfate. The solvent was removed under reduced pressure to give the title reference compound (1.2 g) quantitatively as a yellow solid.

| | |
|---|---|
| 3'-(4-Nitrophenylthio)acetophenone (Reference compound No. 6-1) 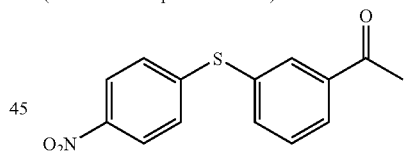 | ¹H-NMR (400 MHz, DMSO-d₆) δ 2.62 (s, 3H), 7.36 (dt, J = 9.3, 2.4 Hz, 2H), 7.69 (t, J = 8.0 Hz, 1H), 7.84 (m, 1H), 8.07-8.10 (m, 2H), 8.16 (dt, J = 9.3, 2.4 Hz, 2H) |

Reference Example 7

2'-Vinylacetophenone (Reference compound No. 7-1)

A solution of 2'-bromoacetophenone (1.6 mL, 12 mmol), sodium hydrogencarbonate (2.5 g, 30 mmol), vinylboronic acid pinacol ester (3.0 mL, 18 mmol) and tetrakis(triphenylphosphine)palladium(0) (0.69 g, 0.60 mmol) in a mixed solvent (50 mL), which consists of water and 1,4-dioxane (1:4), was stirred at 95° C. for 2.5 hours. Water (100 mL) was added to the reaction solution and extracted with ethyl acetate (100 mL). The organic layer was washed with brine (50 mL), dried over anhydrous magnesium sulfate. After the organic layer was filtered with celite and the solvent was removed under reduced pressure, the residue was purified by silica gel column chromatography to give the title reference compound (1.2 g) as an orange oil (Yield 69%).

| | |
|---|---|
| 2'-Vinylacetophenone (Reference compound No. 7-1) 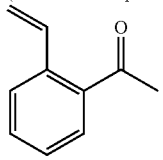 | ¹H-NMR (400 MHz, DMSO-d₆) δ 2.56 (s, 3H), 5.31 (dd, J = 11.0, 1.2 Hz, 1H), 5.71 (dd, J = 17.6, 1.2 Hz, 1H), 7.10 (dd, J = 17.6, 11.0 Hz, 1H), 7.42 (td, J = 7.6, 1.4 Hz, 1H), 7.53 (td, J = 7.6, 1.4 Hz, 1H), 7.66 (d, J = 7.6 Hz, 1H), 7.78 (dd, J = 7.6, 1.4 Hz, 1H) |

Example 1

2-Aminocarbonylamino-5-(4-bromophenyl)pyrrole-3-carboxamide (Compound No. 1-1)

Trichloroacetyl isocyanate (60 μL, 0.50 mmol) was added dropwise to a solution of 2-amino-5-(4-bromophenyl)pyrrole-3-carboxamide (Reference compound No. 1-1, 0.17 g, 0.60 mmol) in anhydrous tetrahydrofuran (3.0 mL) at −40° C. and the mixture was stirred for 1 hour. Furthermore, ammonia solution 2.0 M in methanol (3.0 mL, 6.0 mmol) was added thereto, and the whole was stirred at room temperature for 3 days. Water (20 mL) was added to the reaction solution, then the precipitated solid was filtered off. The obtained solid was dried under reduced pressure to give the target compound (0.070 g) as a brown solid (Yield 36%).

| | |
|---|---|
| 2-Aminocarbonylamino-5-(4-bromophenyl)pyrrole-3-carboxamide (Compound No. 1-1) 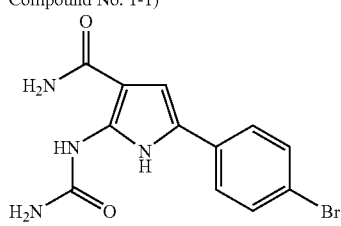 | ¹H-NMR (400 MHz, DMSO-d₆) δ 6.86 (br s, 3H), 6.91 (d, J = 2.8 Hz, 1H), 7.33 (br s, 1H), 7.38 (d, J = 8.8 Hz, 2H), 7.53 (d, J = 8.8 Hz, 2H), 9.65 (s, 1H), 11.20 (s, 1H) |

As described below, using reference compounds selected from No. 1-2 to 1-62, 2-1, 3-1, 5-1 to 5-4, 6-1 or 7-1, compound No. 1-2 to 1-64 were obtained by a method similar to compound No. 1-1.

| | |
|---|---|
| 2-Aminocarbonylamino-5-(pyridin-2-yl)pyrrole-3-carboxamide (Compound No. 1-2) 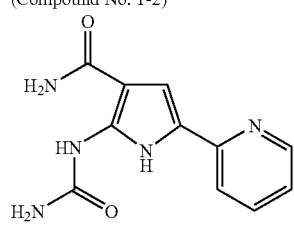 | ¹H-NMR (500 MHz, DMSO-d₆) δ 6.89 (br s, 3H), 7.10 (dd, J = 6.7, 4.6 Hz, 1H), 7.13 (d, J = 3.1 Hz, 1H), 7.38 (br s, 1H), 7.47 (d, J = 7.9 Hz, 1H), 7.74 (td, J = 7.9, 1.5 Hz, 1H), 8.46 (d, J = 4.6 Hz, 1H), 9.73 (s, 1H), 11.34 (s, 1H) |
| 2-Aminocarbonylamino-5-(pyridin-3-yl)pyrrole-3-carboxamide (Compound No. 1-3) 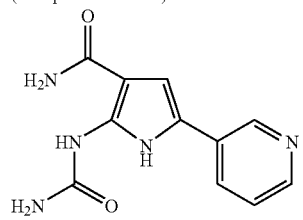 | ¹H-NMR (500 MHz, DMSO-d₆) δ 6.87 (br s, 3H), 6.98 (d, J = 3.1 Hz, 1H), 7.35 (br s, 1H), 7.36 (dd, J = 7.9, 4.9 Hz, 1H), 7.82 (dt, J = 7.9, 1.8 Hz, 1H), 8.33 (dd, J = 4.9, 1.8 Hz, 1H), 8.70 (d, J = 1.8 Hz, 1H), 9.66 (s, 1H), 11.28 (s, 1H) |
| 2-Aminocarbonylamino-5-phenylpyrrole-3-carboxamide (Compound No. 1-4) 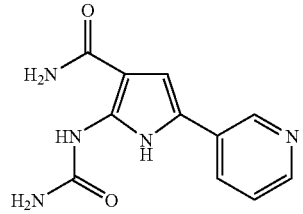 | ¹H-NMR (400 MHz, DMSO-d₆) δ 6.85 (br s, 3H), 6.87 (d, J = 2.7 Hz, 1H), 7.15 (td, J = 8.3, 1.2 Hz, 1H), 7.31 (br s, 1H), 7.36 (t, J = 8.3 Hz, 2H), 7.42 (dd, J = 8.3, 1.2 Hz, 2H), 9.63 (s, 1H), 11.16 (s, 1H) |

-continued

| | |
|---|---|
| 2-Aminocarbonylamino-5-(4-biphenyl)pyrrole-3-carboxamide (Compound No. 1-5)<br>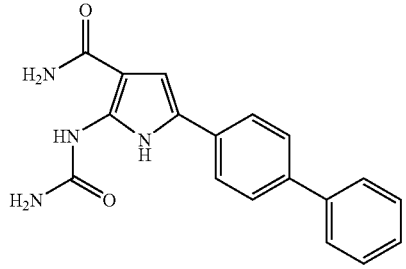 | $^1$H-NMR (500 MHz, DMSO-d$_6$) δ 6.86 (br s, 3H), 6.94 (d, J = 3.1 Hz, 1H), 7.27-7.41 (m, 2H), 7.42-7.50 (m, 2H), 7.52 (d, J = 8.6 Hz, 2H), 7.57-7.81 (m, 4H), 9.67 (s, 1H, 11.22 (s, 1H) |
| 2-Aminocarbonylamino-5-(3-nitrophenyl)pyrrole-3-carboxamide (Compound No. 1-6)<br>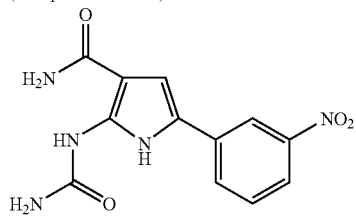 | $^1$H-NMR (400 MHz, DMSO-d$_6$) δ 6.90 (br s, 3H), 7.13 (d, J = 2.9 Hz, 1H), 7.37 (br s, 1H), 7.63 (t, J = 8.1 Hz, 1H), 7.88 (ddd, J = 8.1, 2.2, 1.0 Hz, 1H), 7.95 (ddd, J = 8.1, 2.2, 1.0 Hz, 1H), 8.28 (t, J = 2.2 Hz, 1H), 9.67 (s, 1H), 11.43 (s, 1H) |
| 2-Aminocarbonylamino-5-(4-nitrophenyl)pyrrole-3-carboxamide (Compound No. 1-7)<br>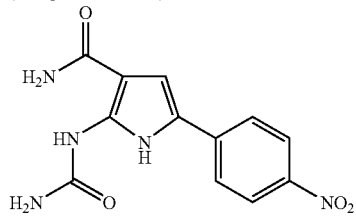 | $^1$H-NMR (400 MHz, DMSO-d$_6$) δ 6.97 (br s, 3H), 7.24 (d, J = 2.9 Hz, 1H), 7.45 (br s, 1H), 7.64 (dd, J = 7.1, 2.0 Hz, 2H), 8.18 (dd, J = 7.1, 2.0 Hz, 2H), 9.75 (s, 1H), 11.45 (s, 1H) |
| 2-Aminocarbonylamino-5-(4-fluorophenyl)pyrrole-3-carboxamide (Compound No. 1-8)<br>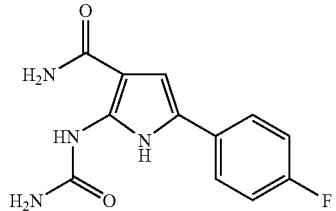 | $^1$H-NMR (500 MHz, DMSO-d$_6$) δ 6.80 (d, J = 2.7 Hz, 1H), 6.81 (br s, 3H), 7.17-7.22 (m, 2H), 7.28 (br s, 1H), 7.43-7.47 (m, 2H), 9.61 (s, 1H), 11.13 (s, 1H) |
| 2-Aminocarbonylamino-5-(2-methoxyphenyl)pyrrole-3-carboxamide (Compound No. 1-9)<br>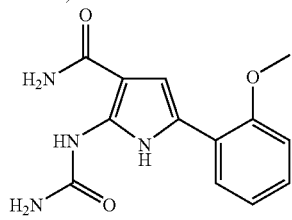 | $^1$H-NMR (500 MHz, DMSO-d$_6$) δ 3.89 (s, 3H), 6.77 (br s, 3H), 6.91 (d, J = 2.7 Hz, 1H), 6.97 (m, 1H), 7.08 (d, J = 7.6 Hz, 1H), 7.14 (m, 1H), 7.27 (br s, 1H), 7.47 (dd, J = 7.6, 1.5 Hz, 1H), 9.59 (s, 1H), 11.76 (s, 1H) |

| | |
|---|---|
| 2-Aminocarbonylamino-5-(4-methoxyphenyl) pyrrole-3-carboxamide (Compound No. 1-10) 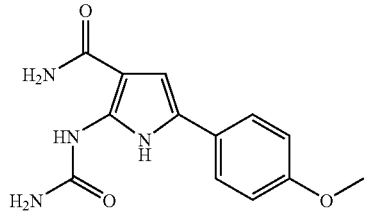 | $^1$H-NMR (500 MHz, DMSO-d$_6$) δ 3.76 (s, 3H), 6.69 (d, J = 2.7 Hz, 1H), 6.82 (br s, 3H), 6.95 (d, J = 8.9 Hz, 2H), 7.25 (br s, 1H), 7.35 (d, J = 8.9 Hz, 2H), 9.60 (s, 1H), 11.02 (s, 1H) |
| 2-Aminocarbonylamino-5-(4-methylphenyl) pyrrole-3-carboxamide (Compound No. 1-11) 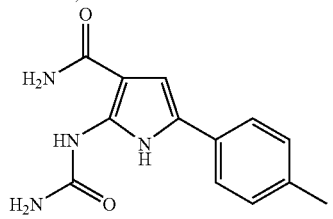 | $^1$H-NMR (500 MHz, DMSO-d$_6$) δ 2.28 (s, 3H), 6.79 (d, J = 2.7 Hz, 1H), 6.80 (br s, 3H), 7.17 (d, J = 8.1 Hz, 2H), 7.30 (br s, 1H), 7.31 (d, J = 8.1 Hz, 2H), 9.62 (s, 1H), 11.09 (s, 1H) |
| 2-Aminocarbonylamino-5-(3-methoxyphenyl) pyrrole-3-carboxamide (Compound No. 1-12) 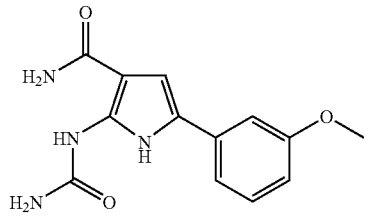 | $^1$H-NMR (400 MHz, DMSO-d$_6$) δ 3.79 (s, 3H), 6.74 (dd, J = 7.9, 1.8 Hz, 1H), 6.84 (br s, 3H), 6.87 (d, J = 2.8 Hz, 1H), 6.96-7.02 (m, 2H), 7.27 (t, J = 7.9 Hz, 1H), 7.28 (br s, 1H), 9.62 (s, 1H), 11.14 (s, 1H) |
| 2-Aminocarbonylamino-5-(2-trifluoromethylphenyl)pyrrole-3-carboxamide (Compound No. 1-13) 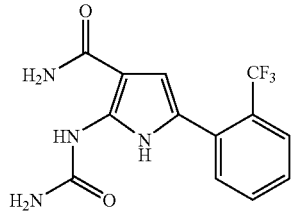 | $^1$H-NMR (500 MHz, DMSO-d$_6$) δ 6.71 (d, J = 3.1 Hz, 1H), 6.83 (br s, 3H), 7.38 (br s, 1H), 7.47 (t, J = 7.6 Hz, 1H), 7.57 (d, J = 7.6 Hz, 1H), 7.68 (t, J = 7.6 Hz, 1H), 7.77 (d, J = 7.6 Hz, 1H), 9.68 (s, 1H), 11.24 (s, 1H) |
| 2-Aminocarbonylamino-5-(4-chlorophenyl) pyrrole-3-carboxamide (Compound No. 1-14) 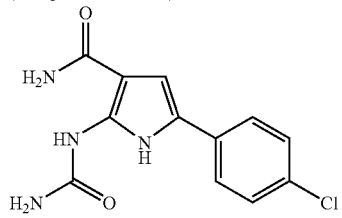 | $^1$H-NMR (400 MHz, DMSO-d$_6$) δ 6.86 (br s, 3H), 6.89 (d, J = 2.9 Hz, 1H), 7.31 (br s, 1H), 7.40 (d, J = 8.8 Hz, 2H), 7.44 (d, J = 8.8 Hz, 2H), 9.64 (s, 1H), 11.19 (s, 1H) |

| | |
|---|---|
| 2-Aminocarbonylamino-5-(4-cyanophenyl)pyrrole-3-carboxamide (Compound No. 1-15) 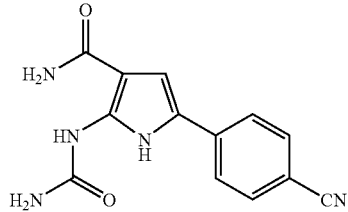 | $^1$H-NMR (400 MHz, DMSO-d$_6$) δ 6.93 (br s, 3H), 7.12 (d, J = 2.9 Hz, 1H), 7.38 (br s, 1H), 7.57 (d, J = 8.5 Hz, 2H), 7.77 (d, J = 8.5 Hz, 2H), 9.70 (s, 1H), 11.36 (s, 1H) |
| 2-Aminocarbonylamino-5-(thiophen-2-yl)pyrrole-3-carboxamide (Compound No. 1-16) 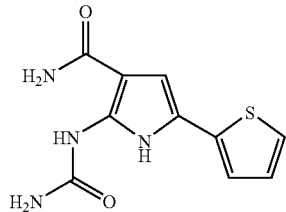 | $^1$H-NMR (400 MHz, DMSO-d$_6$) δ 6.67 (d, J = 2.8 Hz, 1H), 6.81 (br s, 3H), 7.01 (dd, J = 5.0, 3.5 Hz, 1H), 7.15 (dd, J = 3.5, 1.1 Hz, 1H), 7.30 (dd, J = 5.0, 1.1 Hz, 1H), 7.33 (br s, 1H), 9.65 (s, 1H), 11.06 (s, 1H) |
| 2-Aminocarbonylamino-5-(2,5-dimethoxyphenyl)pyrrole-3-carboxamide (Compound No. 1-17) 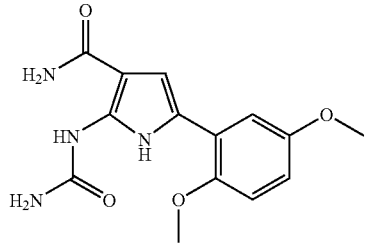 | $^1$H-NMR (400 MHz, DMSO-d$_6$) δ 3.74 (s, 3H), 3.84 (s, 3H), 6.72 (dd, J = 8.9, 2.9 Hz, 1H), 6.81 (br s, 3H), 6.95 (d, J = 2.7 Hz, 1H), 7.01 (d, J = 8.9 Hz, 1H), 7.02 (d, J = 2.9 Hz, 1H), 7.25 (br s, 1H), 9.59 (s, 1H), 11.82 (s, 1H) |
| 2-Aminocarbonylamino-5-(4-fluoro-2-methoxyphenyl)pyrrole-3-carboxamide (Compound No. 1-18) 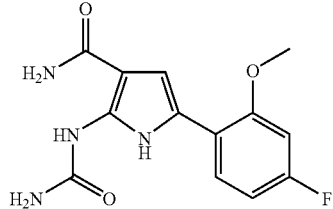 | $^1$H-NMR (500 MHz, DMSO-d$_6$) δ 3.91 (s, 3H), 6.79 (br s, 3H), 6.81-6.89 (m, 2H), 7.01 (dd, J = 11.3, 2.4 Hz, 1H), 7.27 (br s, 1H), 7.45 (dd, J = 8.6, 6.7 Hz, 1H), 9.59 (s, 1H), 11.67 (s, 1H) |
| 2-Aminocarbonylamino-5-(5-fluoro-2-methoxyphenyl)pyrrole-3-carboxamide (Compound No. 1-19) 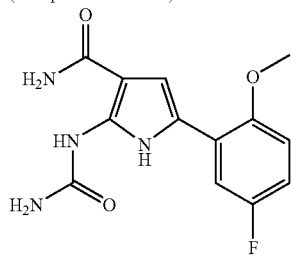 | $^1$H-NMR (400 MHz, DMSO-d$_6$) δ 3.88 (s, 3H), 6.84 (br s, 3H), 6.95 (td, J = 9.0, 3.1 Hz, 1H), 7.00 (d, J = 2.7 Hz, 1H), 7.09 (dd, J = 9.0, 4.9 Hz, 1H), 7.21 (dd, J = 10.0, 3.1 Hz, 1H), 7.22 (br s, 1H), 9.59 (s, 1H), 11.84 (s, 1H) |

| | |
|---|---|
| 2-Aminocarbonylamino-5-(2-trifluoromethoxyphenyl)pyrrole-3-carboxamide (Compound No. 1-20)<br>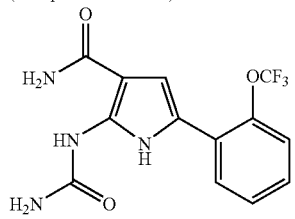 | ¹H-NMR (500 MHz, DMSO-d₆)<br>δ 6.87 (br s, 3H), 7.01 (d, J = 3.1 Hz, 1H), 7.27 (m, 1H), 7.34-7.50 (m, 3H), 7.61 (dd, J = 7.9, 1.8 Hz, 1H), 9.69 1H), (s, 1H), 11.48 (s, 1H) |
| 2-Aminocarbonylamino-5-(4-bromophenyl)-4-methylpyrrole-3-carboxamide (Compound No. 1-21)<br>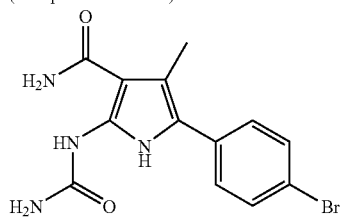 | ¹H-NMR (400 MHz, DMSO-d₆)<br>δ 2.28 (s, 3H), 6.74 (br s, 4H), 7.31 (d, J = 8.7 Hz, 2H), 7.58 (d, J = 8.7 Hz, 2H), 9.59 (s, 1H), 10.92 (s, 1H) |
| 2-Aminocarbonylamino-5-(5-chloro-2-methoxyphenyl)pyrrole-3-carboxamide (Compound No. 1-22)<br>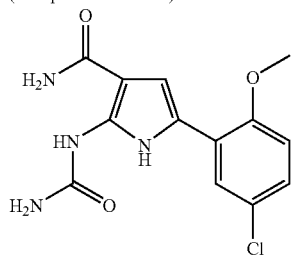 | ¹H-NMR (400 MHz, DMSO-d₆)<br>δ 3.90 (s, 3H), 6.84 (br s, 3H), 7.04 (d, J = 2.9 Hz, 1H), 7.10 (d, J = 8.8 Hz, 1H), 7.16 (dd, J = 8.8, 2.4 Hz, 1H), 7.24 (br s, 1H), 7.45 (d, J = 2.4 Hz, 1H), 9.59 (s, 1H), 11.80 (s, 1H) |
| 2-Aminocarbonylamino-5-(3-bromo-5-chloro-2-methoxyphenyl)pyrrole-3-carboxamide (Compound No. 1-23)<br>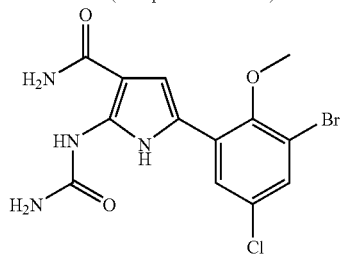 | ¹H-NMR (400 MHz, DMSO-d₆)<br>δ 3.72 (s, 3H), 6.91 (br s, 3H), 7.15 (d, J = 2.9 Hz, 1H), 7.29 (br s, 1H), 7.50 (d, J = 2.4 Hz, 1H), 7.51 (d, J = 2.4 Hz, 1H), 9.66 (s, 1H), 11.73 (s, 1H) |
| 2-Aminocarbonylamino-5-(5-chloro-2-methoxy-4-methylphenyl)pyrrole-3-carboxamide (Compound No. 1-24)<br>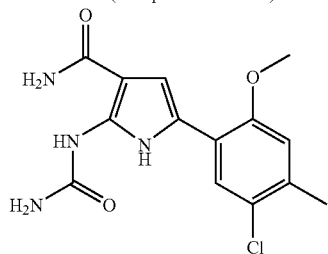 | ¹H-NMR (400 MHz, DMSO-d₆)<br>δ 2.31 (s, 3H), 3.89 (s, 3H), 6.81 (br s, 3H), 6.97 (d, J = 2.9 Hz, 1H), 7.08 (s, 1H), 7.23 (br s, 1H), 7.43 (s, 1H), 9.57 (s, 1H), 11.73 (s, 1H) |

| | |
|---|---|
| 2-Aminocarbonylamino-5-(3-chlorophenyl)pyrrole-3-carboxamide (Compound No. 1-25) 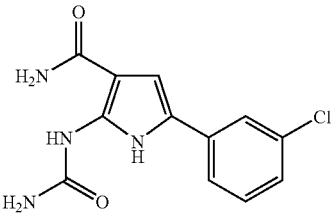 | ¹H-NMR (400 MHz, DMSO-d₆) δ 6.86 (br s, 3H), 6.96 (d, J = 2.9 Hz, 1H), 7.18 (dt, J = 6.8, 2.2 Hz, 1H), 7.29 (br s, 1H), 7.33-7.44 (m, 2H), 7.50 (m, 1H), 9.63 (s, 1H), 11.23 (s, 1H) |
| 2-Aminocarbonylamino-5-(2-methoxy-5-nitrophenyl)pyrrole-3-carboxamide (Compound No. 1-26) 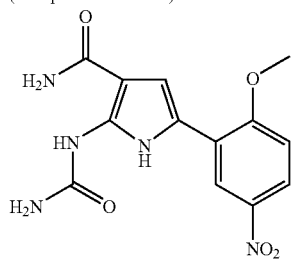 | ¹H-NMR (500 MHz, DMSO-d₆) δ 4.05 (s, 3H), 6.85 (br s, 3H), 7.22 (d, J = 3.1 Hz, 1H), 7.30 (d, J = 9.2 Hz, 1H), 7.38 (br s, 1H), 8.03 (dd, J = 9.2, 2.7 Hz, 1H), 8.31 (d, J = 2.7 Hz, 1H), 9.63 (s, 1H), 11.86 (s, 1H) |
| 2-Aminocarbonylamino-5-(2,5-dichlorophenyl)pyrrole-3-carboxamide (Compound No. 1-27) 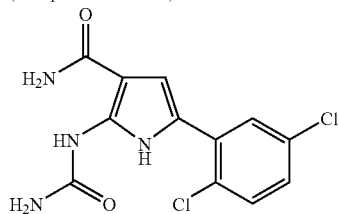 | ¹H-NMR (400 MHz, DMSO-d₆) δ 6.88 (br s, 3H), 7.12 (d, J = 2.9 Hz, 1H), 7.24 (dd, J = 8.5, 2.7 Hz, 1H), 7.37 (br s, 1H), 7.49 (d, J = 8.5 Hz, 1H), 7.54 (d, J = 2.7 Hz, 1H), 9.69 (s, 1H), 11.62 (s, 1H) |
| 2-Aminocarbonylamino-5-(3-fluorophenyl)pyrrole-3-carboxamide (Compound No. 1-28) 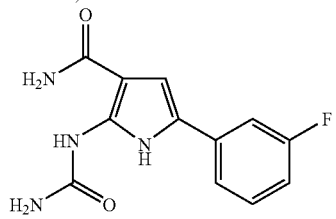 | ¹H-NMR (500 MHz, DMSO-d₆) δ 6.85 (br s, 3H), 6.91-6.99 (m, 2H), 7.19-7.34 (m, 2H), 7.35-7.49 (m, 2H), 9.63 (s, 1H), 11.20 (s, 1H) |
| 2-Amiocarbonylamino-5-(5-chloro-2-methoxyphenyl)-1-methylpyrrole-3-carboxamide (Compound No. 1-29) 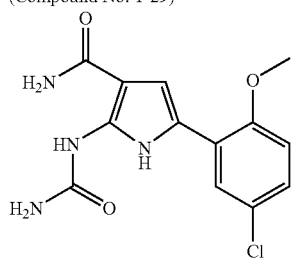 | ¹H-NMR (500 MHz, DMSO-d₆) δ 3.16 (s, 3H), 3.78 (s, 3H), 6.29 (s, 2H), 6.42 (s, 1H), 6.80 (br s, 1H), 7.13 (br s, 1H), 7.13 (d, J = 8.9 Hz, 1H), 7.21 (d, J = 2.7 Hz, 1H), 7.43 (dd, J = 8.9, 2.7 Hz, 1H), 8.26 (s, 1H) |

| | |
|---|---|
| 2-Aminocarbonylamino-5-(4-ethoxycarbonylphenyl)pyrrole-3-carboxamide (Compound No. 1-30) 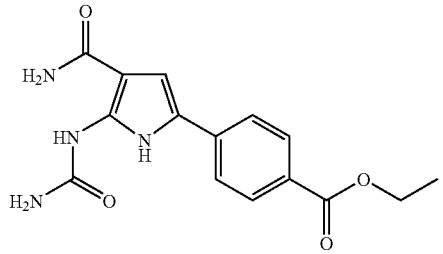 | $^1$H-NMR (400 MHz, DMSO-d$_6$) δ 1.32 (t, J = 7.2 Hz, 3H), 4.30 (q, J = 7.2 Hz, 2H), 6.90 (br s, 3H), 7.08 (s, 1H), 7.38 (br s, 1H), 7.54 (d, J = 8.5 Hz, 2H), 7.93 (d, J = 8.5 Hz, 2H), 9.69 (s, 1H), 11.31 (s, 1H) |
| 2-Aminocarbonylamino-5-(3-bromophenyl)pyrrole-3-carboxamide (Compound No. 1-31) 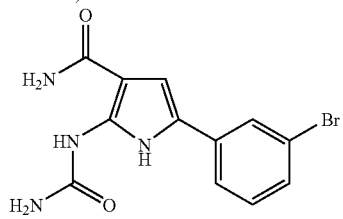 | $^1$H-NMR (400 MHz, DMSO-d$_6$) δ 6.84 (br s, 3H), 6.95 (s, 1H), 7.29 (br s, 1H), 7.29-7.32 (m, 2H), 7.43 (m, 1H), 7.64 (s, 1H), 9.62 (s, 1H), 11.22 (s, 1H) |
| 2-Aminocarbonylamino-5-(3-methylphenyl)pyrrole-3-carboxamide (Compound No. 1-32) 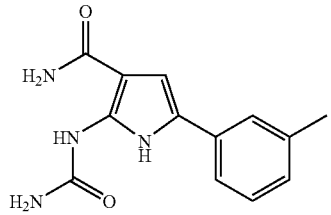 | $^1$H-NMR (400 MHz, DMSO-d$_6$) δ 2.32 (s, 3H), 6.83 (br s, 3H), 6.85 (d, J = 2.9 Hz, 1H), 6.97 (d, J = 7.3 Hz, 1H), 7.19-7.27 (m, 3H), 7.28 (br s, 1H), 9.63 (s, 1H), 11.11 (s, 1H) |
| 2-Aminocarbonylamino-5-(3-trifluoromethylphenyl)pyrrole-3-carboxamide (Compound No. 1-33) 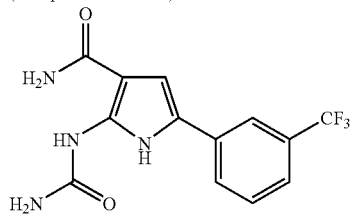 | $^1$H-NMR (500 MHz, DMSO-d$_6$) δ 6.87 (br s, 3H), 7.05 (d, J = 1.8 Hz, 1H), 7.31 (br s, 1H), 7.46 (d, J = 7.8 Hz, 1H), 7.57 (t, J = 7.8 Hz, 1H), 7.72 (d, J = 7.8 Hz, 1H), 7.79 (s, 1H), 9.64 (s, 1H), 11.33 (s, 1H) |
| 2-Aminocarbonylamino-5-(thiophen-3-yl)pyrrole-3-carboxamide (Compound No. 1-34) 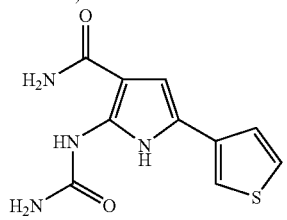 | $^1$H-NMR (400 MHz, DMSO-d$_6$) δ 6.68 (d, J = 2.9 Hz, 1H), 6.80 (br s, 3H), 7.23 (dd, J = 5.0, 1.3 Hz, 1H), 7.25 (br s, 1H), 7.52 (dd, J = 2.9, 1.3 Hz, 1H), 7.55 (dd, J = 5.0, 2.9 Hz, 1H), 9.62 (s, 1H), 10.99 (s, 1H) |

| | |
|---|---|
| 2-Aminocarbonylamino-5-(3-ethoxycarbonylphenyl)pyrrole-3-carboxamide (Compound No. 1-35) 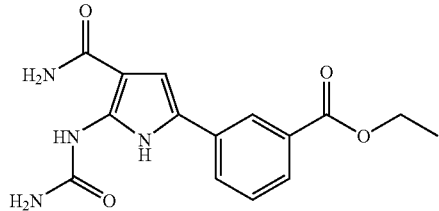 | ¹H-NMR (400 MHz, DMSO-d₆) δ 1.34 (t, J = 7.2 Hz, 3H), 4.35 (q, J = 7.2 Hz, 2H), 6.86 (br s, 3H), 7.00 (d, J = 2.4 Hz, 1H), 7.37 (br s, 1H), 7.50 (t, J = 7.8 Hz, 1H), 7.69 (m, 1H), 7.72 (d, J = 7.8 Hz, 1H), 8.01 (t J = 1.6 Hz, 1H), 9.65 (s, 1H), 11.29 (s, 1H) |
| 2-Aminocarbonylamino-5-(3-chloro-4-fluorophenyl)pyrrole-3-carboxamide (Compound No. 1-36) 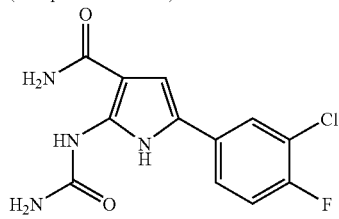 | ¹H-NMR (500 MHz, DMSO-d₆) δ 6.85 (br s, 3H), 6.90 (d, J = 2.7 Hz, 1H), 7.27 (br s, 1H), 7.32-7.47 (m, 2H), 7.66 (dd, J = 7.0, 2.1 Hz, 1H), 9.61 (s, 1H), 11.20 (s, 1H) |
| 2-Aminocarbonylamino-5-(3-chloro-4-methoxyphenyl)pyrrole-3-carboxamide (Compound No. 1-37) 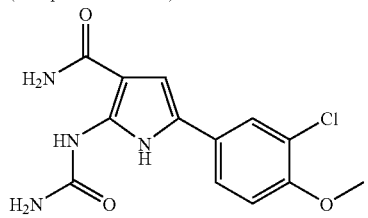 | ¹H-NMR (400 MHz, DMSO-d₆) δ 3.85 (s, 3H), 6.78 (d, J = 3.2 Hz, 1H), 6.81 (br s, 3H), 7.15 (d, J = 8.8 Hz, 1H), 7.23 (br s, 1H), 7.37 (dd, J = 8.8, 2.4 Hz, 1H), 7.51 (d, J = 2.4 Hz, 1H), 9.58 (s, 1H), 11.09 (s, 1H) |
| 2-Aminocarbonylamino-5-(2,3-dichlorophenyl)pyrrole-3-carboxamide (Compound No. 1-38) 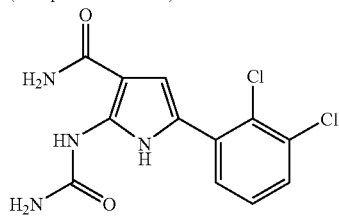 | ¹H-NMR (400 MHz, DMSO-d₆) δ 6.87 (br s, 3H), 7.05 (d, J = 3.2 Hz, 1H), 7.37 (t, J = 7.8 Hz, 1H), 7.42 (br s, 1H), 7.44-7.49 (m, 2H), 9.71 (s, 1H), 11.51 (s, 1H) |
| 2-Aminocarbonylamino-5-(3-cyanophenyl)pyrrole-3-carboxamide (Compound No. 1-39) 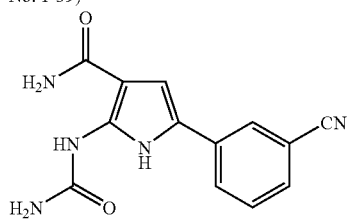 | ¹H-NMR (400 MHz, DMSO-d₆) δ 6.88 (br s, 3H), 7.02 (d, J = 3.2 Hz, 1H), 7.30 (br s, 1H), 7.47-7.60 (m, 2H), 7.75 (dt, J = 7.1, 2.1 Hz, 1H), 7.92 (s, 1H), 9.65 (s, 1H), 11.29 (s, 1H) |

-continued

| | |
|---|---|
| 2-Aminocarbonylamino-5-(2-chlorophenyl) pyrrole-3-carboxamide (Compound No. 1-40) 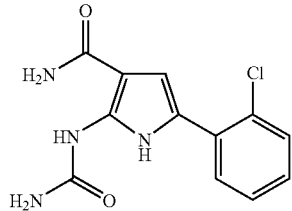 | ¹H-NMR (400 MHz, DMSO-d₆) δ 6.86 (br s, 3H), 7.01 (d, J = 3.2 Hz, 1H), 7.21 (td, J = 8.0, 1.6 Hz, 1H), 7.36 (td, J = 8.0, 1.2 Hz, 1H), 7.40 (br s, 1H), 7.47 (dd, J = 8.0, 1.2 Hz, 1H), 7.51 (dd, J = 8.0, 1.6 Hz, 1H), 9.69 (s, 1H), 11.53 (s, 1H) |
| 2-Aminocarbonylamino-5-(5-methylthiophen-2-yl) pyrrole-3-carboxamide (Compound No. 1-41) 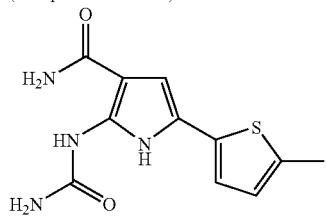 | ¹H-NMR (400 MHz, DMSO-d₆) δ 2.41 (s, 3H), 6.56 (d, J = 2.8 Hz, 1H), 6.68 (dd, J = 3.4, 1.2 Hz, 1H), 6.80 (br s, 3H), 6.91 (d, J = 3.4 Hz, 1H), 7.31 (br s, 1H), 9.63 (s, 1H), 10.97 (s; -1H) |
| 2-Aminocarbonylamino-5-(2-methylphenyl) pyrrole-3-carboxamide (Compound No. 1-42) 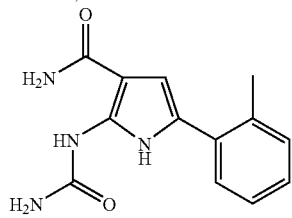 | ¹H-NMR (400 MHz, DMSO-d₆) δ 2.42 (s, 3H), 6.69 (d, J = 3.2 Hz, 1H), 6.83 (br s, 3H), 7.13 (td, J = 7.6, 1.5 Hz, 1H), 7.21-7.25 (m, 2H), 7.29 (d, J = 7.6 Hz, 1H), 7.36 (br s, 1H), 9.65 (s, 1H), 11.07 (s, 1H) |
| 2-Aminocarbonylamino-5-(3-methylthiophenyl) pyrrole-3-carboxamide (Compound No. 1-43) 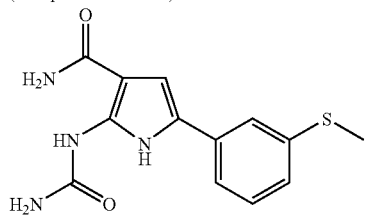 | ¹H-NMR (400 MHz, DMSO-d₆) δ 2.51 (s, 3H), 6.84 (br s, 3H), 6.91 (d, J = 2.7 Hz, 1H), 7.04 (ddd, J = 7.8, 1.7, 1.2 Hz, 1H), 7.19 (ddd, J = 7.8, 1.7, 1.2 Hz, 1H), 7.29 (br s, 1H), 7.30 (t, J = 7.8 Hz, 1H), 7.31 (t, J = 1.7 Hz, 1H), 9.61 (s, 1H), 11.17 (s, 1H) |
| 2-Aminocarbonylamino-5-(3-ethylthiophenyl) pyrrole-3-carboxamide (Compound No. 1-44) 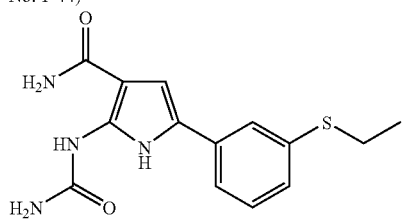 | ¹H-NMR (400 MHz, DMSO-d₆) δ 1.26 (t, J = 7.3 Hz, 3H), 3.01 (q, J = 7.3 Hz, 2H), 6.84 (br s, 3H), 6.91 (d, J = 2.4 Hz, 1H), 7.09 (d, J = 7.7 Hz, 1H), 7.23 (d, J = 7.7 Hz, 1H), 7.29 (br s, 1H), 7.30 (t, J = 7.7 Hz, 1H), 7.36 (t, J = 1.7 Hz, 1H), 9.61 (s, 1H), 11.18 (s, 1H) |

| | |
|---|---|
| 2-Aminocarbonylamino-5-(2-fluorophenyl)pyrrole-3-carboxamide (Compound No. 1-45) 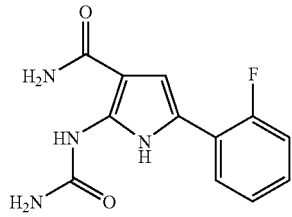 | ¹H-NMR (400 MHz, DMSO-d₆) δ 6.87 (br s, 3H), 7.00 (d, J = 2.0 Hz, 1H), 7.18-7.28 (m, 3H), 7.39 (br s, 1H), 7.53 (m, 1H), 9.69 (s, 1H), 11.38 (s, 1H) |
| 2-Aminocarbonylamino-5-(4-chloro-2-methoxyphenyl)pyrrole-3-carboxamide (Compound No. 1-46) 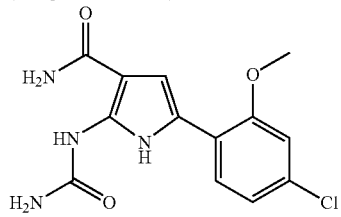 | ¹H-NMR (400 MHz, DMSO-d₆) δ 3.92 (s, 3H), 6.82 (br s, 3H), 6.94 (d, J = 2.9 Hz, 1H), 7.05 (dd, J = 8.5, 2.0 Hz, 1H), 7.15 (d, J = 2.0 Hz, 1H), 7.28 (br s, 1H), 7.44 (d, J = 8.5 Hz, 1H), 9.60 (s, 1H), 11.74 (s, 1H) |
| 2-Aminocarbonylamino-5-(pyrazin-2-yl)pyrrole-3-carboxamide (Compound No. 1-47) 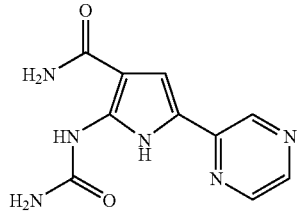 | ¹H-NMR (400 MHz, DMSO-d₆) δ 6.97 (br s, 3H), 7.32 (s, 1H), 7.42 (br s, 1H), 8.30 (d, J = 2.7 Hz, 1H), 8.47 (dd, J = 2.7, 1.7 Hz, 1H), 8.77 (d, J = 1.7 Hz, 1H), 9.78 (s, 1H), 11.41 (s, 1H) |
| 2-Aminocarbonylamino-5-(5-chlorothiophen-2-yl)pyrrole-3-carboxamide (Compound No. 1-48) 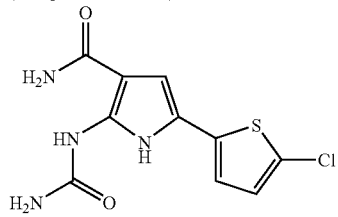 | ¹H-NMR (400 MHz, DMSO-d₆) δ 6.66 (d, J = 3.2 Hz, 1H), 6.83 (br s, 3H), 7.01 (d, J = 3.9 Hz, 1H), 7.06 (d, J = 3.9 Hz, 1H), 7.34 (br s, 1H), 9.66 (s, 1H), 11.13 (s, 1H) |
| 2-Aminocarbonylamino-5-[4-(pyrrolidin-1-yl)phenyl]pyrrole-3-carboxamide (Compound No. 1-49) 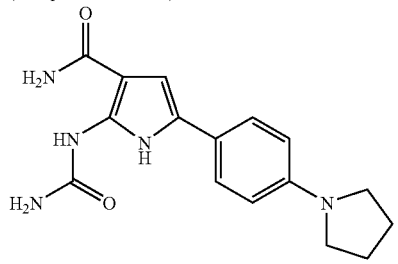 | ¹H-NMR (400 MHz, DMSO-d₆) δ 1.94-1.97 (m, 4H), 3.20-3.26 (m, 4H), 6.55 (d, J = 2.9 Hz, 1H), 6.56 (d, J = 8.8 Hz, 2H), 6.79 (br s, 3H), 7.19 (br s, 1H), 7.24 (d, J = 8.8 Hz, 2H), 9.58 (s, 1H), 10.91 (s, 1H) |

| | |
|---|---|
| 2-Aminocarbonylamino-5-[3-(4-nitrophenylthio)phenyl]pyrrole-3-carboxamide (Compound No. 1-50) 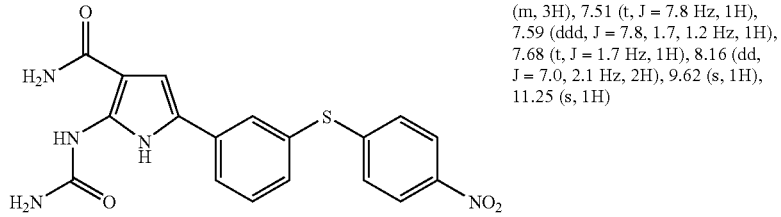 | ¹H-MNR (400 MHz, DMSO-d₆) δ 6.85 (br s, 3H), 6.97 (d, J = 2.4 Hz, 1H), 7.28 (br s, 1H), 7.32-7.36 (m, 3H), 7.51 (t, J = 7.8 Hz, 1H), 7.59 (ddd, J = 7.8, 1.7, 1.2 Hz, 1H), 7.68 (t, J = 1.7 Hz, 1H), 8.16 (dd, J = 7.0, 2.1 Hz, 2H), 9.62 (s, 1H), 11.25 (s, 1H) |
| 2-Aminocarbonylamino-5-(2,5-dimethylthiophen-3-yl)pyrrole-3-carboxamide (Compound No. 1-51)  | ¹H-NMR (400 MHz, DMSO-d₆) δ 2.38 (s, 3H), 2.42 (s, 3H), 6.55 (d, J = 3.2 Hz, 1H), 6.78 (d, J = 1.2 Hz, 1H), 6.80 (br s, 3H), 7.30 (br s, 1H), 9.61 (s, 1H), 10.94 (s, 1H) |
| 2-Aminocarbonylamino-5-(2,4,5-trifluorophenyl)pyrrole-3-carboxamide (Compound No. 1-52) 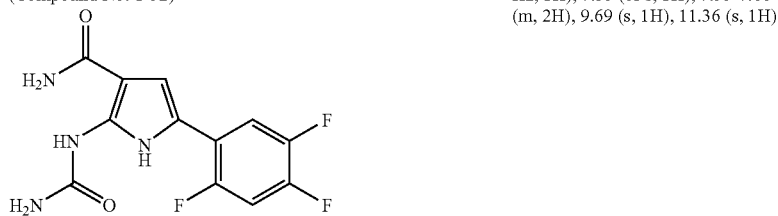 | ¹H-NMR (400 MHz, DMSO-d₆) δ 6.89 (br s, 3H), 6.99 (d, J = 1.5 Hz, 1H), 7.35 (br s, 1H), 7.55-7.66 (m, 2H), 9.69 (s, 1H), 11.36 (s, 1H) |
| 2-Aminocarbonylamino-5-(2,5-difluorophenyl)pyrrole-3-carboxamide (Compound No. 1-53) 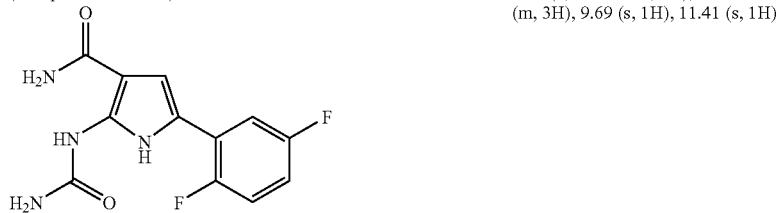 | ¹H-NMR (400 MHz, DMSO-d₆) δ 6.90 (br s, 3H), 7.01 (m, 1H), 7.07 (d, J = 2.0 Hz, 1H), 7.27-7.34 (m, 3H), 9.69 (s, 1H), 11.41 (s, 1H) |
| 2-Aminocarbonylamino-5-(3-methylthiophen-2-yl)pyrrole-3-carboxamide (Compound No. 1-54)  | ¹H-NMR (400 MHz, DMSO-d₆) δ 2.29 (s, 3H), 6.63 (d, J = 3.2 Hz, 1H), 6.81 (br s, 3H), 6.91 (d, J = 4.9 Hz, 1H), 7.26 (d, J = 4.9 Hz, 1H), 7.37 (s, 1H), 9.66 (s, 1H), 11.02 (s, 1H) |

| | |
|---|---|
| 2-Aminocarbonylamino-5-(2-fluoro-4-methoxyphenyl)pyrrole-3-carboxamide (Compound No. 1-55)<br>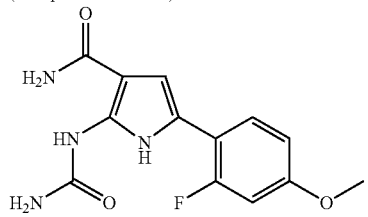 | ¹H-NMR (400 MHz, DMSO-d₆) δ 3.78 (s, 3H), 6.82 (d, J = 2.7 Hz, 1H), 6.84 (br s, 3H), 6.84 (dd, J = 8.9, 2.6 Hz, 1H), 6.90 (dd, J = 14.0, 2.6 Hz, 1H), 7.32 (br s, 1H), 7.42 (t, J = 8.9 Hz, 1H), 9.65 (s, 1H), 11.24 (s, 1H) |
| 2-Aminocarbonylamino-5-(3,4-difluorophenyl)pyrrole-3-carboxamide (Compound No. 1-56)<br>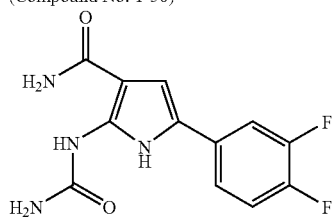 | ¹H-NMR (500 MHz, DMSO-d₆) δ 6.85 (br s, 3H), 6.88 (d, J = 3.1 Hz, 1H), 7.25-7.27 (m, 2H), 7.41 (dt, J = 10.7, 8.6 Hz, 1H), 7.50 (ddd, J = 12.2, 7.6, 2.1 Hz, 1H), 9.62 (s, 1H), 11.18 (s, 1H) |
| 2-Aminocarbonylamino-5-(3-cyanomethylthiophenyl)pyrrole-3-carboxamide (Compound No. 1-57)<br>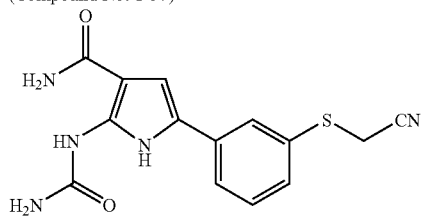 | ¹H-NMR (400 MHz, DMSO-d₆) δ 4.27 (s, 2H), 6.85 (br s, 3H), 6.95 (d, J = 3.2 Hz, 1H), 7.27 (dt, J = 6.3, 2.2 Hz, 1H), 7.37-7.41 (m, 3H), 7.56 (s, 1H), 9.64 (s, 1H), 11.21 (s, 1H) |
| 2-Aminocarbonylamino-5-(2-methylthiophenyl)pyrrole-3-carboxamide (Compound No. 1-58)<br>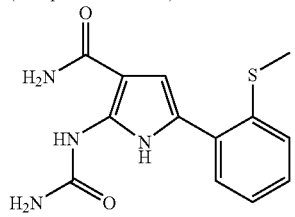 | ¹H-NMR (400 MHz, DMSO-d₆) δ 2.43 (s, 3H), 6.80 (d, J = 3.2 Hz, 1H), 6.81 (br s, 3H), 7.17-7.25 (m, 2H), 7.30-7.38 (m, 3H), 9.68 (s, 1H), 11.39 (s, 1H) |
| 2-Aminocarbonylamino-5-(2-vinylphenyl)pyrrole-3-carboxamide (Compound No. 1-59)<br>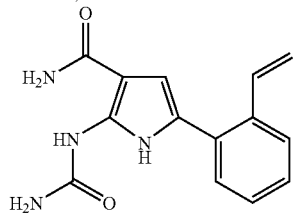 | ¹H-NMR (400 MHz, DMSO-d₆) δ 5.33 (dd, J = 11.0, 1.2 Hz, 1H), 5.75 (dd, J = 17.3, 1.2 Hz, 1H), 6.59 (d, J = 2.9 Hz, 1H), 6.83 (br s, 3H), 6.98 (dd, J = 17.3, 11.0 Hz, 1H), 7.25 (m, 1H), 7.32-7.34 (m, 2H), 7.37 (br s, 1H), 7.56 (d, J = 7.8 Hz, 1H), 9.67 (s, 1H), 11.03 (s, 1H) |

| | |
|---|---|
| 2-Aminocarbonylamino-5-(3,4-dichlorophenyl)pyrrole-3-carboxamide (Compound No. 1-60) 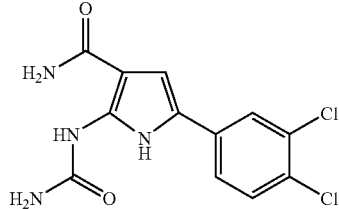 | $^1$H-NMR (400 MHz, DMSO-d$_6$) δ 6.87 (br s, 3H), 6.99 (d, J = 2.7 Hz, 1H), 7.29 (br s, 1H), 7.41 (dd, J = 8.3, 2.2 Hz, 1H), 7.58 (d, J = 8.3 Hz, 1H), 7.71 (d, J = 2.2 Hz, 1H), 9.63 (s, 1H), 11.26 (s, 1H) |
| 2-Aminocarbonylamino-5-(2,4-difluorophenyl)pyrrole-3-carboxamide (Compound No. 1-61) 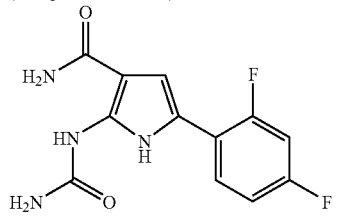 | $^1$H-NMR (400 MHz, DMSO-d$_6$) δ 6.87 (br s, 3H), 6.93 (d, J = 2.0 Hz, 1H), 7.14 (td, J = 8.4, 2.6 Hz, 1H), 7.31 (ddd, J = 12.2, 9.3, 2.6 Hz, 1H), 7.38 (br s, 1H), 7.55 (td, J = 9.3, 6.6 Hz, 1H), 9.68 (s, 1H), 11.34 (s, 1H) |
| 2-Aminocarbonylamino-5-(4-methylthiophen-2-yl)pyrrole-3-carboxamide (Compound No. 1-62) 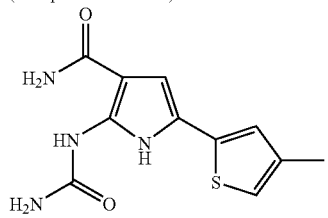 | $^1$H-NMR (400 MHz, DMSO-d$_6$) δ 2.18 (d, J = 1.2 Hz, 3H), 6.63 (d, J = 3.2 Hz, 1H), 6.82 (br s, 3H), 6.87 (t, J = 1.2 Hz, 1H), 6.96 (d, J = 1.2 Hz, 1H), 7.31 (br s, 1H), 9.64 (s, 1H), 11.01 (s, 1H) |
| 2-Aminocarbonylamino-5-(3-fluoro-4-methoxyphenyl)pyrrole-3-carboxamide (Compound No. 1-63) 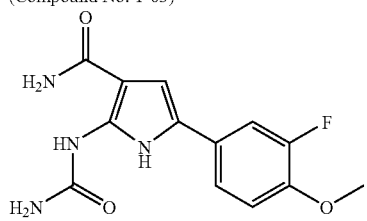 | $^1$H-NMR (400 MHz, DMSO-d$_6$) δ 3.83 (s, 3H), 6.76 (d, J = 2.9 Hz, 1H), 6.82 (br s, 3H), 7.16 (t, J = 8.5 Hz, 1H), 7.20 (dd, J = 8.5, 2.0 Hz, 1H), 7.21 (br s, 1H), 7.28 (dd, J = 13.0, 2.0 Hz, 1H), 9.59 (s, 1H), 11.07 (s, 1H) |
| 2-Aminocarbonylamino-5-(3,5-difluorophenyl)pyrrole-3-carboxamide (Compound No. 1-64) 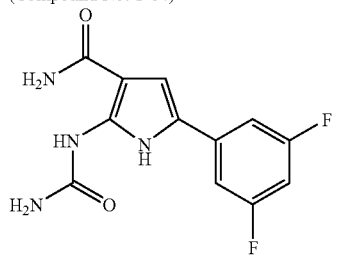 | $^1$H-NMR (500 MHz, DMSO-d$_6$) δ 6.89 (br s, 3H), 6.95 (tt, J = 9.3, 2.2 Hz, 1H), 7.02 (d, J = 3.1 Hz, 1H), 7.16 (dt, J = 7.3, 2.2 Hz, 2H), 7.26 (br s, 1H), 9.63 (s, 1H), 11.25 (s, 1H) |

Example 2

2-Aminocarbonylamino-5-(3-aminophenyl)pyrrole-3-carboxamide (Compound No. 2-1)

5% Palladium on activated carbon (30 mg) was added to a solution of 2-aminocarbonylamino-5-(3-nitrophenyl)pyrrole-3-carboxamide (Compound No. 1-6, 0.15 g, 0.52 mmol) in methanol (10 mL) and the mixture was stirred at room temperature for 6.5 hours under hydrogen gas atmosphere. After the insoluble solid was filtered out, the solvent was removed under reduced pressure. The obtained solid was washed with a mixed solvent (6 mL) which consists of chloroform and methanol (5:1), and dried under reduced pressure to give the target compound (0.072 g) as a pale yellow solid (Yield 53%).

| 2-Aminocarbonylamino-5-(3-aminophenyl)pyrrole-3-carboxamide (Compound No. 2-1) 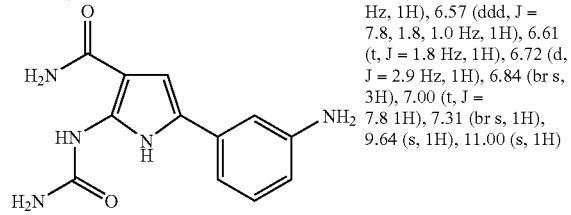 | $^1$H-NMR (400 MHz, DMSO-$d_6$) δ 5.13 (s, 2H), 6.37 (ddd, J = 7.8, 1.8, 1.0 Hz, 1H), 6.57 (ddd, J = 7.8, 1.8, 1.0 Hz, 1H), 6.61 (t, J = 1.8 Hz, 1H), 6.72 (d, J = 2.9 Hz, 1H), 6.84 (br s, 3H), 7.00 (t, J = 7.8 1H), 7.31 (br s, 1H), 9.64 (s, 1H), 11.00 (s, 1H) |
|---|---|

As described below, using compound No. 1-7, compound No. 2-2 was obtained by a method similar to compound No. 2-1.

| 2-Aminocarbonylamino-5-(4-aminophenyl aminophenyl)pyrrole-3-carboxamide (Compound No. 2-2) 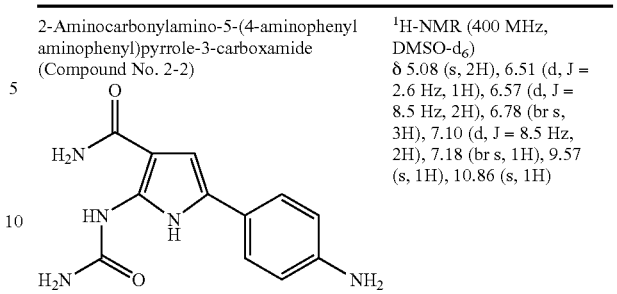 | $^1$H-NMR (400 MHz, DMSO-$d_6$) δ 5.08 (s, 2H), 6.51 (d, J = 2.6 Hz, 1H), 6.57 (d, J = 8.5 Hz, 2H), 6.78 (br s, 3H), 7.10 (d, J = 8.5 Hz, 2H), 7.18 (br s, 1H), 9.57 (s, 1H), 10.86 (s, 1H) |
|---|---|

Example 3

2-Aminocarbonylamino-5-(2-hydroxyphenyl)pyrrole-3-carboxamide (Compound No. 3-1)

Boron tribromide in dichloromethane solution (17%, 5.8 mL, 5.8 mmol) was added dropwise to a suspension of 2-aminocarbonylamino-5-(2-methoxyphenyl)pyrrole-3-carboxamide (Compound No. 1-9, 0.40 g, 1.5 mmol) in anhydrous dichloromethane (8 mL) for 7 minutes at −78° C., and the mixture was stirred for 30 minutes. Moreover, the mixture was stirred under ice-cooling for 5 hours, water (25 mL) was added thereto. The precipitated solid was filtered off with chloroform, dried under reduced pressure to give the target compound (0.39 g) quantitatively as a gray solid.

| 2-Aminocarbonylamino-5-(2-hydroxyphenyl)pyrrole-3-carboxamide (Compound No. 3-1) 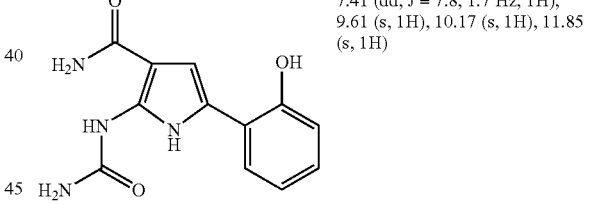 | $^1$H-NMR (400 MHz, DMSO-$d_6$) δ 6.74 (br s, 3H), 6.78-6.89 (m, 3H), 6.96 (m, 1H), 7.17 (br s, 1H), 7.41 (dd, J = 7.8, 1.7 Hz, 1H), 9.61 (s, 1H), 10.17 (s, 1H), 11.85 (s, 1H) |
|---|---|

As described below, using compounds selected from No. 1-12, 1-19, 1-22 or 1-37, compound No. 3-2 to 3-5 were obtained by a method similar to compound No. 3-1.

| 2-Aminocarbonylamino-5-(3-hydroxyphenyl)pyrrole-3-carboxamide (Compound No. 3-2) 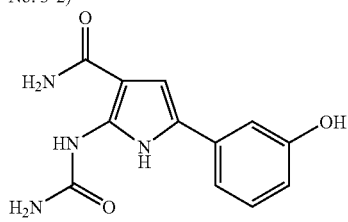 | $^1$H-NMR (400 MHz, DMSO-$d_6$) δ 6.57 (dd, J = 7.8, 1.7 Hz, 1H), 6.75-6.92 (m, 5H), 6.84 (d, J = 7.8 Hz, 1H), 7.15 (t, J = 7.8 Hz, 1H), 7.32 (br s, 1H), 9.44 (s, 1H), 9.64 (s, 1H), 11.10 (s, 1H) |
|---|---|

| | |
|---|---|
| 2-Aminocarbonylamino-5-(5-fluoro-2-hydroxyphenyl)pyrrole-3-carboxamide (Compound No. 3-3)<br>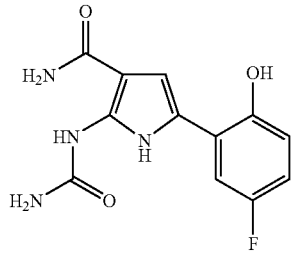 | $^1$H-NMR (400 MHz, DMSO-d$_6$) δ 6.26-7.06 (br s, 4H), 6.72-6.89 (m, 2H), 6.93 (d, J = 2.9 Hz, 1H), 7.12 (dd, J = 10.4, 3.1 Hz, 1H), 9.60 (s, 1H), 10.24 (br s, 1H), 11.92 (s, 1H) |
| 2-Aminocarbonylamino-5-(5-chloro-2-hydroxyphenyl)pyrrole-3-carboxamide (Compound No. 3-4)<br>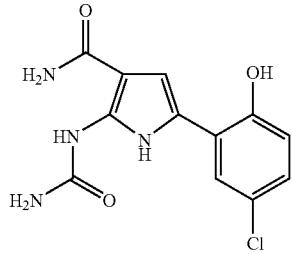 | $^1$H-NMR (400 MHz, DMSO-d$_6$) δ 6.79 (br s, 3H), 6.94-7.02 (m, 3H), 7.18 (br s, 1H), 7.38 (d, J = 2.7 Hz, 1H), 9.60 (s, 1H), 10.53 (s, 1H), 11.88 (s, 1H) |
| 2-Aminocarbonylamino-5-(3-chloro-4-hydroxyphenyl)pyrrole-3-carboxamide (Compound No. 3-5)<br>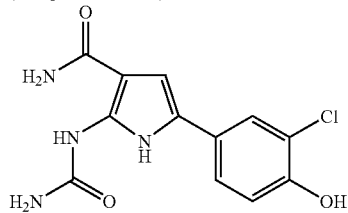 | $^1$H-NMR (400 MHz, DMSO-d$_6$) δ 6.71 (d, J = 2.9 Hz, 1H), 6.84 (br s, 4H), 6.97 (d, J = 8.5 Hz, 1H), 7.22 (dd, J = 8.5, 2.2 Hz, 1H), 7.41 (d, J = 2.2 Hz, 1H), 9.58 (s, 1H), 10.11 (s, 1H), 11.04 (s, 1H) |

Example 4

2-Aminocarbonylamino-5-(2-cyanomethyloxyphenyl)pyrrole-3-carboxamide (Compound No. 4-1)

A suspension of 2-aminocarbonylamino-5-(2-hydroxyphenyl)pyrrole-3-carboxamide (Compound No. 3-1, 52 mg, 0.20 mmol), potassium carbonate (43 mg, 0.31 mmol), bromoacetonitrile (15 μL, 0.22 mmol) in anhydrous N,N-dimethylformamide (1 mL) was stirred at 60° C. for 2.5 hours. After cooling to room temperature, water (10 mL) was added thereto and the precipitated solid was filtered off. The obtained solid was dried under reduced pressure to give the target compound (32 mg) as a pale brown solid (Yield 54%).

| | |
|---|---|
| 2-Aminocarbonylamino-5-(2-cyanomethyloxyphenyl)pyrrole-3-carboxamide (Compound No. 4-1)<br>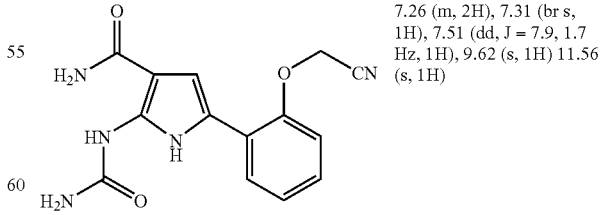 | $^1$H-NMR (400 MHz, DMSO-d$_6$) δ 5.26 (s, 2H), 6.83 (br s, 3H), 6.96 (s, 1H), 7.10 (m, 1H), 7.18-7.26 (m, 2H), 7.31 (br s, 1H), 7.51 (dd, J = 7.9, 1.7 Hz, 1H), 9.62 (s, 1H) 11.56 (s, 1H) |

As described below, using commercially available compounds or compounds selected from No. 3-1 to 3-4, compound No. 4-2 to 4-55 were obtained by a method similar to compound No. 4-1.

| | |
|---|---|
| 2-Aminocarbonylamino-5-[2-(2-phenoxyethyloxy)phenyl]pyrrole-3-carboxamide (Compound No. 4-2)<br/>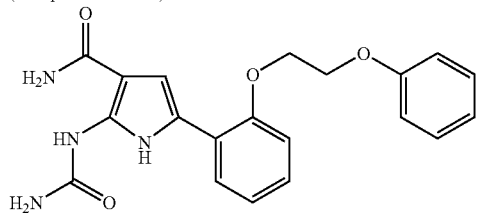 | $^1$H-NMR (500 MHz, DMSO-$d_6$) δ 4.44 (t, J = 5.0 Hz, 2H), 4.54 (t, J = 5.0 Hz, 2H), 6.77 (br s, 3H), 6.90-7.03 (m, 5H), 7.11-7.19 (m, 2H), 7.20-7.36 (m, 3H), 7.50 (dd, J = 7.3, 1.2 Hz, 1H), 9.59 (s, 1H), 11.74 (s, 1H) |
| 2-Aminocarbonylamino-5-[2-(3-pyrrol-1-ylpropyloxy)phenyl]pyrrole-3-carboxamide (Compound No. 4-3)<br/>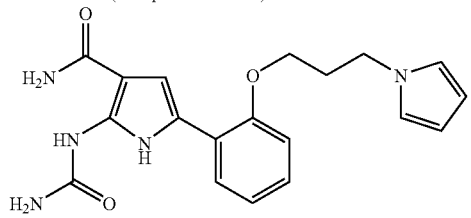 | $^1$H-NMR (500 MHz, DMSO-$d_6$) δ 2.28-2.33 (m, 2H), 3.99 (t, J = 6.1 Hz, 2H), 4.08 (t, J = 6.9 Hz, 2H), 5.96 (t, J = 2.0 Hz, 2H), 6.74 (t, J = 2.0 Hz, 2H), 6.84 (br s, 3H), 6.93 (s, 1H), 6.95-7.02 (m, 2H), 7.11 (m, 1H), 7.29 (br s, 1H), 7.50 (dd, J = 7.8, 1.7 Hz, 1H), 9.66 (s, 1H), 11.70 (s, 1H) |
| 2-Aminocarbonylamino-5-(2-propyloxyphenyl)pyrrole-3-carboxamide (Compound No. 4-4)<br/>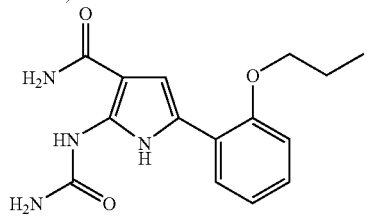 | $^1$H-NMR (400 MHz, DMSO-$d_6$) δ 0.99 (t, J = 7.1 Hz, 3H), 1.85-2.00 (m, 2H), 4.04 (t, J = 7.1 Hz, 2H), 6.81 (br s, 3H), 6.91 (d, J = 2.9 Hz, 1H), 6.95 (m, 1H), 7.06 (d, J = 7.8 Hz, 1H), 7.12 (m, 1H), 7.28 (br s, 1H), 7.50 (dd, J = 7.8, 1.7 Hz, 1H), 9.62 (s, 1H), 11.70 (s, 1H) |
| 2-Aminocarbonylamino-5-[2-(1,3-thiazol-2-ylcarbonylmethyloxy)phenyl]pyrrole-3-carboxamide (Compound No. 4-5)<br/>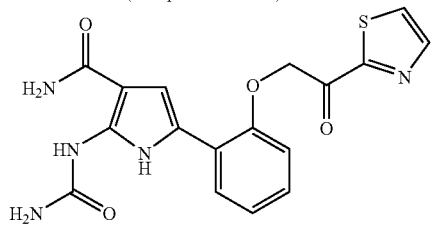 | $^1$H-NMR (400 MHz, DMSO-$d_6$) δ 4.12 (d, J = 12.5 Hz, 1H), 4.27 (d, J = 12.5 Hz, 1H), 6.67-6.97 (m, 4H), 7.02 (dd, J = 7.6, 1.7 Hz, 1H), 7.14-7.22 (m, 2H), 7.54 (dd, J = 7.6, 1.7 Hz, 1H), 7.66 (d, J = 3.2 Hz, 1H), 7.67 (d, J = 3.2 Hz, 1H), 7.81 (br s, 1H), 9.78 (s, 1H), 11.47 (s, 1H) |
| 2-Aminocarbonylamino-5-(2-benzyloxyphenyl)pyrrole-3-carboxamide (Compound No. 4-6)<br/>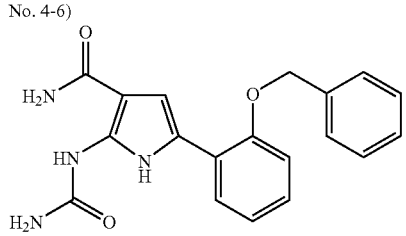 | $^1$H-NMR (500 MHz, DMSO-$d_6$) δ 5.33 (s, 2H), 6.80 (br s, 3H), 6.90 (d, J = 2.7 Hz, 1H), 6.93 (td, J = 7.3, 0.9 Hz, 1H), 7.06 (td, J = 7.6, 1.5 Hz, 1H), 7.12 (d, J = 7.6 Hz, 1H), 7.20-7.40 (m, 4H), 7.44 (dd, J = 7.6, 1.5 Hz, 1H), 7.52 (d, J = 7.3 Hz, 2H), 9.61 (s, 1H), 11.80 (s, 1H) |

| | |
|---|---|
| 2-Aminocarbonylamino-5-(2-phenethyloxyphenyl)pyrrole-3-carboxamide (Compound No. 4-7) 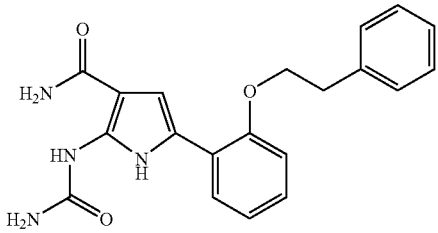 | $^1$H-NMR (500 MHz, DMSO-d$_6$) δ 3.28 (t, J = 7.2 Hz, 2H), 4.27 (t, J = 7.2 Hz, 2H), 6.92 (d, J = 2.9 Hz, 1H), 6.93-7.40 (m, 12H), 7.49 (dd, J = 7.9, 1.2 Hz, 1H), 9.65 (s, 1H), 11.80 (s, 1H) |
| 2-Aminocarbonylamino-5-[2-(4-fluorophenylcarbonylmethyloxy)phenyl]pyrrole-3-carboxamide (Compound No. 4-8) 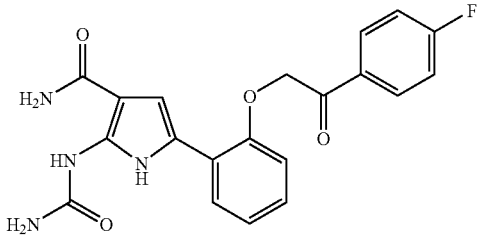 | $^1$H-NMR (400 MHz, DMSO-d$_6$) δ 5.74 (s, 2H), 6.77 (br s, 3H), 6.94 (d, J = 3.1 Hz, 1H), 6.96-7.33 (m, 4H), 7.41 (dd, J = 9.0, 8.9 Hz, 2H), 7.48 (d, J = 7.8 Hz, 1H), 8.13 (dd, J = 8.9, 5.5 Hz, 2H), 9.59 (s, 1H), 11.71 (s, 1H) |
| 2-Aminocarbonylamino-5-(3-cyanomethyloxyphenyl)pyrrole-3-carboxamide (Compound No. 4-9) 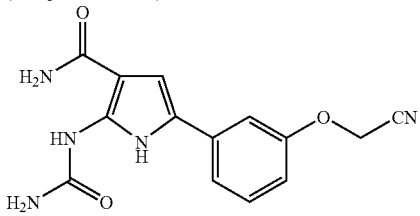 | $^1$H-NMR (400 MHz, DMSO-d$_6$) δ 5.21 (s, 2H), 6.86 (dd, J = 8.1, 1.8 Hz, 1H), 6.87 (br s, 3H), 6.91 (d, J = 2.9 Hz, 1H), 7.09-7.17 (m, 2H), 7.33 (br s, 1H), 7.35 (t, J = 8.1 Hz, 1H), 9.64 (s, 1H), 11.17 (s, 1H) |
| 2-Aminocarbonylamino-5-(2-methoxycarbonylmethyloxyphenyl)pyrrole-3-carboxamide (Compound No. 4-10) 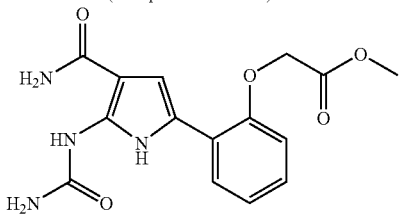 | $^1$H-NMR (400 MHz, DMSO-d$_6$) δ 3.71 (s, 3H), 4.93 (s, 2H), 6.80 (br s, 2H), 6.93 (d, J = 2.9 Hz, 1H), 6.96-7.05 (m, 3H), 7.11 (td, J = 7.7, 1.6 Hz, 1H), 7.27 (br s, 1H), 7.48 (dd, J = 7.7, 1.6 Hz, 1H), 9.60 (s, 1H), 11.63 (s, 1H) |
| 2-Aminocarbonylamino-5-(2-ethoxyphenyl)pyrrole-3-carboxamide (Compound No. 4-11) 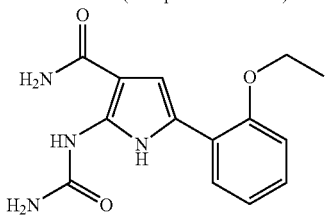 | $^1$H-NMR (400 MHz, DMSO-d$_6$) δ 1.50 (t, J = 7.0 Hz, 3H), 4.13 (q, J = 7.0 Hz, 2H), 6.81 (br s, 3H), 6.92 (d, J = 2.9 Hz, 1H), 6.95 (m, 1H), 7.06 (dd, J = 7.8, 1.7 Hz, 1H), 7.11 (m, 1H), 7.28 (br s, 1H), 7.50 (dd, J = 7.8, 1.7 Hz, 1H), 9.62 (s, 1H), 11.77 (s, 1H) |

| | |
|---|---|
| 2-Aminocarbonylamino-5-(2-cyclohexylmethyloxyphenyl)pyrrole-3-carboxamide (Compound No. 4-12) 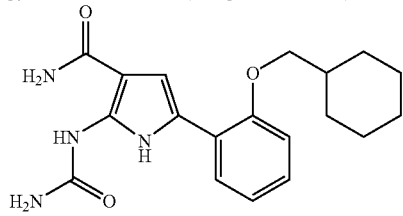 | $^1$H-NMR (400 MHz, DMSO-d$_6$) δ 0.92-1.07 (m, 2H), 1.10-1.40 (m, 4H), 1.50-1.90 (m, 4H), 2.06 (m, 1H), 3.88 (d, J = 6.8 Hz, 2H), 6.77 (br s, 3H), 6.89 (d, J = 2.9 Hz, 1H), 6.95 (m, 1H), 7.05 (d, J = 7.8 Hz, 1H), 7.11 (m, 1H), 7.28 (br s, 1H), 7.48 (dd, J = 7.8, 1.7 Hz, 1H), 9.61 (s, 1H), 11.63 (s, 1H) |
| 2-Aminocarbonylamino-5-[2-(pyridin-4-ylmethyloxy)phenyl]pyrrole-3-carboxamide (Compound No. 4-13) 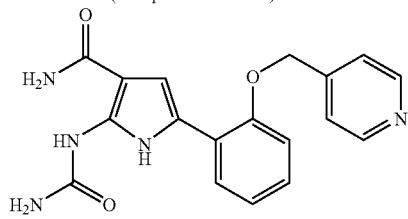 | $^1$H-NMR (400 MHz, DMSO-d$_6$) δ 5.36 (s, 2H), 6.82 (br s, 3H), 6.93 (d, J = 2.9 Hz, 1H), 6.98 (m, 1H), 7.05-7.11 (m, 2H), 7.30 (br s, 1H) 7.45-7.50 (m, 3H), 8.54 (d, J = 5.9 Hz, 2H), 9.63 (s, 1H), 11.73 (s, 1H) |
| 2-Aminocarbonylamino-5-(2-n-pentyloxyphenyl)pyrrole-3-carboxamide (Compound No. 4-14) 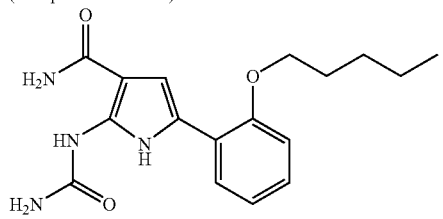 | $^1$H-NMR (400 MHz, DMSO-d$_6$) δ 0.88 (t, J = 7.1 Hz, 3H), 1.29-1.44 (m, 4H), 1.87-1.95 (m, 2H), 4.07 (t, J = 6.7 Hz, 2H), 6.79 (br s, 2H), 6.90 (d, J = 2.9 Hz, 1H), 6.95 (m, 1H), 7.02-7.16 (m, 2H), 7.27 (br s, 2H), 7.49 (dd, J = 7.8, 1.7 Hz, 1H), 9.61 (s, 1H), 11.68 (s, 1H) |
| 2-Aminocarbonylamino-5-[2-(pyridin-3-ylmethyloxy)phenyl]pyrrole-3-carboxamide (Compound No. 4-15) 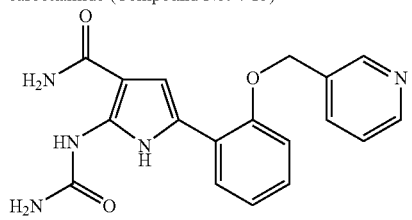 | $^1$H-NMR (400 MHz, DMSO-d$_6$) δ 5.36 (s, 2H), 6.80 (br s, 3H), 6.90 (d, J = 2.9 Hz, 1H), 6.96 (m, 1H), 7.11 (m, 1H), 7.21 (d, J = 7.9 Hz, 1H) 7.28 (br s, 1H), 7.38 (dd, J = 7.8, 4.8 Hz, 1H), 7.44 (td, J = 7.9, 1.6 Hz, 1H), 7.94 (dt, J = 7.9, 1.8 Hz, 1H), 8.50 (dd, J = 4.8, 1.8 Hz, 1H), 8.72 (d, J = 1.8 Hz, 1H), 9.61 (s, 1H), 11.73 (s, 1H) |
| 2-Aminocarbonylamino-5-(2-cyclobutylmethyloxyphenyl)pyrrole-3-carboxamide (Compound No. 4-16) 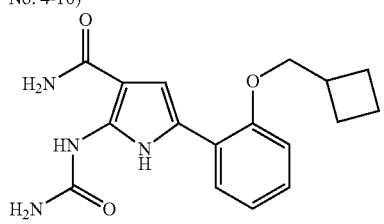 | $^1$H-NMR (400 MHz, DMSO-d$_6$) δ 1.72-2.04 (m, 4H), 2.08-2.22 (m, 2H), 2.97 (m, 1H), 4.08 (d, J = 7.1 Hz, 2H), 6.82 (br s, 3H), 6.90 (d, J = 2.9 Hz, 1H), 6.95 (m, 1H), 7.01-7.15 (m, 2H), 7.37 (m, 1H), 7.48 (dd, J = 7.7, 1.3 Hz, 1H), 9.62 (s, 1H), 11.57 (s, 1H) |

| | |
|---|---|
| 2-Aminocarbonylamino-5-[2-(pyridin-2-ylmethyloxy)phenyl]pyrrole-3-carboxamide (Compound No. 4-17)<br />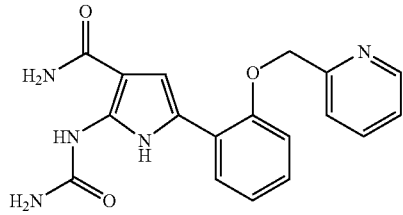 | ¹H-NMR (400 MHz, DMSO-d₆) δ 5.37 (s, 2H), 6.80 (br s, 3H), 6.93 (d, J = 2.9 Hz, 1H), 6.97 (m, 1H), 7.04-7.10 (m, 2H), 7.21 (br s, 1H), 7.32 (ddd, J = 7.6, 4.9, 1.0 Hz, 1H), 7.47 (d, J = 7.3 Hz, 1H), 7.52 (d, J = 7.6 Hz, 1H), 7.79 (td, J = 7.6, 1.7 Hz, 1H), 8.57 (ddd, J = 4.9, 1.7, 1.0 Hz 1H), 9.61 (s, 1H), 11.78 (s, 1H) |
| 2-Aminocarbonylamino-5-[2-(2-chloroethyloxy)phenyl]pyrrole-3-carboxamide (Compound No. 4-18)<br />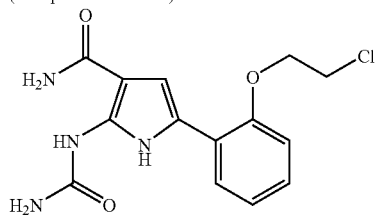 | ¹H-NMR (400 MHz, DMSO-d₆) δ 4.15 (t, J = 5.3 Hz, 2H), 4.38 (t, J = 5.3 Hz, 2H), 6.85 (br s, 3H), 6.94 (d, J = 2.9 Hz, 1H), 7.00 (m, 1H), 7.06-7.16 (m, 2H), 7.28 (br s, 1H) 7.51 (dd J = 7.8, 1.5 Hz, 1H), 9.61 (s, 1H), 11.75 (s, 1H) |
| 2-2Aminocarbonylamino-5-[2-(2-benzyloxyethyloxy)phenyl]pyrrole-3-carboxamide (Compound No. 4-19)<br />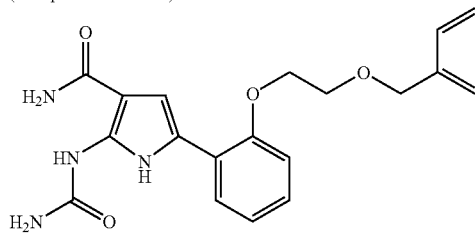 | ¹H-NMR (400 MHz, DMSO-d₆) δ 4.01 (t, J = 4.4 Hz, 2H), 4.26 (t, J = 4.4 Hz, 2H), 4.57 (s, 2H), 6.81 (br s, 3H), 6.93 (d, J = 2.7 Hz, 1H), 6.98 (m, 1H), 7.05-7.15 (m, 2H), 7.19-7.40 (m, 6H), 7.50 (d, J = 6.6 Hz, 1H), 9.63 (s, 1H), 11.76 (s, 1H) |
| 2-Aminocarbonylamino-5-[2-(3-methylbutoxy)phenyl]pyrrole-3-carboxamide (Compound No. 4-20)<br />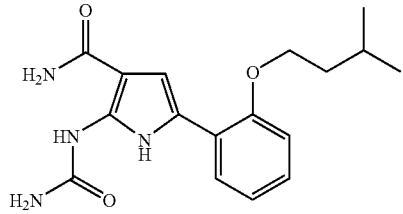 | ¹H-NMR (500 MHz, DMSO-d₆) δ 0.93 (d, J = 6.5 Hz, 6H), 1.72-1.86 (m, 3H), 4.11 (t, J = 6.5 Hz, 2H), 6.78 (br s, 3H), 6.90 (d, J = 3.1 Hz, 1H), 6.95 (m, 1H), 7.05-7.15 (m, 2H), 7.27 (br s, 1H), 7.48 (dd, J = 7.8, 1.5 Hz, 1H), 9.61 (s, 1H), 11.65 (s, 1H) |
| 2-Aminocarbonylamino-5-[2-(2-methylthiazol-4-ylmethyloxy)phenyl]pyrrole-3-carboxamide (Compound No. 4-21)<br />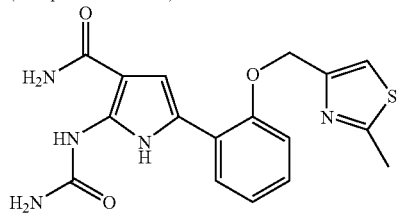 | ¹H-NMR (400 MHz, DMSO-d₆) δ 2.64 (s, 3H), 5.28 (s, 2H), 6.77 (br s, 3H), 6.90 (d, J = 2.9 Hz, 1H), 6.98 (m, 1H), 7.09 (m, 1H), 7.19 (dd, J = 7.8, 1.5 Hz, 1H), 7.27 (br s, 1H), 7.46 (dd, J = 7.8, 1.5 Hz, 1H), 7.54 (s, 1H), 9.60 (s, 1H), 11.57 (s, 1H) |

| | |
|---|---|
| 2-Aminocarbonylamino-5-[2-(3-ethoxycarbonylpropyloxy)phenyl]pyrrole-3-carboxamide (Compound No. 4-22)<br />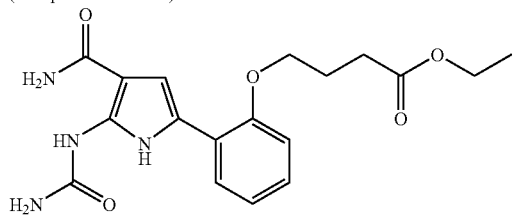 | ¹H-NMR (400 MHz, DMSO-d₆) δ 1.16 (t, J = 7.1 Hz, 3H), 2.11-2.20 (m, 2H), 2.44-2.54 (m, 2H), 4.04 (q, J = 7.1 Hz, 2H), 4.10 (t, J = 6.3 Hz, 2H), 6.80 (br s, 3H), 6.92 (d, J = 3.2 Hz, 1H), 6.96 (m, 1H), 7.05 (m, 1H), 7.12 (m, 1H), 7.29 (br s, 1H), 7.49 (dd, J = 7.8, 1.7 Hz, 1H), 9.62 (s, 1H) 11.69 (s, 1H) |
| 2-Aminocarbonylamino-5-(2-cyclopropylmethyloxyphenyl)pyrrole-3-carboxamide (Compound No. 4-23)<br />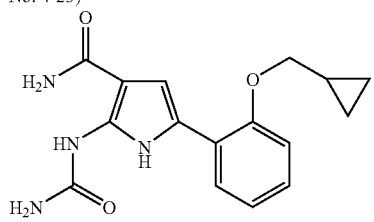 | ¹H-NMR (400 MHz, DMSO-d₆) δ 0.32-0.38 (m, 2H), 0.56-0.61 (m, 2H), 1.44 (m, 1H), 3.93 (d, J = 7.1 Hz, 2H), 6.79 (br s, 3H), 6.92 (d, J = 2.9 Hz, 1H), 6.96 (m, 1H), 7.04 (m, 1H), 7.09 (m, 1H), 7.27 (br s, 1H), 7.49 (dd, J = 7.8, 1.5 Hz, 1H), 9.62 (s, 1H), 11.79 (s, 1H) |
| 2-Aminocarbonylamino-5-[2-(3-fluoropropyloxy)phenyl]pyrrole-3-carboxamide (Compound No. 4-24)<br />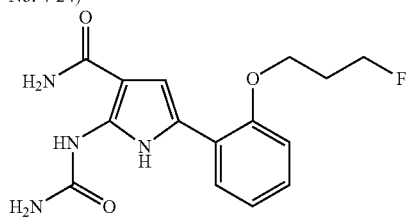 | ¹H-NMR (400 MHz, DMSO-d₆) δ 2.28 (t, J = 6.0 Hz, 1H), 2.35 (t, J = 6.0 Hz, 1H), 4.19 (t, J = 6.0 Hz, 2H), 4.59 (t, J = 5.8 Hz, 1H), 4.71 (t, J = 5.8 Hz, 1H), 6.83 (br s, 3H), 6.93 (d, J = 2.9 Hz, 1H), 6.98 (m, 1H), 7.06-7.18 (m, 2H), 7.30 (br s, 1H), 7.51 (dd, J = 7.7, 1.3 Hz, 1H), 9.63 (s, 1H) 11.68 (s, 1H) |
| 2-Aminocarbonylamino-5-[2-[2-(methoxyethoxy)ethyloxy]phenyl]pyrrole-3-carboxamide (Compound No. 4-25)<br />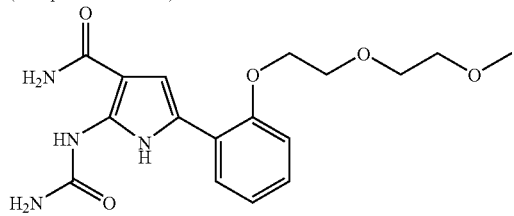 | ¹H-NMR (400 MHz, DMSO-d₆) δ 3.21 (s, 3H), 3.40-3.45 (m, 2H), 3.60-3.65 (m, 2H), 3.96 (t, J = 4.7 Hz, 2H), 4.21 (t, J = 4.7 Hz, 2H), 6.81 (br s, 3H), 6.93 (d, J = 2.9 Hz, 1H), 6.98 (m, 1H), 7.07-7.22 (m, 2H), 7.28 (br s, 1H), 7.50 (dd, J = 7.7, 1.6 Hz, 1H), 9.62 (s, 1H), 11.69 (s, 1H) |
| 2-Aminocarbonylamino-5-[2-(3,5-dimethylisoxazol-4-ylmethyloxy)phenyl]pyrrole-3-carboxamide (Compound No. 4-26)<br />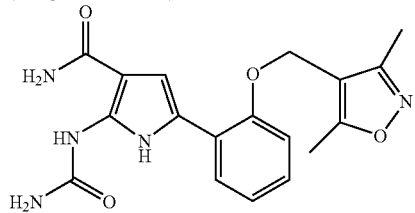 | ¹H-NMR (500 MHz, DMSO-d₆) δ 2.13 (s, 3H), 2.38 (s, 3H), 5.04 (s, 2H), 6.75 (br s, 3H), 6.88 (d, J = 3.1 Hz, 1H), 6.99 (m, 1H), 7.11-7.22 (m, 2H), 7.24 (br s, 1H), 7.47 (dd, J = 7.6, 1.5 Hz, 1H), 9.59 (s, 1H), 11.46 (s, 1H) |

| | |
|---|---|
| 2-Aminocarbonylamino-5-[2-[2-(piperidin-1-yl)ethyloxy]phenyl]pyrrole-3-carboxamide (Compound No. 4-27) 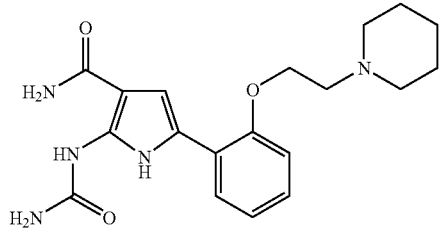 | $^1$H-NMR (500 MHz, DMSO-$d_6$) δ 1.29-1.40 (m, 2H), 1.42-1.53 (m, 4H), 2.39-2.49 (m, 4H), 2.89 (t, J = 6.1 Hz, 2H), 4.17 (t, J = 6.1 Hz, 2H), 6.79 (br s, 3H), 6.91 (d, J = 3.1 Hz, 1H), 6.96 (m, 1H), 7.08-7.21 (m, 2H), 7.26 (br s, 1H), 7.49 (dd, J = 7.8, 1.3 Hz, 1H), 9.60 (s, 1H), 11.63 (s, 1H) |
| 2-Aminocarbonylamino-5-[2-(2-methoxyethyloxy)phenyl]pyrrole-3-carboxamide (Compound No. 4-28) 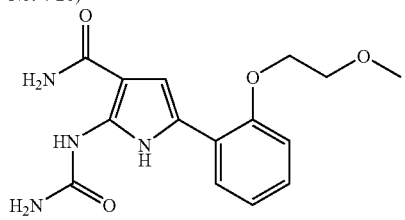 | $^1$H-NMR (400 MHz, DMSO-$d_6$) δ 3.32 (s, 3H), 3.88 (t, J = 4.6 Hz, 2H), 4.20 (t, J = 4.6 Hz, 2H), 6.80 (br s, 3H), 6.92 (d, J = 3.2 Hz, 1H), 6.98 (m, 1H), 7.05-7.21 (m, 2H), 7.28 (br s, 1H), 7.50 (dd, J = 7.8, 1.5 Hz, 1H), 9.61 (s, 1H), 11.69 (s, 1H) |
| 2-Aminocarbonylamino-5-[2-(3-chloropropyloxy)phenyl]pyrrole-3-carboxamide (Compound No. 4-29) 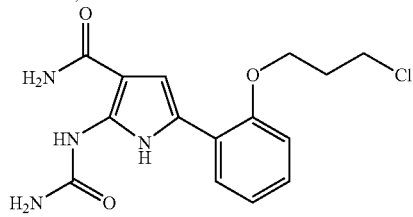 | $^1$H-NMR (500 MHz, DMSO-$d_6$) δ 2.33-2.42 (m, 2H), 3.84 (t, J = 6.3 Hz, 2H), 4.22 (t, J = 6.0 Hz, 2H), 6.81 (br s, 3H), 6.92 (d, J = 3.1 Hz, 1H), 6.99 (m, 1H), 7.08-7.21 (m, 2H), 7.29 (br s, 1H), 7.50 (dd, J = 7.8, 1.4 Hz, 1H), 9.63 (s, 1H), 11.64 (s, 1H) |
| 2-Aminocarbonylamino-5-[2-(3-dimethylaminopropyloxy)phenyl]pyrrole-3-carboxamide (Compound No. 4-30) 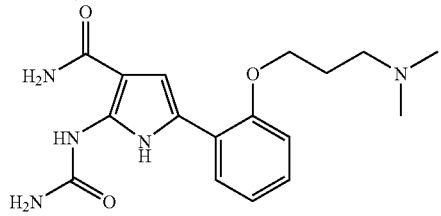 | $^1$H-NMR (400 MHz, DMSO-$d_6$) δ 2.00-2.10 (m, 2H), 2.12 (s, 6H), 2.36 (t, J = 6.7 Hz, 2H), 4.10 (t, J = 6.6 Hz, 2H), 6.80 (br s, 3H), 6.91 (d, J = 3.2 Hz, 1H), 6.96 (t, J = 7.6 Hz, 1H), 7.07 (t, J = 7.6 Hz, 1H), 7.10 (dd, J = 7.6, 1.5 Hz, 1H), 7.27 (br s, 1H), 7.49 (dd, J = 7.6, 1.5 Hz, 1H), 9.62 (s, 1H), 11.68 (s, 1H) |
| 2-Aminocarbonylamino-5-[2-(2-dimethylaminoethyloxy)phenyl]pyrrole-3-carboxamide (Compound No. 4-31) 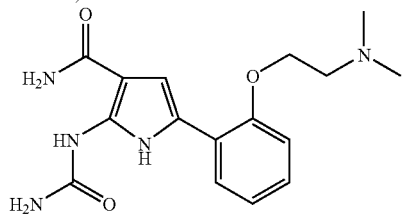 | $^1$H-NMR (400 MHz, DMSO-$d_6$) δ 2.21 (s, 6H), 2.85 (t, J = 5.8 Hz, 2H), 4.15 (t, J = 5.8 Hz, 2H), 6.79 (br s, 3H), 6.91 (d, J = 2.9 Hz, 1H), 6.98 (m, 1H), 7.11 (m, 1H), 7.18 (m, 1H), 7.27 (br s, 1H), 7.50 (m, 1H), 9.60 (s, 1H), 11.65 (s, 1H) |

| | |
|---|---|
| 2-Aminocarbonylamino-5-[2-[2-(1-methylpyrrolidin-2-yl)ethyloxy]phenyl]pyrrole-3-carboxamide (Compound No. 4-32)<br />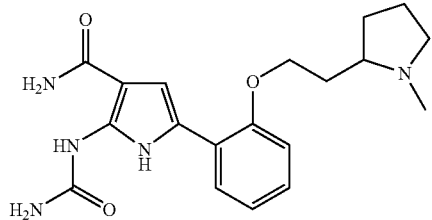 | $^1$H-NMR (400 MHz, DMSO-d$_6$)<br />δ 1.40-2.13 (m, 6H), 2.24 (s, 3H), 2.37-2.66 (m, 3H), 4.11 (m, 1H), 4.71 (m, 1H), 6.82 (br s, 3H), 6.89 (d, J = 2.9 Hz, 1H), 6.95 (m, 1H), 7.01-7.17 (m, 2H) 7.28 (br s, 1H), 7.49 (dd, J = 7.8, 1.7 Hz, 1H), 9.63 (s, 1H), 11.68 (s, 1H) |
| 2-Aminocarbonylamino-5-[2-(2-chloroethyloxy)-5-fluorophenyl]pyrrole-3-carboxamide (Compound No. 4-33)<br />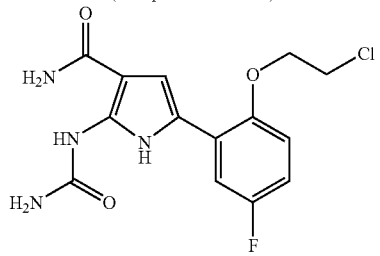 | $^1$H-NMR (400 MHz, DMSO-d$_6$)<br />δ 4.14 (t, J = 5.4 Hz, 2H), 4.37 (t, J = 5.4 Hz, 2H), 6.87 (br s, 3H), 6.92-6.97 (ddd, J = 9.0, 7.9, 3.2 Hz, 1H), 7.02 (d, J = 2.9 Hz, 1H), 7.11 (dd J = 9.0, 4.9 Hz, 1H) 7.24 (dd, J = 10.3, 3.2 Hz, 1H), 7.24 (br s, 1H), 9.61 (s, 1H), 11.80 (s, 1H) |
| 2-Aminocarbonylamino-5-(5-fluoro-2-propyloxyphenyl)pyrrole-3-carboxamide (Compound No. 4-34)<br />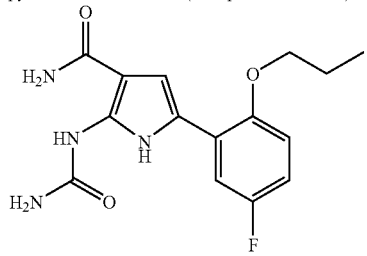 | $^1$H-NMR (400 MHz, DMSO-d$_6$)<br />δ 0.98 (t, J = 7.4 Hz, 3H), 1.86-1.98 (m, 2H), 4.02 (t, J = 6.7 Hz, 2H), 6.86 (br s, 3H), 6.92 (ddd, J = 9.3, 7.8, 3.1 Hz, 1H), 7.00 (d, J = 2.9 Hz, 1H), 7.07 (dd, J = 9.3, 4.9 Hz, 1H), 7.22 (dd, J = 10.1, 3.1 Hz, 1H), 7.22 (br s, 1H), 9.62 (s, 1H), 11.75 (s, 1H) |
| 2-Aminocarbonylamino-5-[5-fluoro-2-(3-hydroxypropyloxy)phenyl]pyrrole-3-carboxamide (Compound No. 4-35)<br />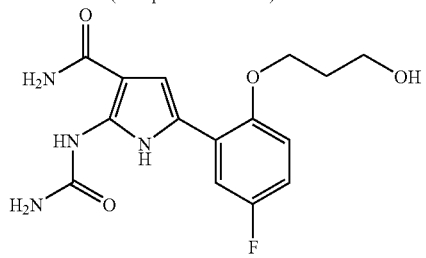 | $^1$H-NMR (400 MHz, DMSO-d$_6$)<br />1.99-2.12 (m, 2H), 3.52-3.64 (m, 2H), 4.13 (t, J = 6.3 Hz, 2H), 4.50 (t, J = 5.1 Hz, 1H), 6.87 (br s, 3H), 6.93 (ddd, J = 9.0, 7.8, 2.9 Hz, 1H), 7.01 (d, J = 2.9 Hz, 1H), 7.09 (dd, J = 9.0, 4.9 Hz, 1H), 7.23 (dd, J = 10.3, 2.9 Hz, 1H), 7.23 (br s, 1H), 9.64 (s, 1H), 11.75 (s, 1H) |
| 2-Aminocarbonylamino-5-[2-(pyridin-3-ylmethyloxy)-5-fluorophenyl]pyrrole-3-carboxamide (Compound No. 4-36)<br />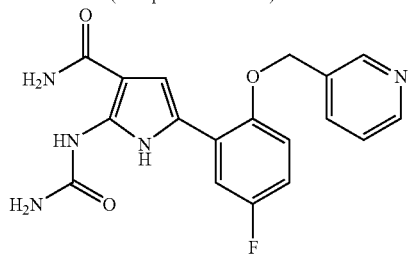 | $^1$H-NMR (400 MHz, DMSO-d$_6$)<br />δ 5.34 (s, 2H), 6.85 (br s, 4H), 6.92 (ddd, J = 9.2, 7.9, 3.2 Hz, 1H), 6.98 (d, J = 2.9 Hz, 1H), 7.19 (dd, J = 10.0, 3.2 Hz, 1H), 7.23 (dd, J = 9.2, 4.8 Hz, 1H), 7.38 (dd, J = 7.8, 4.9 Hz, 1H), 7.92 (dt, J = 7.8, 2.0 Hz, 1H), 8.51 (dd, J = 4.9, 1.7 Hz, 1H), 8.70 (d, J = 1.7 Hz, 1H), 9.61 (s, 1H), 11.79 (s, 1H) |

| | |
|---|---|
| 2-Aminocarbonylamino-5-(5-chloro-2-propyloxyphenyl)pyrrole-3-carboxamide (Compound No. 4-37) 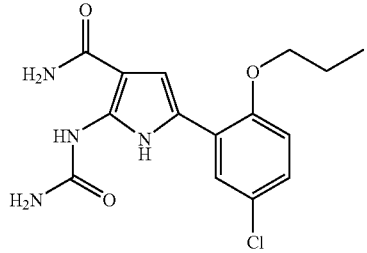 | $^1$H-NMR (400 MHz, DMSO-d$_6$) δ 0.98 (t, J = 7.3 Hz, 3H), 1.84-2.01 (m, 2H), 4.04 (t, J = 6.7 Hz, 2H), 6.85 (br s, 3H), 7.04 (d, J = 2.9 Hz, 1H), 7.09 (d, J = 8.8 Hz, 1H), 7.13 (dd, J = 8.8, 2.4 Hz, 1H), 7.23 (br s, 1H), 7.47 (d, J = 2.4 Hz, 1H), 9.62 (s, 1H), 11.73 (s, 1H) |
| 2-Aminocarbonylamino-5-[5-chloro-2-(3-hydroxypropyloxy)phenyl]pyrrole-3-carboxamide (Compound No. 4-38) 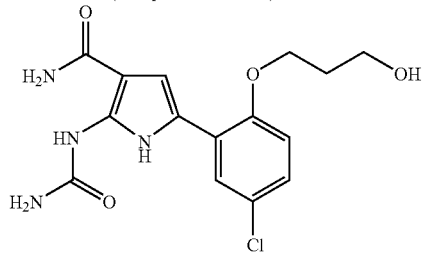 | $^1$H-NMR (400 MHz, DMSO-d$_6$) δ 2.00-2.10 (m, 2H), 3.53-3.63 (m, 2H), 4.15 (t, J = 6.3 Hz, 2H), 4.50 (t, J = 5.1 Hz, 1H), 6.86 (br s, 3H), 7.05 (d, J = 2.9 Hz, 1H), 7.10 (d, J = 8.8 Hz, 1H), 7.13 (dd, J = 8.8, 2.4 Hz, 1H), 7.24 (br s, 1H), 7.47 (d, J = 2.4 Hz, 1H), 9.63 (s, 1H), 11.71 (s, 1H) |
| 2-Aminocarbonylamino-5-[2-(2-chloroethyloxy)-5-chlorophenyl]pyrrole-3-carboxamide (Compound No. 4-39) 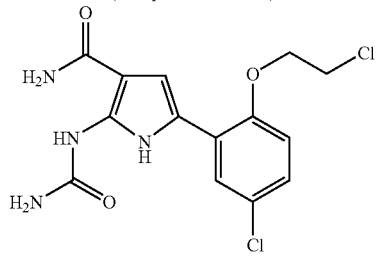 | $^1$H-NMR (500 MHz, DMSO-d$_6$) δ 4.14 (t, J = 5.3 Hz, 2H), 4.39 (t, J = 5.3 Hz, 2H), 6.85 (br s, 3H), 7.06 (d, J = 3.1 Hz, 1H), 7.11-7.15 (m, 2H), 7.23 (br s, 1H), 7.48 (d, J = 2.1 Hz, 1H), 9.60 (s, 1H), 11.77 (s, 1H) |
| 2-Aminocarbonylamino-5-[2-(2-tetrahydrofurfurylmethyloxy)-5-fluorophenyl]pyrrole-3-carboxamide (Compound No. 4-40) 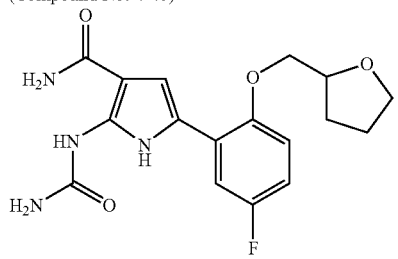 | $^1$H-NMR (400 MHz, DMSO-d$_6$) δ 1.65 (m, 1H), 1.74-1.94 (m, 2H), 2.09 (m, 1H), 3.58-3.82 (m, 2H), 3.92-4.12 (m, 2H), 4.42 (m, 1H), 6.85 (br s, 3H), 6.92 (ddd, J = 9.0, 7.8, 3.2 Hz, 1H), 6.99 (d, J = 2.9 Hz, 1H), 7.10 (dd, J = 9.0, 4.9 Hz, 1H), 7.21 (dd, J = 10.1, 3.2 Hz, 1H), 7.22 (br s, 1H), 9.62 (s, 1H), 11.66 (s, 1H) |

| | |
|---|---|
| 2-Aminocarbonylamino-5-[2-[2-(2-tetrahydro-2H-pyranoxy)ethyloxy]-5-fluorophenyl]pyrrole-3-carboxamide (Compound No. 4-41) 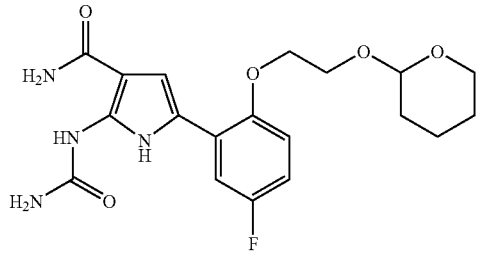 | ¹H-NMR (400 MHz, DMSO-d$_6$) δ 1.27-1.72 (m, 6H), 3.41 (m, 1H), 3.71 (m, 1H), 3.85-4.07 (m, 2H), 4.14-4.33 (m, 2H), 4.71 (m, 1H), 6.84 (br s, 3H), 6.93 (ddd, J = 9.1, 8.1, 3.2 Hz, 1H), 6.99 (d, J = 2.9 Hz, 1H), 7.11 (dd, J = 9.1, 4.9 Hz, 1H), 7.21 (dd, J = 10.3, 3.2 Hz, 1H), 7.22 (br s, 1H), 9.59 (s, 1H) 11.73 (s, 1H) |
| 2-Aminocarbonylamino-5-[2-[2-(2-pyrrolidon-1-yl)ethyloxy]-5-chlorophenyl]pyrrole-3-carboxamide (Compound No. 4-42) 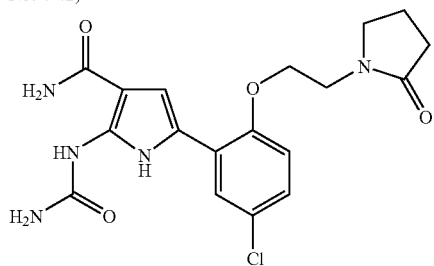 | ¹H-NMR (400 MHz, DMSO-d$_6$) δ 1.79-1.94 (m, 2H), 2.19 (t, J = 8.1 Hz, 2H), 3.43 (t, J = 7.0 Hz, 2H), 3.75 (t, J = 5.5 Hz, 2H), 4.20 (t, J = 5.5 Hz, 2H), 6.86 (br s, 3H), 7.05 (d, J = 3.2 Hz, 1H), 7.10 (d, J = 8.8 Hz, 1H), 7.14 (dd, J = 8.8, 2.4 Hz, 1H), 7.34 (br s, 1H), 7.44 (d, J = 2.4 Hz, 1H), 9.64 (s, 1H), 11.66 (s, 1H) |
| 2-Aminocarbonylamino-5-(5-chloro-2-cyanomethyloxyphenyl)pyrrole-3-carboxamide (Compound No. 4-43) 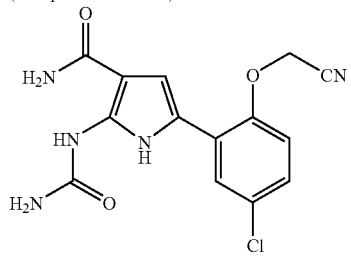 | ¹H-NMR (500 MHz, DMSO-d$_6$) δ 5.28 (s, 2H), 6.87 (br s, 3H), 7.08 (d, J = 3.1 Hz, 1H), 7.24 (dd, J = 8.9, 2.1 Hz, 1H), 7.27 (br s, 1H), 7.27 (d, J = 8.9 Hz, 1H), 7.50 (d, J = 2.1 Hz, 1H), 9.62 (s, 1H), 11.60 (s, 1H) |
| 2-Aminocarbonylamino-5-[2-(2-bromoethyloxy)-5-fluorophenyl]pyrrole-3-carboxamide (Compound No. 4-44) 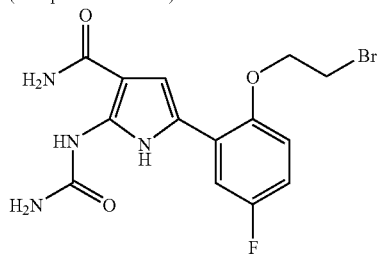 | ¹H-NMR (400 MHz, DMSO-d$_6$) δ 3.99 (t, J = 5.7 Hz, 2H), 4.43 (t, J = 5.7 Hz, 2H), 6.87 (br s, 3H), 6.94 (m, 1H), 7.02 (d, J = 2.9 Hz, 1H), 7.10 (dd, J = 9.2, 4.8 Hz, 1H), 7.22 (br s, 1H), 7.23 (dd, J = 10.0, 3.1 Hz, 1H), 9.60 (s, 1H), 11.80 (s, 1H) |
| 2-Aminocarbonylamino-5-[2-(3-hydroxypropyloxy)phenyl]pyrrole-3-carboxamide (Compound No. 4-45) 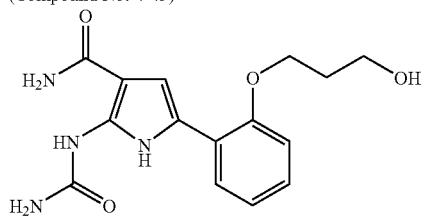 | ¹H-NMR (400 MHz, DMSO-d$_6$) δ 2.00-2.14 (m, 2H), 3.54-3.64 (m, 2H), 4.09-4.17 (m, 2H), 4.48 (t, J = 5.2 Hz, 1H), 6.83 (br s, 3H), 6.92 (d, J = 2.9 Hz, 1H), 6.92-6.99m, 1H), 7.06-7.16 (m, 2H), 7.28 (br s, 1H), 7.50 (dd, J = 7.8, 1.5 Hz, 1H), 9.63 (s, 1H), 11.68 (s, 1H) |

| | |
|---|---|
| 2-Aminocarbonylamino-5-[5-chloro-2-[2-(pyrrol-1-yl)ethyloxy]phenyl]pyrrole-3-carboxamide (Compound No. 4-46)<br>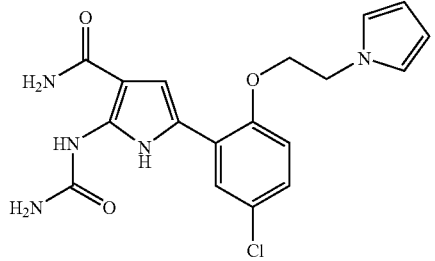 | $^1$H-NMR (500 MHz, DMSO-$d_6$) δ 4.34 (t, J = 5.3 Hz, 2H), 4.51 (t, J = 5.3 Hz, 2H), 5.94 (t, J = 2.0 Hz, 2H), 6.87 (t, J = 2.0 Hz, 2H), 6.92 (br s, 3H), 7.02-7.06 (m, 2H), 7.11 (dd, J = 8.9, 2.4 Hz, 1H), 7.24 (br s, 1H), 7.46 (d, J = 2.4 Hz, 1H), 9.67 (s, 1H), 11.84 (s, 1H) |
| 2-Aminocarbonylamino-5-(2-ethoxy-5-fluorophenyl)pyrrole-3-carboxamide (Compound No. 4-47)<br>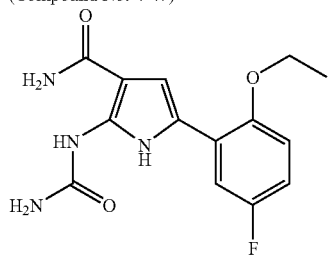 | $^1$H-NMR (500 MHz, DMSO-$d_6$) δ 1.48 (t, J = 7.0 Hz, 3H), 4.11 (q, J = 7.0 Hz, 2H), 6.84 (br s, 3H), 6.92 (ddd, J = 9.2, 7.9, 3.1 Hz, 1H), 7.00 (d, J = 3.1 Hz, 1H), 7.06 (dd, J = 9.2, 4.9 Hz, 1H), 7.21 (br s, 1H), 7.22 (dd, J = 10.1, 3.1 Hz, 1H), 9.62 (s, 1H), 11.81 (s, 1H) |
| 2-Aminocarbonylamino-5-(5-chloro-2-ethoxyphenyl)pyrrole-3-carboxamide (Compound No. 4-48)<br>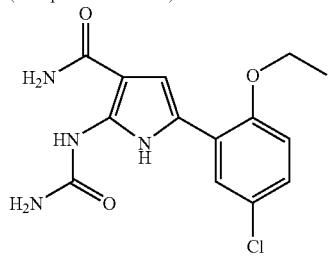 | $^1$H-NMR (500 MHz, DMSO-$d_6$) δ 1.49 (t, J = 7.0 Hz, 3H), 4.13 (q, J = 7.0 Hz, 2H), 6.83 (br s, 3H), 7.04 (d, J = 3.1 Hz, 1H), 7.08 (d, J = 8.9 Hz, 1H), 7.12 (dd, J = 8.9, 2.4 Hz, 1H), 7.22 (br s, 1H), 7.47 (d, J = 2.4 Hz, 1H), 9.61 (s, 1H), 11.78 (s, 1H) |
| 5-(2-Allyloxy-5-chlorophenyl)-2-(aminocarbonylamino)pyrrole-3-carboxamide (Compound No. 4-49)<br>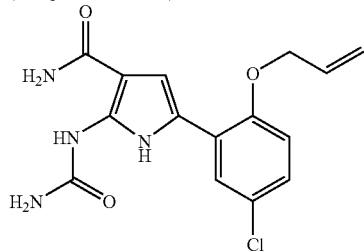 | $^1$H-NMR (500 MHz, DMSO-$d_6$) δ 4.71 (d, J = 5.8 Hz, 2H), 5.27 (dd, J = 10.4, 1.3 Hz, 1H), 5.40 (dd, J = 17.3, 1.3 Hz, 1H), 6.26 (ddt, J = 17.3, 10.4, 5.8 Hz, 1H), 6.84 (br s, 3H), 7.04 (d, J = 3.1 Hz, 1H), 7.10 (d, J = 8.9 Hz, 1H), 7.14 (dd, J = 8.9, 2.4 Hz, 1H), 7.23 (br s, 1H), 7.46 (d, J = 2.4 Hz, 1H), 9.61 (s, 1H), 11.73 (s, 1H) |
| 2-Aminocarbonylamino-5-[5-chloro-2-(2-propynyloxy)phenyl]pyrrole-3-carboxamide (Compound No. 4-50)<br>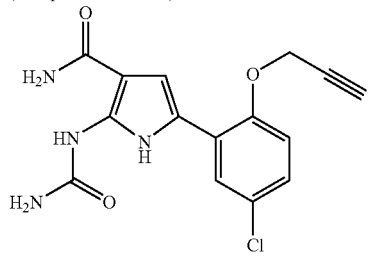 | $^1$H-NMR (400 MHz, DMSO-$d_6$) δ 3.61 (t, J = 2.4 Hz, 1H), 4.94 (d, J = 2.4 Hz, 2H), 6.84 (br s, 3H), 7.04 (d, J = 3.2 Hz, 1H), 7.16-7.21 (m, 2H), 7.24 (br s, 1H), 7.47 (s, 1H), 9.60 (s, 1H), 11.69 (s, 1H) |

| | |
|---|---|
| 2-Aminocarbonylamino-5-[2-(2-butynyloxy)-5-chlorophenyl]pyrrole-3-carboxamide (Compound No. 4-51) 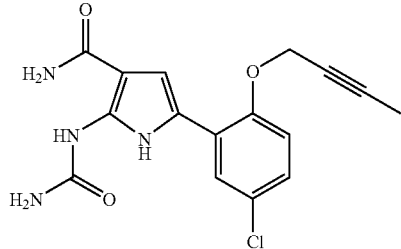 | $^1$H-NMR (400 MHz, DMSO-d$_6$) δ 1.83 (s, 3H), 4.88 (s, 2H), 6.82 (br s, 3H), 7.04 (d, J = 2.9 Hz, 1H), 7.09-7.30 (m, 3H), 7.46 (d, J = 1.7 Hz, 1H), 9.60 (s, 1H), 11.71 (s, 1H) |
| 2-Aminocarbonylamino-5-[5-chloro-2-(3-fluoropropyloxy)phenyl]pyrrole-3-carboxamide (Compound No. 4-52) 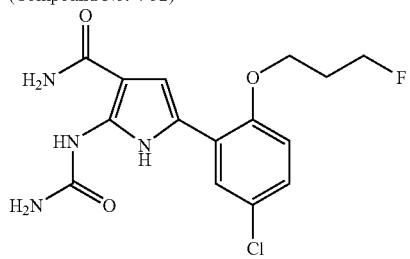 | $^1$H-NMR (400 MHz, DMSO-d$_6$) δ 2.20-2.42 (m, 2H), 4.19 (t, J = 6.2 Hz, 2H), 4.58 (t, J = 5.7 Hz, 1H), 4.70 (t, J = 5.7 Hz, 1H), 6.86 (br s, 3H), 7.05 (d, J = 2.9 Hz, 1H), 7.10-7.18 (m, 2H), 7.24 (br s, 1H), 7.48 (m, 1H), 9.62 (s, 1H), 11.70 (s, 1H) |
| 2-Aminocarbonylamino-5-[5-chloro-2-(3,3,3-trifluoropropyloxy)phenyl]pyrrole-3-carboxamide (Compound No. 4-53) 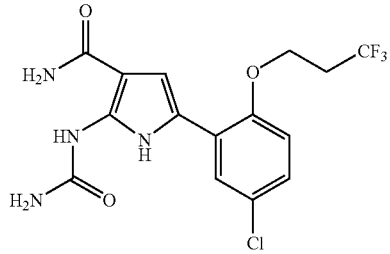 | $^1$H-NMR (400 MHz, DMSO-d$_6$) δ 2.93-3.14 (m, 2H), 4.33 (t, J = 6.1 Hz, 2H), 6.86 (br s, 3H), 7.05 (d, J = 2.9 Hz, 1H), 7.14 (dd, J = 9.0, 2.4 Hz, 1H), 7.17 (d, J = 9.0 Hz, 1H), 7.22 (br s, 1H), 7.48 (d, J = 2.4 Hz, 1H), 9.60 (br s, 1H), 11.73 (s, 1H) |
| 2-Aminocarbonylamino-5-[5-fluoro-2-(2-hydroxyethyloxy)phenyl]pyrrole-3-carboxamide (Compound No. 4-54) 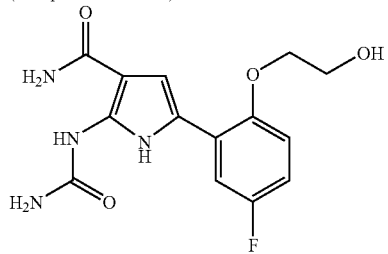 | $^1$H-NMR (400 MHz, DMSO-d$_6$) δ 3.90 (t, J = 5.1 Hz, 2H), 4.07 (t, J = 5.1 Hz, 2H), 4.79 (s, 1H), 6.87 (br s, 3H), 6.93 (ddd, J = 9.1, 7.8, 3.2 Hz, 1H), 7.02 (d, J = 2.9 Hz, 1H), 7.08 (dd, J = 9.1, 4.8 Hz, 1H), 7.20 (br s, 1H), 7.23 (dd, J = 10.3, 3.2 Hz, 1H), 9.67 (s, 1H), 11.79 (s, 1H) |
| 2-Aminocarbonylamino-5-(3-ethoxyphenyl)pyrrole-3-carboxamide (Compound No. 4-55) 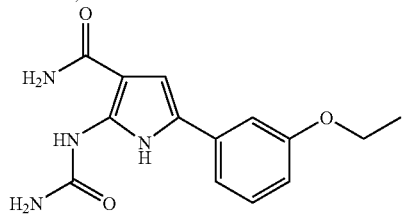 | $^1$H-NMR (400 MHz, DMSO-d$_6$) δ 1.34 (t, J = 7.0 Hz, 3H), 4.05 (q, J = 7.0 Hz, 2H), 6.72 (dd, J = 8.3, 2.0 Hz, 1H), 6.84 (br s, 3H), 6.87 (d, J = 2.9 Hz, 1H), 6.95 (s, 1H), 6.98 (d, J = 8.3 Hz, 1H), 7.26 (t, J = 8.3 Hz, 1H), 7.26 (br s, 1H), 9.61 (s, 1H), 11.13 (s, 1H) |

Example 5

2-Aminocarbonylamino-5-(2-acetoxyphenyl)pyrrole-3-carboxamide (Compound No. 5-1)

Triethylamine (80 μL, 0.57 mmol) and acetyl chloride (33 μL, 0.46 mmol) were added to a solution of 2-aminocarbonylamino-5-(2-hydroxyphenyl)pyrrole-3-carboxamide (Compound No. 3-1, 100 mg, 0.39 mmol) in anhydrous N,N-dimethylformamide (2 mL), and the mixture was stirred overnight at room temperature. After the reaction solution was concentrated in vacuo, the residue was purified by silica gel column chromatography to give the target compound (41 mg) as a green-brown solid (Yield 35%).

| Compound | Structure | $^1$H-NMR |
|---|---|---|
| 2-Aminocarbonylamino-5-(2-acetoxyphenyl)pyrrole-3-carboxamide (Compound No. 5-1) | 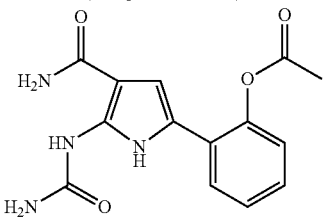 | $^1$H-NMR (400 MHz, DMSO-$d_6$) δ 2.41 (s, 3 H), 6.86 (br s, 3 H), 6.92 (d, J = 2.9 Hz, 1 H), 7.14 (dd, J = 7.5, 1.5 Hz, 1 H), 7.20 (td, J = 7.5, 1.5 Hz, 1 H), 7.27 (td, J = 7.5, 1.5 Hz, 1 H), 7.38 (br s, 1 H), 7.54 (dd, J = 7.5, 1.5 Hz, 1 H), 9.68 (s, 1 H), 11.41 (s, 1 H) |

As described below, using compounds selected from No. 3-3 or 3-4, compound No. 5-2 and 5-3 were obtained by a method similar to compound No. 5-1.

| Compound | Structure | $^1$H-NMR |
|---|---|---|
| 2-Aminocarbonylamino-5-(2-acetoxy-5-fluorophenyl)pyrrole-3-carboxamide (Compound No. 5-2) | 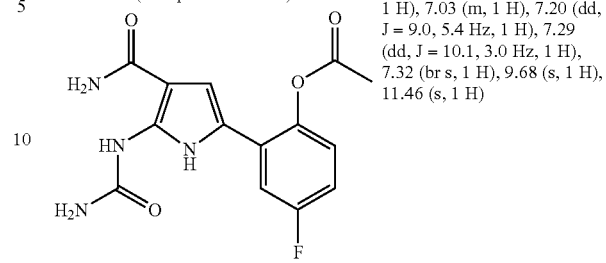 | $^1$H-NMR (400 MHz, DMSO-$d_6$) δ 2.41 (s, 3 H), 6.92 (br s, 3 H), 7.00 (d, J = 3.2 Hz, 1 H), 7.03 (m, 1 H), 7.20 (dd, J = 9.0, 5.4 Hz, 1 H), 7.29 (dd, J = 10.1, 3.0 Hz, 1 H), 7.32 (br s, 1 H), 9.68 (s, 1 H), 11.46 (s, 1 H) |
| 2-Aminocarbonylamino-5-(2-acetoxy-5-chlorophenyl)pyrrole-3-carboxamide (Compound No. 5-3) | 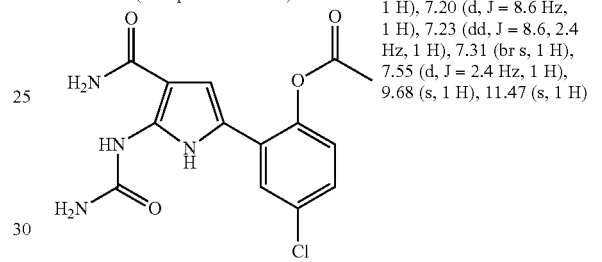 | $^1$H-NMR (500 MHz, DMSO-$d_6$) δ 2.42 (s, 3 H), 6.90 (br s, 3 H), 7.04 (d, J = 3.1 Hz, 1 H), 7.20 (d, J = 8.6 Hz, 1 H), 7.23 (dd, J = 8.6, 2.4 Hz, 1 H), 7.31 (br s, 1 H), 7.55 (d, J = 2.4 Hz, 1 H), 9.68 (s, 1 H), 11.47 (s, 1 H) |

Example 6

2-Aminocarbonylamino-5-(2-propylaminocarbonyloxyphenyl)pyrrole-3-carboxamide (Compound No. 6-1)

Triethylamine (43 μL, 0.31 mmol) and propyl isocyanate (17 μL, 0.18 mmol) were added to a solution of 2-aminocarbonylamino-5-(2-hydroxyphenyl)pyrrole-3-carboxamide (Compound No. 3-1, 40 mg, 0.15 mmol) in anhydrous N,N-dimethylformamide (2 mL), and the mixture was stirred overnight at room temperature. After the reaction solution was concentrated in vacuo, the residue was purified by silica gel column chromatography to give the target compound (29 mg) as a pale blue solid (Yield 54%).

| Compound | Structure | $^1$H-NMR |
|---|---|---|
| 2-Aminocarbonylamino-5-(2-propylaminocarbonyloxyphenyl)pyrrole-3-carboxamide (Compound No. 6-1) | 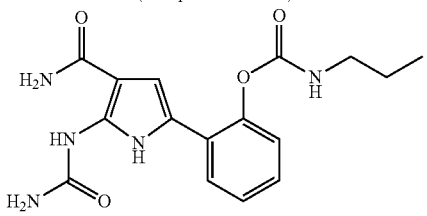 | $^1$H-NMR (400 MHz, DMSO-$d_6$) δ 0.86 (t, J = 7.4 Hz, 3 H), 1.39-1.56 (m, 2 H), 2.96-3.10 (m, 2 H), 6.85 (br s, 3 H), 6.92 (d, J = 3.2 Hz, 1 H), 6.96-7.29 (m, 4 H), 7.47 (dd, J = 7.8, 1.7 Hz, 1 H), 7.53 (t, J = 5.7 Hz, 1 H), 9.63 (s, 1 H), 11.31 (s, 1 H) |

Example 7

2-Aminocarbonylamino-5-(4-bromophenyl)-4-chloropyrrole-3-carboxamide (Compound No. 7-1)

N-Chlorosuccinimide (48 mg, 0.36 mmol) was added to a solution of 2-aminocarbonylamino-5-(4-bromophenyl)pyrrole-3-carboxamide (Compound No. 1-1, 97 mg, 0.30 mmol) in anhydrous N,N-dimethylformamide (2 mL), and the mixture was stirred overnight at 50° C. After cooling, water (4 mL) was added thereto, the precipitated solid was filtered off, and washed with water (5 mL). The obtained solid was dried under reduced pressure to give the target compound (54 mg) as a pale brown solid (Yield 51%).

| 2-Aminocarbonylamino-5-(4-bromophenyl)-4-chloropyrrole-3-carboxamide (Compound No. 7-1) 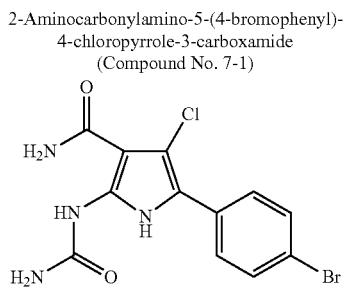 | $^1$H-NMR (400 MHz, DMSO-$d_6$) δ 6.92 (s, 2 H), 7.55 (d, J = 8.8 Hz, 2 H), 7.63 (d, J = 8.8 Hz, 2 H), 9.79 (s, 1 H), 11.45 (s, 1 H) |
|---|---|

As described below, using compounds selected from No. 1-8, 1-9 or 1-25, compound No. 7-2 to 7-4 were obtained by a method similar to compound No. 7-1.

| 2-Aminocarbonylamino-4-chloro-5-(2-methoxyphenyl)pyrrole-3-carboxamide (Compound No. 7-2) 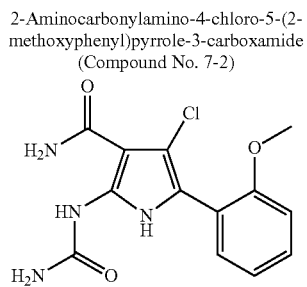 | $^1$H-NMR (400 MHz, DMSO-$d_6$) δ 3.84 (s, 3 H), 6.72 (br s, 1 H), 6.90 (br s, 2 H), 7.03 (t, J = 7.7 Hz, 1 H), 7.13 (d, J = 7.7 Hz, 1 H), 7.26-7.38 (m, 2 H), 7.73 (dd, J = 7.7, 1.6 Hz, 1 H), 9.84 (s, 1 H), 11.66 (s, 1 H) |
|---|---|
| 2-Aminocarbonylamino-4-chloro-5-(4-fluorophenyl)pyrrole-3-carboxamide (Compound No. 7-3) 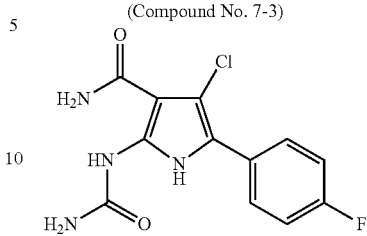 | $^1$H-NMR (400 MHz, DMSO-$d_6$) δ 6.90 (s, 2 H), 7.28 (dd, J = 9.0, 8.8 Hz, 2 H), 7.62 (dd, J = 8.8, 5.4 Hz, 2 H), 9.78 (s, 1 H), 11.39 (s, 1 H) |
| 2-Aminocarbonylamino-4-chloro-5-(3-chlorophenyl)pyrrole-3-carboxamide (Compound No. 7-4) 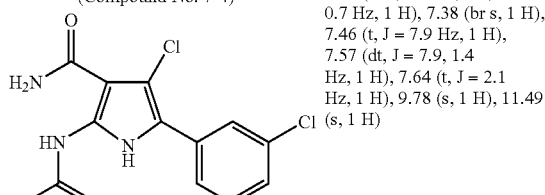 | $^1$H-NMR (500 MHz, DMSO-$d_6$) δ 6.91 (br s, 3 H), 7.35 (ddd, J = 7.9, 2.1, 0.7 Hz, 1 H), 7.38 (br s, 1 H), 7.46 (t, J = 7.9 Hz, 1 H), 7.57 (dt, J = 7.9, 1.4 Hz, 1 H), 7.64 (t, J = 2.1 Hz, 1 H), 9.78 (s, 1 H), 11.49 (s, 1 H) |

Example 8

2-Aminocarbonylamino-5-[2-[3-(pyrrolidin-1-yl)propyloxy]phenyl]pyrrole-3-carboxamide (Compound No. 8-1)

Pyrrolidine (0.5 mL) was added to 2-aminocarbonylamino-5-[2-(3-chloropropyloxy)phenyl]pyrrole-3-carboxamide (Compound No. 4-29, 30 mg, 0.090 mmol), the whole was sealed and stirred at 120° C. for 5 hours. This mixture was purified by silica gel column chromatography to give the target compound (14 mg) as a brown amorphous Powder (Yield 42%).

| 2-Aminocarbonylamino-5-[2-[3-(pyrrolidin-1-yl)propyloxy]phenyl]pyrrole-3-carboxamide (Compound No. 8-1) 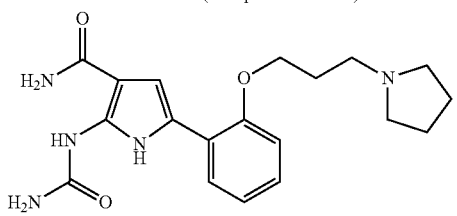 | $^1$H-NMR (400 MHz, DMSO-$d_6$) δ 1.59-1.74 (m, 4 H), 2.02-2.14 (m, 2 H), 2.36-2.44 (m, 4 H), 2.53 (t, J = 6.8 Hz, 2 H), 4.12 (t, J = 6.6 Hz, 2 H), 6.80 (br s, 3 H), 6.90 (d, J = 2.9 Hz, 1 H), 6.95 (t, J = 7.6 Hz, 1 H), 7.06 (d, J = 7.6 Hz, 1 H), 7.12 (t, J = 7.6 Hz, 1 H), 7.28 (br s, 1 H), 7.48 (dd, J = 7.6, 1.5 Hz, 1 H), 9.61 (s, 1 H), 11.68 (s, 1 H) |
|---|---|

As described below, using commercially available compounds or compounds selected from No. 4-18, 4-29, 4-33, 4-39 or 4-44, compound No. 8-2 to 8-23 were obtained by a method similar to compound No. 8-1.

2-Aminocarbonylamino-5-[2-[2-(4-methyl-piperazin-1-yl)ethyloxy]phenyl]pyrrole-3-carboxamide (Compound No. 8-2)

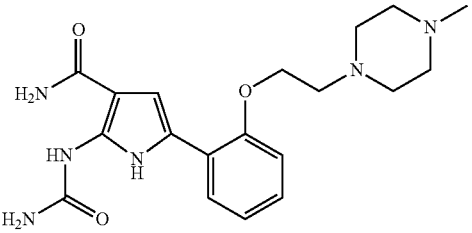

$^1$H-NMR (500 MHz, DMSO-$d_6$)
δ 2.11 (s, 3 H), 2.50 (s, 8 H), 2.91 (t, J = 5.8 Hz, 2 H), 4.17 (t, J = 6.0 Hz, 2 H), 6.79 (br s, 3 H), 6.91 (d, J = 2.7 Hz, 1 H), 6.96 (ddd, J = 8.2, 5.1, 2.5 Hz, 1 H), 7.08-7.15 (m, 2 H), 7.27 (br s, 1 H), 7.49 (d, J = 8.2 Hz, 1 H), 9.60 (s, 1 H), 11.63 (s, 1 H)

2-Aminocarbonylamino-5-[2-[2-(morpholin-4-yl)ethyloxy]phenyl]pyrrole-3-carboxamide (Compound No. 8-3)

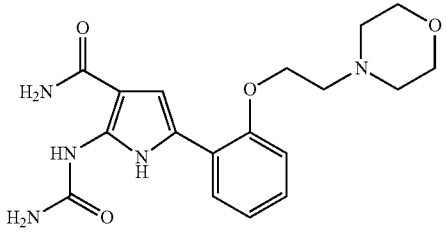

$^1$H-NMR (400 MHz, DMSO-$d_6$)
δ 2.40-2.56 (m, 4 H), 2.91 (t, J = 5.8 Hz, 2 H), 3.53 (t, J = 4.6 Hz, 4 H), 4.20 (t, J = 5.8 Hz, 2 H), 6.80 (br s, 3 H), 6.91 (d, J = 2.9 Hz, 1 H), 6.96 (m, 1 H), 7.08-7.16 (m, 2 H), 7.28 (br s, 1 H), 7.49 (d, J = 7.6 Hz, 1 H), 9.61 (s, 1 H), 11.65 (s, 1 H)

2-Aminocarbonylamino-5-[2-[2-(pyrrolidin-1-yl)ethyloxy]phenyl]pyrrole-3-carboxamide (Compound No. 8-4)

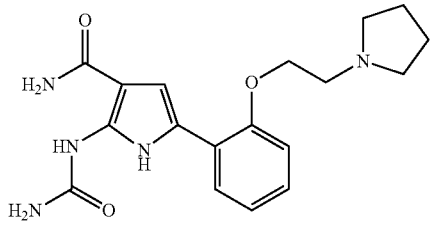

$^1$H-NMR (400 MHz, DMSO-$d_6$)
δ 1.58-1.72 (m, 4 H), 2.45-2.59 (m, 4 H), 3.00 (t, J = 6.1 Hz, 2 H), 4.17 (t, J = 6.1 Hz, 2 H), 6.79 (br s, 3 H), 6.91 (d, J = 2.9 Hz, 1 H), 6.96 (m, 1 H), 7.07-7.16 (m, 2 H), 7.27 (br s, 1 H), 7.49 (dd, J = 7.7, 1.3 Hz, 1 H), 9.60 (s, 1 H), 11.65 (s, 1 H)

2-Aminocarbonylamino-5-[2-[3-(morpholin-4-yl)propyloxy]phenyl]pyrrole-3-carboxamide (Compound No. 8-5)

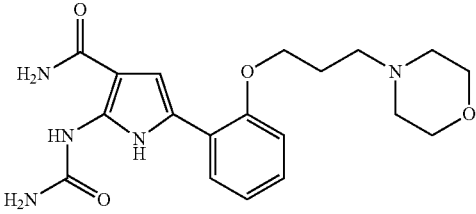

$^1$H-NMR (500 MHz, DMSO-$d_6$)
δ 2.02-2.13 (m, 2 H), 2.34 (s, 4 H), 2.43 (t, J = 6.9 Hz, 2 H), 3.55 (t, J = 4.6 Hz, 4 H), 4.12 (t, J = 6.4 Hz, 2 H), 6.79 (br s, 3 H), 6.90 (d, J = 2.7 Hz, 1 H), 6.97 (m, 1 H), 7.03-7.16 (m, 2 H), 7.27 (br s, 1 H), 7.48 (dd, J = 7.6, 1.5 Hz, 1 H), 9.61 (s, 1 H), 11.67 (s, 1 H)

2-Aminocarbonylamino-5-[2-[2-(isoindolin-2-yl)ethyloxy]phenyl]pyrrole-3-carboxamide (Compound No. 8-6)

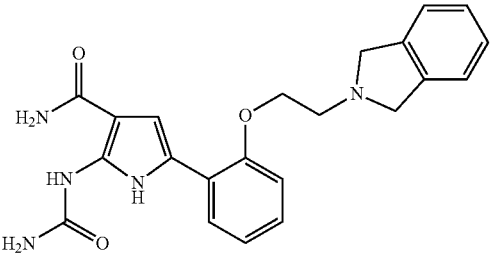

$^1$H-NMR (400 MHz, DMSO-$d_6$)
δ 3.30 (t, J = 5.9 Hz, 2 H), 3.96 (s, 4 H), 4.27 (t, J = 5.9 Hz, 2 H), 6.80 (br s, 3 H), 6.92 (d, J = 2.9 Hz, 1 H), 6.97 (m, 1 H), 7.12-7.23 (m, 6 H), 7.28 (br s, 1 H), 7.50 (dd, J = 7.4, 1.2 Hz, 1 H), 9.62 (s, 1 H), 11.70 (s, 1 H)

| | |
|---|---|
| 2-Aminocarbonylamino-5-[2-[2-(N-benzyl-N-methylamino)ethyloxy]phenyl]pyrrole-3-carboxamide (Compound No. 8-7)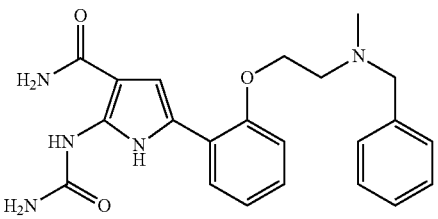 | $^1$H-NMR (400 MHz, DMSO-$d_6$) δ 2.17 (s, 3 H), 3.02 (t, J = 6.0 Hz, 2 H), 3.57 (s, 2 H), 4.22 (t, J = 6.0 Hz, 2 H), 6.80 (br s, 3 H), 6.92 (d, J = 2.9 Hz, 1 H), 6.97 (m, 1 H), 7.06-7.36 (m, 8 H), 7.49 (d, J = 7.3 Hz, 1 H), 9.61 (s, 1 H), 11.70 (s, 1 H) |
| 2-Aminocarbonylamino-5-[2-[2-N-ethyl-N-(pyridin-4-ylmethyl)amino]ethyloxy]phenyl]pyrrole-3-carboxamide (Compound No. 8-8)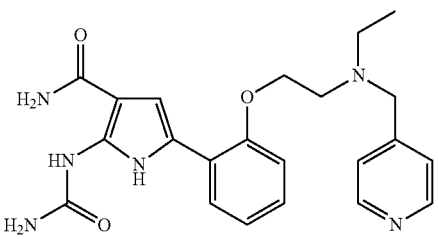 | $^1$H-NMR (400 MHz, DMSO-$d_6$) δ 0.95 (t, J = 7.1 Hz, 3 H), 2.41-2.59 (m, 2 H), 3.06 (t, J = 6.2 Hz, 2 H), 3.68 (s, 2 H), 4.19 (t, J = 6.2 Hz, 2 H), 6.81 (br s, 3 H), 6.91 (d, J = 2.9 Hz, 1 H), 6.92-7.34 (m, 4 H), 7.27 (d, J = 6.1 Hz, 2 H), 7.48 (d, J = 7.6 Hz, 1 H), 8.40 (dd, J = 4.4, 1.7 Hz, 2 H), 9.60 (s, 1 H), 11.67 (s, 1 H) |
| 2-Aminocarbonylamino-5-[2-[2-[N-methyl-N-(2-dimethylaminoethyl)amino]ethyloxy]phenyl]pyrrole-3-carboxamide (Compound No. 8-9)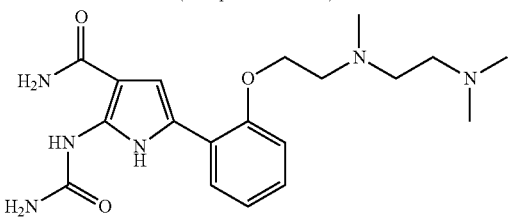 | $^1$H-NMR (500 MHz, DMSO-$d_6$) δ 2.05 (s, 6 H), 2.15 (s, 3 H), 2.20 (t, J = 7.0 Hz, 2 H), 2.25 (t, J = 6.7 Hz, 2 H), 2.71 (t, J = 5.8 Hz, 2 H), 4.03 (t, J = 5.7 Hz, 2 H), 6.59 (d, J = 0.9 Hz, 1 H), 6.75 (br s, 3 H), 6.99 (t, J = 7.3 Hz, 1 H), 7.03 (br s, 1 H), 7.09 (d, J = 8.2 Hz, 1 H), 7.21 (dd, J = 7.3, 1.5 Hz, 1 H), 7.30 (m, 1 H), 9.97 (s, 1 H), 10.87 (s, 1 H) |
| 2-Aminocarbonylamino-5-[2-[2-(4-methyl-piperidin-1-yl)ethyloxy]phenyl]pyrrole-3-carboxamide (Compound No. 8-10)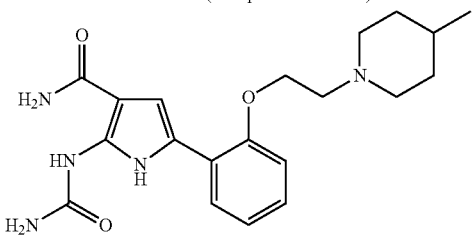 | $^1$H-NMR (400 MHz, DMSO-$d_6$) δ 0.86 (d, J = 6.6 Hz, 3 H), 0.99-1.34 (m, 3 H), 1.43-1.62 (m, 2 H), 1.93-2.07 (m, 2 H), 2.88 (t, J = 6.1 Hz, 4 H), 4.16 (t, J = 6.2 Hz, 2 H), 6.79 (br s, 3 H), 6.91 (d, J = 2.9 Hz, 1 H), 6.97 (m, 1 H), 7.06-7.15 (m, 2 H), 7.27 (br s, 1 H), 7.48 (d, J = 7.3 Hz, 1 H), 9.60 (s, 1 H), 11.63 (s, 1 H) |
| 2-Aminocarbonylamino-5-[2-[2-[N-(2-hydroxyethyl)-N-methylamino]ethyloxy]phenyl]pyrrole-3-carboxamide (Compound No. 8-11)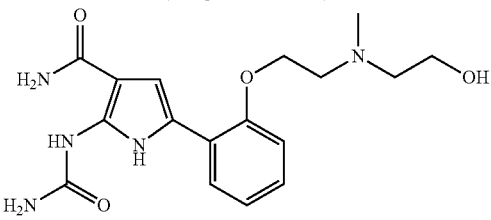 | $^1$H-NMR (400 MHz, DMSO-$d_6$) δ 2.28 (s, 3 H), 2.42 (t, J = 6.2 Hz, 1 H), 2.97 (t, J = 6.2 Hz, 2 H), 3.37-3.51 (m, 4 H), 4.16 (t, J = 6.2 Hz, 2 H), 6.80 (br s, 3 H), 6.91 (d, J = 2.9 Hz, 1 H), 6.93-6.99 (m, 2 H), 7.11 (m, 1 H), 7.29 (br s, 1 H), 7.48 (d, J = 7.3 Hz, 1 H), 9.61 (s, 1 H), 11.64 (s, 1 H) |

| | |
|---|---|
| 2-Aminocarbonylamino-5-[5-fluoro-2-[2-(pyrrolidin-1-yl)ethyloxy]phenyl]pyrrole-3-carboxamide (Compound No. 8-12) 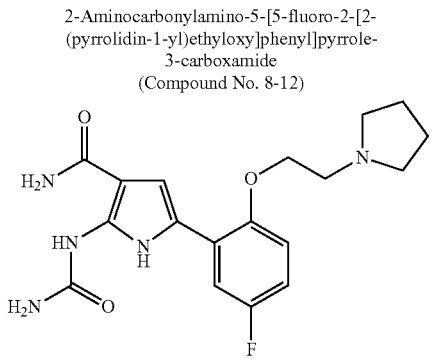 | ¹H-NMR (400 MHz, DMSO-d₆) δ 1.53-1.76 (m, 4 H), 2.40-2.60 (m, 4 H), 2.98 (t, J = 6.1 Hz, 2 H), 4.16 (t, J = 6.1 Hz, 2 H), 6.83 (br s, 3 H), 6.92 (ddd, J = 9.2, 7.8, 3.2 Hz, 1 H), 6.99 (d, J = 2.7 Hz, 1 H), 7.11 (dd, J = 9.2, 4.8 Hz, 1 H), 7.21 (dd, J = 10.3, 3.2 Hz, 1 H), 7.21 (br s, 1 H), 9.60 (s, 1 H), 11.71 (s, 1 H) |
| 2-Aminocarbonylamino-5-[5-fluoro-2-[2-(4-methylpiperidin-1-yl)ethyloxy]phenyl]pyrrole-3-carboxamide (Compound No. 8-13) 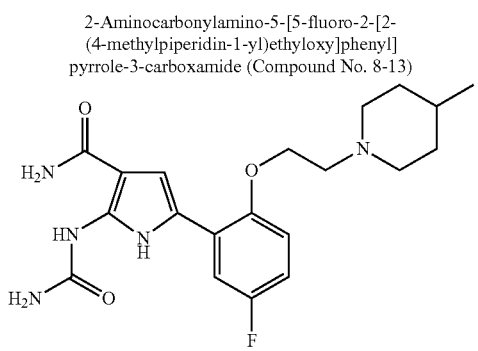 | ¹H-NMR (400 MHz, DMSO-d₆) δ 0.85 (d, J = 6.3 Hz, 3 H), 0.98-1.15 (m, 2 H), 1.29 (m, 1 H), 1.44-1.60 (m, 2 H), 1.92-2.07 (m, 2 H), 2.80-2.95 (m, 4 H), 4.15 (t, J = 6.1 Hz, 2 H), 6.84 (br s, 3 H), 6.92 (ddd, J = 9.0, 8.1, 3.2 Hz, 1 H), 6.99 (d, J = 2.9 Hz, 1 H), 7.12 (dd, J = 9.0, 4.9 Hz, 1 H), 7.21 (dd, J = 10.3, 3.2 Hz, 1 H), 7.21 (br s, 1 H), 9.60 (s, 1 H), 11.69 (s, 1 H) |
| 2-Aminocarbonylamino-5-[5-chloro-2-[2-(piperidin-1-yl)ethyloxy]phenyl]pyrrole-3-carboxamide (Compound No. 8-14) 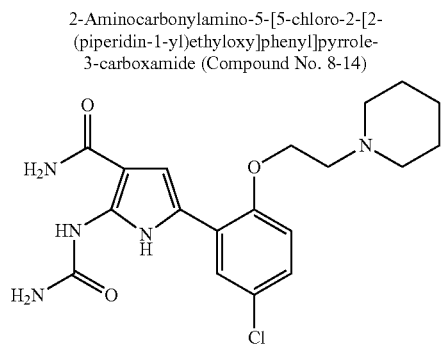 | ¹H-NMR (400 MHz, DMSO-d₆) δ 1.29-1.51 (m, 6 H), 2.35-2.54 (m, 4 H), 2.86 (t, J = 6.1 Hz, 2 H), 4.17 (t, J = 6.1 Hz, 2 H), 6.84 (br s, 3 H), 7.03 (d, J = 2.9 Hz, 1 H), 7.11 (dd, J = 9.0, 2.2 Hz, 1 H), 7.14 (d, J = 9.0 Hz, 1 H), 7.22 (br s, 1 H), 7.46 (d, J = 2.2 Hz, 1 H), 9.60 (s, 1 H), 11.67 (s, 1 H) |
| 2-Aminocarbonylamino-5-[5-chloro-2-[2-(4-methylpiperazin-1-yl)ethyloxy]phenyl]pyrrole-3-carboxamide (Compound No. 8-15) 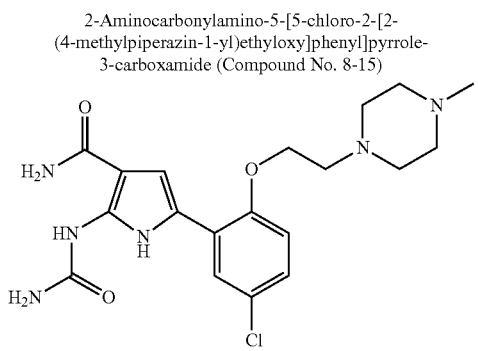 | ¹H-NMR (400 MHz, DMSO-d₆) δ 2.11 (s, 3 H), 2.14-2.60 (m, 8 H), 2.89 (t, J = 5.9 Hz, 2 H), 4.18 (t, J = 5.9 Hz, 2 H), 6.84 (br s, 3 H), 7.03 (d, J = 2.9 Hz, 1 H), 7.09-7.16 (m, 2 H), 7.23 (br s, 1 H), 7.46 (d, J = 2.0 Hz, 1 H), 9.60 (s, 1 H), 11.67 (s, 1 H) |

| Compound | ¹H-NMR |
|---|---|
| 2-Aminocarbonylamino-5-[5-chloro-2-[2-(4-hydroxyethylpiperidin-1-yl)ethyloxy]phenyl]pyrrole-3-carboxamide (Compound No. 8-16)<br>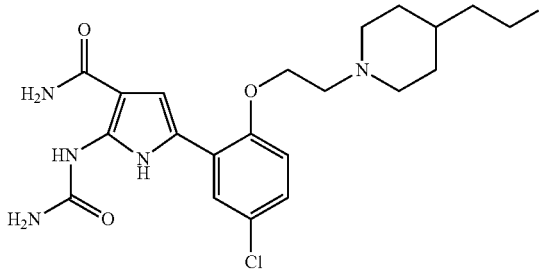 | ¹H-NMR (400 MHz, DMSO-d₆) δ 0.98-1.14 (m, 2 H), 1.23-1.36 (m, 3 H), 1.48-1.65 (m, 2 H), 1.90-2.06 (m, 2 H), 2.80-2.97 (m, 4 H), 3.36-3.46 (m, 2 H), 4.17 (t, J = 6.1 Hz, 2 H), 4.30 (t, J = 5.1 Hz, 1 H), 6.84 (br s, 3 H), 7.03 (d, J = 2.9 Hz, 1 H), 7.11 (dd, J = 9.0, 2.2 Hz, 1 H), 7.14 (d, J = 9.0 Hz, 1 H), 7.23 (br s, 1 H), 7.46 (d, J = 2.2 Hz, 1 H), 9.60 (s, 1 H), 11.67 (s, 1 H) |
| 2-Aminocarbonylamino-5-[5-fluoro-2-[2-[N-(2-hydroxyethyl)-N-methylamino]ethyloxy]phenyl]pyrrole-3-carboxamide (Compound No. 8-17)<br>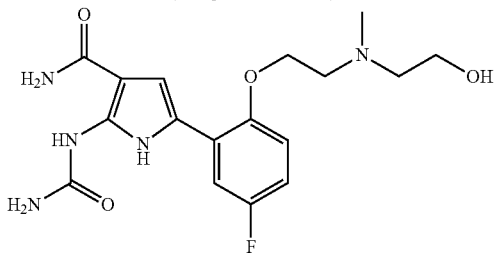 | ¹H-NMR (500 MHz, DMSO-d₆) δ 2.27 (s, 3 H), 2.45-2.57 (m, 2 H), 2.95 (t, J = 6.1 Hz, 2 H), 3.40-3.49 (m, 2 H), 4.14 (t, J = 6.3 Hz, 2 H), 4.30 (t, J = 5.5 Hz, 1 H), 6.84 (br s, 3 H), 6.93 (ddd, J = 9.0, 7.9, 3.2 Hz, 1 H), 6.99 (d, J = 3.1 Hz, 1 H), 7.12 (dd, J = 9.0, 4.7 Hz, 1 H), 7.21 (dd, J = 10.2, 3.2, Hz, 1 H), 7.21 (br s, 1 H), 9.61 (s, 1 H), 11.69 (s, 1 H) |
| 2-Aminocarbonylamino-5-[5-fluoro-2-(2-methylthioethyloxy)phenyl]pyrrole-3-carboxamide (Compound No. 8-18)<br>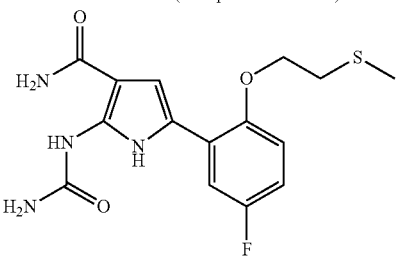 | ¹H-NMR (400 MHz, DMSO-d₆) δ 2.12 (s, 3 H), 3.04 (t, J = 7.0 Hz, 2 H), 4.23 (t, J = 7.0 Hz, 2 H), 6.86 (br s, 3 H), 6.93 (m, 1 H), 7.00 (d, J = 2.9 Hz, 1 H), 7.13 (dd, J = 9.0, 4.9 Hz, 1 H), 7.22 (dd, J = 10.1, 3.1 Hz, 1 H), 7.22 (br s, 1 H), 9.61 (s, 1 H), 11.78 (s, 1 H) |
| 2-Aminocarbonylamino-5-[5-chloro-2-(2-methoxycarbonylmethylthioethyloxy)phenyl]pyrrole-3-carboxamide (Compound No. 8-19)<br>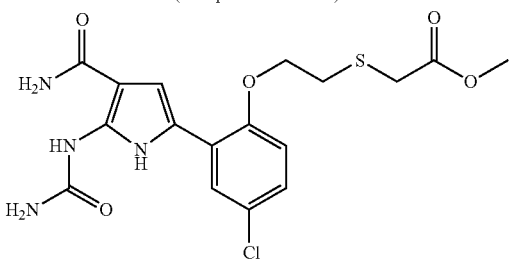 | ¹H-NMR (400 MHz, DMSO-d₆) δ 3.16 (t, J = 6.7 Hz, 2 H), 3.47 (s, 2 H), 3.60 (s, 3 H), 4.27 (t, J = 6.7 Hz, 2 H), 6.86 (br s, 3 H), 7.05 (d, J = 2.9 Hz, 1 H), 7.11 (d, J = 9.0 Hz, 1 H), 7.14 (dd, J = 9.0, 2.4 Hz, 1 H), 7.14 (dd, J = 9.0, 2.4 Hz, 1 H), 7.22 (br s, 1 H), 7.47 (d, J = 2.4 Hz, 1 H), 9.60 (s, 1 H), 11.75 (s, 1 H) |

| | |
|---|---|
| 2-Aminocarbonylamino-5-[5-chloro-2-(2-isopropylthioethyloxy)phenyl]pyrrole-3-carboxamide (Compound No. 8-20) 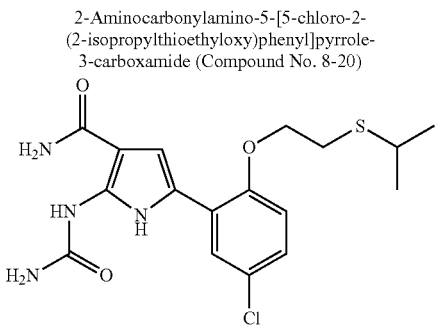 | $^1$H-NMR (400 MHz, DMSO-$d_6$) δ 1.21 (d, J = 6.6 Hz, 6 H), 3.04 (m, 1 H), 3.08 (t, J = 7.3 Hz, 2 H), 4.21 (t, J = 7.3 Hz, 2 H), 6.86 (br s, 3 H), 7.04 (d, J = 2.9 Hz, 1 H), 7.12-7.14 (m, 2 H), 7.22 (br s, 1 H), 7.47 (m, 1 H), 9.60 (s, 1 H), 11.76 (s, 1 H) |
| 2-Aminocarbonylamino-5-[2-[2-(N-benzyl-N-methylamino)ethyloxy]-5-chlorophenyl]pyrrole-3-carboxamide (Compound No. 8-21) 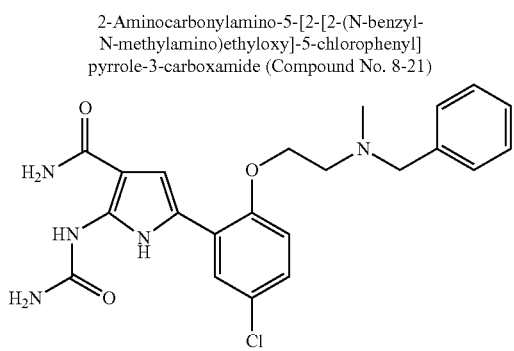 | $^1$H-NMR (400 MHz, DMSO-$d_6$) δ 2.16 (s, 3 H), 3.00 (t, J = 6.0 Hz, 2 H), 3.56 (s, 2 H), 4.23 (t, J = 6.0 Hz, 2 H), 6.82 (br s, 3 H), 7.04 (d, J = 3.2 Hz, 1 H), 7.12-7.31 (m, 8 H), 7.47 (d, J = 2.2 Hz, 1 H), 9.60 (s, 1 H), 11.73 (s, 1 H) |
| 2-Aminocarbonylamino-5-[2-[2-(N-cyclohexyl-N-methylamino)ethyloxy]-5-fluorophenyl]pyrrole-3-carboxamide (Compound No. 8-22) 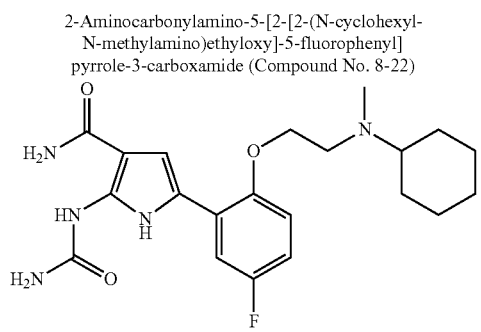 | $^1$H-NMR (400 MHz, DMSO-$d_6$) δ 0.93-1.29 (m, 5 H), 1.41-1.84 (m, 5 H), 2.22 (s, 3 H), 2.34 (m, 1 H), 2.95 (t, J = 6.2 Hz, 2 H), 4.09 (t, J = 6.2 Hz, 2 H), 6.82 (br s, 3 H), 6.92 (ddd, J = 9.3, 7.8, 3.2 Hz, 1 H), 6.97 (d, J = 2.9 Hz, 1 H), 7.10 (dd, J = 9.3, 4.9 Hz, 1 H), 7.19 (br s, 1 H), 7.20 (dd, J = 10.3, 3.2 Hz, 1 H), 9.60 (s, 1 H), 11.68 (s, 1 H) |
| 2-Aminocarbonylamino-5-[5-fluoro-2-[2-(4-hydroxypiperidin-1-yl)ethyloxy]phenyl]pyrrole-3-carboxamide (Compound No. 8-23) 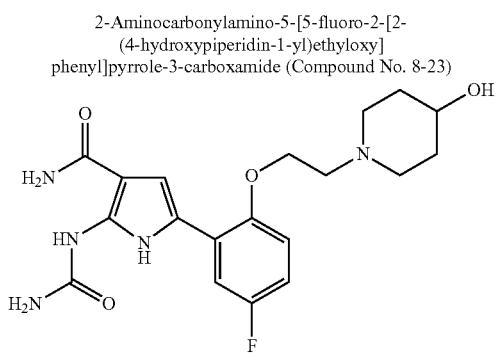 | $^1$H-NMR (400 MHz, DMSO-$d_6$) δ 1.24-1.48 (m, 2 H), 1.56-1.87 (m, 2 H), 2.75-2.84 (m, 2 H), 2.86 (t, J = 5.7 Hz, 2 H), 3.05-3.23 (m, 2 H), 4.16 (t, J = 5.7 Hz, 2 H), 4.49 (m, 1 H), 4.80 (d, J = 3.2 Hz, 1 H), 6.88-6.99 (m, 4 H), 7.02 (d, J = 2.7 Hz, 1 H), 7.13 (dd, J = 9.2, 5.0 Hz, 1 H), 7.22 (dd, J = 10.3, 3.2 Hz, 1 H), 7.40 (br s, 1 H), 10.59 (s, 1 H), 11.55 (s, 1 H) |

Example 9

2-Aminocarbonylamino-5-(4-vinylphenyl)pyrrole-3-carboxamide (Compound No. 9-1)

2-Aminocarbonylamino-5-(4-bromophenyl)pyrrole-3-carboxamide (Compound No. 1-1, 80 mg, 0.25 mmol), sodium hydrogencarbonate (52 mg, 0.62 mmol), vinylboronic acid pinacol ester (63 μL, 0.37 mmol) and tetrakis(triphenylphosphine)palladium(0) (14 mg, 0.012 mmol) in mixed solvent (4 mL), which consists of water and 1,4-dioxane (1:3), were stirred overnight at 95° C. The brine (10 mL) was added to the reaction solution, extracted with ethyl acetate (10 mL), and then the organic layer was dried over magnesium sulfate. The layer was filtered with celite and the solvent was removed under reduced pressure. The obtained solid was washed with diethyl ether (2 mL), and dried under reduced pressure to give the target compound (22 mg) as a pale brown solid (Yield 33%).

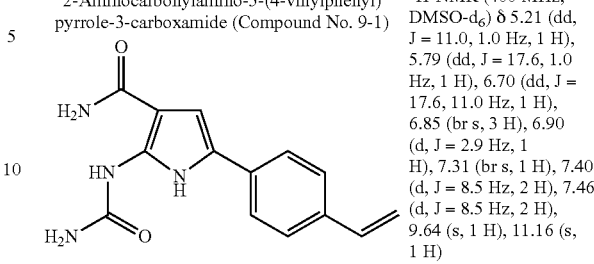

2-Aminocarbonylamino-5-(4-vinylphenyl)pyrrole-3-carboxamide (Compound No. 9-1)

$^1$H-NMR (400 MHz, DMSO-$d_6$) δ 5.21 (dd, J = 11.0, 1.0 Hz, 1 H), 5.79 (dd, J = 17.6, 1.0 Hz, 1 H), 6.70 (dd, J = 17.6, 11.0 Hz, 1 H), 6.85 (br s, 3 H), 6.90 (d, J = 2.9 Hz, 1 H), 7.31 (br s, 1 H), 7.40 (d, J = 8.5 Hz, 2 H), 7.46 (d, J = 8.5 Hz, 2 H), 9.64 (s, 1 H), 11.16 (s, 1 H)

As described below, using commercially available compounds or compounds selected from No. 1-1 or 1-31, compound No. 9-2 to 9-6 were obtained by a method similar to compound No. 9-1.

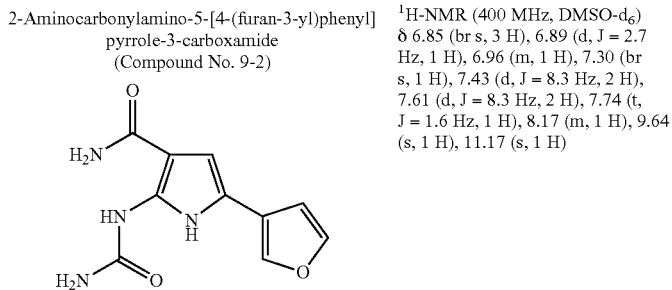

2-Aminocarbonylamino-5-[4-(furan-3-yl)phenyl]pyrrole-3-carboxamide (Compound No. 9-2)

$^1$H-NMR (400 MHz, DMSO-$d_6$) δ 6.85 (br s, 3 H), 6.89 (d, J = 2.7 Hz, 1 H), 6.96 (m, 1 H), 7.30 (br s, 1 H), 7.43 (d, J = 8.3 Hz, 2 H), 7.61 (d, J = 8.3 Hz, 2 H), 7.74 (t, J = 1.6 Hz, 1 H), 8.17 (m, 1 H), 9.64 (s, 1 H), 11.17 (s, 1 H)

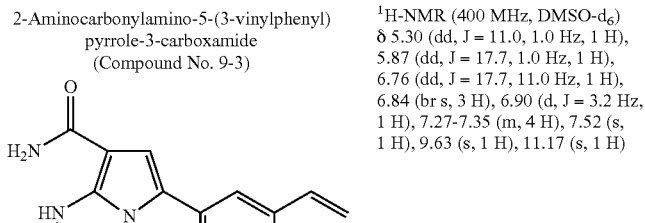

2-Aminocarbonylamino-5-(3-vinylphenyl)pyrrole-3-carboxamide (Compound No. 9-3)

$^1$H-NMR (400 MHz, DMSO-$d_6$) δ 5.30 (dd, J = 11.0, 1.0 Hz, 1 H), 5.87 (dd, J = 17.7, 1.0 Hz, 1 H), 6.76 (dd, J = 17.7, 11.0 Hz, 1 H), 6.84 (br s, 3 H), 6.90 (d, J = 3.2 Hz, 1 H), 7.27-7.35 (m, 4 H), 7.52 (s, 1 H), 9.63 (s, 1 H), 11.17 (s, 1 H)

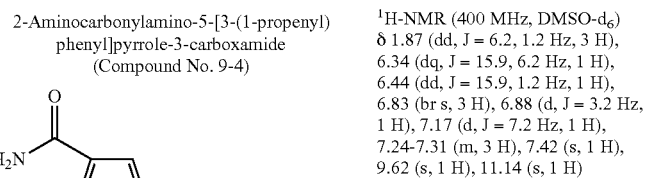

2-Aminocarbonylamino-5-[3-(1-propenyl)phenyl]pyrrole-3-carboxamide (Compound No. 9-4)

$^1$H-NMR (400 MHz, DMSO-$d_6$) δ 1.87 (dd, J = 6.2, 1.2 Hz, 3 H), 6.34 (dq, J = 15.9, 6.2 Hz, 1 H), 6.44 (dd, J = 15.9, 1.2 Hz, 1 H), 6.83 (br s, 3 H), 6.88 (d, J = 3.2 Hz, 1 H), 7.17 (d, J = 7.2 Hz, 1 H), 7.24-7.31 (m, 3 H), 7.42 (s, 1 H), 9.62 (s, 1 H), 11.14 (s, 1 H)

| | |
|---|---|
| 2-Aminocarbonylamino-5-[3-(pyridin-3-yl)phenyl]pyrrole-3-carboxamide (Compound No. 9-5) 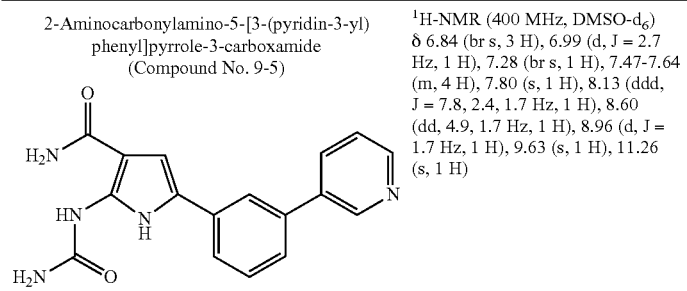 | $^1$H-NMR (400 MHz, DMSO-$d_6$) δ 6.84 (br s, 3 H), 6.99 (d, J = 2.7 Hz, 1 H), 7.28 (br s, 1 H), 7.47-7.64 (m, 4 H), 7.80 (s, 1 H), 8.13 (ddd, J = 7.8, 2.4, 1.7 Hz, 1 H), 8.60 (dd, 4.9, 1.7 Hz, 1 H), 8.96 (d, J = 1.7 Hz, 1 H), 9.63 (s, 1 H), 11.26 (s, 1 H) |
| 2-Aminocarbonylamino-5-[3-(furan-3-yl)phenyl]pyrrole-3-carboxamide (Compound No. 9-6) 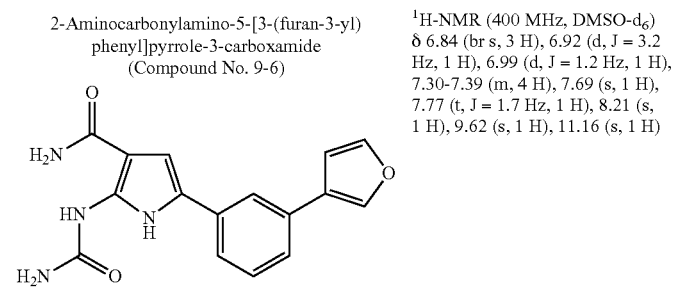 | $^1$H-NMR (400 MHz, DMSO-$d_6$) δ 6.84 (br s, 3 H), 6.92 (d, J = 3.2 Hz, 1 H), 6.99 (d, J = 1.2 Hz, 1 H), 7.30-7.39 (m, 4 H), 7.69 (s, 1 H), 7.77 (t, J = 1.7 Hz, 1 H), 8.21 (s, 1 H), 9.62 (s, 1 H), 11.16 (s, 1 H) |

Example 10

2-Aminocarbonylamino-5-(4-phenylethynylphenyl)pyrrole-3-carboxamide (Compound No. 10-1)

2-Aminocarbonylamino-5-(4-bromophenyl)pyrrole-3-carboxamide (Compound No. 1-1, 100 mg, 0.31 mmol), sodium carbonate (69 mg, 0.65 mmol), copper(I) iodide (12 mg, 0.063 mmol), phenylacetylene (68 μL 0.62 mmol) and tetrakis(triphenylphosphine)palladium(0) (38 mg, 0.033 mmol) in mixed solvent (8 mL), which consists of water and 1,4-dioxane (1:3), were stirred at 95° C. for 5 hours. The brine (5 mL) was added to the reaction solution, extracted with ethyl acetate (10 mL), and then the organic layer was dried over magnesium sulfate. The layer was filtered with celite and the solvent was removed under reduced pressure. The obtained solid was washed with ethyl acetate (2 mL), and dried under reduced pressure to give the target compound (61 mg) as a pale yellow solid (Yield 57%).

| | |
|---|---|
| 2-Aminocarbonylamino-5-[4-(phenylethynyl)phenyl]pyrrole-3-carboxamide (Compound No. 10-1) 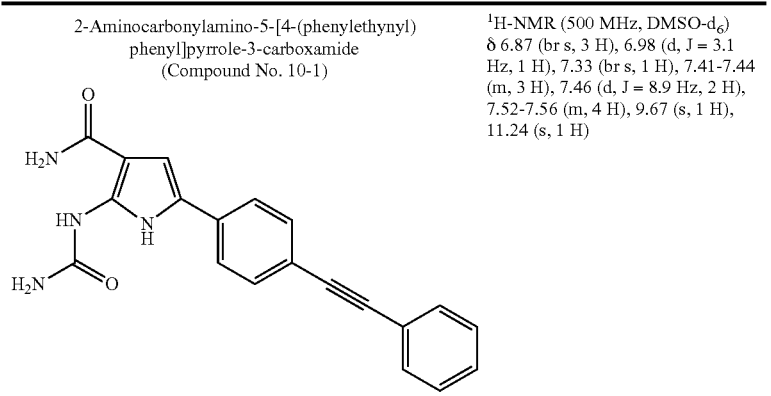 | $^1$H-NMR (500 MHz, DMSO-$d_6$) δ 6.87 (br s, 3 H), 6.98 (d, J = 3.1 Hz, 1 H), 7.33 (br s, 1 H), 7.41-7.44 (m, 3 H), 7.46 (d, J = 8.9 Hz, 2 H), 7.52-7.56 (m, 4 H), 9.67 (s, 1 H), 11.24 (s, 1 H) |

As described below, using commercially available compounds or compounds selected from No. 1-1 or 1-31, compound No. 10-2 to 10-4 were obtained by a method similar to compound No. 10-1.

| Compound | NMR |
|---|---|
| 2-Aminocarbonylamino-5-[4-(3-hydroxypropynyl)phenyl]pyrrole-3-carboxamide (Compound No. 10-2) 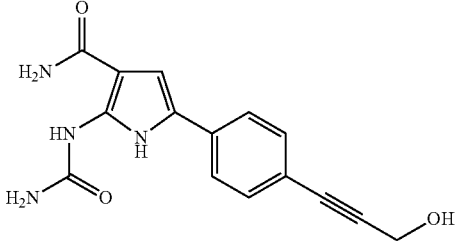 | $^1$H-NMR (400 MHz, DMSO-$d_6$) δ 4.30 (d, J = 6.0 Hz, 2 H), 5.31 (t, J = 6.0 Hz, 1 H), 6.86 (br s, 3 H), 6.93 (d, J = 2.9 Hz, 1 H), 7.33 (br s, 1 H), 7.39-7.41 (m, 4 H), 9.65 (s, 1 H), 11.21 (s, 1 H) |
| 2-Aminocarbonylamino-5-[3-(3-hydroxypropynyl)phenyl]pyrrole-3-carboxamide (Compound No. 10-3) 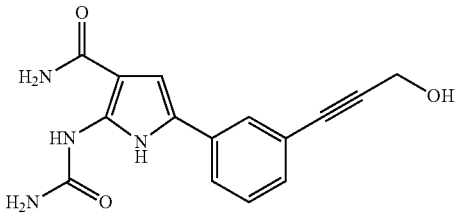 | $^1$H-NMR (500 MHz, DMSO-$d_6$) δ 4.32 (d, J = 6.0 Hz, 2 H), 5.35 (t, J = 6.0 Hz, 1 H), 6.85 (br s, 3 H), 6.93 (d, J = 3.1 Hz, 1 H), 7.18 (d, J = 7.8 Hz, 1 H), 7.27 (br s, 1 H), 7.36 (t, J = 7.8 Hz, 1 H), 7.43 (d, J = 7.8 Hz, 1 H), 7.47 (s, 1 H), 9.62 (s, 1 H), 11.20 (s, 1 H) |
| 2-Aminocarbonylamino-5-[3-(3-dimethylaminopropynyl)phenyl]pyrrole-3-carboxamide (Compound No. 10-4) 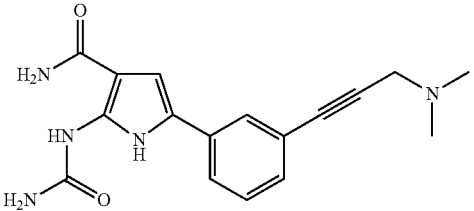 | $^1$H-NMR (400 MHz, DMSO-$d_6$) δ 2.26 (s, 6 H), 3.47 (s, 2 H), 6.85 (br s, 3 H), 6.94 (d, J = 2.7 Hz, 1 H), 7.19 (d, J = 7.8 Hz, 1 H), 7.28 (br s, 1 H), 7.35 (t, J = 7.8 Hz, 1 H), 7.42 (d, J = 7.8 Hz, 1 H), 7.49 (s, 1 H), 9.61 (s, 1 H), 11.20 (s, 1 H) |

Example 11

2-Aminocarbonylamino-5-(3-ethynylphenyl)pyrrole-3-carboxamide (Compound No. 11-1)

2-Aminocarbonylamino-5-(3-bromophenyl)pyrrole-3-carboxamide (Compound No. 1-31, 200 mg, 0.62 mmol), sodium hydrogencarbonate (133 mg, 1.6 mmol), copper (I) iodide (16 mg, 0.084 mmol), (triisopropylsilyl)acetylene (0.28 mL, 1.2 mmol) and tetrakis(triphenylphosphine)palladium(0) (38 mg, 0.033 mmol) in mixed solvent (12 mL), which consists of water and 1,4-dioxane (1:5), were stirred at 95° C. for 4.5 hours. The brine (5 mL) and water (5 mL) were added to the reaction solution, extracted with ethyl acetate (15 mL), and then the organic layer was dried over magnesium sulfate. The layer was filtered with celite, the solvent was removed under reduced pressure, and then the obtained solid was washed with diethyl ether (2 mL) to give the intermediate 2-aminocarbonylamino-5-(3-triisopropylsilylethynylphenyl)pyrrole-3-carboxamide as a yellow solid. Moreover, 1.0M tetrabutylammonium fluoride in tetrahydrofuran solution (0.48 mL, 0.48 mmol) was added to a solution of this intermediate in tetrahydrofuran (5 mL) and the mixture was stirred at 75° C. for 3.5 hours. The reaction solution was concentrated in vacuo, the obtained residue was purified by silica gel column chromatography to give the target compound (47 mg) as a colorless solid (Yield 29%).

| 2-Aminocarbonylamino-5-(3-ethynylphenyl)pyrrole-3-carboxamide (Compound No. 11-1) 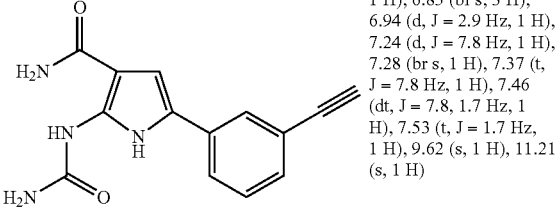 | $^1$H-NMR (400 MHz, DMSO-$d_6$) δ 4.22 (s, 1 H), 6.85 (br s, 3 H), 6.94 (d, J = 2.9 Hz, 1 H), 7.24 (d, J = 7.8 Hz, 1 H), 7.28 (br s, 1 H), 7.37 (t, J = 7.8 Hz, 1 H), 7.46 (dt, J = 7.8, 1.7 Hz, 1 H), 7.53 (t, J = 1.7 Hz, 1 H), 9.62 (s, 1 H), 11.21 (s, 1 H) |

Example 12

2-Aminocarbonylamino-5-(4-ethylphenyl)pyrrole-3-carboxamide (Compound No. 12-1)

10% Palladium on activated carbon (6 mg) was added to a solution of 2-aminocarbonylamino-5-(4-vinylphenyl)pyrrole-3-carboxamide (Compound No. 9-1, 16 mg, 0.059 mmol) in methanol (2 mL) and the mixture was stirred at room temperature for 4.5 hours under hydrogen gas atmosphere. After the reaction solution was filtered, the filterate was concentrated in vacuo. The obtained solid was washed with diethyl ether (2 mL) and dried under reduced pressure to give the target compound (10 mg) as a colorless solid (Yield 62%).

| | |
|---|---|
| 2-Aminocarbonylamino-5-(4-ethylphenyl)pyrrole-3-carboxamide (Compound No. 12-1) 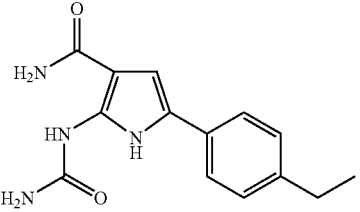 | $^1$H-NMR (400 MHz, DMSO-$d_6$) δ 1.18 (t, J = 7.6 Hz, 3 H), 2.58 (q, J = 7.6 Hz, 2 H), 6.79 (d, J = 2.9 Hz, 1 H), 6.82 (br s, 3 H), 7.20 (d, J = 8.0 Hz, 2 H), 7.28 (br s, 1 H), 7.34 (d, J = 8.0 Hz, 2 H), 9.62 (s, 1 H), 11.09 (s, 1 H) |

As described below, using compound No. 1-59 or 9-3, compound No. 12-2 and 12-3 were obtained by a method similar to compound No. 12-1.

| | |
|---|---|
| 2-Aminocarbonylamino-5-(3-ethylphenyl)pyrrole-3-carboxamide (Compound No. 12-2) 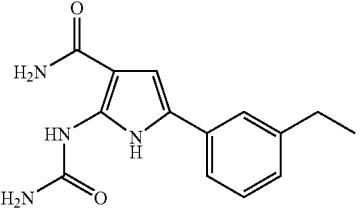 | $^1$H-NMR (400 MHz, DMSO-$d_6$) δ 1.21 (t, J = 7.7 Hz, 3 H), 2.62 (q, J = 7.7 Hz, 2 H), 6.82 (br s, 3 H), 6.86 (d, J = 2.9 Hz, 1 H), 7.01 (d, J = 7.3 Hz, 1 H), 7.21-7.29 (m, 4 H), 9.63 (s, 1 H), 11.12 (s, 1 H) |
| 2-Aminocarbonylamino-5-(2-ethylphenyl)pyrrole-3-carboxamide (Compound No. 12-3) 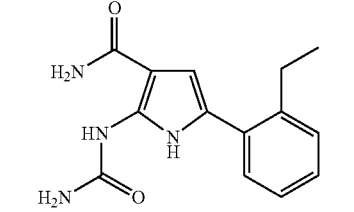 | $^1$H-NMR (400 MHz, DMSO-$d_6$) δ 1.18 (t, J = 7.6 Hz, 3 H), 2.75 (q, J = 7.6 Hz, 2 H), 6.58 (d, J = 3.2 Hz, 1 H), 6.81 (br s, 3 H), 7.20-7.22 (m, 2 H), 7.26-7.29 (m, 2 H), 7.37 (br s, 1 H), 9.64 (s, 1 H), 10.98 (s, 1 H) |

Example 13

2-Aminocarbonylamino-5-(4-hydroxymethylphenyl)pyrrole-3-carboxamide (Compound No. 13-1)

Under ice-cooling, 1.0M diisobutylaluminum hydride in toluene solution (3.2 mL, 3.2 mmol) was added to a solution of 2-aminocarbonylamino-5-(4-ethoxycarbonylphenyl)pyrrole-3-carboxamide (Compound No. 1-30, 0.28 g, 0.89 mmol) in anhydrous tetrahydrofuran (5 mL) and the mixture was stirred for 2 hours. Moreover, 1.0M diisobutylaluminum hydride in toluene solution (3.2 mL, 3.2 mmol) was added thereto and the whole was stirred for 2 hours, and then water (2 mL) and methanol (2 mL) were added thereto. The mixture was filtered with celite with 1,4-dioxane (10 mL) and the filtrate was concentrated in vacuo. The obtained solid was washed with diethyl ether (2 mL), dried under reduced pressure to give the target compound (0.16 g) as a pale yellow solid (Yield 66%).

| | |
|---|---|
| 2-Aminocarbonylamino-5-(4-hydroxymethylphenyl)pyrrole-3-carboxamide (Compound No. 13-1) 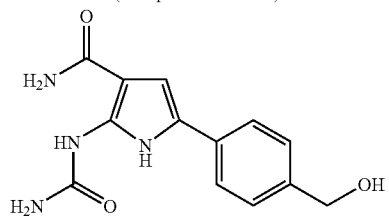 | $^1$H-NMR (400 MHz, DMSO-$d_6$) δ 4.47 (d, J = 5.8 Hz, 2 H), 5.14 (t, J = 5.8 Hz, 1 H), 6.82 (br s, 3 H), 6.83 (d, J = 3.2 Hz, 1 H), 7.30 (br s, 1 H), 7.30 (d, J = 8.3 Hz, 2 H), 7.38 (d, J = 8.3 Hz, 2 H), 9.63 (s, 1 H), 11.12 (s, 1 H) |

As described below, using compound No. 1-35, compound No. 13-2 was obtained by a method similar to compound No. 13-1.

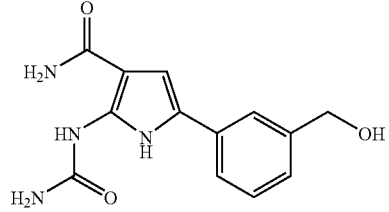

| 2-Aminocarbonylamino-5-(3-hydroxymethyl-phenyl)pyrrole-3-carboxamide (Compound No. 13-2) | $^1$H-NMR (500 MHz, DMSO-$d_6$) δ 4.51 (d, J = 5.8 Hz, 2 H), 5.23 (t, J = 5.8 Hz, 1 H), 6.81 (br s, 3 H), 6.88 (d, J = 3.1 Hz, 1 H), 7.09 (d, J = 7.0 Hz, 1 H), 7.27-7.32 (m, 3 H), 7.40 (s, 1 H), 9.64 (s, 1 H), 11.14 (s, 1 H) |
|---|---|

Example 14

2-Aminocarbonylamino-5-(4-formylphenyl)pyrrole-3-carboxamide (Compound No. 14-1)

2-Iodoxybenzoic acid (150 mg, 0.53 mmol) was added to a solution of 2-aminocarbonylamino-5-(4-hydroxymethylphe-nyl)pyrrole-3-carboxamide (Compound No. 13-1, 130 mg, 0.47 mmol) in dimethyl sulfoxide (5 mL) and the mixture was stirred at room temperature for 1 hour. Water (15 mL) was added to the reaction solution, the precipitated solid was filtered off. The obtained solid was washed with 0.25N aqueous sodium hydroxide (2 mL) and water (2 mL), dried under reduced pressure to give the target compound (86 mg) as a yellow solid (Yield 67%).

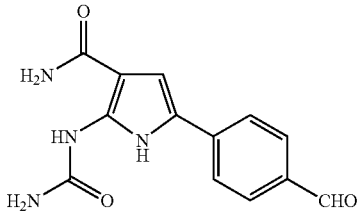

| 2-Aminocarbonylamino-5-(4-formylphenyl) pyrrole-3-carboxamide (Compound No. 14-1) | $^1$H-NMR (400 MHz, DMSO-$d_6$) δ 6.93 (br s, 3 H), 7.16 (d, J = 2.9 Hz, 1 H), 7.39 (br s, 1 H), 7.61 (d, J = 8.5 Hz, 2 H), 7.87 (d, J = 8.5 Hz, 2 H), 9.72 (s, 1 H), 9.91 (s, 1 H), 11.37 (s, 1 H) |
|---|---|

As described below, using compound No. 13-2, compound No. 14-2 was obtained by a method similar to compound No. 14-1.

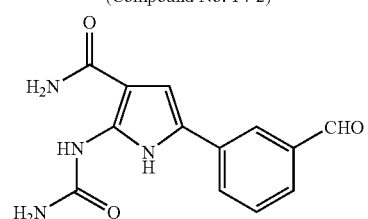

| 2-Aminocarbonylamino-5-(3-formylphenyl) pyrrole-3-carboxamide (Compound No. 14-2) | $^1$H-NMR (400 MHz, DMSO-$d_6$) δ 6.87 (br s, 3 H), 7.03 (d, J = 2.9 Hz, 1 H), 7.35 (br s, 1 H), 7.59 (t, J = 7.7 Hz, 1 H), 7.68 (dt, J = 7.7, 1.6 Hz, 1 H), 7.76 (dt, J = 7.7, 1.6 Hz, 1 H), 7.96 (t, J = 1.6 Hz, 1 H), 9.66 (s, 1 H), 10.03 (s, 1 H), 11.31 (s, 1 H) |
|---|---|

Example 15

2-Aminocarbonylamino-5-(3-methylthiomethylphe-nyl)pyrrole-3-carboxamide (Compound No. 15-1)

Under a solution of 2-aminocarbonylamino-5-(3-formylphenyl)pyrrole-3-carboxamide (Compound No. 14-2, 50 mg, 0.18 mmol) in trifluoroacetic acid (4 mL) was added to a solution of sodium methanethiolate (14 mg, 0.20 mmol) in dichloromethane (2 mL) and the mixture was stirred for 10 minutes. Moreover, borane-pyridine complex (41 μL, 0.41 mmol) was added thereto and the whole was stirred for 10 minutes. The reaction solution was concentrated in vacuo. Saturated aqueous sodium hydrogencarbonate (3 mL) and water (2 mL) were added to the residue, extracted with ethyl acetate (10 mL). After the organic layer was dried over anhydrous magnesium sulfate, the solvent was removed under reduced pressure. The obtained residue was purified by silica gel column chromatography to give the target compound (22 mg) as a colorless solid (Yield 39%).

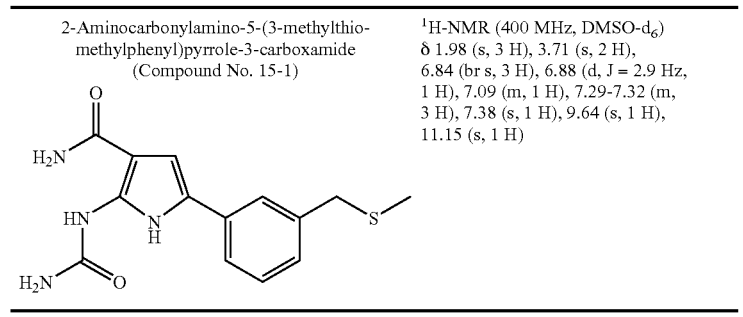

| 2-Aminocarbonylamino-5-(3-methylthio-methylphenyl)pyrrole-3-carboxamide (Compound No. 15-1) | $^1$H-NMR (400 MHz, DMSO-$d_6$) δ 1.98 (s, 3 H), 3.71 (s, 2 H), 6.84 (br s, 3 H), 6.88 (d, J = 2.9 Hz, 1 H), 7.09 (m, 1 H), 7.29-7.32 (m, 3 H), 7.38 (s, 1 H), 9.64 (s, 1 H), 11.15 (s, 1 H) |
|---|---|

As described below, using commercially available compounds and compound No. 14-2, compound No. 15-2 was obtained by a method similar to compound No. 15-1.

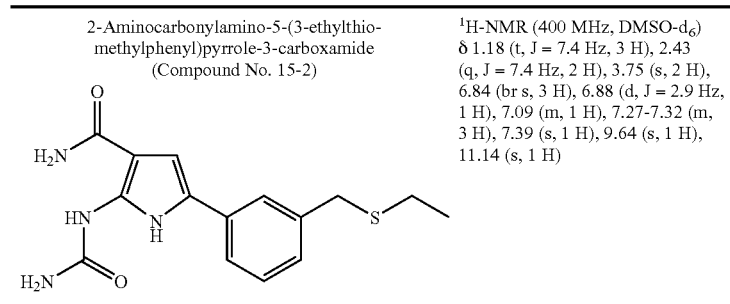

| 2-Aminocarbonylamino-5-(3-ethylthio-methylphenyl)pyrrole-3-carboxamide (Compound No. 15-2) | $^1$H-NMR (400 MHz, DMSO-$d_6$) δ 1.18 (t, J = 7.4 Hz, 3 H), 2.43 (q, J = 7.4 Hz, 2 H), 3.75 (s, 2 H), 6.84 (br s, 3 H), 6.88 (d, J = 2.9 Hz, 1 H), 7.09 (m, 1 H), 7.27-7.32 (m, 3 H), 7.39 (s, 1 H), 9.64 (s, 1 H), 11.14 (s, 1 H) |
|---|---|

Example 16

2-Aminocarbonylamino-5-[4-[N-benzyl-N-(2-hydroxyethyl)aminomethyl]phenyl]pyrrole-3-carboxamide (Compound No. 16-1)

Acetic acid (30 μl N-benzylethanolamine (79 μL, 0.55 mmol) and sodium cyanoborohydride (35 mg, 0.55 mmol) were added to a solution of 2-aminocarbonylamino-5-(4-formylphenyl)pyrrole-3-carboxamide (Compound No. 14-1, 50 mg, 0.18 mmol) in N,N-dimethylformamide (3 mL) and the mixture was stirred overnight at room temperature. Saturated aqueous sodium hydrogencarbonate (10 mL) and water (10 mL) were added to the reaction solution, extracted with ethyl acetate (20 mL). The organic layer was washed with brine (10 mL), dried over anhydrous magnesium sulfate. The solvent was removed under reduced pressure, the obtained residue was purified by silica gel column chromatography to give the target compound (26 mg) as a colorless solid (Yield 36%)

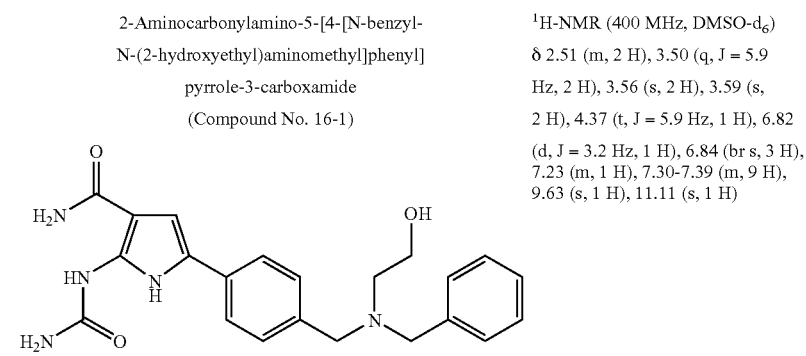

| 2-Aminocarbonylamino-5-[4-[N-benzyl-N-(2-hydroxyethyl)aminomethyl]phenyl] pyrrole-3-carboxamide (Compound No. 16-1) | $^1$H-NMR (400 MHz, DMSO-$d_6$) δ 2.51 (m, 2 H), 3.50 (q, J = 5.9 Hz, 2 H), 3.56 (s, 2 H), 3.59 (s, 2 H), 4.37 (t, J = 5.9 Hz, 1 H), 6.82 (d, J = 3.2 Hz, 1 H), 6.84 (br s, 3 H), 7.23 (m, 1 H), 7.30-7.39 (m, 9 H), 9.63 (s, 1 H), 11.11 (s, 1 H) |
|---|---|

Example 17

2-Aminocarbonylamino-5-(3-chlorophenyl)-4-formylpyrrole-3-carboxamide (Compound No. 17-1)

1.0M Titanium tetrachloride in dichloromethane solution (2 mL, 2.0 mmol) was added to a suspension of 2-aminocarbonylamino-5-(3-chlorophenyl)pyrrole-3-carboxamide (Compound No. 1-25, 140 mg, 0.50 mmol) in dichloromethane (3 mL) at −30° C. and the mixture was stirred for 40 minutes. Moreover, dichloromethyl methyl ether (0.27 mL, 3.0 mmol) was added thereto and the whole was stirred overnight at 4° C. Under ice-cooling, 1N hydrochloric acid (4 mL) was added thereto and the mixture was stirred for 1 hour, and then water (10 mL) was add thereto. The precipitated solid was filtered off, washed with chloroform (10 mL) and water (10 mL), and dried under reduced pressure to give the target compound (120 mg) as a brown solid (Yield 77%).

| 2-Aminocarbonylamino-5-(3-chlorophenyl)-4-formylpyrrole-3-carboxamide (Compound No. 17-1) | $^1$H-NMR (400 MHz, DMSO-$d_6$) δ 7.01 (br s, 2 H), 7.47-7.62 (m, 5 H), 7.69 (s, 1 H), 9.47 (s, 1 H), 10.37 (s, 1 H), 12.10 (s, 1 H) |
|---|---|

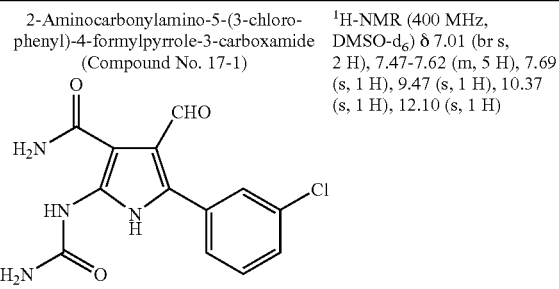

Example 18

2-Aminocarbonylamino-5-(3-chlorophenyl)-4-(hydroxymethyl)pyrrole-3-carboxamide (Compound No. 18-1)

Sodium borohydride (18 mg, 0.48 mmol) was added to a solution of 2-aminocarbonylamino-5-(3-chlorophenyl)-4-formylpyrrole-3-carboxamide (Compound No. 17-1, 50 mg, 0.16 mmol) in the mixed solvent (tetrahydrofuran methanol=2:1, 1.5 mL) and the mixture was stirred at room temperature for 4 hours. Saturated aqueous ammonium chloride solution (50 mL) was added to the reaction solution, extracted with ethyl acetate (50 mL). The organic layer was dried over anhydrous magnesium sulfate, and the solvent was removed under reduced pressure. The obtained solid was washed with chloroform (15 mL) and dried under reduced pressure to give the target compound (19 mg) as an orange solid (Yield 37%).

| 2-Aminocarbonylamino-5-(3-chlorophenyl)-4-(hydroxymethyl)pyrrole-3-carboxamide (Compound No. 18-1) | $^1$H-NMR (500 MHz, DMSO-$d_6$) δ 4.46 (d, J = 4.9 Hz, 2 H), 5.82 (t, J = 4.9 Hz, 1 H), 6.82 (br s, 2 H), 6.99 (br s, 1 H), 7.31-7.56 (m, 4 H), 7.78 (br s, 1 H), 9.74 (s, 1 H), 11.03 (s, 1 H) |
|---|---|

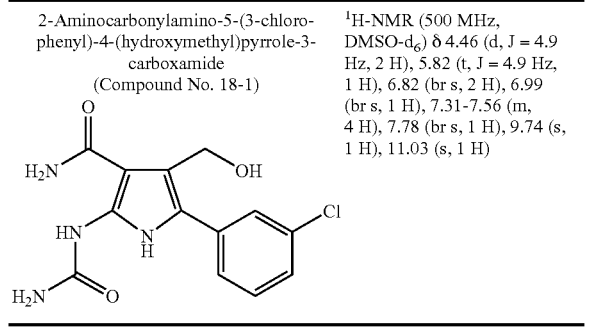

Example 19

2-Aminocarbonylamino-5-(3-chlorophenyl)-4-(methylaminomethyl)pyrrole-3-carboxamide (Compound No. 19-1)

40% Methylamine in methanol (1 mL, 9.8 mmol) was added to a suspension of 2-aminocarbonylamino-5-(3-chlorophenyl)-4-formylpyrrole-3-carboxamide (Compound No. 17-1, 45 mg, 0.15 mmol) in tetrahydrofuran (1 mL), and the mixture was sealed and stirred at 40° C. for 3 hours. Moreover, sodium borohydride (25 mg, 0.66 mmol) was added thereto and the whole was stirred at room temperature for 3 hours. Acetone (5 mL) was added to the reaction solution and concentrated in vacuo. Water (10 mL) was added to the obtained residue, and the precipitated solid was filtered off. The solid was washed with water (10 mL) and the mixed solvent (5.5 mL), which consists of chloroform and ethanol (10:1), dried under reduced pressure to give the target compound (17 mg) as an orange solid (Yield 36%).

| 2-Aminocarbonylamino-5-(3-chlorophenyl)-4-(methylaminomethyl)pyrrole-3-carboxamide (Compound No. 19-1) | $^1$H-NMR (500 MHz, DMSO-$d_6$) δ 2.31 (s, 3 H), 3.53 (s, 2 H), 6.77 (br s, 3 H), 7.29-7.56 (m, 5 H), 9.81 (s, 1 H), 10.95 (s, 1 H) |
|---|---|

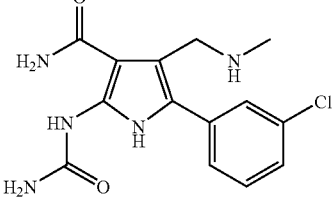

Example 20

2-Aminocarbonylamino-5-[2-(2-methylaminoethyloxy)phenyl]pyrrole-3-carboxamide hydrochloride (Compound No. 20-1)

Palladium on activated carbon (10 mg) was added to a solution of 2-aminocarbonylamino-5-[2-[2-(N-benzyl-N-methylamino)ethyloxy]-5-chlorophenyl]pyrrole-3-carboxamide (Compound No. 8-21, 26 mg, 0.059 mmol) in the mixed solvent (methanol:N,N-dimethylformamide=10:1, 2.2 mL) and the mixture was stirred at room temperature for 2.5 hours under hydrogen gas atmosphere. After the reaction solution was filtered, the filtrate was concentrated in vacuo. The obtained solid was washed with a mixed solvent (6 mL), which consists of chloroform and diethyl ether (1:1), and dried under reduced pressure to give the target compound (23 mg) quantitatively as a colorless solid.

| 2-Aminocarbonylamino-5-[2-(2-methylamino-ethyloxy)phenyl]pyrrole-3-carboxamide hydrochloride (Compound No. 20-1) | ¹H-NMR (500 MHz, DMSO-d₆) δ 2.72 (s, 3 H), 3.54 (t, J = 3.8 Hz, 2 H), 4.35 (t, J = 4.6 Hz, 2 H), 6.81 (br s, 3 H), 6.94 (d, J = 2.7 Hz, 1 H), 6.99-7.20 (m, 3 H), 7.30 (br s, 1 H), 7.53 (dd, J = 7.9, 1.5 Hz, 1 H), 8.72 (s, 2 H), 9.65 (s, 1 H), 11.75 (s, 1 H) |
|---|---|
| 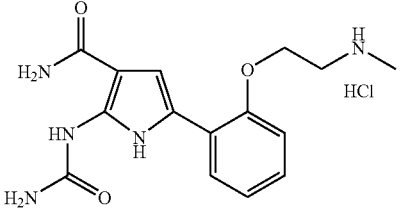 | |

Example 21

2-Aminocarbonylamino-5-[3-(4-nitrophenyloxy)phenyl]pyrrole-3-carboxamide (Compound No. 21-1)

Under ice-cooling, a solution of 2-aminocarbonylamino-5-(3-hydroxyphenyl)pyrrole-3-carboxamide (Compound No. 3-2, 100 mg, 0.38 mmol) in N,N-dimethylformamide (1.5 mL) was added to a suspension of 60% sodium hydride (23 mg, 0.58 mmol) in N,N-dimethylformamide (1.5 mL) and the mixture was stirred for 35 minutes. Moreover, 4-fluoronitrobenzene (61 μL, 0.57 mmol) was added thereto and the whole was stirred overnight at 50° C. Saturated aqueous ammonium chloride solution (3 mL) and water (3 mL) were added to the reaction solution, extracted with ethyl acetate (10 mL). The organic layer was washed with brine (10 mL) and dried over anhydrous magnesium sulfate. The solvent was removed under reduced pressure, and the residue was purified by silica gel column chromatography to give the target compound (12 mg) as a yellow solid (Yield 8%).

| 2-Aminocarbonylamino-5-[3-(4-nitrophenyloxy)phenyl]pyrrole-3-carboxamide (Compound No. 21-1) | ¹H-NMR (400 MHz, DMSO-d₆) δ 6.84 (br s, 3 H), 6.92-6.97 (m, 2 H), 7.18 (d, J = 9.3 Hz, 2 H), 7.26 (s, 1 H), 7.27 (br s, 1 H), 7.36 (d, J = 7.9 Hz, 1 H), 7.47 (t, J = 7.9 Hz, 1 H), 8.27 (d, J = 9.3 Hz, 2 H), 9.61 (s, 1 H), 11.20 (s, 1 H) |
|---|---|
| 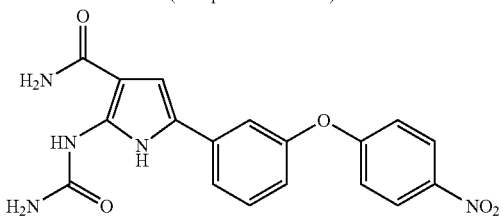 | |

Example 22

2-Aminocarbonylamino-5-(3-methylaminomethylphenyl)pyrrole-3-carboxamide hydrochloride (Compound No. 22-1)

40% Methylamine in methanol (0.4 mL, 3.9 mmol) was added to a solution of 2-aminocarbonylamino-5-(3-formylphenyl)pyrrole-3-carboxamide (Compound No. 14-2, 100 mg, 0.37 mmol) in anhydrous methanol (5 mL) and the mixture was stirred at 60° C. for 6.5 hours. The reaction solution was concentrated in vacuo, sodium borohydride (30 mg, 0.79 mmol) was added to the residue in anhydrous methanol (5 mL) and the whole was stirred overnight at room temperature. Water (1 mL) was added to the reaction mixture, and concentrated in vacuo. Water (10 mL) was added to the residue. The mixture was extracted with ethyl acetate (20 mL); the organic layer was washed with water (10 mL) and brine (10 mL) and then dried over anhydrous magnesium sulfate. The solvent was removed under reduced pressure, 2N hydrochloric acid (10 mL) was added to the residue. After the mixture was washed with ethyl acetate (10 mL, twice), 4N sodium hydroxide (20 mL) was added to the aqueous layer, and extracted with ethyl acetate (20 mL). The organic layer was washed with brine (10 mL), dried over anhydrous magnesium sulfate, and then the solvent was removed under reduced pressure. Ethanol (5 mL) and 2N hydrochloric acid (2 mL) were added to the obtained residue, the whole was concentrated in vacuo to give the target compound (7.7 mg) as a pale brown amorphous (Yield 7%).

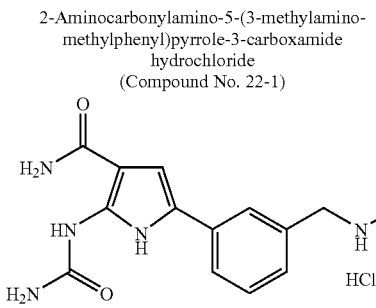

| 2-Aminocarbonylamino-5-(3-methylaminomethylphenyl)pyrrole-3-carboxamide hydrochloride (Compound No. 22-1) | $^1$H-NMR (400 MHz, DMSO-$d_6$) δ 2.58 (t, J = 5.7 Hz, 3 H), 4.13 (t, J = 5.7 Hz, 2 H), 6.91 (br s, 3 H), 6.92 (d, J = 3.2 Hz, 1 H), 7.25 (d, J = 7.7 Hz, 1 H), 7.34 (br s, 1 H), 7.43 (t, J = 7.7 Hz, 1 H), 7.49 (d, J = 7.7 Hz, 1 H), 7.55 (s, 1 H), 8.83 (br s, 2 H), 9.71 (s, 1 H), 11.16 (s, 1 H) |
|---|---|

Further, commercially available compounds are compounds which listed on product catalogs published by Sigma-Ardrich, Wako Pure Chemical Industries Ltd., Kanto Chemical Co., Inc., Tokyo Chemical Industry Co., Ltd., Nacalai Tesque Inc., and so on from 2006 to 2008.

Preparation Examples

Hereinafter, typical preparation examples of the present compound will be shown.

| 1) Tablet (in 150 mg) | |
|---|---|
| The present compound | 1 mg |
| Lactose | 100 mg |
| Cornstarch | 40 mg |
| Calcium carboxymethyl cellulose | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol or a silicone resin), whereby a desired tablet can be obtained. In addition, a desired tablet can be obtained by appropriately changing the kinds and/or amounts of the present compound and additives.

| 2) Capsule (in 150 mg) | |
|---|---|
| The present compound | 5 mg |
| Lactose | 135 mg |
| Calcium carboxymethyl cellulose | 4.5 mg |
| Hydroxypropyl cellulose | 4 mg |
| Magnesium stearate | 1.5 mg |

A desired capsule can be obtained by appropriately changing the kinds and/or amounts of the present compound and additives.

| 3) Eye drop (in 100 mL) | |
|---|---|
| The present compound | 100 mg |
| Sodium chloride | 900 mg |

| -continued | |
|---|---|
| 3) Eye drop (in 100 mL) | |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kinds and the amounts of the present compound and additives.

[Pharmacological Tests]

1. Test for Measurement of Inhibitory Activity Against IL-6 Production

An inhibitory effect on TNF-α-induced IL-6 production in normal human skin fibroblast-derived CCD-1059Sk cells (ATCC No. CRL-2072) was evaluated. The amount of IL-6 was determined by the homogeneous time-resolved fluorescence method using HTRF™ Human IL-6 kit (Cat. No. 62IL6PEB, manufactured by CIS-Bio international, Inc.). Specific test methods will be described below.

(Preparation of Test Compound Solution)

After a test compound was dissolved in dimethyl sulfoxide, the resulting solution was diluted with D-MEM medium containing 0.1% heat-inactivated fetal bovine serum, 0.1 mM MEM non-essential amino acid solution, 100 U/mL penicillin and 100 μg/mL streptomycin (hereinafter referred to as "medium"), whereby a 40 μM test compound solution was prepared.

(Test Method and Measurement Method)

1) CCD-1059Sk cells prepared at a density of $3 \times 10^5$ cells/mL were inoculated in a 384-well plate in an amount of 10 μL per well such that the cell density was $3 \times 10^3$ cells/well.

2). After the plate was incubated at 37° C. for several hours in a $CO_2$ incubator, 5 μL of the test compound was added to each well.

3) After the plate was incubated at 37° C. for 1 hour in a $CO_2$ incubator, 5 μL of a 40 ng/mL TNF-α solution was added to each well.

4) After the plate was incubated at 37° C. for 16 hours in a $CO_2$ incubator, 10 μL of a cryptate-labeled anti-IL-6 antibody and an XL665-labeled anti-IL-6 antibody containing potassium fluoride was added to each well.

5) After the plate was incubated at room temperature for several hours, a fluorescence intensity ratio (665 nm/620 nm) was determined for each well using a multimode plate reader Analyse™ HT (manufactured by Molecular Device Corporation) and Criterion Host software version 2.00 (manufactured by Molecular Device Corporation), and then, the amount of IL-6 was calculated.

6) The same procedures as in the above 1) to 5) were performed except that 0.4% dimethyl sulfoxide was added in place of the test compound, and the obtained result was designated as the control.

7) The same procedures as in the above 1) to 5) were performed except that 0.4% dimethyl sulfoxide and the medium were added in place of the test compound and the TNF-α solution, respectively, and the obtained result was designated as the background.

(Calculation Formula of IL-6 Production Inhibition Ratio)

An IL-6 production inhibition ratio (%) was calculated from the following formula.

IL-6 Production Inhibition Ratio (%)=100×{1−[(Amount of IL-6 for Test Compound)−(Amount of IL-6 for Background)/(Amount of IL-6 for Control)−(Amount of IL-6 for Background)]}

(Evaluation Results)

As an example of the evaluation results, the IL-6 production inhibition ratios (%) for the test compounds (Compounds 1-1, 1-2, 1-4, 1-5, 1-6, 1-8, 1-9, 1-11, 1-13, 1-15, 1-16, 1-17, 1-19, 1-21, 1-22, 1-24, 1-25, 1-27, 1-28, 1-29, 1-30, 1-36, 1-37, 1-39, 1-40, 1-41, 1-42, 1-43, 1-44, 1-45, 1-48, 1-51, 1-52, 1-53, 2-2, 3-1, 3-3, 3-4, 4-1, 4-4, 4-9, 4-11, 4-15, 4-23, 4-24, 4-27, 4-30, 4-31, 4-32, 4-34, 4-35, 4-37, 4-43, 4-47, 4-48, 4-49, 4-50, 4-54, 5-1, 6-1, 7-3, 8-1, 8-2, 8-3, 8-4, 8-10, 8-11, 8-12, 8-13, 8-14, 8-15, 8-16, 8-17, 8-18, 8-22, 9-1, 9-2, 10-3, 11-1, 13-2, 15-1, 17-1, 18-1, 19-1 and 20-1) at 10 μM are shown in Table I.

TABLE I

| | Inhibition ratio (%) |
|---|---|
| Compound 1-1 | 94 |
| Compound 1-2 | 85 |
| Compound 1-4 | 88 |
| Compound 1-5 | 67 |
| Compound 1-6 | 92 |
| Compound 1-8 | 93 |
| Compound 1-9 | 100 |
| Compound 1-11 | 88 |
| Compound 1-13 | 93 |
| Compound 1-15 | 80 |
| Compound 1-16 | 94 |
| Compound 1-17 | 96 |
| Compound 1-19 | 100 |
| Compound 1-21 | 88 |
| Compound 1-22 | 100 |
| Compound 1-24 | 99 |
| Compound 1-25 | 99 |
| Compound 1-27 | 100 |
| Compound 1-28 | 97 |
| Compound 1-29 | 54 |
| Compound 1-30 | 90 |
| Compound 1-36 | 100 |
| Compound 1-37 | 98 |
| Compound 1-39 | 99 |
| Compound 1-40 | 99 |
| Compound 1-41 | 96 |
| Compound 1-42 | 94 |
| Compound 1-43 | 88 |
| Compound 1-44 | 92 |
| Compound 1-45 | 95 |
| Compound 1-48 | 98 |
| Compound 1-51 | 96 |
| Compound 1-52 | 93 |
| Compound 1-53 | 94 |
| Compound 2-2 | 85 |
| Compound 3-1 | 95 |
| Compound 3-3 | 100 |
| Compound 3-4 | 100 |
| Compound 4-1 | 96 |
| Compound 4-4 | 90 |
| Compound 4-9 | 89 |
| Compound 4-11 | 97 |
| Compound 4-15 | 91 |
| Compound 4-23 | 97 |
| Compound 4-24 | 99 |
| Compound 4-27 | 99 |
| Compound 4-30 | 99 |
| Compound 4-31 | 98 |
| Compound 4-32 | 99 |
| Compound 4-34 | 100 |
| Compound 4-35 | 100 |
| Compound 4-37 | 97 |
| Compound 4-43 | 99 |
| Compound 4-47 | 100 |
| Compound 4-48 | 100 |
| Compound 4-49 | 100 |
| Compound 4-50 | 100 |
| Compound 4-54 | 96 |
| Compound 5-1 | 94 |
| Compound 6-1 | 99 |
| Compound 7-3 | 98 |
| Compound 8-1 | 97 |
| Compound 8-2 | 77 |
| Compound 8-3 | 95 |
| Compound 8-4 | 99 |
| Compound 8-10 | 98 |
| Compound 8-11 | 96 |
| Compound 8-12 | 100 |
| Compound 8-13 | 100 |
| Compound 8-14 | 100 |
| Compound 8-15 | 98 |
| Compound 8-16 | 100 |
| Compound 8-17 | 100 |
| Compound 8-18 | 100 |
| Compound 8-22 | 98 |
| Compound 9-1 | 100 |
| Compound 9-2 | 87 |
| Compound 10-3 | 100 |
| Compound 11-1 | 100 |
| Compound 13-2 | 94 |
| Compound 15-1 | 98 |
| Compound 17-1 | 98 |
| Compound 18-1 | 90 |
| Compound 19-1 | 97 |
| Compound 20-1 | 95 |

The inhibition ratio which is 100% or more is indicated to be 100%.

As shown in Table I, the present compounds exhibited an excellent inhibitory activity against IL-6 production. Accordingly, the present compounds can be used as an inhibitor of IL-6 production and are useful as a prophylactic and/or therapeutic agent for a disease considered to be associated with IL-6.

2. Evaluation Test for Inhibitory Effect on Choroidal Neovascularization

As one of the methods widely used for evaluating an inhibitory effect on choroidal neovascularization, a rat model of choroidal neovascularization induced by krypton laser irradiation has been reported in Graefe's Arch. Cli. Exp. Ophthalmol., 235, 313-319 (1997). According to the method described in this document, a ratio of incidence of choroidal neovascularization of a present compound administration group to that of a vehicle administration group was calculated using the rat model of choroidal neovascularization, and an inhibitory effect of the present compound on choroidal neovascularization was evaluated using the calculated value as an index. Specific test methods will be described below.

(Preparation of Administration Liquid of Test Compound)

A test compound was suspended in a 1% aqueous methyl cellulose solution, whereby a 6 mg/mL test compound suspension was prepared.

(Preparation of Rat Model of Choroidal Neovascularization Induced by Krypton Laser)

1) To a Brown Norway rat (male, 7 to 8 weeks of age), a mixed solution of a 5% ketamine hydrochloride injection solution and a 2% xylazine hydrochloride injection solution (7:1) was intramuscularly administered at a dose of 1 mL/kg to effect systemic anesthesia.

2) After a 0.5% tropicamide-0.5% phenylephrine hydrochloride eye drop was instilled into the eyes to cause mydriasis, photocoagulation was performed using a krypton laser photocoagulation apparatus (MC-7000, manufactured by NIDEK Co., Ltd.). The krypton laser irradiation was performed at eight spots per eye sparsely by focusing on the retinal deep layer avoiding large retinal vessels in a posterior section of ocular fundus. The photocoagulation conditions were set such that the spot size was 100 μm, the output was 100 mW and the coagulation time was 0.1 sec.

3) After the photocoagulation, the ocular fundus photography was performed (PRO III, manufactured by Kowa Company, Ltd.) to confirm the photocoagulation (krypton laser irradiation) sites.

(Administration Method of Test Compound)

1) The test compound suspension (30 mg/kg/day) was orally administered once a day for 7 consecutive days from the day of krypton laser irradiation (day 0) until day 6.

2) A 1% aqueous methyl cellulose solution was administered in the same manner as in 1) in place of the test compound suspension, and the obtained result was designated as the vehicle administration group.

(Evaluation Method)

1). On day 7 after the photocoagulation, 0.1 mL of a 10% aqueous fluorescein solution was injected into the tail vein, and fluorescein fundus angiography was performed (PRO III, manufactured by Kowa Company, Ltd.).

2) In the fluorescein fundus angiography, a spot where fluorescence leakage was not observed was determined to be negative and a spot where fluorescence leakage was observed was determined to be positive. With respect to photocoagulation sites where a little fluorescence leakage was observed, in the case where there were two such photocoagulation sites, it was determined to be positive.

(Calculation Formula of Incidence of Neovascularization)

An incidence (%) of neovascularization of each administration group and a ratio of incidence of neovascularization of the test compound administration group to that of the vehicle administration group were calculated from the following formulae, respectively.

Incidence of Neovascularization of Each Administration Group (%)=[(Number of Positive Photocoagulation. Sites)/(Number of Total Photocoagulation Sites)]×100

Ratio of Incidence of Neovascularization of Test Compound Administration Group to that of Vehicle Administration Group (% of Control)= [(Incidence of Neovascularization of Test Compound Administration Group)/(Incidence of Neovascularization of Vehicle Administration Group)]×100

(Evaluation Results)

As an example of the evaluation results, the ratios (% of control) of incidence of neovascularization of the test compound administration group to that of the vehicle administration group with respect to the test compounds (Compounds 1-8, 1-9, 1-25, 4-4, 4-34, 4-37, 4-43 and 4-54) are shown in Table II.

TABLE II

|  | Ratio of incidence of neovascularization (% of control) |
| --- | --- |
| Compound 1-8 | 31 |
| Compound 1-9 | 40 |
| Compound 1-25 | 52 |
| Compound 4-4 | 71 |
| Compound 4-34 | 75 |
| Compound 4-37 | 69 |
| Compound 4-43 | 57 |
| Compound 4-54 | 86 |

(Each numerical value is an average of 5 to 8 eyes of 3 to 4 rats.)

As shown in Table II, the present compounds exhibited an excellent inhibitory effect on choroidal neovascularization. Accordingly, the present compounds are useful as a prophylactic and/or therapeutic agent for an ocular inflammatory disease and/or a retinal disease such as age-related macular degeneration, diabetic retinopathy or diabetic macular edema.

INDUSTRIAL APPLICABILITY

The present compound has an excellent inhibitory activity against IL-6 production and/or inhibitory effect on choroidal neovascularization, and is therefore useful as an inhibitor of IL-6 production, a prophylactic and/or therapeutic agent for a disease considered to be associated with IL-6, a prophylactic and/or therapeutic agent for an ocular inflammatory disease and a prophylactic and/or therapeutic agent for a retinal disease.

More specifically, the present compound is useful as a prophylactic and/or therapeutic agent for age-related macular degeneration, retinopathy of prematurity, polypoidal choroidal vasculopathy, retinal vein occlusion, diabetic retinopathy, diabetic macular edema, keratitis, conjunctivitis, uveitis or the like.

The invention claimed is:

1. A compound represented by the following general formula (I) or a salt thereof:

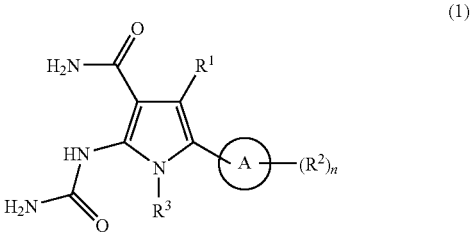

[wherein the ring A represents a benzene ring or a monocyclic aromatic heterocyclic ring;

$R^1$ represents a halogen atom, a hydrogen atom, a lower alkyl group which may have a substituent, a formyl group or a lower alkylcarbonyl group which may have a substituent;

R² represents a halogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a hydroxy group, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent, a heterocyclic oxy group which may have a substituent, a formyl group, a lower alkylcarbonyl group which may have a substituent, an arylcarbonyl group which may have a substituent, a carboxy group, a lower alkoxycarbonyl group which may have a substituent, an aryloxycarbonyl group which may have a substituent, a lower alkylcarbonyloxy group which may have a substituent, an arylcarbonyloxy group which may have a substituent, a mercapto group, a lower alkylthio group which may have a substituent, a lower cycloalkylthio group which may have a substituent, an arylthio group which may have a substituent, a lower alkylsulfinyl group which may have a substituent, an arylsulfinyl group which may have a substituent, a lower alkylsulfonyl group which may have a substituent, an arylsulfonyl group which may have a substituent, a cyano group, a nitro group, —NR$^{a1}$R$^{a2}$, —CONR$^{b1}$R$^{b2}$, —SON$^{c1}$R$^{c2}$, —SO$_2$NR$^{d1}$R$^{d2}$ or —OCONR$^{e1}$R$^{e2}$;

R³ represents a hydrogen atom, a lower alkyl group which may have a substituent, an aryl group which may have a substituent or an acyl group which may have a substituent;

R$^{a1}$, R$^{a2}$, R$^{b1}$, R$^{b2}$, R$^{c1}$, R$^{c2}$, R$^{d1}$, R$^{d2}$, R$^{e1}$ and R$^{e2}$ are the same or different and represent a hydrogen atom, a lower alkyl group which may have a substituent or an aryl group which may have a substituent, and further, R$^{a1}$ and R$^{a2}$, R$^{b1}$ and R$^{b2}$, R$^{c1}$ and R$^{c2}$, R$^{d1}$ and R$^{d2}$ or R$^{e1}$ and R$^{e2}$ may be joined to each other to form a nitrogen-containing heterocyclic ring which may have a substituent;

n represents 0, 1, 2, 3, 4 or 5; and provided that when n is 2, 3, 4 or 5, R² may be the same or different].

2. The compound or a salt thereof according to claim 1, wherein, in the general formula (1), the ring A represents a benzene ring or a monocyclic aromatic heterocyclic ring;

R¹ represents a halogen atom, a hydrogen atom, a lower alkyl group which may have a substituent, a formyl group or a lower alkylcarbonyl group;

R² represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group which may have a substituent, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group which may have a substituent, a lower cycloalkylthio group, an arylthio group which may have a substituent, a lower alkylsulfinyl group, an arylsulfinyl group, a lower alkylsulfonyl group, an arylsulfonyl group, a cyano group, a nitro group, —NR$^{a1}$R$^{a2}$, —CONR$^{b1}$R$^{b2}$, —SONR$^{c1}$R$^{c2}$, —SO$_2$NR$^{d1}$R$^{d2}$ or —OCONR$^{e1}$R$^{e2}$;

R³ represents a hydrogen atom, a lower alkyl group, an aryl group or an acyl group;

R$^{a1}$, R$^{a2}$, R$^{b1}$, R$^{b2}$, R$^{c1}$, R$^{c2}$, R$^{d1}$, R$^{d2}$, R$^{e1}$ and R$^{e2}$ are the same or different and represent a hydrogen atom, a lower alkyl group or an aryl group, and further, R$^{a1}$ and R$^{a2}$, R$^{b1}$ and R$^{b2}$, R$^{c1}$ and R$^{c2}$, R$^{d1}$ and R$^{d2}$ or R$^{e1}$ and R$^{e2}$ may be joined to each other to form a nitrogen-containing heterocyclic ring;

n represents 0, 1, 2, 3, 4 or 5; and provided that when n is 2, 3, 4 or 5, R² may be the same or different.

3. The compound or a salt thereof according to claim 1, wherein, in the general formula (1), the ring A represents a benzene ring or a monocyclic aromatic heterocyclic ring;

R¹ represents a halogen atom, a hydrogen atom, a lower alkyl group which may have a substituent, a formyl group or a lower alkylcarbonyl group;

R² represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group which may have a substituent, a lower cycloalkylthio group, an arylthio group, an arylthio group substituted with a nitro group, a lower alkylsulfinyl group, an arylsulfinyl group, a lower alkylsulfonyl group, an arylsulfonyl group, a cyano group, a nitro group, —NR$^{a1}$R$^{a2}$, —CONR$^{b1}$R$^{b2}$, —SONR$^{c1}$R$^{c2}$, —SO$_2$NR$^{d1}$R$^{d2}$ or —OCONR$^{e1}$R$^{e2}$;

provided that when R¹ and/or R² represents a lower alkyl group which may have a substituent, a lower alkynyl group which may have a substituent, a lower alkoxy group which may have a substituent or a lower alkylthio group which may have a substituent, the lower alkyl group, the lower alkynyl group, the lower alkoxy group or the lower alkylthio group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a heterocyclic group substituted with a carbonyl group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, a lower alkylthio group substituted with a lower alkoxycarbonyl group, an arylthio group, a cyano group and —$NR^{f1}R^{f2}$;

$R^3$ represents a hydrogen atom, a lower alkyl group, an aryl group or an acyl group;

$R^{a1}$, $R^{a2}$, $R^{b1}$, $R^{b2}$, $R^{c1}$, $R^{c2}$, $R^{d1}$, $R^{d2}$, $R^{e1}$ and $R^{e2}$ are the same or different and represent a hydrogen atom, a lower alkyl group or an aryl group, and further, $R^{a1}$ and $R^{a2}$, $R^{b1}$ and $R^{b2}$, $R^{c1}$ and $R^{c2}$, $R^{d1}$ and $R^{d2}$ or $R^{e1}$ and $R^{e2}$ may be joined to each other to form a nitrogen-containing heterocyclic ring;

$R^{f1}$ and $R^{f2}$ are the same or different and represent a hydrogen atom, a lower alkyl group which may have a substituent, a lower cycloalkyl group or an aryl group, and further, $R^{f1}$ and $R^{f2}$ may be joined to each other to form a nitrogen-containing heterocyclic ring which may have a lower alkyl group substituted with a hydroxy group or a carbonyl group as a substituent;

provided that when $R^{f1}$ and/or $R^{f2}$ represents a lower alkyl group which may have a substituent, the lower alkyl group represents a group which may be substituted with one or plural groups selected from the group consisting of a lower cycloalkyl group, an aryl group, a heterocyclic group, a hydroxy group, a lower alkoxy group, a lower cycloalkyloxy group, an aryloxy group, a heterocyclic oxy group and —$NR^{g1}R^{g2}$;

$R^{g1}$ and $R^{g2}$ are the same or different and represent a hydrogen atom or a lower alkyl group, and further, $R^{g1}$ and $R^{g2}$ may be joined to each other to form a nitrogen-containing heterocyclic ring;

n represents 0, 1, 2, 3, 4 or 5; and provided that when n is 2, 3, 4 or 5, $R^2$ may be the same or different.

4. The compound or a salt thereof according to claim 1, wherein, in the general formula (I), the ring A represents a benzene ring or a monocyclic aromatic heterocyclic ring;

$R^1$ represents a halogen atom, a hydrogen atom, a lower alkyl group, a lower alkyl group substituted with a hydroxy group, a lower alkyl group substituted with a lower alkoxy group, a lower alkyl group substituted with —$NR^{h1}R^{h2}$, a formyl group or a lower alkylcarbonyl group;

$R^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group, a lower alkylthio group substituted with a cyano group, a lower cycloalkylthio group, an arylthio group, an arylthio group substituted with a nitro group, a lower alkylsulfinyl group, an arylsulfinyl group, a lower alkylsulfonyl group, an arylsulfonyl group, a cyano group, a nitro group, —$NR^{a1}R^{a2}$, —$CONR^{b1}R^{b2}$, —$SONR^{c1}R^{c2}$, —$SO_2NR^{d1}R^{d2}$ or —$OCONR^{e1}R^{e2}$;

provided that when $R^2$ represents a lower alkyl group which may have a substituent, the lower alkyl group represents a group which may be substituted with one or plural groups selected from the group consisting of a halogen atom, a hydroxy group, a lower alkoxy group, a mercapto group, a lower alkylthio group and —$NR^{f1}R^{f2}$;

provided that when $R^2$ represents a lower alkynyl group which may have a substituent, the lower alkynyl group represents a group which may be substituted with one or plural groups selected from the group consisting of a lower cycloalkyl group, an aryl group, a hydroxy group, a lower alkoxy group, a lower cycloalkyloxy group, an aryloxy group and —$NR^{f1}R^{f2}$;

provided that when $R^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a heterocyclic group substituted with a carbonyl group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, a lower alkylthio group substituted with a lower alkoxycarbonyl group, an arylthio group, a cyano group and —$NR^{f1}R^{f2}$;

provided that when $R^2$ represents a lower alkylthio group which may have a substituent, the lower alkylthio group represents a group which may be substituted with one or plural groups selected from the group consisting of a hydroxy group, a lower alkoxy group, a mercapto group, a lower alkylthio group and a cyano group;

$R^3$ represents a hydrogen atom, a lower alkyl group, an aryl group or an acyl group;

$R^{a1}$, $R^{a2}$, $R^{b1}$, $R^{b2}$, $R^{c1}$, $R^{c2}$, $R^{d1}$, $R^{d2}$, $R^{e1}$ and $R^{e2}$ are the same or different and represent a hydrogen atom, a lower alkyl group or an aryl group, and further, $R^{a1}$ and $R^{a2}$, $R^{b1}$ and $R^{b2}$, $R^{c1}$ and $R^{c2}$, $R^{d1}$ and $R^{d2}$ or $R^{e1}$ and $R^{e2}$ may be joined to each other to form a nitrogen-containing heterocyclic ring;

$R^{f1}$ and $R^{f2}$ are the same or different and represent a hydrogen atom, a lower alkyl group, a lower alkyl group substituted with a lower cycloalkyl group, a lower alkyl group substituted with an aryl group, a lower alkyl group substituted with a heterocyclic group, a lower alkyl group substituted with a hydroxy group, a lower alkyl group substituted with a lower alkoxy group, a lower alkyl group substituted with a lower cycloalkyloxy group, a lower alkyl group substituted with an aryloxy group, a lower alkyl group substituted with a heterocyclic oxy group, a lower alkyl group substituted with —$NR^{g1}R^{g2}$, a lower cycloalkyl group or an aryl group, and further, $R^{f1}$ and $R^{f2}$ may be joined to each other to form a nitrogen-containing heterocyclic ring which may have a lower alkyl group substituted with a hydroxy group or a carbonyl group as a substituent;

$R^{g1}$ and $R^{g2}$ are the same or different and represent a hydrogen atom or a lower alkyl group, and further, $R^{g1}$ and $R^{g2}$ may be joined to each other to form a nitrogen-containing heterocyclic ring;

$R^{h1}$ and $R^{h2}$ are the same or different and represent a hydrogen atom or a lower alkyl group, and further, $R^{h1}$ and $R^{h2}$ may be joined to each other to form a nitrogen-containing heterocyclic ring;

$R^{i1}$ and $R^{i2}$ are the same or different and represent a hydrogen atom, a lower alkyl group, a lower alkyl group substituted with a lower cycloalkyl group, a lower alkyl group substituted with an aryl group, a lower alkyl group substituted with a hydroxy group, a lower alkyl group substituted with a lower alkoxy group, a lower alkyl group substituted with a lower cycloalkyloxy group or a lower alkyl group substituted with an aryloxy group, and further, $R^{i1}$ and $R^{i2}$ may be joined to each other to form a nitrogen-containing heterocyclic ring;

$R^{j1}$ and $R^{j2}$ are the same or different and represent a hydrogen atom or a lower alkyl group, and further, $R^{j1}$ and $R^{j2}$ may be joined to each other to form a nitrogen-containing heterocyclic ring;

n represents 0, 1, 2 or 3; and provided that when n is 2 or 3, $R^2$ may be the same or different.

5. The compound or a salt thereof according to claim 1, wherein, in the general formula (1), the ring A represents a benzene ring or a monocyclic aromatic heterocyclic ring;

$R^1$ represents a halogen atom, a hydrogen atom, a lower alkyl group, a lower alkyl group substituted with a hydroxy group, a lower alkyl group substituted with a lower alkoxy group, a lower alkyl group substituted with $—NR^{h1}R^{h2}$, a formyl group or a lower alkylcarbonyl group;

$R^2$ represents a halogen atom, a lower alkyl group which may have a substituent, a lower alkenyl group, a lower alkynyl group which may have a substituent, a lower cycloalkyl group, an aryl group, a heterocyclic group, a hydroxy group, a lower alkoxy group which may have a substituent, a lower alkenyloxy group, a lower alkynyloxy group, a lower cycloalkyloxy group, an aryloxy group, an aryloxy group substituted with a nitro group, a heterocyclic oxy group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, a mercapto group, a lower alkylthio group, a lower alkylthio group substituted with a cyano group, an arylthio group, an arylthio group substituted with a nitro group, a cyano group, a nitro group, $—NR^{11}R^{a2}$ or $—OCONR^{e1}R^{e2}$;

provided that when $R^2$ represents a lower alkyl group which may have a substituent, the lower alkyl group represents a group which may be substituted with one or plural groups selected from the group consisting of a halogen atom, a hydroxy group, a lower alkoxy group, a mercapto group, a lower alkylthio group and $—NR^{i1}R^{i2}$;

provided that when $R^2$ represents a lower alkynyl group which may have a substituent, the lower alkynyl group represents a group which may be substituted with one or plural groups selected from the group consisting of a lower cycloalkyl group, an aryl group, a hydroxy group, a lower alkoxy group, a lower cycloalkyloxy group, an aryloxy group and $—NR^{j1}R^{j2}$;

provided that when $R^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a heterocyclic group substituted with a lower alkoxy group, a hydroxy group, a lower alkoxy group, a lower alkoxy group substituted with a lower cycloalkyl group, a lower alkoxy group substituted with an aryl group, a lower alkoxy group substituted with a lower alkoxy group, a lower alkoxy group substituted with a lower cycloalkyloxy group, a lower alkoxy group substituted with an aryloxy group, a lower cycloalkyloxy group, an aryloxy group, a heterocyclic oxy group, a formyl group, a lower alkylcarbonyl group, an arylcarbonyl group, an arylcarbonyl group substituted with a halogen atom, a heterocyclic carbonyl group, a carboxy group, a lower alkoxycarbonyl group, an aryloxycarbonyl group, a heterocyclic oxy carbonyl group, a mercapto group, a lower alkylthio group, an arylthio group, a cyano group and $—NR^{f1}R^{f2}$;

$R^3$ represents a hydrogen atom or a lower alkyl group;

$R^{a1}$, $R^{a2}$, $R^{e1}$ and $R^{e2}$ are the same or different and represent a hydrogen atom or a lower alkyl group;

$R^{f1}$ and $R^{f2}$ are the same or different and represent a hydrogen atom, a lower alkyl group, a lower alkyl group substituted with a lower cycloalkyl group, a lower alkyl group substituted with an aryl group, a lower alkyl group substituted with a heterocyclic group, a lower alkyl group substituted with a hydroxy group, a lower alkyl group substituted with a lower alkoxy group, a lower alkyl group substituted with a lower cycloalkyloxy group, a lower alkyl group substituted with an aryloxy group, a lower alkyl group substituted with a heterocyclic oxy group, a lower alkyl group substituted with $—NR^{g1}R^{g2}$ or a lower cycloalkyl group, and further, $R^{f1}$ and $R^{f2}$ may be joined to each other to form a nitrogen-containing heterocyclic ring;

$R^{g1}$ and $R^{g2}$ are the same or different and represent a hydrogen atom or a lower alkyl group;

$R^{h1}$ and $R^{h2}$ are the same or different and represent a hydrogen atom or a lower alkyl group;

$R^{i1}$ and $R^{i2}$ are the same or different and represent a hydrogen atom, a lower alkyl group, a lower alkyl group substituted with a lower cycloalkyl group, a lower alkyl group substituted with an aryl group, a lower alkyl group substituted with a hydroxy group, a lower alkyl group substituted with a lower alkoxy group, a lower alkyl group substituted with a lower cycloalkyloxy group or a lower alkyl group substituted with an aryloxy group;

$R^{j1}$ and $R^{j2}$ are the same or different and represent a hydrogen atom or a lower alkyl group;

n represents 0, 1, 2 or 3; and provided that when n is 2 or 3, $R^2$ may be the same or different.

6. The compound or a salt thereof according to claim 1, wherein, in the general formula (I), the ring A represents a benzene ring or a monocyclic aromatic heterocyclic ring;

$R^1$ represents a halogen atom, a hydrogen atom, a lower alkyl group, a lower alkyl group substituted with a hydroxy group, a lower alkyl group substituted with $—NR^{h1}R^{h2}$ or a formyl group;

$R^2$ represents a halogen atom, a lower alkyl group which may have a substituent, a lower alkenyl group, a lower alkynyl group which may have a substituent, an aryl group, a heterocyclic group, a hydroxy group, a lower alkoxy group which may have a substituent, a lower alkenyloxy group, a lower alkynyloxy group, an aryloxy group substituted with a nitro group, a formyl group, a lower alkoxycarbonyl group, a lower alkylcarbonyloxy group, a lower alkylthio group, a lower alkylthio group substituted with a cyano group, an arylthio group substituted with a nitro group, a cyano group, a nitro group, —$NR^{a1}R^{a2}$ or —$OCONR^{e1}R^{e2}$;

provided that when $R^2$ represents a lower alkyl group which may have a substituent, the lower alkyl group represents a group which may be substituted with one or plural groups selected from the group consisting of a halogen atom, a hydroxy group, a lower alkylthio group and —$NR^{i1}R^{i2}$;

provided that when $R^2$ represents a lower alkynyl group which may have a substituent, the lower alkynyl group represents a group which may be substituted with one or plural groups selected from the group consisting of an aryl group, a hydroxy group and —$NR^{j1}R^{j2}$;

provided that when $R^2$ represents a lower alkoxy group which may have a substituent, the lower alkoxy group represents a group which may be substituted with one or plural groups selected from the group consisting of a halogen atom, a lower cycloalkyl group, an aryl group, a heterocyclic group, a heterocyclic group substituted with a lower alkyl group, a heterocyclic group substituted with a hydroxy group, a hydroxy group, a lower alkoxy group, a lower alkoxy group substituted with an aryl group, a lower alkoxy group substituted with a lower alkoxy group, an aryloxy group, a heterocyclic oxy group, an arylcarbonyl group substituted with a halogen atom, a heterocyclic carbonyl group, a lower alkoxycarbonyl group, a lower alkylthio group, a cyano group and —$NR^{f1}R^{f2}$;

$R^3$ represents a hydrogen atom;
$R^{a1}$ and $R^{a2}$ represent a hydrogen atom;
$R^{e1}$ and $R^{e2}$ are the same or different and represent a hydrogen atom or a lower alkyl group;
$R^{f1}$ and $R^{f2}$ are the same or different and represent a hydrogen atom, a lower alkyl group, a lower alkyl group substituted with an aryl group, a lower alkyl group substituted with a heterocyclic group, a lower alkyl group substituted with a hydroxy group, a lower alkyl group substituted with —$NR^{g1}R^{g2}$ or a lower cycloalkyl group, and further, $R^{f1}$ and $R^{f2}$ may be joined to each other to form a nitrogen-containing heterocyclic ring;
$R^{g1}$ and $R^{g2}$ represent a lower alkyl group;
$R^{h1}$ and $R^{h2}$ are the same or different and represent a hydrogen atom or a lower alkyl group;
$R^{i1}$ and $R^{i2}$ are the same or different and represent a hydrogen atom, a lower alkyl group, a lower alkyl group substituted with an aryl group or a lower alkyl group substituted with a hydroxy group;
$R^{j1}$ and $R^{j2}$ represent a lower alkyl group;
n represents 0, 1, 2 or 3; and
provided that when n is 2 or 3, $R^2$ may be the same or different.

7. The compound or a salt thereof according to claim 1, wherein, in the general formula (1),
the ring A represents a benzene ring or a monocyclic aromatic heterocyclic ring;
$R^1$ represents a halogen atom, a hydrogen atom, a lower alkyl group, a lower alkyl group substituted with a hydroxy group, a lower alkyl group substituted with —$NR^{h1}R^{h2}$ or a formyl group;

$R^2$ represents a halogen atom, a lower alkyl group which may have a substituent, a lower alkenyl group, a lower alkynyl group, a lower alkynyl group substituted with a hydroxy group, an aryl group, a heterocyclic group, a hydroxy group, a lower alkoxy group which may have a substituent, a lower alkenyloxy group, a lower alkynyloxy group, a lower alkoxycarbonyl group, a lower alkylcarbonyloxy group, a lower alkylthio group, a cyano group, a nitro group, —$NR^{a1}R^{a2}$ or —$OCONR^{e1}R^{e2}$;

provided that when $R^2$ represents a lower alkyl group which may have a substituent, the lower alkyl group represents a group which may be substituted with one or plural groups selected from the group consisting of a halogen atom, a hydroxy group and a lower alkylthio group;

provided that when $R^2$ represents a lower alkoxy group which may have a substituent, the lower alkoxy group represents a group which may be substituted with one or plural groups selected from the group consisting of a halogen atom, a lower cycloalkyl group, a heterocyclic group, a heterocyclic group substituted with a lower alkyl group, a hydroxy group, a lower alkylthio group, a cyano group and —$NR^{f1}R^{f2}$;

$R^3$ represents a hydrogen atom;
$R^{a1}$ and $R^{a2}$ represent a hydrogen atom;
$R^{e1}$ and $R^{e2}$ are the same or different and represent a hydrogen atom or a lower alkyl group;
$R^{f1}$ and $R^{f2}$ are the same or different and represent a hydrogen atom, a lower alkyl group, a lower alkyl group substituted with a hydroxy group or a lower cycloalkyl group, and further, $R^{f1}$ and $R^{f2}$ may be joined to each other to form a nitrogen-containing heterocyclic ring;
$R^{h1}$ and $R^{h2}$ are the same or different and represent a hydrogen atom or a lower alkyl group;
n represents 0, 1, 2 or 3; and
provided that when n is 2 or 3, $R^2$ may be the same or different.

8. The compound or a salt thereof according to claim 1, wherein, in the general formula (1),
the ring A represents benzene, pyridine, pyrazine or thiophene.

9. The compound or a salt thereof according to claim 1, wherein, in the general formula (1),
the ring A represents benzene, pyridine or thiophene.

10. The compound or a salt thereof according to claim 1, wherein, in the general formula (1),
the ring A represents benzene.

11. The compound or a salt thereof according to claim 1, wherein, in the general formula (1),
$R^1$ represents a hydrogen atom; and
$R^3$ represents a hydrogen atom.

12. The compound or a salt thereof according to claim 1, wherein, in the general formula (1),
n represents 0, 1 or 2.

13. The compound or a salt thereof according to claim 1, wherein, in the general formula (1),
n represents 1 or 2.

14. The compound or a salt thereof according to claim 1, wherein, in the general formula (1),
the ring A represents a benzene ring;
$R^1$ represents a hydrogen atom;
$R^2$ represents a halogen atom, a lower alkynyl group, a hydroxy group, a lower alkoxy group which may have a substituent, a lower alkylthio group which may have a substituent or a cyano group;

provided that when R² represents a lower alkoxy group which may have a substituent or a lower alkylthio group which may have a substituent, the lower alkoxy group or the lower alkylthio group represents a group which may be substituted with one or plural groups selected from the group consisting of a hydroxy group, a lower alkoxy group, a mercapto group, a lower alkylthio group and a cyano group;

R³ represents a hydrogen atom;

n represents 0, 1 or 2; and provided that when n is 2, R² may be the same or different.

15. The compound or a salt thereof according to claim 1, wherein, in the general formula (1), the ring A represents a benzene ring;

R¹ represents a hydrogen atom;

R² represents a halogen atom, a lower alkynyl group, a hydroxy group, a lower alkoxy group, a lower alkoxy group substituted with a hydroxy group, a lower alkoxy group substituted with a cyano group, a lower alkylthio group or a cyano group;

R³ represents a hydrogen atom;

n represents 0, 1 or 2; and provided that when n is 2, R² may be the same or different.

16. The compound or a salt thereof according to claim 1, wherein, in the general formula (1), the ring A represents a benzene ring;

R¹ represents a hydrogen atom;

R² represents a fluorine atom, a chlorine atom, a bromine atom, an ethynyl group, a hydroxy group, a methoxy group, an ethoxy group, a propoxy group, a hydroxyethyloxy group, a cyanomethyloxy group or a cyano group;

R³ represents a hydrogen atom;

n represents 1 or 2; and provided that when n is 2, R² may be the same or different.

17. A compound or a salt thereof selected from

2-Aminocarbonylamino-5-(4-bromophenyl)pyrrole-3-carboxamide,
2-Aminocarbonylamino-5-(pyridin-2-yl)pyrrole-3-carboxamide,
2-Aminocarbonylamino-5-phenylpyrrole-3-carboxamide,
2-Aminocarbonylamino-5-(4-biphenyl)pyrrole-3-carboxamide,
2-Aminocarbonylamino-5-(3-nitrophenyl)pyrrole-3-carboxamide,
2-Aminocarbonylamino-5-(4-fluorophenyl)pyrrole-3-carboxamide,
2-Aminocarbonylamino-5-(2-methoxyphenyl)pyrrole-3-carboxamide,
2-Aminocarbonylamino-5-(4-methylphenyl)pyrrole-3-carboxamide,
2-Aminocarbonylamino-5-(2-trifluoromethylphenyl)pyrrole-3-carboxamide,
2-Aminocarbonylamino-5-(4-cyanophenyl)pyrrole-3-carboxamide,
2-Aminocarbonylamino-5-(thiophen-2-yl)pyrrole-3-carboxamide,
2-Aminocarbonylamino-5-(2,5-dimethoxyphenyl)pyrrole-3-carboxamide,
2-Aminocarbonylamino-5-(5-fluoro-2-methoxyphenyl)pyrrole-3-carboxamide,
2-Aminocarbonylamino-5-(4-bromophenyl)-4-methylpyrrole-3-carboxamide,
2-Aminocarbonylamino-5-(5-chloro-2-methoxyphenyl)pyrrole-3-carboxamide,
2-Aminocarbonylamino-5-(5-chloro-2-methoxy-4-methylphenyl)pyrrole-3-carboxamide,
2-Aminocarbonylamino-5-(3-chlorophenyl)pyrrole-3-carboxamide,
2-Aminocarbonylamino-5-(2,5-dichlorophenyl)pyrrole-3-carboxamide,
2-Aminocarbonylamino-5-(3-fluorophenyl)pyrrole-3-carboxamide,
2-Aminocarbonylamino-5-(5-chloro-2-methoxyphenyl)-1-methylpyrrole-3-carboxamide,
2-Aminocarbonylamino-5-(4-ethoxycarbonylphenyl)pyrrole-3-carboxamide,
2-Aminocarbonylamino-5-(3-chloro-4-fluorophenyl)pyrrole-3-carboxamide,
2-Aminocarbonylamino-5-(3-chloro-4-methoxyphenyl)pyrrole-3-carboxamide,
2-Aminocarbonylamino-5-(3-cyanophenyl)pyrrole-3-carboxamide,
2-Aminocarbonylamino-5-(2-chlorophenyl)pyrrole-3-carboxamide,
2-Aminocarbonylamino-5-(5-methylthiophen-2-yl)pyrrole-3-carboxamide,
2-Aminocarbonylamino-5-(2-methylphenyl)pyrrole-3-carboxamide,
2-Aminocarbonylamino-5-(3-methylthiophenyl)pyrrole-3-carboxamide,
2-Aminocarbonylamino-5-(3-ethylthiophenyl)pyrrole-3-carboxamide,
2-Aminocarbonylamino-5-(2-fluorophenyl)pyrrole-3-carboxamide,
2-Aminocarbonylamino-5-(5-chlorothiophen-2-yl)pyrrole-3-carboxamide,
2-Aminocarbonylamino-5-(2,5-dimethylthiophen-3-yl)pyrrole-3-carboxamide,
2-Aminocarbonylamino-5-(2,4,5-trifluorophenyl)pyrrole-3-carboxamide,
2-Aminocarbonylamino-5-(2,5-difluorophenyl)pyrrole-3-carboxamide,
2-Aminocarbonylamino-5-(4-aminophenyl)pyrrole-3-carboxamide,
2-Aminocarbonylamino-5-(2-hydroxyphenyl)pyrrole-3-carboxamide,
2-Aminocarbonylamino-5-(5-fluoro-2-hydroxyphenyl)pyrrole-3-carboxamide,
2-Aminocarbonylamino-5-(5-chloro-2-hydroxyphenyl)pyrrole-3-carboxamide,
2-Aminocarbonylamino-5-(2-cyanomethyloxyphenyl)pyrrole-3-carboxamide,
2-Aminocarbonylamino-5-(2-propyloxyphenyl)pyrrole-3-carboxamide,
2-Aminocarbonylamino-5-(3-cyanomethyloxyphenyl)pyrrole-3-carboxamide,
2-Aminocarbonylamino-5-(2-ethoxyphenyl)pyrrole-3-carboxamide,
2-Aminocarbonylamino-5-[2-(pyridin-3-ylmethyloxy)phenyl]pyrrole-3-carboxamide,
2-Aminocarbonylamino-5-(2-cyclopropylmethyloxyphenyl)pyrrole-3-carboxamide,
2-Aminocarbonylamino-5-[2-(3-fluoropropyloxy)phenyl]pyrrole-3-carboxamide,
2-Aminocarbonylamino-5-[2-[2-(piperidin-1-yl)ethyloxy]phenyl]pyrrole-3-carboxamide,
2-Aminocarbonylamino-5-[2-(3-dimethylaminopropyloxy)phenyl]pyrrole-3-carboxamide,
2-Aminocarbonylamino-5-[2-(2-dimethylaminoethyloxy)phenyl]pyrrole-3-carboxamide,
2-Aminocarbonylamino-5-[2-[2-(1-methylpyrrolidin-2-yl)ethyloxy]phenyl]pyrrole-3-carboxamide, 2-Aminocarbonylamino-5-(5-fluoro-2-propyloxyphenyl)pyrrole-3-carboxamide,
2-Aminocarbonylamino-5-[5-fluoro-2-(3-hydroxypropyloxy)phenyl]pyrrole-3-carboxamide,
2-Aminocarbonylamino-5-(5-chloro-2-propyloxyphenyl)pyrrole-3-carboxamide,
2-Aminocarbonylamino-5-(5-chloro-2-cyanomethyloxyphenyl)pyrrole-3-carboxamide,
2-Aminocarbonylamino-5-(5-fluoro-2-ethoxyphenyl)pyrrole-3-carboxamide,
2-Aminocarbonylamino-5-(5-chloro-2-ethoxyphenyl)pyrrole-3-carboxamide,
2-Allyloxy-5-chlorophenyl)-2-(aminocarbonylamino)pyrrole-3-carboxamide,
2-Aminocarbonylamino-5-[5-chloro-2-(2-propynyloxy)phenyl]pyrrole-3-carboxamide,
2-Aminocarbonylamino-5-[5-fluoro-2-(2-hydroxyethyloxy)phenyl]pyrrole-3-carboxamide,
2-Aminocarbonylamino-5-(2-acetoxyphenyl)pyrrole-3-carboxamide,
2-Aminocarbonylamino-5-(2-propylaminocarbonyloxyphenyl)pyrrole-3-carboxamide,
2-Aminocarbonylamino-4-chloro-5-(4-fluorophenyl)pyrrole-3-carboxamide,
2-Aminocarbonylamino-5-[2-[3-(pyrrolidin-1-yl)propyloxy]phenyl]pyrrole-3-carboxamide,
2-Aminocarbonylamino-5-[2-[2-(4-methylpiperazin-1-yl)ethyloxy]phenyl]pyrrole-3-carboxamide,
2-Aminocarbonylamino-5-[2-[2-(morpholin-4-yl)ethyloxy]phenyl]pyrrole-3-carboxamide,
2-Aminocarbonylamino-5-[2-[2-(pyrrolidin-1-yl)ethyloxy]phenyl]pyrrole-3-carboxamide,
2-Aminocarbonylamino-5-[2-[2-(4-methylpiperidin-1-yl)ethyloxy]phenyl]pyrrole-3-carboxamide,
2-Aminocarbonylamino-5-[2-[2-[N-(2-hydroxyethyl)-N-methylamino]ethyloxy]phenyl]pyrrole-3-carboxamide,
2-Aminocarbonylamino-5-[5-fluoro-2-[2-(pyrrolidin-1-yl)ethyloxy]phenyl]pyrrole-3-carboxamide,
2-Aminocarbonylamino-5-[5-fluoro-2-[2-(4-methylpiperidin-1-yl)ethyloxy]phenyl]pyrrole-3-carboxamide,
2-Aminocarbonylamino-5-[5-chloro-2-[2-(piperidin-1-yl)ethyloxy]phenyl]pyrrole-3-carboxamide,
2-Aminocarbonylamino-5-[5-chloro-2-[2-(4-methylpiperazin-1-yl)ethyloxy]phenyl]pyrrole-3-carboxamide,
2-Aminocarbonylamino-5-[5-chloro-2-[2-(4-hydroxyethylpiperidin-1-yl)ethyloxy]phenyl]pyrrole-3-carboxamide,
2-Aminocarbonylamino-5-[5-fluoro-2-[2-[N-(2-hydroxyethyl)-N-methylamino]ethyloxy]phenyl]pyrrole-3-carboxamide,
2-Aminocarbonylamino-5-[5-fluoro-2-(2-methylthioethyloxy)phenyl]pyrrole-3-carboxamide,
2-Aminocarbonylamino-5-[2-[2-(N-cyclohexyl-N-methylamino)ethyloxy]-5-fluorophenyl]pyrrole-3-carboxamide,
2-Aminocarbonylamino-5-(4-vinylphenyl)pyrrole-3-carboxamide,
2-Aminocarbonylamino-5-[4-(furan-3-yl)phenyl]pyrrole-3-carboxamide,
2-Aminocarbonylamino-5-[3-(3-hydroxypropynyl)phenyl]pyrrole-3-carboxamide,
2-Aminocarbonylamino-5-(3-ethynylphenyl)pyrrole-3-carboxamide,
2-Aminocarbonylamino-5-(3-hydroxymethylphenyl)pyrrole-3-carboxamide,
2-Aminocarbonylamino-5-(3-methylthiomethylphenyl)pyrrole-3-carboxamide,
2-Aminocarbonylamino-5-(3-chlorophenyl)-4-formylpyrrole-3-carboxamide,
2-Aminocarbonylamino-5-(3-chlorophenyl)-4-(hydroxymethyl)pyrrole-3-carboxamide,
2-Aminocarbonylamino-5-(3-chlorophenyl)-4-(methylaminomethyl)pyrrole-3-carboxamide, and
2-Aminocarbonylamino-5-[2-(2-methylaminoethyloxy)phenyl]pyrrole-3-carboxamide.

18. A pharmaceutical composition comprising the compound or a salt thereof according to claim 1 and a pharmaceutical carrier.

19. An inhibitor of IL-6 production comprising the compound or a salt thereof according to claim 1 as an active ingredient.

20. A therapeutic agent for an ocular inflammatory disease comprising the compound or a salt thereof according to claim 1 as an active ingredient wherein the ocular inflammatory disease is age-related macular degeneration, diabetic retinopathy, diabetic macular edema, keratitis, conjunctivitis or uveitis.

21. A therapeutic agent for a retinal disease comprising the compound or a salt thereof according to claim 1 as an active ingredient wherein the retinal disease is age-related macular degeneration, diabetic retinopathy or diabetic macular edema.

22. A method for treating an ocular inflammatory disease comprising administering to a patient in need thereof a pharmaceutically effective amount of the compound or a salt thereof according to claim 1 wherein the ocular inflammatory disease is age-related macular degeneration, diabetic retinopathy, diabetic macular edema, keratitis, conjunctivitis or uveitis.

23. A method for treating a retinal disease comprising administering to a patient in need thereof a pharmaceutically effective amount of the compound or a salt thereof according to claim 1 wherein the retinal disease is age-related macular degeneration, diabetic retinopathy or diabetic macular edema.

* * * * *